US010697979B2

(12) United States Patent
Ichiyanagi

(10) Patent No.: US 10,697,979 B2
(45) Date of Patent: Jun. 30, 2020

(54) METHOD FOR MEASUREMENT OF HBA1C USING AMADORIASE THAT REACTS WITH GLYCATED PEPTIDE

(71) Applicant: Kikkoman Corporation, Noda-shi, Chiba (JP)

(72) Inventor: Atsushi Ichiyanagi, Noda (JP)

(73) Assignee: Kikkoman Corporation, Chiba (JP)

( * ) Notice: Subject to any disclaimer, the term of this patent is extended or adjusted under 35 U.S.C. 154(b) by 220 days.

(21) Appl. No.: 15/031,385

(22) PCT Filed: Oct. 24, 2014

(86) PCT No.: PCT/JP2014/078367
§ 371 (c)(1),
(2) Date: Apr. 22, 2016

(87) PCT Pub. No.: WO2015/060431
PCT Pub. Date: Apr. 30, 2015

(65) Prior Publication Data

US 2016/0274129 A1 Sep. 22, 2016

(30) Foreign Application Priority Data

Oct. 25, 2013 (JP) ................................ 2013-222789

(51) Int. Cl.
*G01N 33/72* (2006.01)
*C12N 9/06* (2006.01)
*C07K 14/37* (2006.01)

(52) U.S. Cl.
CPC ........... *G01N 33/723* (2013.01); *C07K 14/37* (2013.01); *C12N 9/0032* (2013.01); *G01N 2333/805* (2013.01); *G01N 2333/90672* (2013.01)

(58) Field of Classification Search
CPC .................. C07K 14/37; C12N 9/0032; G01N 2333/805; G01N 2333/90672; G01N 33/723
See application file for complete search history.

(56) References Cited

U.S. PATENT DOCUMENTS

| | | | |
|---|---|---|---|
| 5,370,990 A | 12/1994 | Staniford et al. | |
| 7,070,948 B1 | 7/2006 | Sakaue et al. | |
| 2006/0172367 A1* | 8/2006 | Yoshida | C12N 9/0022 435/27 |
| 2006/0239989 A1 | 10/2006 | Badet-Denisot et al. | |
| 2006/0240501 A1 | 10/2006 | Ebinuma | |
| 2007/0054344 A1 | 3/2007 | Ebinuma | |
| 2008/0113381 A1 | 5/2008 | Matsuoka et al. | |
| 2008/0233605 A1 | 9/2008 | Taniguchi et al. | |
| 2009/0317851 A1* | 12/2009 | Matsuoka | C12N 9/0004 435/23 |
| 2011/0003361 A1 | 1/2011 | Kurosawa et al. | |
| 2011/0195444 A1 | 8/2011 | Hirao et al. | |
| 2013/0267007 A1 | 10/2013 | Ichiyanagi et al. | |
| 2014/0234886 A1 | 8/2014 | Aisaka et al. | |
| 2015/0118700 A1 | 4/2015 | Ichiyanagi et al. | |

FOREIGN PATENT DOCUMENTS

| | | | |
|---|---|---|---|
| EP | 1555325 | A1 | 7/2005 |
| JP | 05-033997 | B2 | 5/1993 |
| JP | 11-127895 | A | 5/1999 |
| JP | 2001-095598 | A | 4/2001 |
| JP | 2003-235585 | A | 8/2003 |
| JP | 2003-274943 | A | 9/2003 |
| JP | 2004-275013 | A | 10/2004 |
| JP | 2004-275063 | A | 10/2004 |
| JP | 2007-515931 | A | 6/2007 |
| JP | 2010-035469 | A | 2/2010 |

(Continued)

OTHER PUBLICATIONS

Sunil et al. (2008) Bulletin of Environmental Contamination and Toxicology 81(4): 422-426.*

(Continued)

*Primary Examiner* — Lisa J Hobbs
(74) *Attorney, Agent, or Firm* — Foley & Lardner LLP

(57) ABSTRACT

This invention provides an amadoriase that can react with a wide variety of glycated peptides generated upon hydrolysis of the β chain of hemoglobin A1c (HbA1c) to generate hydrogen peroxide, a method for measurement of HbA1c using such amadoriase, and a reagent kit for measurement of HbA1c using such amadoriase. Provided is an amadoriase obtained by substitution of one or more amino acids at positions corresponding to amino acids selected from the group consisting of amino acids 62, 63, 102, 106, 110, 113, and 355 in the amino acid sequence of the amadoriase derived from the genus *Coniochaeta* or the like which amadoriase is capable of oxidizing a wide variety of glycated peptides to generate hydrogen peroxide. Further provided is a method for measurement of HbA1c comprising using such amadoriase as well as a reagent kit for measurement of HbA1c comprising such amadoriase. This invention can provide a method for measurement of HbA1c that enables quantification of HbA1c to be performed rapidly, simply, and accurately with the use of a small amount of a protease and a kit used for such measurement. This invention can also provide a method for measurement of HbA1c that enables quantification of HbA1c to be performed rapidly, simply, and accurately, with high sensitivity with the use of a small amount of a protease and a kit used for such measurement.

9 Claims, 16 Drawing Sheets

Specification includes a Sequence Listing.

(56) References Cited

FOREIGN PATENT DOCUMENTS

| | | | |
|---|---|---|---|
| JP | 2010-057474 | A | 3/2010 |
| JP | 2011-229526 | A | 11/2011 |
| JP | 2013-500729 | A | 1/2013 |
| JP | 2013-176351 | A | 9/2013 |
| WO | WO 97/13872 | A1 | 4/1997 |
| WO | WO 2004/038033 | A1 | 5/2004 |
| WO | WO 2004/038034 | A1 | 5/2004 |
| WO | WO 2004/104203 | A1 | 12/2004 |
| WO | WO 2005/049857 | A1 | 6/2005 |
| WO | WO 2008/108385 | A1 | 9/2008 |
| WO | WO 2010/041419 | A1 | 4/2010 |
| WO | WO 2010/041715 | A1 | 4/2010 |
| WO | WO 2011/015325 | A1 | 2/2011 |
| WO | WO 2011/015326 | A2 | 2/2011 |
| WO | WO 2012/018094 | A1 | 2/2012 |
| WO | WO 2013/162035 | A1 | 10/2013 |

OTHER PUBLICATIONS

Hirakawa et al. (2003) Biochem. Biophys,. Res. Comm 311(1): 104-111 (Year: 2003).*

Supplementary European Search Report dated Mar. 17, 2017, in EP 14853677.8.

Hirokawa et al., "Distribution and properties of novel deglycating enzymes for fructosyl peptide in fungi," Arch. Microbiol., Jul. 17, 2003, 180(3):227-231.

Nanjo et al., "An enzymatic method for the rapid measurement of the hemoglobin $A_{1c}$ by a flow-injection system comprised of an electrochemical detector with a specific enzyme-reactor and a spectrophotometer," Analytica Chimica Acta, Jan. 30, 2007, 583(1):45-54.

International Search Report dated Jan. 6, 2015 in PCT/JP2014/078367.

Ferri et al., "Cloning and Expression of Fructosyl-amine Oxidase from Marine Yeast *Pichia* Species N1-1," Mar. Biotechnol., 2004, 6:625-632.

Ferri et al., "Isolation and characterization of a fructosyl-amine oxidase from an *Arthrobacter* sp.," Biotechnology Letters, 2005, 27:27-32.

Fujiwara et al., "Alteration of Substrate Specificity of Fructosyl-Amino Acid Oxidase from *Ulocladium* sp. JS-103, Journal of Bioscience and Bioengineering," 2006, 102(3):241-243.

Fujiwara et al., "Alteration of substrate specificity of fructosyl-amino acid oxidase from *Fusarium oxysporum*," Appl. Microbiol. Biotechnol., 2007, 74:813-819.

Hirokawa et al., "Molecular cloning and expression of novel fructosyl peptide oxidases and their application for the measurement of glycated protein," Biochemical and Biophysical Research Communications, 2003, 311:104-111.

Hirokawa et al., "Recombinant *Agrobacterium* AgaE-like Protein with Fructosyl Amino Acid Oxidase Activity," Biosci. Biotechnol. Biochem., 2002, 66(11):2323-2329.

Kim et al., "Motif-Based Search for a Novel Fructosyl Peptide Oxidase from Genome Databases," Biotechnology and Bioengineering, Jun. 15, 2010, 106(3):358-366.

Sakaue et al., "Cloning and Expression of Fructosyl-amino Acid Oxidase Gene from *Corynebacterium* sp. 2-4-1 in *Escherichia coli*," Biosci. Biotechnol. Biochem., 2002, 66(6):1256-1261.

Yoshida et al., "Primary structures of fungal fructosyl amino acid oxidases and their application to the measurement of glycated proteins," Eur. J. Biochem., 1996, 242:499-505.

Office Action dated Sep. 4, 2018, in JP 2015-543926.

Office Action dated Feb. 18, 2020, in JP 2015-543926.

* cited by examiner

Fig. 1-4

| | | | |
|---|---|---|---|
| Co | 299 | SPKRISVPRSHAKHPTDTYPDASEVSIKKAIATFLPRFQDKELFNRALCW | 348 |
| Et | 299 | SPKMISVPRSHAKHPTDTYPDASEVTIRKAIARFLPEFKDKELFNRTMCW | 348 |
| Py | 297 | APKRISVPRSHAKHPTDTYPHASEASIKKAIAAFLPQFKDKELFNRAMCW | 346 |
| Ar | 300 | APTRVSVPRSHAKHPTDTYPDASEQSIRRAVAAFLPRFQSKELFNRAMCW | 349 |
| Cc | 297 | APKRISVPRSAAKHPTDTYPDASEKSIRKAIATFLPKFTEKELFNRHLCW | 346 |
| Nv | 299 | APKPVSVPRSHAKHPTDTYPDASEESIKRAVSTFLPRFKDKPLFNRALCW | 348 |
| Cn | 299 | STKHISFPRSHAKHPTDTIPDESDASIRRAISAFLPRFKEKELFNRALCW | 348 |
| Pn | 295 | APKRISVPRSHAKHPTDTIPDASDVSIRRAIATFMPQFKNKKMFNQAMCW | 344 |
| An | 299 | APKPISVPRSHAKHPTDTYPHASEVTIKKAINRFLPRFNDKELFNRAMCW | 348 |
| En | 299 | VPKLISVPRSHAKHPTDTYPHASEVTIKKAINRFLPRFNDKELFNRAMCW | 348 |
| Ul | 297 | APKRISVPRSAAKHPTDTYPDASEVSIRKAIATFLPKFTEKEVFNRHLCW | 346 |
| Pj | 299 | SPKLISVPRSHAKHPTDTYPDSSEETIRKAIARFMPRFKDKELFNRSMCW | 348 |
| Co | 349 | CTDTADAALLMCEHPKWKNFILATGDSGHSFKILPNVGKYVVELIEGRLP | 398 |
| Et | 349 | CTDTADANLLICEHPKWKNFILATGDSGHSFKLLPNIGKHVVELLEGSLS | 398 |
| Py | 347 | CTDTADAALLICEHPQWKNFMLATGDSGHSFKLLPNIGKHVVELIEGTLA | 396 |
| Ar | 350 | CTDTADAALLICEHPRWRNFILATGDSGHSFKLLPNIGKHVVELLEGRLA | 399 |
| Cc | 347 | CTDTADAALLMCEHPEWKNFVLATGDSGHTFKLLPNIGKHVVELLEGTLA | 396 |
| Nv | 349 | CTDTADSALLICEHPRWKNFILATGDSGHSFKLLPIIGKHVVELVEGRLA | 398 |
| Cn | 349 | CTDTADANLLICEHPKWKNFILATGDSGHSFKILPNIGKHVVELIEGTLA | 398 |
| Pn | 345 | CTDTADAALLICEHPEWKNFVLATGDSGHSFKLLPNIGKHVVELLEGTLA | 394 |
| An | 349 | CTDTADANLLVCEHPRWKGFYLATGDSGHSFKLLPNIGKHVVELLEERLE | 398 |
| En | 349 | CTDTADANLLVCEHPRWKGFYLATGDSGHSFKLLPNIGKHVVELLEGRLE | 398 |
| Ul | 347 | CTDTADAALLMCEHPEWKNFVLATGDSGHTFKLLPNIGKHVVELLEGTLA | 396 |
| Pj | 349 | CTDTADANLLICEHPKWKNFILATGDSGHSFKVLPNIGKHVVELIEGRLP | 398 |

Fig. 1-5

```
Co  399  EEMAYQWRWRPG-GDALKSRRAAPPKDLADMPGWKHDPKL----------  437
Et  399  QEMAGAWRWRPG-GDALRSRRGAPAKDLAEMPGWKHDAHL----------  437
Py  397  ADLAHAWRWRPGIGDALQSRRAAPAKDLADMPGWNHD-ESPRAKL-----  440
Ar  400  DDLAQAWRWRPGQGDALKSRRAAPAKDLADMPGWNHDGDSGNATSGTSSE  449
Cc  397  EDLAHAWRWRPGTGDALKSRRAAPAKDLADMPGWKHD-DVVKSKL-----  440
Nv  399  DDLAEAWRWRPGQGDARKSIRAAPAKDLADMPGWKHDQDSESR-------  441
Cn  399  EDLAESWRWRPGSGDPLISRRAAPARDLADLPGWNHDEPSDDDMDVKDVA  448
Pn  395  DDLAHAWRWRPGSGDALKSRRSAPAKDLADMPGWNHD--KPRANL-----  437
An  399  SVFKDAWRWRPGSGDALKSRRAAPAKDLADMPGWRNEAKM----------  438
En  399  SVFKDAWRWRPGSGDALKSRRAAPAKDLADMPGWRNEAKM----------  438
Ul  397  DDLAHAWRWRPGTGDALKSRRAARAKDLADMPGWNHDGEAPRAKL-----  441
Pj  399  QDLAGAWRWRPG-GDALKSKRSAPAKDLAEMPGWKHDAKL----------  437

Co  437  -----------------------------  437 (SEQ ID NO: 1)
Et  437  -----------------------------  437 (SEQ ID NO: 145)
Py  440  -----------------------------  440 (SEQ ID NO: 113)
Ar  450  HKL--------------------------  452 (SEQ ID NO: 115)
Cc  440  -----------------------------  440 (SEQ ID NO: 117)
Nv  441  -----------------------------  441 (SEQ ID NO: 54)
Cn  449  VSLASVKIGENIGEKVVEDGARVGVKVLA  477 (SEQ ID NO: 149)
Pn  437  -----------------------------  437 (SEQ ID NO: 38)
An  438  -----------------------------  438 (SEQ ID NO: 147)
En  438  -----------------------------  438 (SEQ ID NO: 119)
Ul  441  -----------------------------  441 (SEQ ID NO: 121)
Pj  437  -----------------------------  437 (SEQ ID NO: 123)
```

Fig. 2-2

```
Co  101  PEGIEDLKKQYQALHDAGAGLEKTHAWLDNEDEILSKMPLLQRDQIQGWK  150
Et  101  KEGIENLRRKYQTLLDAGIGLEKTNVWLESEDEILAKAPNFTREQVKGWK  150
Py  101  EKGINDLRQAYQTLLDANAGLEETNEWLDSEDEILARMPLLSREQIKGWK  150
Ar  101  EKGIAALKQQYQTLLDADVGLEKTTEWLDSEDAILAKMPLLERDQIKGWK  150
Cc  101  EEGLADLRQAYQALLDANAGLEETTEWLDSEDEILKKMPLLDREQIKGWK  150
Nv  101  AEGVEGLRREYQKLVEAGVGLEETHEWLDSEEAILEKAPLLQREEIEGWK  150
On  101  PESIASLRKSYEAILKAGSGLEKTHHWLSTEDEILARAPLLDRKQIKGWK  150
Pn  101  EKDIADLKSGYQALVDA--GLDATNEWLDSEDEILKRMPLLSRDQIKGWK  148
An  100  EEGIEGLRKKYQSLLDAGIGLEKTNFMLESEDEILAKAPHFTQEQIKGWK  149
En  100  EEGIKKLRMRYQSLLDAGIGLEKTNFLLESEDEILAKAPHFTREQIKGWK  149
Ul  101  EKGLADLKQAYQALLDANAGLEATTEWLDSEDKILEKMPLLNRDQIKGWK  150
Pj  101  QEGIASLRRKHQDLIDANIGLEKTNIWLESEDDILAKAPHFTREQIKGWK  150

Co  151  AIWSQDGGWLAAAKAINAIGQFLKERGVKFGFGGAGSFKQPLFD-DEGTT  199
Et  151  GLFCTDGGWLAAAKAINAIGIFLQDKGVKFGFGGAGTFQQPLFA-ADGKT  199
Py  151  AVFSRDGGWLAAGKAINAIGEYLRKEGVKFGFGGAGSFQQPLLA-EG--I  197
Ar  151  AIFSQDGGWLAAAKAINAIGEELKRQGVNFGFGGAGAFKKPLFA-PDGST  199
Cc  151  AVYSQDGGWLAAAKAINAIGEYLRAQGVKFGFGGAGSFKQPLLA-EG--V  197
Nv  151  AIWSEEGGWLAAAKAINAIGEELQRQGVRFGFGGAGSFKRPLFA-DDGTT  199
On  151  AIYSEDGGWLAAAKAINSIGQVLKEKGVTFGFGSAGSFKKPLFD-EDGTK  199
Pn  149  AIFSKDGGWLAAAKAINAVGEYLRDQGVRFGFYGAGSFKAPLLA-EG--V  195
An  150  GLFCGDGGWLAAAKAINAIGQFLKEQGVKFGFGGAGTFKKPLFADAHEKT  199
En  150  GLFCGDGGWLAAAKAINAIGQFLKEQGVKFGFGEAGTFKKPLFADADEKT  199
Ul  151  AVFSEDGGWLAAAKAINAIGRFLRDQGVKFGFGGAGSFKQPLLA-EG--V  197
Pj  151  GLFCGDGGWLAAAKAINAIGTFLKSQGVKFGFGSAGTFKRPLFA-PDGAT  199
```

Fig. 2-5

```
Co  399  EEMAYQWRWRPG-GDALKSRRAAPPKDLADMPGWKHDPKL----------  437
Et  399  QEMAGAWRWRPG-GDALRSRRGAPAKDLAEMPGWKHDAHL----------  437
Py  397  ADLAHAWRWRPGIGDALQSRRAAPAKDLADMPGWNHD-ESPRAKL-----  440
Ar  400  DDLAQAWRWRPGQGDALKSRRAAPAKDLADMPGWNHDGDSGNATSGTSSE  449
Cc  397  EDLAHAWRWRPGTGDALKSRRAAPAKDLADMPGWKHD-DVVKSKL-----  440
Nv  399  DDLAEAWRWRPGQGDARKSIRAAPAKDLADMPGWKHDQDSESR-------  441
Cn  399  EDLAESWRWRPGSGDPLISRRAAPARDLADLPGWNHDEPSDDDMDVKDVA  448
Pn  395  DDLAHAWRWRPGSGDALKSRRSAPAKDLADMPGWNHD--KPRANL-----  437
An  399  SVFKDAWRWRPGSGDALKSRRAAPAKDLADMPGWRNEAKM----------  438
En  399  SVFKDAWRWRPGSGDALKSRRAAPAKDLADMPGWRNEAKM----------  438
Ul  397  DDLAHAWRWRPGTGDALKSRRAARAKDLADMPGWNHDGEAPRAKL-----  441
Pj  399  QDLAGAWRWRPG-GDALKSKRSAPAKDLAEMPGWKHDAKL----------  437

Co  437  -----------------------------  437 (SEQ ID NO: 1)
Et  437  -----------------------------  437 (SEQ ID NO: 145)
Py  440  -----------------------------  440 (SEQ ID NO: 113)
Ar  450  HKL--------------------------  452 (SEQ ID NO: 115)
Cc  440  -----------------------------  440 (SEQ ID NO: 117)
Nv  441  -----------------------------  441 (SEQ ID NO: 54)
Cn  449  VSLASVKIGENIGEKVVEDGARVGVKVLA  477 (SEQ ID NO: 149)
Pn  437  -----------------------------  437 (SEQ ID NO: 38)
An  438  -----------------------------  438 (SEQ ID NO: 147)
En  438  -----------------------------  438 (SEQ ID NO: 119)
Ul  441  -----------------------------  441 (SEQ ID NO: 121)
Pj  437  -----------------------------  437 (SEQ ID NO: 123)
```

METHOD FOR MEASUREMENT OF HBA1C USING AMADORIASE THAT REACTS WITH GLYCATED PEPTIDE

CROSS-REFERENCE TO RELATED APPLICATIONS

This application is a National Stage application of PCT/JP2014/078367, filed Oct. 24, 2014, which claims priority from Japanese application JP 2013-222789, filed Oct. 25, 2013.

TECHNICAL FIELD

The present invention relates to a method for measurement of hemoglobin A1c in a sample and a reagent kit used for implementing such method for measurement.

BACKGROUND ART

Glycated proteins are generated by non-enzymatic covalent bonding between aldehyde groups in aldoses, such as glucose (monosaccharides potentially containing aldehyde groups and derivatives thereof), and amino groups in proteins, followed by Amadori rearrangement. Examples of amino groups in proteins include α-amino groups of the amino terminus and side chain ε-amino groups of the lysine residue in proteins. Examples of known glycated proteins generated in vivo include glycated hemoglobin resulting from glycation of hemoglobin and glycated albumin resulting from glycation of albumin in the blood.

Among such glycated proteins generated in vivo, hemoglobin A1c (HbA1c) has drawn attention as a glycemic control marker significant for diagnosis of diabetic patients and control of conditions in the field of clinical diagnosis of diabetes mellitus. HbA1c is a protein comprising glucose bound to the α-amino group at the N-terminal (amino-terminal) valine (Val) residue of the hemoglobin "β chain." The blood HbA1c level reflects the average blood glucose level for a given period of time in the past, and the measured value thereof serves as a significant indicator for diagnosis and control of diabetes conditions.

Several types of enzymatic methods involving the use of amadoriases have heretofore been known as methods for rapidly and simply measuring HbA1c.

Enzymes that oxidize iminodiacetic acid or a derivative thereof (also referred to as an "Amadori compound") in the presence of oxygen to catalyze a reaction to generate glyoxylic acid or α-ketoaldehyde, amino acid or peptide, and hydrogen peroxide are collectively referred to as "amadoriases." Amadoriases are known to be useful for measuring HbA1c by an enzymatic method. An example of a substrate that is known to be oxidized by amadoriases is α-fructosyl valyl histidine (hereafter referred to as "αFVH").

Amadoriases have been found in bacteria, yeast, and fungi. For example, amadoriases derived from the genera *Coniochaeta, Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophiobolus, Pleospora, Coniochaelidium, Pichia, Debaryomyces, Corynehacterium, Agrobacterium*, and *Arthrobacter* have been reported (e.g., Patent Documents 1 and 6 to 15 and Non-Patent Documents 1 to 9). These genera may be referred to as the genera *Coniochaeta* etc. in this description. In some of the aforementioned documents, an amadoriase may also be referred to as, for example, ketoamine oxidase, fructosyl amino acid oxidase, fructosyl peptide oxidase, or fructosyl amine oxidase. These terms are synonymously used herein.

As a method for rapidly and readily measuring HbA1c with the use of various types of amadoriases as described above, a method in which HbA1c is degraded with a cleavage enzyme such as a protease or the like, and a particular target substance released from the β-chain amino terminus of HbA1c is quantified with the use of amadoriases as described above is known (e.g., Patent Documents 1 to 7).

Specifically, a method in which HbA1c is degraded with a particular protease or the like, αFVH is released from the β-chain amino terminus thereof, and the released αFVH is quantified has been known. At present, such method is a major technique for measuring HbA1c by an enzymatic method.

However, in order to sufficiently hydrolyze the HbA1c β chain down to αFVH within a short period of time, it is necessary to formulate the assay reagent with large quantities of proteases and/or many different types of proteases exhibiting different types of reactivity. However, such inclusion is not preferable for the reasons described below.

That is, a protease is capable of protein hydrolysis and, therefore, enzymes which are proteins are also hydrolyzed by a protease. As such, amadoriases will also be hydrolized by a protease and inactivated, and, as a result, the reaction consuming a glycated peptide and oxygen to generate hydrogen peroxide will be inhibited. In order to address such problem, it is possible to increase the amount of amadoriases, and to complete the measurement before amadoriases are completely inactivated. However, increasing the amount of amadoriases will lead to preferential hydrolysis of amadoriases rather than HbA1c, which intrinsically is not preferable.

When measuring HbA1c by allowing an amadoriase to react with αFVH and quantifying the resulting hydrogen peroxide, hydrogen peroxide may be quantified using a peroxidase. In such a case, the peroxidase will also be hydrolyzed by the protease and be inactivated, which is not preferable.

As another aspect, when measuring HbA1c using enzymes, it is commonplace to use an automated analyzer. In such a case, a single sample is simultaneously subjected to analysis of various biomarkers including HbA1c. Since each biomarker is analyzed using an enzyme or antibody, upon contamination of a protease, the enzyme or antibody contained in the biomarker reagent may be hydrolyzed. In such a case, biomarkers other than HbA1c may not be accurately analyzed. Accordingly, it is preferable not to include a protease in a reagent to be mounted on an automated analyzer.

For the reasons described above, it was desired to minimize the amount and the types of proteases to be applied in the method comprising degrading HbA1c with a particular type of protease or the like, releasing αFVH from the β chain amino terminus thereof, and quantifying the released αFVH. If the amount and the types of proteases to be applied are minimized, however, the HbA1c β chain may not be sufficiently hydrolyzed down to αFVH, and, as a result, a wide variety of glycated peptides generated during the process of hydrolysis would also be present.

In addition, the speed of the hydrolysis reaction by a protease depends on the substrate concentration. Therefore, if the majority of HbA1c is hydrolyzed, then the protease reaction speed will be lowered significantly. Accordingly, at the time of completion of measurement of HbA1c, i.e., quantification of αFVH, it is deduced that although the majority of HbA1c is hydrolyzed down to αFVH, glycated peptides that are not hydrolyzed down to αFVH also remain.

As such, if remaining glycated peptides derived from the HbA1c β chain that were not hydrolyzed down to αFVH can be simultaneously quantified, then the amount of proteases to be applied can be reduced, and/or the sensitivity of the method for measurement of HbA1c using an amadoriase can be enhanced. However, no amadoriases exhibiting enzymatic activity on a wide variety of glycated peptides have been found in the past.

PRIOR ART DOCUMENTS

Patent Documents

Patent Document 1: WO 2004/104203
Patent Document 2: WO 2005/49857
Patent Document 3: JP 2001-95598 A
Patent Document 4: JP H05-33997 B (1993)
Patent Document 5: JP H11-127895 A (1999)
Patent Document 6: WO 97/13872
Patent Document 7: JP 2011-229526 A
Patent Document 8: JP 2003-235585 A
Patent Document 9: JP 2004-275013 A
Patent Document 10: JP 2004-275063 A
Patent Document 11: JP 2010-35469 A
Patent Document 12: JP 2010-57474 A
Patent Document 13: WO 2010/41715
Patent Document 14: WO 2010/41419
Patent Document 15: WO 2011/15325

Non-Patent Documents

Non-Patent Document 1: Biochem. Biophys. Res. Commun. 311, 104-11, 2003
Non-Patent Document 2: Biotechnol. Bioeng. 106, 358-66, 2010
Non-Patent Document 3: J. Biosci. Bioeng. 102, 241-3, 2006
Non-Patent Document 4: Appl. Microbiol. Biotechnol. 74, 813-9, 2007
Non-Patent Document 5: Eur. J. Biochem. 242, 499-505, 1996
Non-Patent Document 6: Mar. Biotechnol. 6, 625-32, 2004
Non-Patent Document 7: Biosci. Biotechnol. Biochem. 66, 1256-61, 2002
Non-Patent Document 8: Biosci. Biotechnol. Biochem. 66, 2323-29, 2002
Non-Patent Document 9: Biotechnol. Letters 27, 27-32, 2005

SUMMARY OF THE INVENTION

Objects to be Attained by the Invention

It is an object of the present invention to discover an amadoriase that exhibits enzymatic activity on a wide variety of glycated peptides, and it is another object to construct a method for measurement of HbA1c using such amadoriase.

Means for Attaining the Objects

The present inventors have conducted concentrated studies in order to attain the above objects. As a result, the present inventors found that a modified amadoriase having several amino acid substitutions introduced into the amadoriase derived from the genus *Coniochaeta* or the like has the activity of oxidizing a wide variety of glycated peptides to generate hydrogen peroxide, and the present inventors established a method for measurement of HbA1c with the use of such modified amadoriase. By this the present invention has been accomplished.

Specifically, the present invention encompasses the following.

[1] A method for measurement of α-fructosyl oligopeptide in a sample, said method comprising allowing an amadoriase capable of reacting with one or more α-fructosyl oligopeptides selected from among αF3P to αF16P below to react with a sample comprising one or more α-fructosyl oligopeptides selected from among αF3P to αF16P and measuring the amount of hydrogen peroxide generated or enzyme consumed in such reaction:

α-fructosyl-valyl-histidyl-leucine (αF3P);
α-fructosyl-valyl-histidyl-leucyl-threonine (αF4P);
α-fructosyl-valyl-histidyl-leucyl-threonyl-proline (αF5P);
α-fructosyl-valyl-histidyl-leucyl-threonyl-proryl-glutamic acid (αF6P);
α-fructosyl-valyl-histidyl-leucyl-threonyl-proryl-glutamyl-glutamic acid (αF7P);
α-fructosyl-valyl-histidyl-leucyl-threonyl-proryl-glutamyl-glutamyl-lysine (αF8P);
α-fructosyl-valyl-histidyl-leucyl-threonyl-proryl-glutamyl-glutamyl-lysyl-serine (αF9P);
α-fructosyl-valyl-histidyl-leucyl-threonyl-proryl-glutamyl-glutamyl-lysyl-seryl-alanine (αF10P);
α-fructosyl-valyl-histidyl-leucyl-threonyl-proryl-glutamyl-glutamyl-lysyl-seryl-alanyl-valine (αF11P);
α-fructosyl-valyl-histidyl-leucyl-threonyl-proryl-glutamyl-glutamyl-lysyl-seryl-alanyl-valyl-threonine (αF12P);
α-fructosyl-valyl-histidyl-leucyl-threonyl-proryl-glutamyl-glutamyl-lysyl-seryl-alanyl-valyl-threonyl-alanine (αF13P);
α-fructosyl-valyl-histidyl-leucyl-threonyl-proryl-glutamyl-glutamyl-lysyl-seryl-alanyl-valyl-threonyl-alanyl-leucine (αF14P);
α-fructosyl-valyl-histidyl-leucyl-threonyl-proryl-glutamyl-glutamyl-lysyl-seryl-alanyl-valyl-threonyl-alanyl-leucyl-tryptophane (αF15P); and
α-fructosyl-valyl-histidyl-leucyl-threonyl-proryl-glutamyl-glutamyl-lysyl-seryl-alanyl-valyl-threonyl-alanyl-leucyl-tryptophyl-glycine (αF16P).

[2] A method for measurement of α-fructosyl peptide in a sample, said method comprising allowing an amadoriase capable of reacting with one or more α-fructosyl peptides selected from among (a) to (f) below to react with a sample comprising one or more α-fructosyl peptides selected from among (a) to (f) and measuring the amount of hydrogen peroxide generated or enzyme consumed in such reaction:

(a) α-fructosyl-valyl-histidyl-leucine (αF3P);
(b) α-fructosyl-valyl-histidyl-leucyl-threonine (αF4P);
(c) α-fructosyl-valyl-histidyl-leucyl-threonyl-proline (αF5P);
(d) α-fructosyl-valyl-histidyl-leucyl-threonyl-proryl-glutamic acid (αF6P);
(e) α-fructosyl-valyl-histidyl-leucyl-threonyl-proryl-glutamyl-glutamyl-lysine (αF8P); and
(f) α-fructosyl-valyl-histidyl-leucyl-threonyl-proryl-glutamyl-glutamyl-lysyl-scryl-alanyl-valyl-threonyl-alanyl-leucyl-tryptophyl-glycine (αF16P).

[3] The method according to [1] or [2], wherein the sample further comprises α-fructosyl-valine (αF1P) or α-fructosyl-valyl-histidine (αF2P), the amadoriase is further capable of reacting with α-fructosyl-valine (αF1P) or α-fructosyl-valyl-histidine (αF2P), and the amount of hydrogen peroxide generated or enzyme consumed in such reaction is also measured.

[4] A method for measurement of hemoglobin A1c in a sample, said method comprising treating a sample with a protease to release α-fructosyl oligopeptide comprising one or more α-fructosyl oligopeptides selected from among αF3P to αF16P below, allowing an amadoriase capable of oxidizing one or more of the released α-fructosyl oligopeptides to react therewith, and measuring the amount of hydrogen peroxide generated or enzyme consumed in such reaction:

α-fructosyl-valyl-histidyl-leucine (αF3P);
α-fructosyl-valyl-histidyl-leucyl-threonine (αF4P);
α-fructosyl-valyl-histidyl-leucyl-threonyl-proline (αF5P);
α-fructosyl-valyl-histidyl-leucyl-threonyl-proryl-glutamic acid (αF6P);
α-fructosyl-valyl-histidyl-leucyl-threonyl-proryl-glutamyl-glutamic acid (αF7P);
α-fructosyl-valyl-histidyl-leucyl-threonyl-proryl-glutamyl-glutamyl-lysine (αF8P);
α-fructosyl-valyl-histidyl-leucyl-threonyl-proryl-glutamyl-glutamyl-lysyl-serine (αF9P);
α-fructosyl-valyl-histidyl-leucyl-threonyl-proryl-glutamyl-glutamyl-lysyl-seryl-alanine (αF10P);
α-fructosyl-valyl-histidyl-leucyl-threonyl-proryl-glutamyl-glutamyl-lysyl-seryl-alanyl-valine (αF11P);
α-fructosyl-valyl-histidydyl-leucyl-threonyl-proryl-glutamyl-glutamyl-lysyl-seryl-alanyl-valyl-threonine (αF12P);
α-fructosyl-valyl-histidyl-leucyl-threonyl-proryl-glutamyl-glutamyl-lysyl-seryl-alanyl-valyl-threonyl-alanine (αF13P);
α-fructosyl-valyl-histidyl-leucyl-threonyl-proryl-glutamyl-glutamyl-lysyl-seryl-alanyl-valyl-threonyl-alanyl-leucine (αF14P);
α-fructosyl-valyl-histidyl-leucyl-threonyl-proryl-glutamyl-glutamyl-lysyl-seryl-alanyl-valyl-threonyl-alanyl-leucyl-tryptophane (αF15P); and
α-fructosyl-valyl-histidyl-leucyl-threonyl-proryl-glutamyl-glutayl-yl-lysyl-seryl-alanyl-valyl-threonyl-alanyl-leucyl-tryptophyl-glycine (αF16P).

[5] A method for measurement of hemoglobin A1c in a sample, said method comprising treating a sample with a protease to release a glycated peptide comprising one or more α-fructosyl peptides selected from among (a) to (f), allowing an amadoriase capable of oxidizing a released glycated peptide comprising one or more α-fructosyl peptides selected from among (a) to (f) to react therewith, and measuring the amount of hydrogen peroxide generated or enzyme consumed in such reaction:

(a) α-fructosyl-valyl-histidyl-leucine (αF3P);
(b) α-fructosyl-valyl-histidyl-leucyl-threonine (αF4P);
(c) α-fructosyl-valyl-histidyl-leucyl-threonyl-proline (αF5P);
(d) α-fructosyl-valyl-histidyl-leucyl-threonyl-proryl-glutamic acid (αF6P);
(e) α-fructosyl-valyl-histidyl-leucyl-threonyl-proryl-glutamyl-glutamyl-lysine (αF8P); and
(f) α-fructosyl-valyl-histidyl-leucyl-threonyl-proryl-glutamyl-glutamyl-lysyl-seryl-alanyl-valyl-threonyl-alanyl-leucyl-tryptophyl-glycine (αF16P).

[6] The method according to [4] or [5], wherein α-fructosyl-valine (αF1P) or α-fructosyl-valyl-histidine (αF2P) is further released by treatment with the protease, the amadoriase is one that is further capable of reacting with α-fructosyl-valine (αF1P) or α-fructosyl-valyl-histidine (αF2P), and the amount of hydrogen peroxide generated or enzyme consumed in such reaction is also measured.

[7] The method for measurement according to any one of [1] to [6], wherein the amadoriase is derived from the genus *Coniochaeta, Eupenicillium, Pyrenochaeta, Arthrinium, Curvularia, Neocosmospora, Cryptococcus, Phaeosphaeria, Aspergillus, Emericella, Ulocladium*, or *Penicillium.*

[8] The method for measurement according to any one of [1] to [6], wherein the amadoriase is derived from *Coniochaeta* sp., *Eupenicillium terrenum, Pyrenochaeta* sp., *Arthrinium* sp., *Curvularia clavata, Neocosmospora vasinfecta, Cryptococcus neoformans, Phaeosphaeria nodorum, Aspergillus nidulans, Emericella nidulans, Ulocladium* sp., or *Penicillium janthinelum.*

[9] The method for measurement according to any one of [1] to [6,] wherein the amadoriase is an amadoriase selected from the group consisting of (i) and (ii) below:

(i) an amadoriase comprising an amino acid sequence derived from the amino acid sequence as shown in SEQ ID NO: 141 by substitution, deletion, or addition of one or several amino acids; and (ii) the amadoriase as defined in (i), wherein the amadoriase comprises an amino acid sequence having 70% or higher sequence identity with the amino acid sequence as shown in SEQ ID NO: 141 over the full length and having 90% or higher sequence identity between the amino acid sequence of a homologous region consisting of amino acids at positions 10 to 32, 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of SEQ ID NO: 141 and the amino acid sequence of the homologous region in corresponding positions of the amadoriase.

[10] The method according to any one of [1], [2], [4], [5], and [7] to [9], further comprising using an amadoriase that oxidizes α-fructosyl-valine or α-fructosyl-valyl-histidine.

[11] A reagent kit for measurement of α-fructosyl peptide in a sample, said kit comprising ingredients (1) and (2) below:

(1) an amadoriase that has activity of oxidizing one or more of αF3P to αF16P below to generate hydrogen peroxide; and (2) a reagent for measurement of hydrogen peroxide:

α-fructosyl-valyl-histidyl-leucine (αF3P);
α-fructosyl-valyl-histidyl-leucyl-threonine (αF4P);
α-fructosyl-valyl-histidyl-leucyl-threonyl-proline (αF5P);
α-fructosyl-valyl-histidyl-leucyl-threonyl-proryl-glutamic acid (αF6P);
α-fructosyl-valyl-histidyl-leucyl-threonyl-proryl-glutamyl-glutamic acid (αF7P);
α-fructosyl-valyl-histidyl-leucyl-threonyl-proryl-glutamyl-glutamyl-lysine (αF8P);
α-fructosyl-valyl-histidyl-leucyl-threonyl-proryl-glutamyl-glutamyl-lysyl-serine (αF9P);
α-fructosyl-valyl-histidyl-leucyl-threonyl-proryl-glutamyl-glutamyl-lysyl-seryl-alanine (αF10P):
α-fructosyl-valyl-histidyl-leucyl-threonyl-proryl-glutamyl-glutamyl-lysyl-seryl-alanyl-valine (αF11P);
α-fructosyl-valyl-histidy-leucyl-threonyl-proryl-glutamyl-glutamyl-lysyl-seryl-alanyl-valyl-threonine (αF12P);
α-fructosyl-valyl-histidyl-leucyl-threonyl-proryl-glutamyl-glutamyl-lysyl-seryl-alanyl-valyl-threonyl-alanine (αF13P);

α-fructosyl-valyl-histidyl-leucyl-threonyl-proryl-glutamyl-glutamyl-lysyl-seryl-alanyl-valyl-threonyl-alanyl-leucine (αF14P);

α-fructosyl-valyl-histidyl-leucyl-threonyl-proryl-glutamyl-glutamyl-lysyl-seryl-alanyl-valyl-threonyl-alanyl-leucyl-tryptophane (αF15P); and α-fructosyl-valyl-histidyl-leucyl-threonyl-proryl-glutamyl-glutal-lmy-lysyl-sery-alanyl-valyl-threonyl-alanyl-leucyl-tryptophyl-glycine (αF16P).

[12] A reagent kit for measurement of α-fructosyl peptide in a sample, said kit comprising ingredients (1) and (2) below:

(1) an amadoriase that has activity of oxidizing a glycated peptide comprising one or more α-fructosyl peptides selected from among (a) to (f) to generate hydrogen peroxide; and (2) a reagent for measurement of hydrogen peroxide:

(a) α-fructosyl-valyl-histidyl-leucine (αF3P);

(b) α-fructosyl-valyl-histidyl-leucyl-threonine (αF4P);

(c) α-fructosyl-valyl-histidyl-leucyl-threonyl-proline (αF5P);

(d) α-fructosyl-valyl-histidyl-leucyl-threonyl-proryl-glutamic acid (αF6P);

(e) α-fructosyl-valyl-histidyl-leucyl-threonyl-proryl-glutamyl-glutamyl-lysine (αF8P); and (f) α-fructosyl-valyl-histidyl-leucyl-threonyl-proryl-glutamyl-glutamyl-lysyl-seryl-alanyl-valyl-threonyl-alanyl-leucyl-tryptophyl-glycine (αF16P).

[13] The kit according to [11] or [12], wherein the amadoriase further has activity of oxidizing α-fructosyl-valine (αF1P) or α-fructosyl-valyl-histidine (αF2P) to generate hydrogen peroxide.

[14] A reagent kit for measurement of hemoglobin A1c in a sample, said kit comprising ingredients (1) to (3) below:

(1) a protease capable of hydrolyzing the 3 chain of HbA1c to release a glycated peptide comprising one or more α-fructosyl oligopeptides selected from among αF3P to αF16P below;

(2) an amadoriase that has activity of oxidizing one or more of αF3P to αF16P below to generate hydrogen peroxide; and (3) a reagent for measurement of hydrogen peroxide, α-fructosyl-valyl-histidyl-leucine (αF3P);

α-fructosyl-valyl-histidyl-leucyl-threonine (αF4P);

α-fructosyl-valyl-histidyl-leucyl-threonyl-proline (αF5P);

α-fructosyl-valyl-histidyl-leucyl-threonyl-proryl-glutamic acid (αF6P);

α-fructosyl-valyl-histidyl-leucyl-threonyl-proryl-glutamyl-glutamic acid (αF7P);

α-fructosyl-valyl-histidyl-leucyl-threonyl-proryl-glutamyl-glutamyl-lysine (αF8P);

α-fructosyl-valyl-histidyl-leucyl-threonyl-proryl-glutamyl-glutamyl-lysyl-serine (αF9P);

α-fructosyl-valyl-histidyl-leucyl-threonyl-proryl-glutamyl-glutamyl-lysyl-seryl-alanine (αF10P);

α-fructosyl-valyl-histidyl-leucyl-threonyl-proryl-glutamyl-glutamyl-lysyl-seryl-alanyl-valine (αF1P);

α-fructosyl-valyl-histidyl-leucyl-threonyl-proryl-glutamyl-glutamyl-lysyl-scryl-alanyl-valyl-threonine (αF12P);

α-fructosyl-valyl-histidyl-leucyl-threonyl-proryl-glutamyl-glutamyl-lysyl-seryl-alanyl-valyl-threonyl-alanine (αF13P);

α-fructosyl-valyl-histidyl-leucyl-threonyl-proryl-glutamyl-glutamyl-lysyl-seryl-alanyl-valyl-threonyl-alanyl-leucine (αF14P);

α-fructosyl-valyl-histidyl-leucyl-threonyl-proryl-glutamyl-glutamyl-lysyl-seryl-alanyl-valyl-threonyl-alanyl-leucyl-tryptophane (αF15P); and α-fructosyl-valyl-histidyl-leucyl-threonyl-proryl-glutamyl-glutamyl-lysyl-seryl-alanyl-valyl-threonyl-alanyl-leucyl-tryptophyl-glycine (αF16P).

[15] A reagent kit for measurement of hemoglobin A1c in a sample, said kit comprising ingredients (1) to (3) below:

(1) a protease that is capable of hydrolyzing the β chain of HbA1c to release a glycated peptide comprising one or more α-fructosyl peptides selected from among (a) to (f);

(2) an amadoriase that has activity of oxidizing a glycated peptide comprising one or more α-fructosyl peptides selected from among (a) to (f) to generate hydrogen peroxide; and (3) a reagent for measurement of hydrogen peroxide, (a) α-fructosyl-valyl-histidyl-leucine (αF3P);

(b) α-fructosyl-valyl-histidyl-leucyl-threonine (αF4P);

(c) α-fructosyl-valyl-histidyl-leucyl-threonyl-proline (αF5P);

(d) α-fructosyl-valyl-histidyl-leucyl-threonyl-proryl-glutamic acid (αF6P);

(e) α-fructosyl-valyl-histidyl-leucyl-threonyl-proryl-glutamyl-glutamyl-lysine (αF8P); and (f) acfructosyl-valvl-histidyl-leucyl-threonyl-proryl-glutamyl-glutamyl-lvsyl-seryl-alanyl-valyl-threonyl-alanyl-leucyl-tryptophyl-glycine (αF16P).

[16] The kit according to [14] or [15], wherein (1) the protease is further capable of hydrolyzing the HbA1c β chain to release α-fructosyl-valine (αF1P) or α-fructosyl-valyl-histidine (αF2P) and (2) the amadoriase further has activity of oxidizing α-fructosyl-valine (αF1P) or α-fructosyl-valyl-histidine (αF2P) to generate hydrogen peroxide.

[17] The kit according to any one of [11] to [16], wherein the amadoriase is derived from the genus *Coniochaeta, Eupenicillium, Pyrenochaeta, Arthrinium, Curvularia, Neocosmospora, Cryptococcus, Phaeosphaeria, Aspergillus, Emericella, Ulocladium*, or *Penicillium.*

[18] The kit according to any one of [11] to [16], wherein the amadoriase is an amadoriase selected from the group consisting of (i) and (ii) below:

(i) an amadoriase comprising an amino acid sequence derived from the amino acid sequence as shown in SEQ ID NO: 141 by substitution, deletion, or addition of one or several amino acids; and (ii) the amadoriase as defined in (i), wherein the amadoriase comprises an amino acid sequence having 70% or higher sequence identity with the amino acid sequence as shown in SEQ ID NO: 141 over the full length and having 90% or higher sequence identity between the amino acid sequence of a homologous region consisting of amino acids at positions 10 to 32, 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of SEQ ID NO: 141 and the amino acid sequence of the homologous region in corresponding positions of the amadoriase.

[19] A method for measurement of α-fructosyl oligopeptide in a sample, said method comprising allowing an amadoriase capable of reacting with one or more α-fructosyl oligopeptides selected from among αF1P to αF32P below to react with a sample comprising one or more α-fructosyl oligopeptides selected from among αF1P to αF32P and measuring the amount of hydrogen peroxide generated or enzyme consumed in such reaction:

α-fructosyl-valine (αF1P);

α-fructosyl-valyl-histidine (αF2P);

α-fructosyl-valyl-histidyl-leucine (αF3P);

α-fructosyl-valyl-histidyl-leucyl-threonine (αF4P);

α-fructosyl-valyl-histidyl-leucyl-threonyl-proline (αF5P);

α-fructosyl-valyl-histidyl-leucyl-threonyl-proryl-glutamic acid (αF6P);

α-fructosyl-valyl-histidyl-leucyl-threonyl-proryl-glutainyl-glutamic acid (αF7P):

α-fructosyl-valyl-histidyl-leucyl-threonyl-proryl-glutamyl-glutamyl-lysine (αF8P);

α-fructosyl-valyl-histidyl-leucyl-threonyl-proryl-glutamyl-glutamyl-ysl-serine (αF9P);

α-fructosyl-valyl-histidyl-leucyl-threonyl-proryl-glutamyl-glutamyl-lysyl-seryl-alanine (αF10P);

α-fructosyl-valyl-histidyl-leucyl-threonyl-proryl-glutamyl-glutamyl-lysyl-scryl-alanyl-valin (αF11P);

α-fructosyl-valyl-histidyl-leucyl-threonyl-proryl-glutamyl-glutamyl-lysyl-seryl-alanyl-valyl-threonine (αF12P);

α-fructosyl-valyl-histidyl-leucyl-threonyl-proryl-glutamyl-glutamyl-lysyl-seryl-alanyl-valyl-threonyl-alanine (αF13P);

α-fructosyl-valyl-histidyl-leucyl-threonyl-proryl-glutamyl-glutamyl-lysyl-seryl-alanyl-valyl-threonyl-alanyl-leucine (αF14P);

α-fructosyl-valyl-histidyl-leucyl-threonyl-proryl-glutamyl-glutamyl-lysyl-seryl-alanyl-valyl-threonyl-alanyl-leucyl-tryptophane (αF15P);

α-fructosyl-valyl-histidyl-leucyl-threonyl-proryl-glutamyl-glutamyl-lysyl-seryl-alanyl-valyl-threonyl-alanyl-leucyl-tryptophyl-glycine (αF16P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysine (αF17P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valine (αF18P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparagine (αF19P);

α-fructosyl-valyl-histidyl-leucyl-threonyl-proryl-glutamyl-glutamyl-lysyl-sryl-alanyl-valyl-threonyl-alanyl-leucyl-tryptophyl-glycyl-lysyl-valyl-asparaginyl-valine (αF20P);

α-fructosyl-valyl-histidyl-leucyl-threonyl-proryl-gutamyl-glutamyl-lysyl-seryl-alanyl-valyl-threonyl-alanyl-leucyl-tryptophyl-glycyl-lysyl-valyl-asparaginyl-valyl-aspartic acid (αF21P);

α-fructosyl-valyl-histidyl-leucyl-thronyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutamic acid (αF22P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutamyl-valine (αF23P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutanyl-valyl-glycine (αF24P);

α-fructosyl-valyl-histidyl-leucyl-threonyl-proryl-glutamyl-glutamyl-lysyl-stryl-alanyl-valyl-threonyl-alanyl-leucyl-tryptophyl-glycyl-lysyl-valyl-asparaginyl-valyl-aspartyl-glutamyl-valyl-glycyl-glycine (αF25P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutamyl-valyl-glycyl-glycyl-glutamic acid (αF26P);

α-fructosyl-valyl-hitidyl-leucyl-tronyl-proryl-glutamyl-glutamyl-lysyl-seryl-alanyl-valyl-treonyl-alanyl-leucyl-tryptophyl-glycyl-lysyl-valyl-asparaginyl-valyl-aspartyl-glutamyl-valyl-glycyl-glycyl-glutamyl-alanine (αF27P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutamyl-valyl-glycyl-glycyl-glutamyl-alanyl- leucine (αF28P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-aspuraginyl-valyl-aspartyl-glutamyl-valyl-glycyl-glycyl-glutamyl-alanyl- leucyl-glycine (αF29P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutamyl-valyl-glycyl-glycyl-glutamyl-alanyl- leucyl-glycyl-arginine (αF30P);

α-fructosyl-valyl-histidyl-leucyl-threonyl-proryl-glutamyl-glutamyl-lysyluseryl-alanyl-valyl-threonyl-alanyl-leucyl-tryptophyl-glycyl-lysyl-valyl-asparaginyl-valyl-aspartyl-glutamyl-valyl-glycyl-glycyl-glutamyl-alanyl- leucyl-glycyl-arginyl-leucine (αF31P); and α-fructosyl-valyl-histidyl-leucyl-threonyl-proryl-glutamyl-glutamyl-lysyl-sryalanyl-valyl-threonyl-alanyl-leucyl-tryptophyl-glycyl-lysyl-valyl-asparaginyl-valyl-aspartyl-glutamyl-valyl-glycyl-glycyl-glutamyl-alanyl-leucyl-glycyl-arginyl-leucyl-leucine (αF32P).

This description includes part or all of the content as disclosed in the description and/or drawings of Japanese Patent Application No. 2013-222789, which is a priority document of the present application.

Effects of the Invention

The present invention can provide an amadoriase that has activity of oxidizing a wide variety of glycated peptides to generate hydrogen peroxide. With the use of such amadoriase, the present invention can provide a method for measurement of HbA1c that enables quantification of HbA1c to be performed rapidly, simply, and accurately and a kit used for such measurement or a method for measurement of HbA1c that enables quantification of HbA1c to be performed rapidly, simply, and accurately, with high sensitivity and a kit used for such measurement, with the use of a small amount of a protease. A protease that reacts with HbA1c but exhibits low cleavage specificity or poor cleavage efficiency can also be used. Also, a protease that is less likely to react with an amadoriase or peroxidase can be used for HbA1c cleavage. For example, even if the HbA1c β chain is not sufficiently hydrolyzed down to αFVH because of a reduced amount of applied protease, and, as a result, a wide variety of glycated peptides are generated during the hydrolysis reaction are also present, the amadoriase of the present invention is capable of reacting with a wide variety of glycated peptides (αF1P to αF32P, such as αF1P to αF16P) in addition to αFV or αFVH and, therefore, HbA1c can be quantified with high accuracy.

BRIEF DESCRIPTION OF THE DRAWINGS

FIG. 1-2 is a continuation from FIG. 1-1.

FIG. 1-3 is a continuation from FIG. 1-2.

FIG. 1-4 is a continuation from FIG. 1-3.

FIG. 1-5 is a continuation from FIG. 1-4.

FIG. 2-1 is a second diagram showing amino acid sequence identity and similar amino acids among various known amadoriases. In addition to Co, Et, Py, Ar, Cc, and Nv; Cn, Pn, An, En, Ul, and Pj were also aligned.

FIG. 2-2 is a continuation from FIG. 2-1.

FIG. 2-3 is a continuation from FIG. 2-2.

FIG. 2-4 is a continuation from FIG. 2-3.

FIG. 2-5 is a continuation from FIG. 2-4.

FIG. 3-1 shows the results of αF3P measurement using the amadoriase of the present invention.

FIG. 3-2 shows the results of αF4P measurement using the amadoriase of the present invention.

FIG. 3-3 shows the results of αF5P measurement using the amadoriase of the present invention.

FIG. 3-4 shows the results of αF6P measurement using the amadoriase of the present invention.

FIG. 3-5 shows the results of αF8P measurement using the amadoriase of the present invention.

FIG. 3-6 shows the results of αF16P measurement using the amadoriase of the present invention.

EMBODIMENTS FOR CARRYING OUT THE INVENTION

Figure 1:
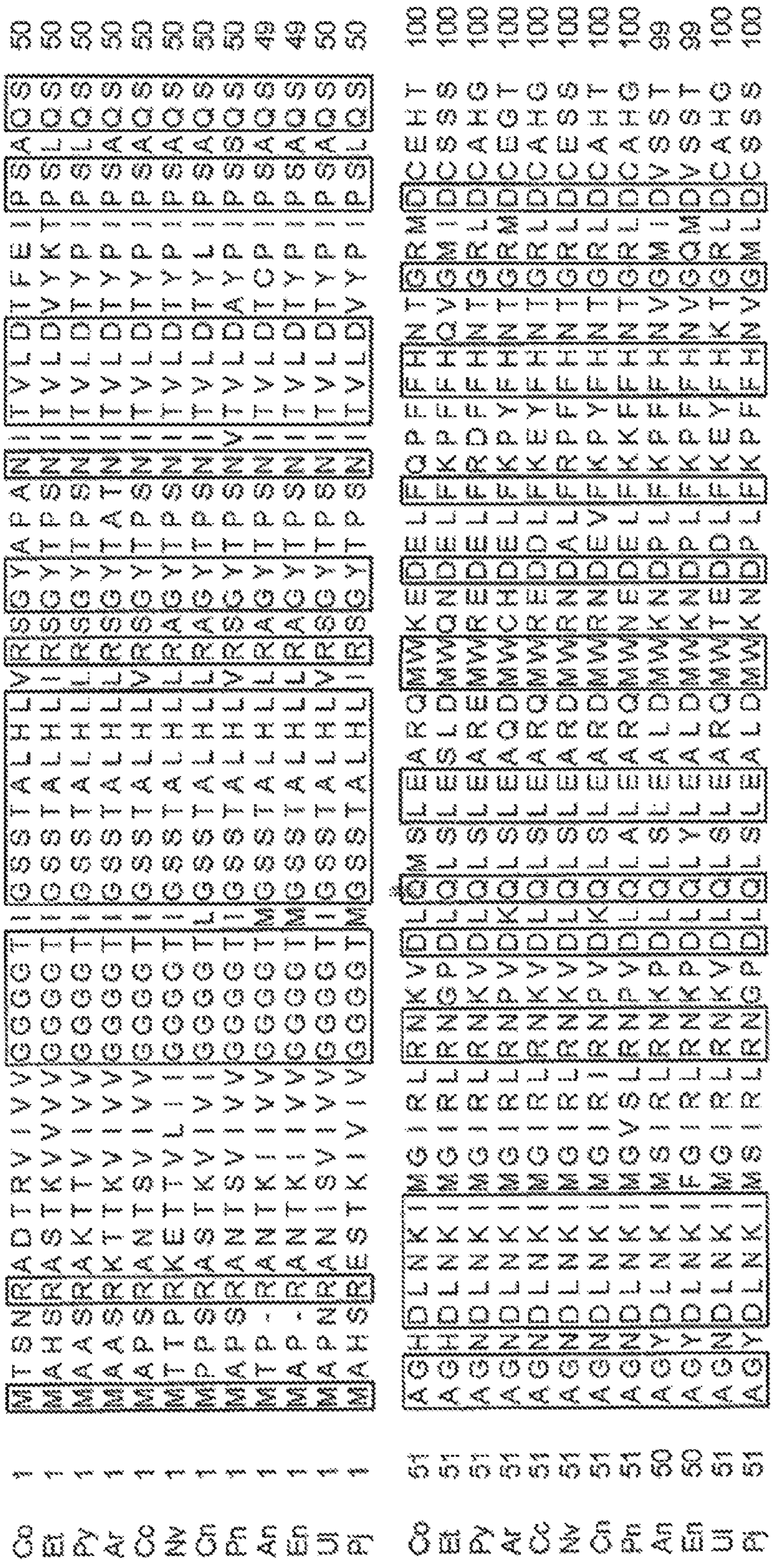
FIG. 1-1 is a first diagram showing amino acid sequence identity among various known amadoriases. In addition to Co (*Coniochaeta* sp.), Et (*Eupenicillium terrenum*), Py (*Pyrenochaeta* sp.), Ar (*Arthrinium* sp.), Cc (*Curvularia clavata*), and Nv (*Neocosmospora vasinfecta*), Cn (*Cryptococcus neoformans*), Pn (*Phaeosphaeria nodorum*), An (*Aspergillus nidulans*), En (*Emericella nidulans*), Ul (*Ulocladium* sp.), and Pj (*Penicillium janthinelum*) were aligned.

The present invention is described in detail as follows.

(Glycated Protein and Hemoglobin A1c)

The term “glycated protein” used herein refers to a protein glycated non-enzymatically. Glycated proteins exist in vivo and ex vivo. Examples of glycated proteins existing in vivo include glycated hemoglobin and glycated albumin in the blood. In particular, glycated hemoglobin comprising glycated valine at the β-chain amino terminus of hemoglobin is referred to as hemoglobin A1c (HbA1c). Examples of glycated proteins existing ex vivo include foods and drinks, such as liquid flavors, and infusion solutions in which a protein or peptide exists together with sugar.

(Glycated Peptide and Fructosyl Peptide)

The term “glycated peptide” used herein encompasses a peptide that is directly and non-enzymatically glycated, a product of degradation of a glycated protein by a protease or the like, and a product of glycation of (poly)peptides constituting a glycated protein. A “glycated peptide” is also referred to as a “fructosyl peptide.” In the present invention, more specifically, the glycated peptide is an α-glycated peptide (α-fructosyl peptide). For example, when the target glycated protein is hemoglobin A1c (HbA1c), the corresponding α-glycated peptide is a glycated peptide having a glycated N terminus. In particular, from the perspective of HbA1c quantification, it is a glycated peptide cleaved from the HbA1c β chain having the glycated N terminus. Examples of a glycated peptide that is cleaved from the HbA1c β chain having a glycated N terminus include α-fructosyl-valyl-histidine (αFVH) having a peptide chain length of 2 amino acids and include α-fructosyl-valyl-histidyl-leucine (αF3P) having a peptide chain length of 3 amino acids, α-fructosyl-valyl-histidyl-leucyl-threonine (αF4P) having a peptide chain length of 4 amino acids, α-fructosyl-valyl-histidyl-leucyl-threonyl-proline (αF5P) having a peptide chain length of 5 amino acids, α-fructosyl-valyl-histidyl-leucyl-threonyl-proryl-glutamic acid (αF6P) having a peptide chain length of 6 amino acids, α-fructosyl-valyl-histidyl-leucyl-threonyl-proryl-glutamyl-glutamyl-lysine (αF8P) having a peptide chain length of 8 amino acids, and α-fructosyl-valyl-histidyl-leucyl-threonyl-proryl-glutamyl-glutamyl-lysyl-seryl-alanyl-valyl-threonyl-alanyl-leucyl-tryptophyl-glycine (αF16P) having a peptide chain length of 16 amino acids and the like. For the convenience of description, αFV, αFVH, αF3P, αF4P, αF5P, αF6P, αF8P, and αF16P are collectively referred to as “α-fructosyl peptides such as αF6P and the like” or “α-fructosyl peptides such as αF6P and the like (αFV, αFVH, αF3P, αF4P, αF5P, αF6P, αF8P, and αF16P).”

In addition, examples of glycated peptides cleaved from the hemoglobin β chain with a glycated N terminus include:

α-fructosyl-valyl-histidyl-leucyl-threonyl-proryl-glutamyl-glutamic acid (αF7P);

α-fructosyl-valyl-histidyl-leucyl-threonyl-proryl-glutamyl-glutamyl-lysyl-serine (αF9P);

α-fructosyl-valyl-histidyl-leucyl-threonyl-proryl-glutamyl-glutamyl-lysyl-seryl-alanine (αF10P);

α-fructosyl-valyl-histidyl-leucyl-threonyl-proryl-glutamyl-glutamyl-lysyl-seryl-alanyl-valine (αF11P);

α-fructosyl-valyl-histidyl-leucyl-threonyl-proryl-glutamyl-glutamyl-lysyl-seryl-alanyl-valyl-threonine (αF12P);

α-fructosyl-valyl-histidyl-leucyl-threonyl-proryl-glutamyl-glutamyl-lysyl-seryl-alanyl-valyl-threonyl-alanine (αF13P);

α-fructosyl-valyl-histidyl-leucyl-threonyl-proryl-glutamyl-glutamyl-lysyl-seryl-alanyl-valyl-threonyl-alanyl-leucine (αF14P); and α-fructosyl-valyl-histidyl-leucyl-threonyl-proryl-glutamyl-glutamyl-lysyl-seryl-alanyl-valyl-threonyl-alanyl-leucyl-tryptophane (αF15P).

For the convenience of description, when referring to a particular range of α-fructosyl peptides with chains of certain lengths, this is expressed, for example, as “αF1P to αF16P,” and this expression encompasses all α-fructosyl peptides within the range, including an α-fructosyl peptide with the shortest chain length, α-fructosyl peptides with intermediate chain lengths, and an α-fructosyl peptide with the longest chain length within the range. For example, αF3P to αF16P may collectively be referred to herein as “α-fructosyl oligopeptides” or “α-fructosyl oligopeptides (αF3P to αF16P)”, and these expressions encompass α-fructosyl peptides of all chain lengths from αF31' to αF16P. Likewise, the expressions “α-fructosyl peptides (αF1P to αF16P)” or “α-fructosyl peptides (αFV to αF16P)” encompass α-fructosyl peptides of all chain lengths from αFV (αF1P) to αF16P.

To give examples, αF1P to αF8P, αF2P to αF8P, αF3P to αF8P, and αF2P to F16P are also defined in the same manner.

While it is not common to refer a compound consisting of a single amino acid as a peptide, in the present specification, α-fructosyl-valine (αFV), which is an α-fructosyl amino acid, and various types of α-fructosyl peptides comprising 2 or more amino acid residues, are collectively referred to as α-fructosyl peptides. Therefore, for the convenience of description, the above definition is given and, accordingly, αFV is defined to be within the scope of the “α-fructosyl peptide.”

The HbA1c β chain with a glycated N terminus is composed of 146 amino acid residues (see SEQ ID NO: 193). This means that, potentially, up to αF145P composed of 145 amino acid residues can exist as a glycated peptide cleaved from the hemoglobin β chain with a glycated N terminus. Accordingly, the HbA1c β chain composed of 145 amino acids (αF145P) is also within the scope of the α-glycated peptide.

In the present description, particularly when collectively referring to from αFV (αF1P) to α-glycated peptide comprising 32 amino acid residues (αF32P), this is referred to as "α-fructosyl peptides (αF1P to αF32P)." Further, α-glycated peptides from αF3P to αF32P, are referred to as "α-fructosyl peptides (αF3P to αF32P)." To give examples, ranges such as αF2P to αF32P, αF16P to αF32P, and αF17P to αF32P are also described in the same manner. Incidentally, αF17P to αF32P are as described below:

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysine (αF17P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valinc (αF18P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparagine (αF19P);

α-fructosyl-valyl-histidyl-leucyl-thrreonyl-proryl-glutamyl-glutamyl-lysyl-seryl-alanyl-valyl-threonyl-alanyl-leucyl-tryptophyl-glycyl-lysyl-valyl-asparaginyl-valine (αF20P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartic acid (αF21P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutamic acid (αF22P);

α-fructosyl-valyl-histidyl-leucyl-threonyl-proryl-glutamyl-glutamvl-lysyl-seryl-alanyl-valyl-threonyl-alanyl-leucyl-tryptophyl-glycyl-lysyl-valyI-asparaginvl-valyl-aspartyl-glutamyvl-valine (αF23P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutamyl-valyl-glycine (αF24P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutamyl-valyl-glycyl-glycine (αF25P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutamyl-valyl-glycyl-glycyl-glutamic acid (αF26P);

α-fructosyl-valyl-histidyl-leucyl-threonyl-proryl-glutamyl-glutamyl-lysyl-scryl-alanyl-valyl-threonyl-alanyl-leucyl-tryptophyl-glycyl-lysyl-valyl-asparaginyl-valyl-aspartyl-glutamyl-valyl-glycyl-glycyl-glutamyl-alanine (αF27P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutanyl-valyl-glycyl-glycyl-glutamyl-alanyl- leucine (αF28P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutamyl-valyl-glycyl-glycyl-glutamyl-alanyl- leucyl-glycine (αF29P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutamyl-valyl-glycyl-glycyl-glutamyl-alanyl- leucyl-glycyl-arginine (αF30P);

α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutamyl-valyl-glycyl-glycyl-glutamyl-alanyl- leucyl-glycyl-arginyl-leucine (αF31P); and α-fructosyl-valyl-histidyl-leucyl-threonyl-proryl-glutamyl-glutamyl-lysyl-seryl-alanyl-valyl-threonyl-alanyl-leucyl-tryptophyl-glycyl-lysyl-valyl-asparaginyl-valyl-aspartyl-glutamyl-valyl-glycyl-glycyl-glutamyl-alanyl- leucyl-glycyl-arginyl-leucyl-leucine (αF32P).

These α-fructosyl peptides (αF1P to αF32P), such as αF1P to αF16P and the like, can serve as substrates for the amadoriase of the present invention.

An embodiment of the present invention provides a method for measurement of α-fructosyl oligopeptide in a sample comprising allowing an amadoriase that reacts with one or more α-fructosyl oligopeptides selected from among αF3P to αF5P and αF7P to αF16P to react with a sample containing one or more α-fructosyl oligopeptides selected from among αF3P to αF5P and αF7P to αF16P and measuring the amount of hydrogen peroxide generated or enzyme consumed in such reaction.

An embodiment of the present invention provides a method for measurement of α-fructosyl oligopeptide in a sample comprising allowing an amadoriase that reacts with one or more α-fructosyl oligopeptides selected from among αF3P, αF4P, αF5P, αF6P, αF8P, and αF16P to react with a sample containing one or more α-fructosyl oligopeptides selected from among αF3P, αF4P, αF5P, αF6P, αF8P, and αF16P and measuring the amount of hydrogen peroxide generated or enzyme consumed in such reaction.

An embodiment of the present invention provides a method for measurement of α-fructosyl oligopeptide in a sample comprising allowing an amadoriase that reacts with one or more α-fructosyl oligopeptides selected from among αF3P, αF4P, αF5P, αF8P, and αF16P to react with a sample containing one or more α-fructosyl oligopeptides selected from among αF3P, αF4P, αF5P, αF8P, and αF16P and measuring the amount of hydrogen peroxide generated or enzyme consumed in such reaction.

An embodiment of the present invention provides a method for measurement of α-fructosyl oligopeptide in a sample comprising allowing an amadoriase that reacts with one or more α-fructosyl oligopeptides selected from among αF3P, αF4P, and αF5P to react with a sample containing one or more α-fructosyl oligopeptides selected from among αF3P, αF4P, and αF5P and measuring the amount of hydrogen peroxide generated or enzyme consumed in such reaction.

(Amadoriase)

An amadoriase is also referred to as ketoamine oxidase, fructosyl amino acid oxidase, fructosyl peptide oxidase, or fructosyl amine oxidase, and it is an enzyme that oxidizes iminodiacetic acid or a derivative thereof (Amadori compound) in the presence of oxygen to catalyze a reaction to generate glyoxylic acid or α-ketoaldehyde, amino acid or peptide, and hydrogen peroxide. Amadoriases are widely distributed in nature and can be obtained by searching for enzymes from sources of microorganisms, animals, or plants. With regard to microorganisms, amadoriases can be obtained from, for example, filamentous fungi, yeast, or bacteria. The amadoriase of the present invention can react with a wide variety of glycated peptides.

The amadoriase of the present invention can react with αF1P to αF32P, such as αF1P to αF16P. In the present specification, the phrase "an amadoriase reacts with an α-fructosyl peptide with a chain of a particular length" means the amadoriase reacts with the fructosyl group of the α-fructosyl peptide with a chain of said particular length in the presence of oxygen, and 2-keto-D glucose, hydrogen peroxide, and a peptide corresponding to said chain length is generated. It should be noted, however, that this does not exclude such amadoriase from being able to react with an α-fructosyl peptide derived from the HbA1c β chain having a shorter chain length, such as αFV or αFVH. That is, the amadoriase of the present invention can react not only with an α-fructosyl peptide with a chain of a particular length, such as αF3P, αF4P, αF5P, αF6P, αF7P, αF8P, αF9P, αF10P, αF11P, αF12P, αF13P, αF14P, αF15P, or αF16P, but also with an α-fructosyl peptide derived from the HbA1c β chain with a shorter chain length, such as αFV or αFVH.

(Modified Amadoriase)

The present invention provides a modified amadoriase with modified substrate specificity, which is prepared based on a wild-type amadoriase comprising the amino acid sequence as shown in SEQ ID NO: 1, SEQ ID NO: 38, SEQ ID NO: 40, SEQ ID NO: 54, SEQ ID NO: 62, SEQ ID NO: 89, or SEQ ID NO: 99 wherein said modified amadoriase has a high degree of reactivity with α-fructosyl peptides such as αF6P and the like (αFV, αFVH, αF3P, αF4P, αF5P, αF6P, αF8P, and αF16P). In this description, the term "modified amadoriase" is interchangeably used with the term "amadoriase variant" and these refer to a modified amadoriase having substitution, deletion, or addition of some amino acids when comparing the amino acid sequence thereof with the amino acid sequence of a wild-type amadoriase. The term "addition" used in this context encompasses "insertion." Such modified amadoriase is able to react not only with αFV and αFVH but also with α-fructosyl oligopeptides (αF3P to αF16P).

Further, the present invention provides a modified amadoriase with modified substrate specificity, which is prepared based on a wild-type amadoriase comprising the amino acid sequence as shown in SEQ ID NO: 113, SEQ ID NO: 115, SEQ ID NO: 117, SEQ ID NO: 119, SEQ ID NO: 121, SEQ ID NO: 123, SEQ ID NO: 145, or SEQ ID NO: 149, wherein said modified amadoriase has a high degree of reactivity with α-fructosyl peptides such as αF6P and the like (αFV, αFVH, αF3P, αF4P, αF5P, αF6P, αF8P, and αF16P).

Based on findings of the present invention, and based on other wild-type amadoriases derived from the genus *Coniochaeta* or the like, a modified amadoriase with modified substrate specificity can be obtained wherein such amadoriase has a high degree of reactivity with α-fructosyl peptides such as αF6P and the like (αFV, αFVH, αF3P, αF4P, αF5P, αF6P, αF8P, and αF16P), and further with αF1P to αF32P.

(Modified Amadoriase Prepared from Amadoriase Derived from *Coniochaeta* sp. NISL 9330)

The amadoriase according to an embodiment of the present invention is a modified amadoriase with modified substrate specificity, which is prepared based on the amadoriase derived from the genus *Coniochaeta* comprising the amino acid sequence as shown in SEQ ID NO: 1, wherein said modified amadoriase has a high degree of reactivity with α-fructosyl peptides such as αF61' and the like (αFV, αFVH, αF3P, αF4P, αF5P, αF6P, αF8P, and αF16P). It is thought that such modified amadoriase can also react with α-fructosyl peptides (αF1P to αF32P).

Examples of variants as described above include amadoriases comprising amino acid sequences exhibiting high sequence identity (e.g., sequence identity of 50% or higher, preferably 60% or higher, 70% or higher, 75% or higher, or 80% or higher, more preferably 85% or higher, further preferably 90% or higher, 95% or higher, or 98% or higher, and most preferably 99% or higher) with the amino acid sequences as shown in SEQ ID NO: 151, SEQ ID NO: 153, and SEQ ID NO: 155 (single variants), SEQ ID NO: 157, SEQ ID NO: 159, SEQ ID NO: 161, and SEQ ID NO: 163 (double variants), SEQ ID NO: 137, SEQ ID NO: 139, SEQ ID NO: 165, SEQ ID NO: 167, SEQ ID NO: 169, SEQ ID NO: 171, and SEQ ID NO: 173 (triple variants), SEQ ID NO: 133, SEQ ID NO: 135, SEQ ID NO: 175, and SEQ ID NO: 189 (quadruple variants), SEQ ID NO: 177 and SEQ ID NO: 179 (quintuple variants), SEQ ID NO: 143, SEQ ID NO: 181, SEQ ID NO: 183, SEQ ID NO: 187, and SEQ ID NO: 191 (sextuple variants), and SEQ ID NO: 141 and SEQ ID NO: 185 (septuple variants), and having activity on α-fructosyl peptides (αF1P to αF32P) or α-fructosyl peptides such as αF6P and the like (αFV, αFVH, αF3P, αF4P, αF5P, αF6P, αF8P, and αF16P).

Further examples of amadoriase variants include amadoriases comprising amino acid sequences derived from the amino acid sequences as shown in SEQ ID NO: 151, SEQ ID NO: 153, and SEQ ID NO: 155 (single variants), SEQ ID NO: 157, SEQ ID NO: 159, SEQ ID NO: 161, and SEQ ID NO: 163 (double variants), SEQ ID NO: 137, SEQ ID NO: 139. SEQ ID NO: 165, SEQ ID NO: 167, SEQ ID NO: 169, SEQ ID NO: 171, and SEQ ID NO: 173 (triple variants). SEQ ID NO: 133, SEQ ID NO: 135, SEQ ID NO: 175, and SEQ ID NO: 189 (quadruple variants), SEQ ID NO: 177 and SEQ ID NO: 179 (quintuple variants), SEQ ID NO: 143, SEQ ID NO: 181, SEQ ID NO: 183, SEQ ID NO: 187, and SEQ ID NO: 191 (sextuple variants), and SEQ ID NO: 141 and SEQ ID NO: 185 (septuple variants) by modification, variation, deletion, substitution, addition, and/or insertion of 1 or several amino acids and having activity on α-fructosyl peptides (αF1P to αF32P) or α-fructosyl peptides such as αF6P and the like (αFV, αFVH, αF3P, αF4P, αF5P, αF6P, αF8P, and αF16P). The term "one or several amino acids" used herein refers to 1 to 15, preferably 1 to 10, more preferably 1 to 5, still more preferably 1 to 4, further preferably 1 to 3, and still further preferably 1 or 2 amino acids, when the full-length amino acid sequence comprises more than 400 amino acids. Also, the term "one or several amino acids" refers to 1 to 10, preferably 1 to 7, more preferably 1 to 5, still more preferably 1 to 4, further preferably 1 to 3, and still further preferably 1 or 2 amino acids, when the full-length amino acid sequence comprises 200 to 400 amino acids. The term "one or several amino acids" refers to 1 to 5, preferably 1 to 4, more preferably 1 to 3, and further preferably 1 or 2 amino acids, when the full-length amino acid sequence comprises 40 to less than 200 amino acids. The term "one or several amino acids" refers to 1 or 2 amino acids, when the full-length amino acid sequence comprises less than 40 amino acids.

Furthermore, examples of amadoriase variants include amadoriases encoded by nucleotide sequences which hybridize under stringent conditions to sequences complementary to the nucleotide sequences as shown in SEQ ID NO: 152, SEQ ID NO: 154, and SEQ ID NO: 156 (single variants), SEQ ID NO: 158, SEQ ID NO: 160. SEQ ID NO: 162, and SEQ ID NO: 164 (double variants), SEQ ID NO: 138, SEQ ID NO: 140, SEQ ID NO: 166, SEQ ID NO: 168, SEQ ID NO: 170, SEQ ID NO: 172, and SEQ ID NO: 174 (triple variants), SEQ ID NO: 134, SEQ ID NO: 136, SEQ ID NO: 176, and SEQ ID NO: 190 (quadruple variants), SEQ ID NO: 178 and SEQ ID NO: 180 (quintuple variants), SEQ ID NO: 144, SEQ ID NO: 182, SEQ ID NO: 184, SEQ ID NO: 188, and SEQ ID NO: 192 (sextuple variants), and SEQ ID NO: 142 and SEQ ID NO: 186 (septuple variants) wherein said amadoriases have activity on α-fructosyl peptides (αF1P to αF32P) or α-fructosyl peptides such as αF6P and the like (αFV, αFVH, αF3P, αF4P, αF5P, αF6P, αF8P, and αF16P). Stringent hybridization conditions are described in, for example, Sambrook et al., Molecular Cloning. Vol. 2 (Cold Spring Harbor Laboratory Press) or Current Protocols in Molecular Biology (Frederick, M. Ausubel et al. (ed.), 1987). Under stringent conditions, for example, hybridization is carried out by conducting incubation with the use of a hybridization solution (50% formamide, 6 to 10×SSC (0.15 to 1.5 M NaCl, 15 mM sodium citrate, pH 7.0), 5×Denhardt solution, 1% SDS, 10% dextran sulfate, 10 μg/ml denatured salmon sperm DNA, and 50 mM phosphate buffer (pH 7.5)) at about 42° C. to about 50° C. followed by washing with 0.1×SSC and 0.1% SDS at about 65° C. to about 70° C. Under other stringent conditions, hybridization is carried out with the use of, for example, a hybridization solution of 50% formamide, 5×SSC (0.15 M NaCl, 15 mM sodium citrate, pH 7.0), 1×Denhardt solution, 1% SDS, 10% dextran sulfate, 10 μg/ml denatured salmon sperm DNA, and 50 mM phosphate buffer (pH 7.5).

The variant according to the present invention may be obtained from amadoriases derived from other organism species, such as the genus *Eupenicillium, Pyrenochaeta, Arthrinium, Curvularia, Neocosmospora, Cryptococcus, Phaeosphaeria, Aspergillus, Emericella, Ulocladium, Penicillium, Fusarium, Achaetomiella, Achaetomium, Thielavia, Chaetomium, Gelasinospora, Microascus, Leptosphaeria, Ophinbolus, Pleospora, Coniochaetidium, Pichia, Corynebacterium, Agrobacterium*, or *Arthrobacter*, provided that the conditions concerning substrate specificity and/or amino acid sequences described in the claims are satisfied.

A modified amadoriase obtained from the amadoriase derived from *Coniochaeta* sp. NISL 9330 (SEQ ID NO: 1) can comprise one or a plurality of amino acid substitutions at the positions described below. The term "one or a plurality of amino acid substitutions" used with regard to the modified amadoriase refers to substitution of 1, 2, 3, 4, 5, 6, 7, or 8 amino acids. Preferably, the term refers to substitution of 1, 2, 3, 4, 5, 6, or 7 amino acids:

(a) arginine at position 62;
(b) leucine at position 63;
(c) glutamic acid at position 102;
(d) aspartic acid at position 106;
(e) glutamine at position 110;
(f) alanine at position 113;
(g) alanine at position 355; and
(h) alanine at position 419.

In the amadoriase derived from *Coniochaeta* sp. NISL 9330 (SEQ ID NO: 1), preferably, (a) arginine at position 62 is substituted with alanine, asparagine, or aspartic acid. Preferably, (b) leucine at position 63 is substituted with histidine or alanine. Preferably, (c) glutamic acid at position 102 is substituted with lysine. Preferably, (d) aspartic acid at position 106 is substituted with alanine, lysine, or arginine. Preferably, (e) glutamine at position 110 is substituted with leucine or tyrosine. Preferably, (f) alanine at position 113 is substituted with lysine or arginine. Preferably, (g) alanine at position 355 is substituted with serine. Optionally, (h) alanine at position 419 may be substituted with lysine.

A modified amadoriase obtained from the amadoriase derived from *Phaeosphaeria nodorum* (PnFX, SEQ ID NO: 38) can comprise one or a plurality of amino acid substitutions at the positions described below:

(a) serine at position 62;
(b) leucine at position 63;
(c) lysine at position 102;
(d) aspartic acid at position 106;
(e) glycine at position 110;
(f) alanine at position 113;
(g) alanine at position 351; and
(h) serine at position 416.

In the amadoriase derived from *Phaeosphaeria nodorum* (SEQ ID NO: 38), preferably, (a) serine at position 62 is substituted with alanine or aspartic acid. Preferably, (b) leucine at position 63 is substituted with histidine. According to the circumstances, (c) lysine at position 102 need not be substituted. Preferably, (d) aspartic acid at position 106 is substituted with lysine. Preferably, glycine at position 110 is substituted with leucine. Preferably, alanine at position 113 is substituted with lysine. Preferably, alanine at position 351 is substituted with serine. Optionally, (h) serine at position 416 may be substituted with lysine.

A modified amadoriase obtained from the amadoriase derived from *Neocosmospora vasinfecta* (NvFX, SEQ ID NO: 54) can comprise one or a plurality of amino acid substitutions at the positions described below:

(a) arginine at position 62;
(b) leucine at position 63;
(c) glutamic acid at position 102;
(d) glycine at position 106;
(e) glutamic acid at position 110;
(f) lysine at position 113;
(g) serine at position 355; and
(h) alanine at position 420.

In the amadoriase derived from *Neocosmospora vasinfecta* (SEQ ID NO: 54), preferably, arginine at position 62 is substituted with alanine or aspartic acid. Preferably, (b) leucine at position 63 is substituted with histidine. Preferably, (c) glutamic acid at position 102 is substituted with lysine. Preferably, (d) glycine at position 106 is substituted with lysine. Preferably, glutamic acid at position 110 is substituted with leucine. According to the circumstances, lysine at position 113 need not be substituted, and serine at position 355 need not be substituted. Optionally, (h) alanine at position 420 may be substituted with lysine.

A modified amadoriase obtained from the amadoriase derived from *Aspergillus nidulans* (AnFX, SEQ ID NO: 62) can comprise one or a plurality of amino acid substitutions at the positions described below:

(a) arginine at position 61:
(b) leucine at position 62;
(c) glutamic acid at position 101;
(d) glycine at position 105;
(c) lysine at position 109;
(f) serine at position 112:
(g) alanine at position 355; and
(h) alanine at position 420.

In the amadoriase derived from *Aspergillus nidulans* (SEQ ID NO: 62), preferably, (a) arginine at position 61 is substituted with alanine or aspartic acid. Preferably, (b) leucine at position 62 is substituted with histidine. Preferably, (c) glutamic acid at position 101 is substituted with lysine. Preferably, (d) glycine at position 105 is substituted with lysine. Preferably, lysine at position 109 is substituted with leucine. Preferably, serine at position 112 is substituted with lysine. Preferably, alanine at position 355 is substituted with serine. Optionally, (h) alanine at position 420 may be substituted with lysine.

A modified amadoriase obtained from the amadoriase derived from *Eupenicillium terrenum* (SEQ ID NO: 40) can comprise one or a plurality of amino acid substitutions at the positions described below:

(a) arginine at position 62;
(b) leucine at position 63;
(c) glutamic acid at position 102;
(d) asparagine at position 106;
(e) lysine at position 110;
(f) threonine at position 113;
(g) alanine at position 355; and
(h) glycine at position 419.

In the amadoriase derived from EFP-T5 (SEQ ID NO: 40), preferably, (a) arginine at position 62 is substituted with alanine or aspartic acid. Preferably, (b) leucine at position 63 is substituted with histidine. Preferably, (c) glutamic acid at position 102 is substituted with lysine. Preferably, (d) asparagine at position 106 is substituted with lysine. Preferably, lysine at position 110 is substituted with leucine. Preferably, threonine at position 113 is substituted with lysine. Preferably, alanine at position 355 is substituted with serine. Optionally, (h) glycine at position 419 may be substituted with lysine.

A modified amadoriase obtained from fructosyl amino acid oxidase derived from *Cryptococcus neoformans* (SEQ ID NO: 89 or 149) can comprise one or a plurality of amino acid substitutions at the positions described below:

(a) arginine at position 62;
(b) isoleucine at position 63;
(c) glutamic acid at position 102;
(d) serine at position 106;
(e) serine at position 110;
(f) alanine at position 113;
(g) alanine at position 355; and
(h) alanine at position 420.

In the fructosyl amino acid oxidase derived from *Cryptococcus neoformans* (CnFX, SEQ ID NO: 89 or 149), preferably, (a) arginine at position 62 is substituted with alanine or aspartic acid. Preferably, (b) isoleucine at position 63 is substituted with histidine. Preferably, (c) glutamic acid at position 102 is substituted with lysine. Preferably, (d) serine at position 106 is substituted with lysine. Preferably, serine at position 110 is substituted with leucine. Preferably, alanine at position 113 is substituted with lysine. Preferably, alanine at position 355 is substituted with serine. Optionally, (h) alanine at position 420 may be substituted with lysine.

A modified amadoriase obtained from ketoamine oxidase derived from *Pyrenochaeta* sp. (SEQ ID NO: 113) can comprise one or a plurality of amino acid substitutions at the positions described below:

(a) arginine at position 62;
(b) leucine at position 63;
(c) lysine at position 102;
(d) aspartic acid at position 106;
(e) alanine at position 110;
(f) threonine at position 113;
(g) alanine at position 353; and
(h) alanine at position 418.

In the ketoamine oxidase derived from *Pyrenochaeta* sp. (SEQ ID NO: 113), preferably, (a) arginine at position 62 is substituted with alanine or aspartic acid. Preferably, (b) leucine at position 63 is substituted with histidine. According to the circumstances, (c) lysine at position 102 need not be substituted. Preferably, (d) aspartic acid at position 106 is substituted with lysine. Preferably, alanine at position 110 is substituted with leucine. Preferably, threonine at position 113 is substituted with lysine. Preferably, alanine at position 353 is substituted with serine. Optionally, (h) alanine at position 418 may be substituted with lysine.

A modified amadoriase obtained from ketoamine oxidase derived from *Arthrinium* sp. (SEQ ID NO: 115) can comprise one or a plurality of amino acid substitutions at the positions described below:

(a) arginine at position 62;
(b) leucine at position 63;
(c) lysine at position 102;
(d) alanine at position 106;
(e) glutamine at position 110;
(f) threonine at position 113;
(g) alanine at position 356; and
(h) alanine at position 421.

In the ketoamine oxidase derived from *Arthrinium* sp. (SEQ ID NO: 115), preferably, (a) arginine at position 62 is substituted with alanine or aspartic acid. Preferably, (b) leucine at position 63 is substituted with histidine. According to the circumstances, (c) lysine at position 102 need not be substituted. Preferably, (d) alanine at position 106 is substituted with lysine. Preferably, glutamine at position 110 is substituted with leucine. Preferably, threonine at position 113 is substituted with lysine. Preferably, alanine at position 356 is substituted with serine. Optionally, (h) alanine at position 421 may be substituted with lysine.

A modified amadoriase obtained from ketoamine oxidase derived from *Curvularia clavata* (SEQ ID NO: 117) can comprise one or a plurality of amino acid substitutions at the positions described below:

(a) arginine at position 62;
(b) leucine at position 63;
(c) glutamic acid at position 102;
(d) aspartic acid at position 106;
(e) alanine at position 110:
(f) alanine at position 113;
(g) alanine at position 353; and
(h) alanine at position 418.

In the ketoamine oxidase derived from *Curvularia clavata* (SEQ ID NO: 117), preferably, (a) arginine at position 62 is substituted with alanine or aspartic acid. Preferably, (b) leucine at position 63 is substituted with histidine. Preferably, (c) glutamic acid at position 102 is substituted with lysine. Preferably, (d) aspartic acid at position 106 is substituted with lysine. Preferably, alanine at position 110 is substituted with leucine. Preferably, alanine at position 113 is substituted with lysine. Preferably, alanine at position 353 is substituted with serine. Optionally, (h) alanine at position 418 may be substituted with lysine.

A modified amadoriase obtained from ketoamine oxidase (Cc95FX, SEQ ID NO: 99) having 95% amino acid sequence identity with ketoamine oxidase derived from *Curvularia clavata* (SEQ ID NO: 117) can comprise one or a plurality of amino acid substitutions at the positions described below:

(a) arginine at position 62;
(b) leucine at position 63;
(c) glutamic acid at position 102;
(d) aspartic acid at position 106;
(e) alanine at position 110;
(f) alanine at position 113;
(g) alanine at position 353; and
(h) serine at position 418.

In the ketoamine oxidase (SEQ ID NO: 99) having 95% amino acid sequence identity with the ketoamine oxidase derived from *Curvularia clavata* (SEQ ID NO: 117), preferably, (a) arginine at position 62 is substituted with alanine or aspartic acid. Preferably, (b) leucine at position 63 is substituted with histidine. Preferably, (c) glutamic acid at position 102 is substituted with lysine. Preferably, (d) aspartic acid at position 106 is substituted with lysine. Preferably, alanine at position 110 is substituted with leucine. Preferably, alanine at position 113 is substituted with lysine. Preferably, alanine at position 353 is substituted with serine. Optionally, (h) serine at position 418 may be substituted with lysine.

A modified amadoriase obtained from fructosyl peptide oxidase derived from *Emericella nidulans* (SEQ ID NO: 119) can comprise one or a plurality of amino acid substitutions at the positions described below:

(a) arginine at position 61;
(b) leucine at position 62;
(c) glutamic acid at position 101;
(d) lysine at position 105;
(e) arginine at position 109;
(f) serine at position 112;
(g) alanine at position 355; and
(h) alanine at position 420.

In the fructosyl peptide oxidase derived from *Emericella nidulans* (SEQ ID NO: 119), preferably, (a) arginine at position 61 is substituted with alanine or aspartic acid. Preferably, (b) leucine at position 62 is substituted with histidine. Preferably, (c) glutamic acid at position 101 is substituted with lysine. According to the circumstances, (d) lysine at position 105 need not be substituted. Preferably, arginine at position 109 is substituted with leucine. Preferably, serine at position 112 is substituted with lysine. Preferably, alanine at position 355 is substituted with serine. Optionally, (h) alanine at position 420 may be substituted with lysine.

A modified amadoriase obtained from fructosyl amino acid oxidase derived from *Ulocladium* sp. (SEQ ID NO: 121) can comprise one or a plurality of amino acid substitutions at the positions described below:

(a) arginine at position 62;
(b) leucine at position 63;
(c) lysine at position 102;
(d) aspartic acid at position 106;
(c) alanine at position 110;
(f) alanine at position 113;
(g) alanine at position 353; and
(h) alanine at position 418.

In the fructosyl amino acid oxidase derived from *Ulocladium* sp. (SEQ ID NO: 121), preferably, (a) arginine at position 62 is substituted with alanine or aspartic acid. Preferably, (b) leucine at position 63 is substituted with histidine. According to the circumstances, (c) lysine at position 102 need not be substituted. Preferably, (d) aspartic acid at position 106 is substituted with lysine. Preferably, alanine at position 110 is substituted with leucine. Preferably, alanine at position 113 is substituted with lysine. Preferably, alanine at position 353 is substituted with serine. Optionally, (h) alanine at position 418 may be substituted with lysine.

A modified amadoriase obtained from fructosyl amino acid oxidase derived from *Penicillium janthinellum* (SEQ ID NO: 123) can comprise one or a plurality of amino acid substitutions at the positions described below:

(a) arginine at position 62;
(b) leucine at position 63;
(c) glutamic acid at position 102;
(d) serine at position 106;
(e) lysine at position 110;
(f) aspartic acid at position 113;
(g) alanine at position 355; and
(h) serine at position 419.

In the fructosyl amino acid oxidase derived from *Penicillium janthinellum* (SEQ ID NO: 123), preferably, (a) arginine at position 62 is substituted with alanine or aspartic acid. Preferably, (b) leucine at position 63 is substituted with histidine. Preferably, (c) glutamic acid at position 102 is substituted with lysine. Preferably, (d) serine at position 106 is substituted with lysine. Preferably, lysine at position 110 is substituted with leucine. Preferably, aspartic acid at position 113 is substituted with lysine. Preferably, alanine at position 355 is substituted with serine. Optionally, (h) serine at position 419 may be substituted with lysine.

The amadoriase according to a preferable embodiment of the present invention recognizes an α-fructosyl peptide such as αF6P and the like, specifically, at least one α-fructosyl peptide selected from among αFV, αFVH, and the glycated peptides (a) to (f) below, as a substrate:

(a) α-fructosyl-valyl-histidyl-leucine (αF3P);
(b) α-fructosyl-valyl-histidyl-leucyl-threonine (αF4P);
(c) α-fructosyl-valyl-histidyl-leucyl-threonyl-proline (αF5P);
(d) α-fructosyl-valyl-histidyl-leucyl-threonyl-proryl-glutamic acid (αF6P);
(e) α-fructosyl-valyl-histidyl-leucyl-threonyl-proryl-glutamyl-glutamyl-lysine (αF8P); and
(f) α-fructosyl-valyl-histidyl-eucy-theonyl-prory-glutamyl-glutamyl-lysyl-seryl-alanyl-valyl-threonyl-alanyl-leucyl-tryptophyl-glycine (αF16P), as enzyme activity, oxidizes one or more glycated peptides selected from among (a) to (f) above to generate hydrogen peroxide,
has an optimal pH range between 6 and 8,
has an operable pH range between 5 and 9,
has an operable temperature between 25° C. and 40° C., and
has a molecular weight determined via SDS-PAGE of about 45 to 55 KDa (e.g., about 48 to 50 KDa).

Amadoriases exhibiting no or substantially no activity on αF3P, αF4P, αF5P, αF6P, αF8P, and αF16P, for example, amadoriases having an amino acid sequences as shown in SEQ ID NO: 1, SEQ ID NO: 36, SEQ ID NO: 38, SEQ ID NO: 40, SEQ ID NO: 54, SEQ ID NO: 62, SEQ ID NO: 89, SEQ ID NO: 99, SEQ ID NO: 145, SEQ ID NO: 147, or SEQ ID NO: 149 are excluded from the scope of the amadoriase variant or the modified amadoriase according to the present invention. Also, revertants to wild-type amadoriases, i.e, those whose amino acid sequence has reverted back to the wild-type sequence, are excluded from the scope of the amadoriase variant or the modified amadoriase according to the present invention.

(Obtaining a Gene Encoding an Amadoriase)

In order to obtain a gene of the present invention which encodes the amadoriase described above (hereinafter, also referred to simply as "amadoriase gene"), gene cloning methods used in general can be employed. For example, chromosomal DNA or mRNA can be extracted from a microorganism fungus body or various cells having an ability to produce an amadoriase by a conventional technique, such as a method described in "Current Protocols in Molecular Biology" (WILEY Interscience, 1989). In addition, cDNA can be synthesized using mRNA as a template. A chromosomal DNA or cDNA library can be made using the chromosomal DNA or cDNA obtained in such a manner.

Subsequently, DNA including the entire sequence of a target amadoriase gene can be obtained by a method of synthesizing an appropriate probe DNA based on the amino acid sequence of the aforementioned amadoriase and selecting an amadoriase gene from a chromosomal DNA or cDNA library using the probe DNA. Alternatively, an appropriate primer DNA may be produced based on the aforementioned amino acid sequence, a DNA including the target gene fragment encoding the amadoriase may be amplified by using an appropriate polymerase chain reaction (PCR) technique, such as the 5' RACE or 3' RACE method, and the resulting DNA fragments may then be linked.

A preferable example of a gene encoding an amadoriase thus obtained is an amadoriase gene derived from the genus *Coniochaeta* (JP 2003-235585 A).

Other preferable examples include amadoriase genes derived from the genus *Phaeosphaeria*, amadoriase genes derived from the genus *Neocosmospora*, amadoriase genes derived from the genus *Aspergillus*, amadoriase genes derived from the genus *Cryptococcus*, amadoriase genes derived from the genus *Curvularia*, and amadoriase genes derived from the genus *Eupenicillium*.

Such amadoriase genes are preferably linked to various vectors according to a conventional technique from the viewpoint of handleability. For example, a DNA encoding an amadoriase gene can be obtained by subjecting a recombinant plasmid pKK223-3-CFP-T7 including DNA encoding an amadoriase gene derived from a strain of *Coniochaeta* sp. NISL9330 (WO 2007/125779) to extraction and purification using the GenElute Plasmid Miniprep Kit (Sigma-Aldrich). A person skilled in the art would be able to obtain DNA of amadoriase genes derived from other organisms in a similar manner using conventional techniques. More specifically. DNA encoding an amadoriase gene can be obtained by culturing *E. coli* strains carrying the recombinant plasmid pUTE100K'-EFP-T5 including DNA encoding an amadoriase gene derived from a strain of *Eupenicillium terrenum* ATCC 18547 (WO 2007/125779) and extracting and purifying the recombinant plasmid pUTE100K'-EFP-T5 including DNA encoding an amadoriase gene from the cells using the GenElute Plasmid Miniprep Kit. Also, DNA encoding an amadoriase gene can be obtained by culturing *E. coli* strains carrying the recombinant plasmid pET22b-AnFX including DNA encoding an amadoriase gene derived from a strain of *Aspergillus nidulans* FGSC A26 (WO 2012/018094) and extracting and purifying the recombinant plasmid pET22b-AnFX including DNA encoding an amadoriase gene therefrom with the use of the GenElute Plasmid Miniprep Kit. DNA encoding an amadoriase gene can be obtained by culturing *E. coli* strains carrying the recombinant plasmid pET22b-CnFX including DNA encoding an amadoriase gene derived from a strain of *Cryptococcus neoformans* (WO 2012/018094) and extracting and purifying the recombinant plasmid pET22b-CnFX including DNA encoding an amadoriase gene therefrom with the use of the GenElute Plasmid Miniprep Kit. DNA encoding an amadoriase gene can be obtained by culturing *E. coli* strains carrying the recombinant plasmid pET22b-NvFX including DNA encoding an amadoriase gene derived from a strain of *Neocosmospora vasinfecta* (WO 2012/018094) and extracting and purifying the recombinant plasmid pET22b-NvFX including DNA encoding an amadoriase gene therefrom with the use of the GenElute Plasmid Miniprep Kit.

(Vector)

Vectors that can be used in the present invention are not limited to the aforementioned plasmid vectors. For example, any other vector known in the art, such as bacteriophage or cosmid vectors, can be used. Specifically, for example, pBluescriptII SK+ (manufactured by Stratagene Corporation) is preferable.

(Mutation of Amadoriase Gene)

Mutation of an amadoriase gene can be performed by any known method depending on an intended form of mutation. More specifically, a method of bringing a chemical mutagen into contact with and allowing to act on an amadoriase gene or recombinant DNA comprising such gene integrated therein, an ultraviolet irradiation method, a genetic engineering technique, a method of making full use of a protein engineering technique, or various other methods can be extensively used.

Examples of chemical mutagens used in the aforementioned mutation include hydroxylamine, N-methyl-N'-nitro-N-nitrosoguanidine, nitrous acid, sulfurous acid, hydrazine, formic acid, and 5-bromouracil.

Various conditions for the contact/reactions may be employed depending on the type of a drug to be used, and such conditions are not particularly limited where a desired mutation can be actually induced in an amadoriase gene. In general, the desired mutation can be induced by contact/reactions performed at 20° C. to 80° C. for 10 minutes or longer, and preferably 10 to 180 minutes, with the use of the aforementioned drug at the concentration of 0.5 M to 12 M. The ultraviolet irradiation may be also performed according to a conventional technique as described above (Gendai Kagaku, pp. 24-30, June, 1989).

As the method of making full use of the protein engineering technique, in general, a technique known as site-specific mutagenesis can be used. Examples include the Kramer method (Nucleic Acids Res., 12, 9441, 1984; Methods Enzymol., 154, 350, 1987; Gene, 37, 73, 1985), the Eckstein method (Nucleic Acids Res., 13, 8749, 1985; Nucleic Acids Res., 13, 8765, 1985; Nucleic Acids Res, 14, 9679, 1986), and the Kunkel method (Proc. Natl. Acid. Sci. U.S.A., 82, 488, 1985; Methods Enzymol., 154, 367, 1987).

A technique known as a general PCR technique can also be used (Technique, 1, 11, 1989). In addition to the conventional genetic mutation technique, by an organic synthesis method or synthetic method of an enzyme, the modified amadoriase genes of interest can be also directly synthesized.

The nucleotide sequences of DNAs encoding the amadoriase genes obtained by the aforementioned methods may be determined or verified by, for example, using a multi-capillary DNA analysis system, Applied Biosystems 3130x Genetic Analyzer (Life Technologies).

(Transformation/Transduction)

The amadoriase genes obtained as described above are integrated into a vector such as a bacteriophage vector, a cosmid vector, or a plasmid vector used in transformation of a prokaryotic or eukaryotic cell by a conventional technique, and a host corresponding to each vector can be transformed or transduced by a conventional technique. For example, a microorganism belonging to the genus *Escherichia*, such as the obtained recombinant DNA, is used as the host to transform a strain of *E. coli* K-12, and preferably a strain of *E. coli* JM109 or *E. coli* DH5a (manufactured by Takara Bio Inc.), or such microorganism is transduced into such strain. Thus, transformed or transduced strains of interest can be obtained.

(Amino Acid Sequence Homology, Identity, or Similarity)

The amino acid sequence homology, identity, or similarity can be calculated by a program such as maximum matching or search homology of GENETYX (manufactured by GENETYX), a program such as maximum matching or multiple alignment of DNASIS Pro (manufactured by Hitachi Solutions, Ltd.), or a program such as multiple alignment of CLUSTALW. In order to calculate amino acid sequence identity, two or more amadoriases may be aligned, and the positions of identical amino acids in such two or more amadoriases may be determined. The identical regions in amino acid sequences can be determined based on such information. The percent identity of two or more amino acid sequences is determined by subjecting two or more amino acid sequences to alignment using the algorithm such as Blosum62 by designating the total number of amino acids in the aligned region as the denominator and the number of identical amino acids relative to the total number as the numerator. If no identity is found in parts of the two or more amino acid sequences, for example, an amino acid sequence comprises at its C terminus an additional sequence in which no identity is observed, in general, such regions cannot be aligned. Accordingly, such regions are not used for calculation of the percent identity.

Also, positions of similar amino acids in two or more amadoriases can be inspected. For example, a plurality of amino acid sequences can be subjected to alignment with the use of CLUSTALW. In such a case, Blosum62 is used as the algorithm and a plurality of amino acid sequences are subjected to alignment. Amino acids determined to be similar as a result of alignment may be referred to as "similar amino acids." In the variant of the present invention, amino acid substitution can be carried out between such similar amino acids. Through such alignment, amino acid sequences composed of the identical amino acids or similar amino acids among a plurality of amino acid sequences can be simultaneously investigated. Based on such information, homologous regions (conserved regions) in the amino acid sequences can be determined.

The term "homologous region(s)" used herein refers to region(s) consisting of identical or similar amino acids at corresponding positions in the reference amadoriase and in the comparative amadoriase, when two or more amadoriases are aligned, wherein such region(s) consist(s) of 3 or more, 4 or more, 5 or more, 6 or more, 7 or more, 8 or more, 9 or more, or 10 or more continuous amino acids. For example, FIG. 1 shows the alignment of amadoriases exhibiting sequence identity of 74% or higher over the full-length amino acid sequences. In such sequences, the region of positions 10 to 32 with reference to the sequence of the amadoriase derived from *Coniochaeta* sp. as shown in SEQ ID NO: 1 consists of identical or similar amino acids, and such region falls under a homologous region. Similarly, regions of positions 36 to 41, 49 to 52, 54 to 58, 63 to 65, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 with reference to the sequence of the amadoriase derived from *Coniochaeta* sp. as shown in SEQ ID NO: 1 can be homologous regions.

Preferably, the homologous region of an amadoriase is the region consisting of amino acid sequences of positions 11 to 32, 36 to 41, 50 to 52, 54 to 58, 84 to 86, 88 to 90, 145 to 150, 157 to 168, 202 to 205, 207 to 212, 215 to 225, 236 to 248, 258 to 261, 266 to 268, 270 to 273, 275 to 287, 347 to 354, 357 to 363, 370 to 383, 385 to 387, and 405 to 410 with reference to the sequence of the amadoriase derived from *Coniochaeta* sp. as shown in SEQ ID NO: 1.

More preferably, the homologous region of an amadoriase is the region consisting of amino acid sequences of positions 11 to 18, 20 to 32, 50 to 52, 54 to 58, 266 to 268, 270 to 273, 277 to 286, and 370 to 383 with reference to the sequence of the amadoriase derived from *Coniochaeta* sp. as shown in SEQ ID NO: 1.

When the full-length amino acid sequence of the amadoriase variant of the present invention is aligned with that of the amadoriase comprising the amino acid sequence as shown in SEQ ID NO: 1 or 141, the sequence identity is 50% or higher, preferably 60% or higher, 70% or higher, 75% or higher, 80% or higher, or 85% or higher, more preferably 90% or higher or 95% or higher, and most preferably 99% or higher, and such amadoriase variant has high reactivity with α-fructosyl peptides such as αF6P and the like (αFV, AFVH, αF3P, αF4P, αF5P, αF6P, αF8P, and αF16P). In addition, the amino acid sequence of the homologous region of the amadoriase variant according to the present invention exhibits 80%, preferably 85% or higher, 90%, 95%, or 98%, and further preferably 99% or higher sequence identity with the amino acid sequence of the homologous region of SEQ ID NO: 1 or 141.

According to an embodiment, the homologous region of the amadoriase is the region consisting of amino acids at positions 10 to 32, 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 with reference to the amadoriase sequence as shown in SEQ ID NO: 141. Preferably, the homologous region of the amadoriase is the region consisting of amino acids at positions 11 to 32, 36 to 41, 50 to 52, 54 to 58, 84 to 86, 88 to 90, 145 to 150, 157 to 168, 202 to 205, 207 to 212, 215 to 225, 236 to 248, 258 to 261, 266 to 268, 270 to 273, 275 to 287, 347 to 354, 357 to 363, 370 to 383, 385 to 387, and 405 to 410, and more preferably the homologous region is the region consisting of amino acids at positions 11 to 18, 20 to 32, 50 to 52, 54 to 58, 266 to 268, 270 to 273, 277 to 286, and 370 to 383.

The amadoriase according to an embodiment of the present invention is (i) or (ii) below:

(i) an amadoriase comprising an amino acid sequence in which substitution, deletion, or addition of 1 or several amino acids has been carried out on the amino acid sequence as shown in SEQ ID NO: 141; or (ii) the amadoriase as defined in (i), wherein the amadoriase comprises an amino acid sequence having 70% or higher sequence identity with the amino acid sequence as shown in SEQ ID NO: 141 over the full length and having 90% or higher sequence identity between the amino acid sequence of a homologous region consisting of amino acids at positions 10 to 32, 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of SEQ ID NO: 141 and the amino acid sequence of the homologous region in corresponding positions of the amadoriase. According to one embodiment, the amadoriase of the present invention comprises an amino acid sequence exhibiting 95% or higher sequence identity between the amino acid sequence of the homologous region as defined in (ii) above and the amino acid sequence of the homologous region in corresponding positions of said amadoriase.

(Identifying a Position Corresponding to an Amino Acid Position)

When an amino acid at a particular position in the reference amino acid sequence corresponds to an amino acid at a particular position in another similar amino acid sequence, in the present invention, such amino acid is referred to as a corresponding amino acid, and the position of such amino acid is referred to as the corresponding position or equivalent position. A method of identifying the "position corresponding to an amino acid position" may be also performed by comparing amino acid sequences using a known algorithm such as a Lipman-Pearson method to assign maximum identity to conserved amino acid residues present in the amino acid sequence of each amadoriase. The positions of the homologous amino acid residues in each of the amadoriase sequences can be determined, regardless of insertion or deletion of amino acid residue(s) in the amino acid sequences by aligning the amino acid sequences of the amadoriases by such method. Homologous positions are considered to exist in the same positions in the three-dimensional structures, and amino acid residues at such homologous positions are expected to exert similar effects in terms of specificity of the amadoriase of interest.

In the present invention, the amino acid at "the position corresponding to arginine at position 62 in the amino acid sequence as shown in SEQ ID NO: 1" is the amino acid corresponding to arginine at position 62 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to arginine at position 62 in the amino acid sequence as shown in SEQ ID NO: 1" is arginine at position 62 in the case of the amadoriase derived from *Eupenicillium terrenum* (SEQ ID NOs: 40 and 145), the ketoamine oxidase derived from *Pyrenochaeta* sp. (SEQ ID NO: 113), the ketoamine oxidase derived from *Arthrinium* sp. (SEQ ID NO: 115), the ketoamine oxidase derived from *Curvularia clavata* (SEQ ID NO: 117), the ketoamine oxidase derived from *Neocosmospora vasinfecta* (SEQ ID NO: 54), the fructosyl amino acid oxidase derived from *Cryptococcus neoformans* (SEQ ID NOs: 89 and 149), the fructosyl amino acid oxidase derived from *Ulocladium* sp. (SEQ ID NO: 121), and the fructosyl amino acid oxidase derived from *Penicillium janthinellum* (SEQ ID NO: 123); it is serine at position 62 in the case of the fructosyl peptide oxidase derived from *Phaeosphaeria nodorum* (SEQ ID NO: 38); it is arginine at position 61 in the case of the fructosyl peptide oxidase derived from *Emericella nidulans* (SEQ ID NO: 119); and it is arginine at position 61 in the case of the fructosyl amino acid oxidase derived from *Aspergillus nidulans* (SEQ ID NOs: 62 and 147).

In the present invention, the amino acid at "the position corresponding to leucine at position 63 in the amino acid sequence as shown in SEQ ID NO: 1" is the amino acid corresponding to leucine at position 63 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to leucine at position 63 in the amino acid sequence as shown in SEQ ID NO: 1" is leucine at position 63 in the case of the amadoriase derived from *Eupenicillium terrenum* (SEQ 11) NOs: 40 and 145), the ketoamine oxidase derived from *Pyrenochaeta* sp. (SEQ ID NO: 113), the ketoamine oxidase derived from *Arthrinium* sp. (SEQ ID NO: 115), the ketoamine oxidase derived from *Curvularia clavata* (SEQ ID NO: 117), the ketoamine oxidase derived from *Neocosmospora vasinfecta* (SEQ ID NO: 54), the fructosyl peptide oxidase derived from *Phaeosphaeria nodorum* (SEQ ID NO: 38), the fructosyl amino acid oxidase derived from *Ulocladium* sp. (SEQ ID NO: 121), and the fructosyl amino acid oxidase derived from *Penicillium janthinellum* (SEQ ID NO: 123); it is isoleucine at position 63 in the case of the fructosyl amino acid oxidase derived from *Cryptococcus neoformans* (SEQ ID NOs: 89 and 149); and it is leucine at position 62 in the case of the fructosyl amino acid oxidase derived from *Aspergillus nidulans* (SEQ ID NOs: 62 and 147) and the fructosyl peptide oxidase derived from *Emericella nidulans* (SEQ ID NO: 119).

In the present invention, the amino acid at "the position corresponding to glutamic acid at position 102 in the amino acid sequence as shown in SEQ ID NO: 1" is the amino acid corresponding to glutamic acid at position 102 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to glutamic acid at position 102 in the amino acid sequence as shown in SEQ ID NO: 1" is glutamic acid at position 102 in the case of the amadoriase derived from *Eupenicillium terrenum* (SEQ ID NOs: 40 and 145), the ketoamine oxidase derived from *Curvularia clavata* (SEQ ID NO: 117), the ketoamine oxidase derived from *Neocosmospora vasinfecta* (SEQ ID NO: 54), the fructosyl amino acid oxidase derived from *Cryptococcus neoformans* (SEQ ID NOs: 89 and 149), and the fructosyl amino acid oxidase derived from *Penicillium janthinellum* (SEQ ID NO: 123); it is lysine at position 102 in the case of the ketoamine oxidase derived from *Pyrenochaeta* sp. (SEQ ID NO: 113), the ketoamine oxidase derived from *Arthrinium* sp. (SEQ ID NO: 115), the fructosyl peptide oxidase derived from *Phaeosphaeria nodorum* (SEQ ID NO: 38), and the fructosyl amino acid oxidase derived from *Ulocladium* sp. (SEQ ID NO: 121); and it is glutamic acid at position 101 in the case of the fructosyl peptide oxidase derived from *Emericella nidulans* (SEQ ID NO: 119) and the fructosyl amino acid oxidase derived from *Aspergillus nidulans* (SEQ ID NOs: 62 and 147).

In the present invention, the amino acid at "the position corresponding to aspartic acid at position 106 in the amino acid sequence as shown in SEQ ID NO: 1" is the amino acid corresponding to aspartic acid at position 106 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to aspartic acid at position 106 in the amino acid sequence as shown in SEQ ID NO: 1" is asparagine at position 106 in the case of the amadoriase derived from *Eupenicillium terrenum* (SEQ ID NOs: 40 and 145); it is aspartic acid at position 106 in the case of the ketoamine oxidase derived from *Pyrenochaeta* sp. (SEQ ID NO: 113), the ketoamine oxidase derived from *Curvularia clavata* (SEQ ID NO: 117), the fructosyl peptide oxidase derived from *Phaeosphaeria nodorum* (SEQ ID NO: 38), and the fructosyl amino acid oxidase derived from *Ulocladium* sp. (SEQ ID NO: 121); it is alanine at position 106 in the case of the ketoamine oxidase derived from *Arthrinium* sp. (SEQ ID NO: 115); it is glycine at position 106 in the case of the ketoamine oxidase derived from *Neocosmospora vasinfecta* (SEQ ID NO: 54); it is serine at position 106 in the case of the fructosyl amino acid oxidase derived from *Cryptococcus neoformans* (SEQ ID NOs: 89 and 149) and the fructosyl amino acid oxidase derived from *Penicillium janthinellum* (SEQ ID NO: 123); it is lysine at position 105 in the case of the fructosyl peptide oxidase derived from *Emericella nidulans* (SEQ ID NO: 119); and it is glycine at position 105 in the case of the fructosyl amino acid oxidase derived from *Aspergillus nidulans* (SEQ ID NOs: 62 and 147).

In the present invention, the amino acid at "the position corresponding to glutamine at position 110 in the amino acid sequence as shown in SEQ ID NO: 1" is the amino acid corresponding to glutamine at position 110 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to glutamine at position 110 in the amino acid sequence as shown in SEQ ID NO: 1" is lysine at position 110 in the case of the amadoriase derived from *Eupenicillium terrenum* (SEQ ID NOs: 40 and 145) and the fructosyl amino acid oxidase derived from *Penicillium janthinellum* (SEQ ID NO: 123); it is alanine at position 110 in the case of the ketoamine oxidase derived from *Pyrenochaeta* sp. (SEQ ID NO: 113), the ketoamine oxidase derived from *Curvularia clavata* (SEQ ID NO: 117), and the fructosyl amino acid oxidase derived from *Ulocladium* sp. (SEQ ID NO: 121); it is glutamine at position 110 in the case of the ketoamine oxidase derived from *Arthrinium* sp. (SEQ ID NO: 115); it is glutamic acid at position 110 in the case of the ketoamine oxidase derived from *Neocosmospora vasinfecta* (SEQ ID NO: 54); it is serine at position 110 in the case of the fructosyl amino acid oxidase derived from *Cryptococcus neoformans* (SEQ ID NOs: 89 and 149); it is glycine at position 110 in the case of the fructosyl peptide oxidase derived from *Phaeosphaeria nodorum* (SEQ ID NO: 38); it is arginine at position 109 in the case of the fructosyl peptide oxidase derived from *Emericella nidulans* (SEQ ID NO: 119); and it is lysine at position 109 in the case of the fructosyl amino acid oxidase derived from *Aspergillus nidulans* (SEQ ID NOs: 62 and 147).

In the present invention, the amino acid at "the position corresponding to alanine at position 113 in the amino acid sequence as shown in SEQ ID NO: 1" is the amino acid corresponding to alanine at position 113 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to alanine at position 113 in the amino acid sequence as shown in SEQ ID NO: 1" is threonine at position 113 in the case of the amadoriase derived from *Eupenicillium terrenum* (SEQ ID NOs: 40 and 145), the ketoamine oxidase derived from *Pyrenochaeta* sp. (SEQ ID NO: 113), and the ketoamine oxidase derived from *Arthrinium* sp. (SEQ ID NO: 115); it is alanine at position 113 in the case of the ketoamine oxidase derived from *Curvularia clavata* (SEQ ID NO: 117), the fructosyl amino acid oxidase derived from *Cryptococcus neoformans* (SEQ ID NOs: 89 and 149), the fructosyl peptide oxidase derived from *Phaeosphaeria nodorum* (SEQ ID NO: 38), and the fructosyl amino acid oxidase derived from *Ulocladium* sp. (SEQ ID NO: 121); it is lysine at position 113 in the case of the ketoamine oxidase derived from *Neocosmospora vasinfecta* (SEQ ID NO: 54); it is serine at position 112 in the case of the fructosyl amino acid oxidase derived from *Aspergillus nidulans* (SEQ ID NOs: 62 and 147) and the fructosyl peptide oxidase derived from *Emericella nidulans* (SEQ ID NO: 119); and it is aspartic acid at position 113 in the case of the fructosyl amino acid oxidase derived from *Penicillium janthinellum* (SEQ ID NO: 123).

In the present invention, the amino acid at "the position corresponding to alanine at position 355 in the amino acid sequence as shown in SEQ ID NO: 1" is the amino acid corresponding to alanine at position 355 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to alanine at position 355 in the amino acid sequence as shown in SEQ ID NO: 1" is alanine at position 355 in the case of the amadoriase derived from *Eupenicillium terrenum* (SEQ ID NOs: 40 and 145), the fructosyl amino acid oxidase derived from *Cryptococcus neoformans* (SEQ ID NOs: 89 and 149), the fructosyl amino acid oxidase derived from *Aspergillus nidulans* (SEQ ID NOs: 62 and 147), the fructosyl peptide oxidase derived from *Emericella nidulans* (SEQ ID NO: 119), and the fructosyl amino acid oxidase derived from *Penicillium janthinellum* (SEQ ID NO: 123); it is alanine at position 353 in the case of the ketoamine oxidase derived from *Pyrenochaeta* sp. (SEQ ID NO: 113), the ketoamine oxidase derived from *Curvularia clavata* (SEQ ID NO: 117), and the fructosyl amino acid oxidase derived from *Ulocladium* sp. (SEQ ID NO: 121); it is alanine at position 356 in the case of the ketoamine oxidase derived from *Arthrinium* sp. (SEQ ID NO: 115); it is serine at position 355 in the case of the ketoamine oxidase derived from *Neocosmospora vasinfecta* (SEQ ID NO: 54); and it is alanine at position 351 in the case of the fructosyl peptide oxidase derived from *Phaeosphaeria nodorum* (SEQ ID NO: 38).

In the present invention, the amino acid at "the position corresponding to alanine at position 419 in the amino acid sequence as shown in SEQ ID NO: 1" is the amino acid corresponding to alanine at position 419 in the amadoriase sequence as shown in SEQ ID NO: 1, when the identified amino acid sequence of the amadoriase is compared with the amino acid sequence of the amadoriase derived from the genus *Coniochaeta* as shown in SEQ ID NO: 1. Thus, the amino acid sequences can be aligned and identified by the aforementioned method of identifying "amino acid residues at corresponding positions."

Specifically, the amino acid at "the position corresponding to alanine at position 419 in the amino acid sequence as shown in SEQ ID NO: 1" is glycine at position 419 in the case of the amadoriase derived from *Eupenicillium terrenum* (SEQ ID NOs: 40 and 145); it is alanine at position 418 in the case of the ketoamine oxidase derived from *Pyrenochaeta* sp. (SEQ ID NO: 113), the ketoamine oxidase derived from *Curvularia clavata* (SEQ ID NO: 117), and the fructosyl amino acid oxidase derived from *Ulocladium* sp. (SEQ ID NO: 121); it is alanine at position 421 in the case of the ketoamine oxidase derived from *Arthrinium* sp. (SEQ ID NO: 115); it is alanine at position 420 in the case of the ketoamine oxidase derived from *Neocosmospora vasinfecta* (SEQ ID NO: 54), the fructosyl amino acid oxidase derived from *Cryptococcus neoformans* (SEQ ID NOs: 89 and 149), and the fructosyl peptide oxidase derived from *Emericella nidulans* (SEQ ID NO: 119); it is serine at position 416 in the case of the fructosyl peptide oxidase derived from *Phaeosphaeria nodorum* (SEQ ID NO: 38); it is serine at position 419 in the case of the fructosyl amino acid oxidase derived from *Penicillium janthinellum* (SEQ ID NO: 123); and it is alanine at position 420 in the case of the fructosyl amino acid oxidase derived from *Aspergillus nidulans* (SEQ ID NOs: 62 and 147).

(Synergistic Effects of Substitution)

The amadoriase variant of the present invention may be a single variant or a multiple variant comprising two or more amino acid substitutions, such as double to octuple variants. The present inventors discovered that an amadoriase comprising an amino acid sequence having amino acid substitutions at positions corresponding to positions 62, 63, 102, 106, 110, 113, 355, and 419 in the amino acid sequence as shown in SEQ ID NO: 1 has enhanced activity on αF6P. In particular, as the number of included substitutions increased from 1 to 7, the activity of the resulting mutant (i.e., a single, double, triple, quadruple, quintuple, sextuple, or septuple mutant) on αF6P was found to be enhanced significantly. From the enhancement of activities of the amadoriase variants on αF6P demonstrated in the examples, it is apparent that such amino acid substitutions yield synergistic effects. A person skilled in the art will appreciate that various combinations of amino acid substitutions at positions corresponding to positions 62, 63, 102, 106, 110, 113, 355, and 419 in the amino acid sequence as shown in SEQ ID NO: 1 will also enhance activity on αF6P.

In addition, the present inventors discovered that an amadoriase comprising an amino acid sequence having amino acid substitutions at positions corresponding to positions 62, 63, 102, 106, 110, 113, and 355 in the amino acid sequence as shown in SEQ ID NO: 1 exhibits activity not only on αFV and αFVH, but also on αF3P, αF4P, αF5P, αF6P, αF8P, and αF16P. Thus, variants derived from other strains, such as Co, Et, Py, Ar, Cc, Nv, Cn, Pn, An, En, Ul, and Pj, comprising amino acid sequences having similar substitution of amino acids at positions corresponding to positions 62, 63, 102, 106, 110, 113, and 355 in the amino acid sequence as shown in SEQ ID NO: 1 are also considered to exhibit activity not only on αFV and αFVH but also on αF3P, αF4P, αF5P, αF6P, αF8P, and αF16P. Further, since an amadoriase comprising an amino acid sequence having amino acid substitutions at positions corresponding to positions 62, 63, 102, 106, 110, 113, and 355 in the amino acid sequence as shown in SEQ ID NO: 1 exhibits activity on αFV, αFVH, αF3P, αF4P, αF5P, αF6P, αF8P, and αF16P, such amadoriase is considered to exhibit activity on various α-fructosyl peptides (e.g., αF1P to αF16P and αF1P to αF32P).

(Auxiliary Substitution)

It has been reported that when the amino acid at the position corresponding to position 60 in the amino acid sequence as shown in SEQ ID NO: 1 is serine, substituting the same with glycine renders the amadoriase which did not exhibit activity on αFVH prior to substitution to exhibit activity on αFVH post substitution (see JP 2010-35469 A and WO 2012/018094). Therefore, when an amadoriase used in the present invention comprises serine at the position corresponding to position 60 in the amadoriase sequence as shown in SEQ ID NO: 1, accordingly, such serine may be substituted with glycine in advance. Alternatively, a wild-type amadoriase comprising a sequence in which the amino acid at the position corresponding to position 60 in the sequence as shown in SEQ ID NO: 1 is glycine may be used to introduce mutations into positions corresponding to positions 62, 63, 102, 106, 110, 113, 355, and 419 in SEQ ID NO: 1. Unless otherwise specified, an amadoriase comprising a sequence in which the amino acid at the position corresponding to position 60 in the sequence as shown in SEQ ID NO: 1 is glycine is encompassed within the scope of the amadoriase variant of the present invention. In the case of the amadoriase derived from *Aspergillus nidulans*, for example, the amino acid at position 59 in SEQ ID NO: 147 that corresponds to position 60 in SEQ ID NO: 1 is serine in the wild-type amadoriase. An amadoriase having this serine substituted with glycine (i.e., SEQ ID NO: 62) may be used as a basis amadoriase to obtain a variant of the present invention. The same applies to the amadoriase from *Penicillium janthinellum* (Pj) (SEQ ID NO: 123).

(Production of the Amadoriase of the Present Invention)

In order to produce an amadoriase having improved substrate specificity using a strain having the ability to produce such amadoriase obtained as described above, the strain may be cultured by a conventional solid culture method, although liquid culture is preferable.

Specifically, the present invention provides a method for producing an amadoriase comprising a step of culturing a strain capable of producing an amadoriase with improved substrate specificity under conditions where the amadoriase protein can be expressed and a step of isolating an amadoriase from a culture product or culture solution. In such method, a host cell transformed with a vector comprising a gene encoding the amadoriase of the present invention can be used. Here the phrase "under conditions where the amadoriase protein can be expressed" means an amadoriase gene is transcribed, translation is carried out, and the polypeptide encoded by such gene is produced.

Examples of media to culture the aforementioned strains include media prepared by adding one or more inorganic salts, such as sodium chloride, monopotassium phosphate, dipotassium phosphate, magnesium sulfate, magnesium chloride, ferric chloride, ferric sulfate, and manganese sulfate, to one or more nitrogen sources, such as a yeast extract, tryptone, peptone, a meat extract, a corn steep liquor, and a leaching solution of soybean or wheat bran, and further adding saccharine materials, vitamins, and the like thereto, where necessary.

Further, a substrate with which the amadoriase can react or a compound similar thereto, such as a glycated protein, including a glycated amino acid, a glycated peptide, a degradation product of glycated protein, glycated hemoglobin, or glycated albumin, may be added to the media, so as to increase the production amount of the enzyme of interest.

It is appropriate to adjust the initial pH of the media to 7 to 9. Culture is preferably performed at 20° C. to 42° C., and more preferably at about 25° C. to 37° C. for 4 to 24 hours, and further preferably at about 25° C. to 37° C. for 8 to 16 hours, by, for example, aeration spinner submerged culture, shake culture, or stationary culture.

Following the completion of culture, amadoriases may be collected from the culture products with conventional enzyme collecting means. For example, a strain may be subjected to ultrasonic disintegration treatment or grinding treatment by a conventional method, the enzyme may be extracted using a lytic enzyme such as lysozyme, or bacteriolysis may be performed via shaking or still standing in the presence of toluene to excrete the enzyme from the microorganism body. The solution is filtered or centrifuged to remove solid content, and nucleic acid is removed with the aid of streptomycin sulfate, protamine sulfate, or manganese sulfate, according to need. Ammonium sulfate, alcohol, or acetone is added to the solution, so as to fractionate the solution, and sediments are then collected to obtain the crude enzymes of the amadoriases.

The purified amadoriase enzyme preparation can be obtained from: the crude enzyme of the aforementioned amadoriase by a method appropriately selected from gel filtration methods using Sephadex, Superdex, or Ultrogel; adsorption-elution methods using ion exchange carriers, hydrophobic carriers, or hydroxyapatite; electrophoretic methods using polyacrylamide gels, etc.; sedimentation methods such as sucrose density-gradient centrifugation; affinity chromatography methods; and fractionation methods using a molecular sieve membrane, a hollow-fiber membrane, etc. Alternatively, the aforementioned methods can adequately be performed in combination. Thus, the amadoriase of interest can be obtained.

(Enhancement of Reactivity of the Amadoriase of the Present Invention)

The amadoriase of the present invention obtained by the means described above is characterized by having improved reactivity with α-fructosyl oligopeptides (αF3P to αF16P) or α-fructosyl peptides such as αF6P and the like (αFV, αFVH, αF3P, αF4P, αF5P, αF6P, αF8P, and αF16P), compared with that of amadoriases before modification, as a result of mutations in the amino acid sequence via genetic modification or other means. If the amadoriase has "improved reactivity" with an α-fructosyl oligopeptide or an α-fructosyl peptide such as αF6P and the like in the present invention, this specifically refers to the amadoriase having improved "reactivity with an α-fructosyl oligopeptide" or "reactivity with an α-fructosyl peptide such as αF6P and the like", compared with such reactivity before modification. The "reactivity with αFVH" may also be referred to as "αFVH oxidation activity" or "αFVH activity." The same applies to αFV or the like.

In order to reduce the amount of proteases applied, perform measurement of HbA1c without the need of using a protease which exhibits high cleavage specificity, or perform quantification of HbA1c without complete degradation into αFVH by a protease, it is necessary to obtain an amadoriase that is capable of reacting readily not only with αFVH but also with α-fructosyl peptides, such as αF3P, αF4P, αF5P, αF6P, αF8P, and αF16P.

The ratio of reactivity of the amadoriase of the present invention with αF6P relative to reactivity with αFVH designated to be 1 is indicated as "αF6P/αFVH." The same applies to αF3P/αFVH, αF4P/αFVH, αF5P/αFVH, αF8P/αFVH, and αF16P/αFVH. The same also applies to other α-fructosyl oligopeptides.

The ratio of reactivity of the amadoriase of the present invention with αF6P relative to reactivity with αFV designated to be 1 is indicated as "αF6P/αFV." The "reactivity with αFV" is also referred to as "αFV oxidation activity." The same applies to αF3P/αFV, αF4P/αFV, αF5P/αFV, αF8P/αFV, and αF16P/αFV. The same also applies to other α-fructosyl oligopeptides.

The ratio of reactivity with αF6P relative to reactivity with αFVH (i.e., the ratio of the reactivity with αF6P to the reactivity with αFVH) can be determined by measurement conducted under any conditions in accordance with a conventional assay technique for amadoriase, and the measured value can be compared with the value prior to modification. For example, the activity measured with the addition of 1 mM αF6P at pH 6.5 can be divided by the activity measured with the addition of 1 mM αFVH, so as determine the ratio of the reactivity with αF6P relative to the reactivity with αFVH designated to be 1. The determined ratio before modification can be compared with that after modification. Also, the activity measured with the addition of 1 mM αF6P at pH 6.5 may be divided by the activity measured with the addition of 1 mM αFV, so as to determine the ratio of the reactivity with αF6P relative to the reactivity with αFV designated to be 1, and the determined ratio before modification can be compared with that after modification. The same applies to αF3P/αFVH to αF16P/αFVH and αF3P/αFV to αF16P/αFV.

The specific activity of the amadoriase according to an embodiment of the present invention on αFV (U/mg) is 1.0 or greater, 5.0 or greater, or 10 or greater, and, for example, 13 or greater. The specific activity of the amadoriase according to an embodiment of the present invention on αFVH (U/mg) is 1.0 or greater or 1.5 or greater, and, for example, 1.90 or greater. The specific activity of the amadoriase according to an embodiment of the present invention on αF3P (U/mg) is 1.0 or greater, and for example, 1.20 or greater. The specific activity of the amadoriase according to an embodiment of the present invention on αF4P (U/mg) is 1.0 or greater, 0.2 or greater, or 0.3 or greater and, for example, 0.35 or greater. The specific activity of the amadoriase according to an embodiment of the present invention on αF5P (U/mg) is 1.0 or greater or 2.0 or greater and, for example, 2.10 or greater. The specific activity of the amadoriase according to an embodiment of the present invention on αF6P (U/mg) is 1.0 or greater, 2.0 or greater, 3.0 or greater, or 4.0 or greater and, for example, 4.2 or greater. The specific activity of the amadoriase according to an embodiment of the present invention on αF8P (U/mg) is 1.0 or greater and, for example, 1.5 or greater. The specific activity of the amadoriase according to an embodiment of the present invention on αF16P (U/mg) is 1.0 or greater or 0.2 or greater and, for example, 0.24 or greater.

An example of the amadoriase of the present invention is an amadoriase produced by a strain of *E. coli* JM109 (pKK223-3-CFP-T7-H35). Such amadoriase not only reacts with αFV and αFVH, but also the reactivity of such amadoriase with αF3P, αF4P, αF5P, αF6P, αF8P, and αF16P is improved in comparison with that before modification. Such modified amadoriase enables quantification of HbA1c, without the need to use a protease which exhibits high cleavage specificity, such as a Glu-C protease, by measuring the amount of α-fructosyl oligopeptides or α-fructosyl peptides such as αF6P and the like, generated upon treatment of HbA1c with a protease which exhibits low cleavage specificity and generates α-fructosyl oligopeptides of various lengths. That is, a wide variety of proteases can now be used for quantification of HbA1c, which is very useful at the industrial level. With the use of a protease with low cleavage specificity but high cleavage efficiency, and even if HbA1c is not completely degraded down to αFVH, such amadoriase (CFP-T7-H35) is capable of reacting not only with αFV and αFVH but also with α-fructosyl peptides (αF3P to αF16P) and, therefore, HbA1c can be quantified with high accuracy. In such a case, the amount of proteases to be used can be reduced, and unfavorable reactions caused by proteases with other protein reagents can be avoided.

(Method of Measuring Activity of Amadoriase)

The activity of an amadoriase can be measured by various methods. An example of the method of measuring the activity of an amadoriase as used herein is described below.

Examples of major methods for measuring the enzyme activity of the amadoriase of the present invention include a method of measuring the amount of hydrogen peroxide generated by enzyme reactions and a method of measuring the amount of oxygen consumed in enzyme reactions. An example of the method of measuring the amount of hydrogen peroxide is described below.

For measurement of the activity of the amadoriase of the present invention, αFV, αFVH, αF3P, αF4P, αF5P, αF6P, αF8P, or αF16P is used as the substrate unless otherwise specified. Regarding the enzyme titer, the amount of enzyme used to generate 1 μmol of hydrogen peroxide per minute is defined as 1 U, when measurement is carried out using αFV, αFVH, αF3P, αF4P, αF5P, αF6P, αF8P, or αF16P as a substrate. αF7P, αF9P to αF15P, and αF17P to αF32P can also be used for measurement of activity and the amount of the enzyme (U) is defined in the same manner.

Specific activity (U/mg) is the enzyme titer (U) per mg of enzyme.

As for glycated peptides such as αFV or αFVH, these may be synthesized and purified with reference to the method of, for example, Sakaue et al. (JP 2001-95598 A). αF3P, αF4P, αF5P, αF6P, αF8P, and αF16P, which are provided as synthesized substrates (manufactured by Peptide Institute, Inc.), can also be used. αF7P, αF9P to αF15P, and αF17P to αF32P can also be prepared by obtaining synthesized substrates or via other means.

A: Preparation of Reagents (Preparation Example of Reagent Used for Measuring Activity of Amadoriase)

(Reagent 1) 0.1 M Phosphate Buffer (pH 6.5) Containing 5 U/ml Peroxidase and 0.49 mM 4-Aminoantipyrine Peroxidase (5.0 kU, manufactured by Kikkoman Corporation) and 100 mg of 4-aminoantipyrine (manufactured by Wako Pure Chemical Industries, Ltd.) are dissolved in a 0.1 M potassium phosphate buffer (pH 6.5), and the volume of the solution is fixed to 1,000 ml.

(Reagent 2) 15 mM TOOS Solution 500 mg of TOOS (N-ethyl-N-(2-hydroxy-3-sulfopropyl)-m-toluidine sodium, manufactured by Dojindo Laboratories) is dissolved in ion-exchange water, and the volume of the solution is fixed to 100 ml.

(Reagent 3) Substrate Solution (30 mM; Final Concentration: 1 mM)

αFV (83.8 mg, manufactured by Kikkoman Corporation), αFVH (125 mg, manufactured by Kikkoman Corporation), αF3P (159 mg, manufactured by Peptide Institute, Inc.), αF4P (189 mg, manufactured by Peptide Institute, Inc.), αF5P (218 mg, manufactured by Peptide Institute, Inc.), αF6P (257 mg, manufactured by Peptide Institute, Inc.), αF8P (334 mg, manufactured by Peptide Institute, Inc.), or αF16P (570 mg, manufactured by Peptide Institute, Inc.) is dissolved in ion-exchange water, and the volume of the solution is fixed to 10 ml. αF7P, αF9P to αF15P, and αF17P to αF32P may also be prepared by obtaining synthetic substrates or via other means, and the resultants may be included in Reagent 3.

B: Method for Measurement of Activity (Example of Method for Measurement of Activity of Amadoriase)

Reagent 1 (2.7 ml), 100 μl of Reagent 2, and 100 μl of an enzyme solution are mixed, and the mixture is preliminarily heated at 37° C. for 5 minutes. Subsequently, 100 μl of Reagent 3 is added, the resultant is thoroughly mixed, and the absorbance at 555 nm is then measured using a spectrophotometer (U-3010A, manufactured by Hitachi High-Technologies) with the elapse of time to determine the change in absorbance per minute (ΔAs) at 555 nm. A control solution is prepared in the manner as described above, except that 100 μl of ion-exchange water is added instead of 100 μl of Reagent 3, and the change in absorbance per minute (ΔA0) at 555 nm thereof is determined. The number of micromoles of hydrogen peroxide generated per minute at 37° C. is calculated using the equation shown below in terms of the unit of activity (U) in the enzyme solution.

$$\text{Activity (U/ml)}=\{(\Delta As-\Delta A0)\times 3.0\times df\}/(39.2\times 0.5\times 0.1)$$

ΔAs: the change in absorbance of the reaction solution per minute

ΔA0: the change in absorbance of the control solution per minute 39.2: millimole absorbance index of quinoncimine dye generated by the reaction ($mM^{-1}\cdot cm^{-1}$)

0.5: number of moles of quinoneimine dye generated by 1 mol of hydrogen peroxide df: dilution factor (Preparation of Sample for Measurement Containing α-Fructosyl Oligopeptide)

According to the method of measurement of an embodiment of the present invention, an amadoriase (α-fructosyl peptide oxidase) is allowed to react with a sample containing α-fructosyl oligopeptide derived from a glycated protein, and the amount of substance produced or consumed by the reaction is measured. An example of a preferable method for cleaving α-fructosyl oligopeptide from a target glycated protein for the purpose of measurement of a glycated protein, such as HbA1c, is digestion with the use of a protease or peptidase. Any protease or peptidase can be used, provided that it can be used for clinical testing and it can effectively cleave one or more α-fructosyl oligopeptides (αFV to αF145P) from the HbA1c β chain (146 amino acid residues, SEQ ID NO: 193). Examples of proteases or peptidases that can cleave one or more α-fructosyl oligopeptides (αFVH to αF145P) from the HbA1c β chain include, but are not limited to, endoproteinase Glu-C, V8 protease, proteinase K, proteinase P, pronase, thermolysin, subtilisin, carboxy peptidase, chymotrypsin, Dispase, papain, ficin, bromelin, and aminopeptidase, various proteases shown in Table 1 of JP 2005-110657 A, such as IP enzyme (Kikkoman Corporation), AO protease (Kikkoman Corporation), Peptidase (Kikkoman Corporation), Protease A5 (Kyowa Kasei Co., Ltd.), Umamizyme (Amano Enzyme), Protease A (Amano Enzyme), Protease M (Amano Enzyme), Protease P (Amano Enzyme), Sumizyme MP (Shinnihon Chemicals Corporation), Sumizyme LP-20 (Shinnihon Chemicals Corporation), and Proteinase 6 (Fluka) derived from *Aspergillus*; Peptidase R derived from *Rhizopus* (Amano Enzyme); Dispase (Roche), Proteinase N (Fluka), Proteinase Type VII (Sigma), Proteinase Bacterial Subtilisin (Fluka), Protease N (Amano Enzyme), Protease S (Amano Enzyme), Proteinase Type X (Sigma), Thermolysin (Daiwa Kasei), Pronase E (Kaken Kagaku), and Neutral protease (TOYOBO CO., LTD.) derived from *Bacillus*; Pronase (Boehringer), Proteinase Type XIV (Sigma), and alkaline protease (TOYOBO CO., LTD.) derived from *Streptomyces*; Proteinase K (Roche) and Proteinase K (Wako) derived from *Tritirachium*; Papain (Roche), Papain (Wako), Papain (Sigma), Papain W40 (Amano Enzyme), and Papain (Asahi) derived from *Carica papaya*; Ficin (Sigma) derived from *Ficus carica*; Pancreatin (Wako) derived from porcine pancreas; and Cathepsin B (Sigma) derived from bovine pancreas. Further, two or more types of proteases may be adequately used in combination.

A sample can be treated with a protease or peptidase under any conditions, provided that the protease acts on the target glycated protein and efficiently releases an α-glycated hexapeptide within a short period of time. The amount of protease used is adequately determined in accordance with the HbA1c content in the sample, treatment conditions, or other factors. For example, a protease is added to a final concentration of 0.1 to 50 U/ml, and preferably 1 to 10 U/ml. If necessary, other appropriate proteases may further be added. At the time of treatment with a protease, the pH level need not be adjusted or alternatively, the pH level may be adjusted as 2 to 9, and preferably 3 to 8, so as to be preferable for the protease being used, with the aid of, for example, an adequate pH adjuster, such as hydrochloric acid, acetic acid, sulfuric acid, sodium hydroxide, or potassium hydroxide. Treatment may be carried out at, for example, 20° C. to 50° C., and treatment may be carried out at higher temperature, such as 45° C. to 70° C., in accordance with the enzyme to be used. The duration of treatment is not particularly limited, provided that HbA1c is sufficiently degraded. For example, treatment period may be 5 seconds to 180 minutes, preferably 1 to 60 minutes, and further preferably 1 to 10 minutes. The resulting treated solution can be subjected to a reaction for glycated hexapeptide oxidase per se without treatment or, alternatively, the solution may be subjected to heating, centrifugation, concentration, dilution, or other processing, according to need, and the resultant can then be subjected to the reaction as the sample containing α-fructosyl oligopeptide.

(Measurement of Released α-Fructosyl Peptide)

The amadoriase (α-fructosyl peptide oxidase) used in the method of measurement according to the present invention is allowed to react with the sample containing α-fructosyl peptide. Cleavage of α-fructosyl oligopeptide and the reaction with α-fructosyl peptide oxidase may be carried out continuously or simultaneously. Alternatively, cleavage of α-fructosyl oligopeptide may be followed by the reaction with α-fructosyl peptide oxidase. The duration of the reaction between α-fructosyl peptide and α-fructosyl peptide oxidase may be, for example, 5 seconds or longer, 10 seconds or longer, or 20 seconds or longer, shorter than 180 minutes or shorter than 150 minutes. More specifically, the duration may be, for example, 0.5 to 120 minutes, preferably 0.5 to 60 minutes, and more preferably 1 to 30 minutes. If the duration of the reaction is too short, glycated hexapeptide in the sample cannot be sufficiently measured and proper measurement cannot be carried out. If, on the other hand, the duration of the reaction is too long, the duration of measurement will be prolonged, and measurement efficiency will become poor. In addition thereto, the sample and the reagent will be exposed to the measurement conditions for a long period of time, and this disadvantageously causes problems such as degradation or denaturation of the substrate in the sample or components of the reagent. In addition thereto, the sample and the reagent will be exposed to the measurement conditions for a long period of time, and this disadvantageously causes problems such as degradation or denaturation of the substrate in the sample or components of the reagent. In the case of a microassay system, in particular, the sample may be dehydrated with the elapse of time, which leads to a decrease in the volume of the sample and a change in the concentration thereof. This may cause an error in the measurement. α-fructosyl peptide oxidase may be allowed to react with the sample for preferably 0.5 to 60 minutes, more preferably 1 to 30 minutes, and further preferably 1 to 10 minutes, so that α-fructosyl peptide can be rapidly and sufficiently measured. While the reaction temperature varies depending on the optimal temperature for the enzyme to be used, it may be, for example, 20° C. to 45° C., and a temperature that is generally employed for an enzymatic reaction can be adequately selected.

A preferable amount of the amadoriase (α-fructosyl peptide oxidase) to use in the present invention varies depending on the amount of α-fructosyl peptide(s) contained in the sample solution. For example, the amadoriase (α-fructosyl peptide oxidase) may be added, so as to adjust the final concentration thereof to 0.1 to 50 U/ml, and preferably 0.2 to 10 U/ml in the solution. The pH level is preferably adjusted to an adequate level for the reaction with the use of a buffer by taking the optimal pH level for α-fructosyl peptide oxidase into consideration, although the pH level is not particularly limited, provided that α-fructosyl peptide oxidase is capable of reacting. For example, the pH is preferably 3 to 11, and particularly preferably 5 to 9, such as 6 to 8.

In the method of measurement according to the present invention, it is preferable to use various types of buffers, according to need, in order to adjust and/or maintain the pH level for the purpose of stabilization of an enzyme or a reagent or improvement in reactivity. Examples of buffers that can be used include N-[tris(hydroxymethyl)methyl]glycine, phosphate, acetate, carbonate, tris(hydroxymethyl)-aminomethane, borate, citrate, dimethyl glutamate, Tricine, HEPES, MES, Bis-Tris, ADA, PIPES, ACES, MOPSO, BES, MOPS, TES, DIPSO, TAPSO, POPSO, HEPPSO, EPPS, Tricine, Bicine, TAPS, phthalate, and tartrate. In addition, solubilizers, stabilizers, reaction-improving agents, or the like, such as surfactants (e.g., n-octyl-β-D-glucoside, n-octyl-β-D-thioglucoside, n-dodecyl-β-D-maltoside, n-tetradecyl-β-D-maltoside, n-octyl-β-D-maltoside, 1-dodecylpyridinium salt, hexadecyltrimethylammonium salt, tetradecyltrimethylammonium salt, dodecyltrimethylammonium salt, triton X-100, Brij 35. Tween 80, cholate, n-heptyl-β-D-thioglucoside, 3-oxatridecyl-α-D-mannoside, n-nonyl-β-D-thiomaltoside, n-decyl-β-D-maltoside, n-undecyl-β-D-maltoside, trehalose C8, trehalose C10, trehalose C12, trehalose C14, trehalose C16, BIGCHAP, deoxy-BIGCHAP, MEGA-8, MEGA-9, MEGA-10, hexadecylpyridinium salt, octadecyltrimethylammonium salt, decyltrimethylammonium salt, nonyltrimethylammonium salt, octyltrimethylammonium salt, hexyltrimethylammonium salt, or sodium dodecyl sulfate), reducing agents (e.g., dithiothreitol, mercaptoethanol, or L-cysteine), bovine serum albumin, or saccharides (e.g., glycerine, lactose, or sucrose), may be adequately added, according to need.

An embodiment of the present invention provides a method for measurement of α-fructosyl peptides (αF1P to αF32P, such as αF1P to αF16P) by measuring the amount of substances generated or consumed by the action of the amadoriase (α-fructosyl peptide oxidase). An example of a product that can readily be measured and is preferable as the target of measurement is hydrogen peroxide. Hydrogen peroxide generated by the action of α-fructosyl peptide oxidase may be detected with the use of a color substrate or the like. Examples of color substrates used in the present invention include, in addition to 4-aminoantipyrine, ADOS (N-ethyl-N-(2-hydroxy-3-sulfopropyl)-m-anisidine), ALOS (N-ethyl-N-(2-hydroxy-3-sulfopropyl)aniline), TOOS (N-ethyl-N-(2-hydroxy-3-sulfopropyl)-m-toluidine sodium), DA-67 (10-(carboxymethylaminocarbonyl)-3,7-bis(dimethylamino)-phenothiazine), and DA-64 (N-(carboxymethylaminocarbonyl)-4,4'-bis(dimethylamino)-diphenylamine). ADOS, ALOS, and TOOS develop color upon condensation with 4-aminoantipyrine. DA-64 and DA-67 are each able to develop color alone without 4-aminoantipyrine. Such color development is catalyzed by peroxidase in each case. In general, it is preferable that measurement of hydrogen peroxide be carried out simultaneously with the step of generating hydrogen peroxide, and it is preferable that measurement be allowed to proceed simultaneously with the reaction with α-fructosyl peptide oxidase. An example of the substance consumed by the reaction to be measured is dissolved oxygen, and the amount of dissolved oxygen in the reaction solution can be measured with the use of a dissolved oxygen meter or the like.

The present invention provides reagents for measurement of HbA1c including the measurement reagents amadoriase (α-fructosyl peptide oxidase) and hydrogen peroxide as described above and further supplemented with a buffer or the like, according to need. Such reagent can be adequately supplemented with various known components, such as a surfactant, a salt, a buffer, a pH adjuster, or a preservative. The reagent for measurement according to the present invention may be prepared to separately contain various reagents in different containers. For example, it can be provided in the form of a liquid product, a frozen product of a liquid, or a freeze-dried product. Alternatively, such reagent(s) for measurement may be used in a dried or dissolved state, or may be used by impregnating the same in a carrier on a thin film, such as an impregnatable paper and the like. Enzymes used for the reagent for measurement can be solidified and repeatedly used in accordance with a conventional technique. The reagent for measurement according to the present invention can constitute a part of a reagent kit comprising a protease used for cleaving α-fructosyl peptide from a glycated protein.

The optimal specification or conditions for the use of the reagent for measurement according to the present invention may be selected in accordance with the components thereof or other properties. For example, the reagent can be prepared to be used for measurement conducted at 20° C. to 45° C. The time necessary for measurement can be adequately determined in accordance with various measurement conditions. For example, it is 0.5 to 60 minutes, preferably 0.5 to 30 minutes, and further preferably 1 to 10 minutes. For example, an extent of the reagent colored (i.e., a change in the absorbance) may be measured using a spectrophotometer, and the measured absorbance may be compared with the reference absorbance. Thus, the glycated peptide or glycated protein contained in the sample can be measured. Measurement can be carried out with the use of a common automated analyzer.

(Quantification of HbA1c)

The method for measurement of HbA1c according to the present invention may be a qualitative or quantitative method. The quantitative method for measurement of HbA1c of the present invention refers to a method in which concentration of HbA1c in the sample is determined. That is, an aspect of the present invention provides a method for quantifying HbA1c in a sample involving the use of an amadoriase variant. This quantitative method comprises a step of bringing a sample containing HbA1c-derived α-fructosyl peptide into contact with the amadoriase of the present invention and a step of measuring the amount of substances produced or consumed by the reaction of the amadoriase with the HbA1c-derived α-fructosyl peptide. The "contact" that is carried out in accordance with the quantitative method can be any form of physical contact between the amadoriase of the present invention and a sample, so that the amadoriase can catalyze the oxidation reaction of α-fructosyl peptide. In addition to the case in which a free enzyme is mixed with α-fructosyl peptide in a solution, for example, a liquid sample containing α-fructosyl peptide can be added or added dropwise to the amadoriase of the present invention immobilized to a solid support. This quantitative method also comprises a step of treating HbA1c with an adequate protease, so as to prepare an α-fructosyl peptide. A protease may have a high or low degree of cleavage specificity.

A sample used for the method for measurement of HbA1c of the present invention can be any type of biological sample that can contain glycated hemoglobin, such as a sample derived from blood, body fluid, or lymph. A sample can adequately be a processed sample.

While maintaining the amount of the amadoriase variant used and the duration of the reaction at constant levels and altering the amount of added HbA1c, and by investigating the range of HbA1c concentration in which the absorbance of the detected luminescent substrate proportionally decreases as the amount of HbA1c added is decreased, it is possible to determine the lowest HbA1c concentration that can be detected with the use of the amadoriase. Such concentration is also referred to as the "detectable limit concentration" herein. According to the method for quantification of HbA1c of the present invention, it is preferable to design the amount of the enzyme and the duration of reaction so that the detectable limit concentration of HbA1c is adjusted to a level lower than the concentration of α-fructosyl peptide (e.g., aαF6P) in the sample or the glycated hemoglobin level in the blood.

According to the quantitative method of measurement of HbA1c of the present invention, a calibration curve can be prepared in advance by performing regression analysis such as the method of least squares based on the measured absorbance of the control sample containing HbA1c or α-fructosyl peptide such as αF6P and the like at a known concentration. The measured value of the sample containing an unknown concentration of HbA1c or α-fructosyl peptide such as αF6P and the like may be plotted on the prepared calibration curve to quantify the concentration of HbA1c or an α-fructosyl peptide such as αF6P and the like in the sample.

The present inventors demonstrated that an amadoriase variant derived from *Coniochaeta*, such as Amadoriase 25 of the present invention (CFP-T7-H35) reacts not only with αFV and αFVH but also with αF3P, αF4P, αF5P, αF6P, αF8P, and αF16P. Based on such finding, it is thought that other amadoriase variants of the present invention exhibiting satisfactory activity with αF6P also exhibit activity not only with αFV and αFVH but also with α-fructosyl peptides (αFV to αF16P) of various chain lengths. With the use of such amadoriase exhibiting activity with α-fructosyl peptides (αFV to αF16P), a protease with low cleavage specificity can also be used for quantification of HbA1c. In addition, a person skilled in the art can adequately determine the amount of enzyme (the concentration of enzyme), the duration of reaction, and other conditions for quantitative assays.

In the past, methods for quantitative assays of HbA1c in which HbA1c is first cleaved with a protease to generate αFVH and an amadoriase that reacts with αFVH is then used have been developed (Patent Documents 1 to 7). However, the speed of the hydrolysis reaction by a protease depends on the substrate concentration and, therefore, if the majority of HbA1c is hydrolyzed, then the protease reaction speed decreases. As such, in conventional techniques of HbA1c assays, glycated peptides that are not hydrolyzed down to αFVH may remain. Since the amadoriase of the present invention exhibits activity on an α-fructosyl peptide such as αF6P and the like, not only αFV and αFVH but also α-fructosyl peptides of various chain lengths (αF3P to αF32P, such as αF3P to αF16P) derived from the HbA1c β chain remaining unhydrolyzed to αFVH can be simultaneously quantified with the use of the amadoriase of the present invention. Accordingly, the amount of applied proteases can be reduced, and sensitivity of HbA1c assays with the use of amadoriase can be enhanced.

In one embodiment, although the major component of the HbA1c-derived α-fructosyl peptides in the target sample being subjected to the quantitative assay of HbA1c of the present invention is αFVH, small quantities of α-fructosyl peptides of various chain lengths such as αF3P to αF32P (e.g., αF3P to αF16P) may also be present due to incomplete degradation to αFVH by the protease. Since the amadoriase of the present invention is capable of reacting with such α-fructosyl peptides of various chain lengths, it is possible to perform quantitative assay of HbA1c. In the present specification, the phrase "the major component is αFVH" refers to αFVH accounting for 50% or more, such as 60% or more, 70% or more, 80% or more, or 90% or more, of α-fructosyl peptides of various chain lengths.

In another embodiment, according to the quantitative assay of HbA1c of the present invention, the major components of α-fructosyl peptides in the target sample are αF3P to αF32P, such as αF3P to αF16P. Even for such samples, HbA1c in the sample can be quantified by combining the amadoriase of the present invention with a protease capable of cleaving HbA1c and specifically generating αF3P, αF4P, αF5P, αF8P, or αF16P from the HbA1c β chain N terminus from among various proteases capable of cleaving HbA1c. This is because the amadoriase of the present invention is capable of reacting with α-fructosyl peptides (αF3P to αF32P). Thus, the present invention enables a wider variety of samples to be subjected to HbA1c quantification and a wider variety protease to be applied to HbA1c quantification.

(Screening Method)

According to an embodiment, whether or not an amadoriase of interest reacts with α-fructosyl peptides (e.g., αF1P to αF32P, αF1P to αF64P, αF1P to αF128P, or αF1P to αF145P) can be determined by using the methods described above. Examples of candidate amadoriases include various naturally occurring amadoriases and amadoriases modified therefrom, such as amadoriases having αFV activity, amadoriases having αFVH activity, amadoriases having αF6P activity, amadoriases exhibiting activity on α-fructosyl peptide, and amadoriases modified therefrom (e.g., those described in the (Modified amadoriase) section above). Many candidates may be simultaneously subjected to screening with the use of a 96-well plate or the like, and high-throughput screening can be carried out rapidly. Whether or not a candidate amadoriase reacts with α-fructosyl peptides of adequate chain lengths (e.g., αF1P to αF32P) can be determined via screening. Alternatively, candidate amadoriases may be first subjected to primary selection, so as to determine whether or not they have αFV activity, αFVH activity, αF6P activity, or other activity, and those determined to have such activity may then be subjected to secondary selection, so as to determine whether or not they react with αF8P to αF32P. A crude enzyme extract prepared from a biological sample or a product purified therefrom can be subjected to screening. A gene of an amadoriase exhibiting activity on α-fructosyl peptide may be obtained in accordance with a conventional technique, an enzyme may be produced via genetic engineering, and the resulting enzyme may be used for selection. According to conventional techniques, an amadoriase exhibiting activity on α-fructosyl peptide can be purified, the amino acid sequence thereof can be determined, and primers for PCR can be designed based on the sequence information. Thus, a gene of interest can be obtained. Alternatively, a gene of interest can be obtained from the genomic library or cDNA library of an organism whose PCR primers have already been designed on the basis of the sequence information of a known amadoriase, although the method for obtaining a gene of interest is not limited thereto (see the (Obtaining a gene encoding an amadoriase) section above). An appropriate mutation may be introduced into the obtained amadoriase gene in accordance with a conventional genetic engineering technique, and whether or not the resulting variant reacts with target α-fructosyl peptides (e.g., αF1P to αF32P, αF1P to αF64P, αF1P to αF128P, or αF1P to αF145P) can be investigated. Also, an appropriate mutation may be introduced into the obtained amadoriase gene in accordance with a genetic engineering technique, so as to prepare an amadoriase variant exhibiting activity on long-chain α-fructosyl peptide, such as αF6P, and whether or not the resulting variant reacts with α-fructosyl peptides with longer chains (e.g., αF1P to αF32P, αF1P to αF64P, αF3P to αF128P, or αF3P to αF145P) can be investigated. Such variant may be prepared via, for example, (a) substitution of an amino acid at a position corresponding to position 62 with alanine, asparagine, or aspartic acid, (b) substitution of an amino acid at a position corresponding to position 63 with histidine or alanine, (c) substitution of an amino acid at a position corresponding to position 102 with lysine, (d) substitution of an amino acid at a position corresponding to position 106 with alanine, lysine, or arginine, (e) substitution of an amino acid at a position corresponding to position 110 with leucine or tyrosine. (f) substitution of an amino acid at a position corresponding to position 113 with lysine or arginine, (g) substitution of an amino acid at a position corresponding to position 355 with serine, and/or (h) substitution of an amino acid at a position corresponding to position 419 with lysine in the amino acid sequence as shown in SEQ ID NO: 1. It should be noted that a mutation to be introduced is not limited thereto, and a further mutation may be introduced based on the mutation described above, or a technique involving random introduction of a mutation may also be employed. Introduction of a mutation and examination of activity may be repeated a plurality of times, and a variant having higher activity on α-fructosyl peptides (e.g., αF1P to αF32P, αF1P to αF64P, αF1P to αF128P, or αF1P to αF145P) can be obtained (see the (Mutation of an amadoriase gene) section above).

The kit for measurement of HbA1c of the present invention may include, in addition to the reagent for measurement of α-fructosyl peptide described above, a protease or peptidase used for cleavage, other known stabilizer(s), a system that deletes contaminants, or the like, according to need. Techniques that are employed for various conventional reagents or kits for the purpose of measuring HbA1c by an enzymatic method may be adequately modified, and such modified technique(s) can be employed for the kit for measurement of HbA1c of the present invention Hereafter, the present invention is described in greater detail with reference to the examples, although the technical scope of the present invention is not limited to these examples.

Example 1

(1) Preparation of DNA of Recombinant Plasmid pKK223-3-CFP-T7

A strain of *E. coli* JM109 (pKK223-3-CFP-T7) having the recombinant plasmid of an amadoriase gene derived from the genus *Coniochaeta* (SEQ ID NO: 2) (WO 2007/125779) was inoculated into 3 ml of LB-amp media (1% (w/v) bactotrypton, 0.5% (w/v) peptone, 0.5% (w/v) NaCl, and 50 μg/ml ampicillin) and shake culture was conducted at 37° C. for 16 hours to obtain a culture product.

The culture product was centrifuged at 10,000×g for 1 minute to collect strains. A recombinant plasmid pKK223-3-CFP-T7 was extracted and purified therefrom using the GenElute Plasmid Mini-Prep Kit (manufactured by Sigma-Aldrich Corporation), and 2.5 μl of DNA of the recombinant plasmid pKK223-3-CFP-17 was obtained.

(2) Site-Directed Modification Operation of DNA of Recombinant Plasmid pKK223-3-CFP-T7

PCR was carried out under conditions described below using DNA of the recombinant plasmid pKK223-3-CFP-T7 as a template, synthetic oligonucleotides of SEQ ID NOs: 3 and 4, and KOD-Plus- (Toyobo Co., Ltd.).

Specifically, 5 μl of 10×KOD-Plus-buffer, 5 μl of a dNTPs mixture in which each dNTP was adjusted at 2 mM, 2 μl of a 25 mM $MgSO_4$ solution, 50 ng of DNA of pKK223-3-CFP-7 as a template, 15 pmol each of the synthetic oligonucleotides, and 1 unit of KOD-Plus were mixed, and sterilized water was added thereto in order to bring the total amount of the solution to 50 μl. The prepared reaction solution was subjected to incubation using a thermal cycler (manufactured by Eppendorf Co.) at 94° C. for 2 minutes, and a cycle of 94° C. for 15 seconds, 50° C. for 30 seconds, and 68° C. for 6 minutes was then repeated 30 times.

A part of the reaction solution was electrophoresed on 1.0% agarose gel, and specific amplification of about 6,000 bp DNA was confirmed. The DNAs obtained in such a manner were treated with a restriction enzyme DpnI (manufactured by New England Biolabs), the remaining template DNAs were cleaved, strains of *E. coli* JM109 were transformed, and the transformants were then spread on LB-amp agar media. The grown colonies were inoculated into LB-amp media and shake-cultured therein, and plasmid DNAs were isolated in the same manner as in (1) above. The nucleotide sequences of DNAs encoding amadoriases in the plasmids were determined using a multi-capillary DNA analysis system (Applied Biosystems 3130×1 Genetic Analyzer; manufactured by Life Technologies). Thus, the recombinant plasmid encoding the modified amadoriase resulting from substitution of arginine at position 62 with alanine in the amino acid sequence as shown in SEQ ID NO: 1 was obtained (pKK223-3-CFP-T7-H1).

(3) Production of Various Types of Modified Amadoriases

Strains of *E. coli* JM109 (pKK223-3-CFP-T7-H1) carrying pKK223-3-CFP-T7-H1 were cultured in 3 ml of LB-amp media supplemented with 0.1 mM IPTG (final concentration) at 25° C. for 16 hours. The resulting cultured strains were washed with 10 mM potassium phosphate buffer (pH 7.0), the washed strains were suspended in the same buffer, the resulting suspension was ultrasonically disintegrated, and the resultant was centrifuged at 20,000×g for 10 minutes to prepare 0.6 ml of a crude enzyme solution containing the modified amadoriase (CFP-T7-H1).

(4) Measurement of αF6P/αFVH and αF6P/αFV

The enzyme solution containing CFP-T7-H1 was subjected to measurement of oxidation activity on αFV, αFVH, and αF6P by the method described in the "B: Method of activity measurement" above. For the purpose of comparison, the enzyme solution containing CFP-T7 produced from the *E. coli* JM109 strain (pKK223-3-CFP-T7) was subjected to measurement in the same manner. Table 1 shows the oxidation activity on αFV, αFVH, and αF6P, αF6P/αFVH, and αF6P/αFV of amadoriases, relative to the oxidation activity on αFVH designated to be 100.

TABLE 1

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7 (Comparative Example) | None | 67.1 | 100 | 0 | 0 | 0 |
| CFP-T7-H1 (Amadoriase 1) | R62A | 142 | 100 | 0.0316 | 0.000316 | 0.000222 |

As shown in Table 1. CFP-T7 exhibited αFV oxidation activity and αFVH oxidation activity, although it did not exhibit αF6P oxidation activity. This indicates that CFP-T7 has very high specificity with α-fructosyl dipeptide but it does not react with α-fructosyl hexapeptide.

Variant CFP-T7-H1, on the other hand, exhibited αF6P oxidation activity, in addition to αFV oxidation activity and αFVH oxidation activity.

Thus, it was found that, as a result of introduction of amino acid substitution (R62A) into CFP-T7, a new trait: i.e., αF6P oxidation activity, could be conferred to CFP-T7, and reactivity (substrate specificity) with αF6P was improved.

Subsequently, in the same manner as in (2) above, PCR was carried out with the use of DNA of the recombinant plasmid pKK223-3-CFP-T7-H1 as a template, oligonucleotides as shown in SEQ ID NOs: 5 to 8, and KOD-Plus-, strains of *E. coli* JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of arginine at position 62 with alanine and glutamine at position 110 with leucine, phenylalanine, or tyrosine were obtained (pKK223-3-CFP-T7-H2, pKK223-3-CFP-T7-H3, and pKK223-3-CFP-T7-H4).

Strains of *E. coli* JM109 carrying pKK223-3-CFP-T7-H2, pKK223-3-CFP-T7-H3, or pKK223-3-CFP-T7-H4 were cultured in the manner described in (3) above, and crude enzyme solutions (0.6 ml each) containing various types of modified amadoriases (i.e., CFP-T7-H2, CFP-T7-H3, or CFP-T7-H4) were prepared.

The crude enzyme solutions thus prepared were subjected to measurement of oxidation activity on αFV, αFVH, and αF6P by the method described in the "B: Method of activity measurement" above. For the purpose of comparison, the enzyme solution containing CFP-T7-H1 produced from the *E. coli* JM109 strain (pKK223-3-CFP-T7-H1) was subjected to measurement in the same manner. Table 2 shows the oxidation activity on αFV, αFVH, and αF6P, αF6P/αFVH, and αF6P/αFV of amadoriases, relative to the oxidation activity on αFVH designated to be 100.

TABLE 2

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H1 (Amadoriase 1) | R62A | 142 | 100 | 0.0316 | 0.000316 | 0.000222 |
| CFP-T7-H2 (Amadoriase 2) | R62A, Q110L | 137 | 100 | 0.0735 | 0.000735 | 0.000536 |
| CFP-T7-H3 (Amadoriase 3) | R62A, Q110F | 145 | 100 | 0.0298 | 0.000298 | 0.000205 |
| CFP-T7-H4 (Amadoriase 4) | R62A, Q110Y | 107 | 100 | 0.0341 | 0.000341 | 0.000319 |

Specifically, CFP-T7-H2 and CFP-T7-H4 were found to have improved reactivity (substrate specificity) with αF6P, compared with that of CFP-T7-H1.

Subsequently, in the same manner as in (2) above, PCR was carried out with the use of DNA of the recombinant plasmid pKK223-3-CFP-T7-H2 as a template, oligonucleotides as shown in SEQ ID NOs: 4 and 9 to 12, and KOD-Plus-, strains of *E. coli* JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of glutamine at position 110 with leucine and arginine at position 62 with asparagine, aspartic acid, glutamine, or glutamic acid were obtained (pKK223-3-CFP-T7-H2-62N, pKK223-3-CFP-T7-H6, pKK223-3-CFP-T7-H2-62Q, and pKK223-3-CFP-T7-H2-62E).

Strains of *E. coli* JM109 carrying pKK223-3-CFP-T7-H2-62N, pKK223-3-CFP-T7-H6, pKK223-3-CFP-T7-H2-62Q, or pKK223-3-CFP-T7-H2-62E were cultured in the manner described in (3) above, and crude enzyme solutions (0.6 ml each) containing various types of modified amadoriases (CFP-T7-H2-62N, CFP-T7-H6, CFP-T7-H2-62Q, or CFP-T7-H2-62E) were prepared.

The crude enzyme solutions thus prepared were subjected to measurement of oxidation activity on αF6P by the method described in the "B: Method of activity measurement" above. For the purpose of comparison, the enzyme solution containing CFP-T7-H2 produced from the *E. coli* JM109 strain (pKK223-3-CFP-T7-H2) was subjected to measurement in the same manner. Table 3 shows αF6P oxidation activity of crude enzyme solutions containing amadoriases, relative to αF6P oxidation activity of a crude enzyme solution containing CFP-T7-H2 designated to be 100.

TABLE 3

| Amadoriase | Amino acid substitution | αF6P oxidation activity ratio |
|---|---|---|
| CFP-T7-H2 (Amadoriase 2) | R62A, Q110L | 100 |
| CFP-T7-H2-62N (Amadoriase 5) | R62N, Q110L | 120 |
| CFP-T7-H6 (Amadoriase 6) | R62D, Q110L | 513 |
| CFP-T7-H2-62Q (Amadoriase 7) | R62Q, Q110L | 11 |
| CFP-T7-H2-62E (Amadoriase 8) | R62E, Q110L | 21 |

Specifically, CFP-T7-H2-62N and CFP-T7-H6 were found to have improved αF6P oxidation activity, compared with that of CFP-T7-H2.

A crude enzyme solution containing CFP-T7-H2 or CFP-T7-H6 was subjected to measurement of oxidation activity on αFV, αFVH, and αF6P by the method described in the "B: Method of activity measurement" above. Table 4 shows oxidation activity on substrates, αF6P/αFVH, and αF6P/αFV of amadoriases, relative to αFVH oxidation activity designated to be 100.

TABLE 4

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H2 (Amadoriase 2) | R62A, Q110L | 137 | 100 | 0.0735 | 0.000735 | 0.000536 |
| CFP-T7-H6 (Amadoriase 6) | R62D, Q110L | 864 | 100 | 3.00 | 0.0300 | 0.00347 |

Specifically, CFP-T7-H6 was found to have significantly improved αF6P oxidation activity and improved reactivity (substrate specificity) with αF6P, compared with those of CFP-T7-H2.

Subsequently, in the same manner as in (2) above, PCR was carried out with the use of DNA of the recombinant plasmid pKK223-3-CFP-T7-H6 as a template, oligonucleotides as shown in SEQ ID NOs: 13 to 24, and KOD-Plus-, strains of *E. coli* JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of arginine at position 62 with aspartic acid, glutamine at position 110 with leucine, and arginine at position 64 with alanine, glutamic acid, or histidine were obtained (pKK223-3-CFP-T7-H7, pKK223-3-CFP-T7-H8, and pKK223-3-CFP-T7-H9), recombinant plasmids encoding modified amadoriases each comprising an amino acid sequence derived from the amino acid sequence as shown in SEQ ID NO: 1 by substitution of arginine at position 62 with aspartic acid, glutamine at position 110 with leucine, and aspartic acid at position 106 with alanine, lysine, or arginine were obtained (pKK223-3-CFP-T7-H10, pKK223-3-CFP-T7-H11, and pKK223-3-CFP-T7-H12), and recombinant plasmids encoding modified amadoriases each comprising an amino acid sequence derived from the amino acid sequence as shown in SEQ ID NO: 1 by substitution of arginine at position 62 with aspartic acid, glutamine at position 110 with leucine, and alanine at position 113 with lysine or arginine were obtained (pKK223-3-CFP-T7-H13 and pKK223-3-CFP-T7-H14).

Strains of *E. coli* JM109 carrying pKK223-3-CFP-T7-H7, pKK223-3-CFP-T7-H8, pKK223-3-CFP-T7-H9, pKK223-3-CFP-T7-H10, pKK223-3-CFP-T7-H11, pKK223-3-CFP-T7-H12, pKK223-3-CFP-T7-H13, or pKK223-3-CFP-T7-H14 were cultured in the manner described in (3) above, and crude enzyme solutions (0.6 ml each) containing various types of modified amadoriases (CFP-T7-H7, CFP-T7-H8, CFP-T7-H9, CFP-T7-H10, CFP-T7-H11, CFP-T7-H12, CFP-T7-H13, or CFP-T7-H14) were prepared.

The crude enzyme solutions thus prepared were subjected to measurement of oxidation activity on αF6P by the method described in the "B: Method of activity measurement" above. For the purpose of comparison, the enzyme solution containing CFP-T7-H6 produced from the *E. coli* JM109 strain (pKK223-3-CFP-T7-H6) was subjected to measurement in the same manner. Table 5 shows αF6P oxidation activity of crude enzyme solutions containing amadoriases, relative to the αF6P oxidation activity of a crude enzyme solution containing CFP-T7-H6 designated to be 100.

TABLE 5

| Amadoriase | Amino acid substitution | αF6P oxidation activity ratio |
|---|---|---|
| CFP-T7-H6 (Amadoriase 6) | R62D, Q110L | 100 |
| CFP-T7-H7 (Amadoriase 9) | R62D, R64A, Q110L | 17 |
| CFP-T7-H8 (Amadoriase 10) | R62D, R64E, Q110L | 2 |
| CFP-T7-H9 (Amadoriase 11) | R62D, R64H, Q110L | 44 |
| CFP-T7-H10 (Amadoriase 12) | R62D, D106A, Q110L | 301 |
| CFP-T7-H11 (Amadoriase 13) | R62D, D106K, Q110L | 951 |
| CFP-T7-H12 (Amadoriase 14) | R62D, D106R, Q110L | 636 |
| CFP-T7-H13 (Amadoriase 15) | R62D, Q110L, A113K | 207 |
| CFP-T7-H14 (Amadoriase 16) | R62D, Q110L, A113R | 183 |

Specifically, CFP-T7-H10, CFP-T7-H11, CFP-T7-H12, CFP-T7-H13, and CFP-T7-H14 were each found to exhibit significantly improved αF6P oxidation activity ratio, compared with that of CFP-T7-H6, and the level of improvement in some of the variants was remarkable.

Crude enzyme solutions containing CFP-T7-H6, CFP-T7-H11, CFP-T7-H12, CFP-T7-H13, and CFP-T7-H14 were subjected to measurement of oxidation activity on αFV, αFVH, and αF6P by the method described in the "B: Method of activity measurement" above. Table 6 shows oxidation activity on substrates, αF6P/αFVH, and αF6P/αFV of amadoriases, relative to αFVH oxidation activity designated to be 100.

TABLE 6

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H6 (Amadoriase 6) | R62D, Q110L | 864 | 100 | 3.00 | 0.0300 | 0.00347 |
| CFP-T7-H11 (Amadoriase 13) | R62D, D106K, Q110L | 511 | 100 | 12.5 | 0.125 | 0.0245 |
| CFP-T7-H12 (Amadoriase 14) | R62D, D106R, Q110L | 700 | 100 | 11.6 | 0.116 | 0.0165 |

TABLE 6-continued

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H13 (Amadoriase 15) | R62D, Q110L, A113K | 747 | 100 | 4.33 | 0.0433 | 0.00579 |
| CFP-T7-H14 (Amadoriase 16) | R62D, Q110L, A113R | 814 | 100 | 4.22 | 0.0422 | 0.00519 |

As shown in Table 6, specifically, CFP-T7-H11, CFP-T7-H12, CFP-T7-H13, and CFP-T7-H14 were found to have significantly improved reactivity (substrate specificity) with αF6P, compared with that of CFP-T7-H6.

Subsequently, in the same manner as in (2) above, PCR was carried out with the use of DNA of the recombinant plasmid pKK223-3-CFP-T7-H11 as a template, oligonucleotides as shown in SEQ ID NOs: 21 to 24, and KOD-Plus-, strains of *E. coli* JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of arginine at position 62 with aspartic acid, aspartic acid at position 106 with lysine, glutamine at position 110 with leucine, and alanine at position 113 with lysine or arginine were obtained (pKK223-3-CFP-T7-H20 and pKK223-3-CFP-T7-H21).

Strains of *E. coli* JM109 carrying pKK223-3-CFP-T7-H20 or pKK223-3-CFP-T7-H21 were cultured in the manner described in (3) above, and crude enzyme solutions (0.6 ml each) containing various types of modified amadoriases (CFP-T7-H20 or CFP-T7-H21) were prepared.

Crude enzyme solutions containing CFP-T7-H11, CFP-T7-H20, and CFP-T7-H21 were subjected to measurement of oxidation activity on αFV, αFVH, and αF6P by the method described in the "B: Method of activity measurement" above. Table 7 shows oxidation activity on substrates, αF6P/αFVH, and αF6P/αFV of amadoriases, relative to the αFVH oxidation activity designated to be 100.

TABLE 7

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H11 (Amadoriase 13) | R62D, D106K, Q110L | 511 | 100 | 12.5 | 0.125 | 0.0245 |
| CFP-T7-H20 (Amadoriase 17) | R62D, D106K, Q110L, A113K | 544 | 100 | 20.5 | 0.205 | 0.0377 |
| CFP-T7-H21 (Amadoriase 18) | R62D, D106K, Q110L, A113R | 558 | 100 | 20.8 | 0.208 | 0.0372 |

Specifically, CFP-T7-H20 and CFP-T7-H21 were found to have improved reactivity (substrate specificity) with αF6P, compared with that of CFP-T7-H11.

Subsequently, in the same manner as in (2) above, PCR was carried out with the use of DNA of the recombinant plasmid pKK223-3-CFP-T7-H20 as a template, oligonucleotides as shown in SEQ ID NOs: 25 to 29, and KOD-Plus-, strains of *E. coli* JM109 were transformed, and nucleotide sequences of DNAs encoding amadoriases in the plasmid DNAs carried on the grown colonies were determined. As a result, recombinant plasmids encoding modified amadoriases each comprising an amino acid sequence derived from the amino acid sequence as shown in SEQ ID NO: 1 by substitution of arginine at position 62 with aspartic acid, aspartic acid at position 106 with lysine, glutamine at position 110 with leucine, alanine at position 113 with lysine, and leucine at position 63 with alanine, aspartic acid, histidine, or lysine were obtained (pKK223-3-CFP-T7-H24, pKK223-3-CFP-T7-H25, pKK223-3-CFP-T7-H26, and pKK223-3-CFP-T7-H27).

Strains of *E. coli* JM109 carrying pKK223-3-CFP-T7-H24, pKK223-3-CFP-T7-H25, pKK223-3-CFP-T7-H26, or pKK223-3-CFP-T7-H27 were cultured in the manner described in (3) above, and crude enzyme solutions (0.6 ml each) containing various types of modified amadoriases (CFP-T7-H24, CFP-T7-H25, CFP-T7-H26, or CFP-T7-H27) were prepared.

The crude enzyme solutions thus prepared were subjected to measurement of oxidation activity on αF6P by the method described in the "B: Method of activity measurement" above. For the purpose of comparison, the enzyme solution containing CFP-T7-H20 produced from the *E. coli* JM109 strain (pKK223-3-CFP-T7-H20) was subjected to measurement in the same manner. Table 8 shows αF6P oxidation activity of crude enzyme solutions containing amadoriases, relative to the αF6P oxidation activity of a crude enzyme solution containing CFP-T7-H20 designated to be 100.

TABLE 8

| Amadoriase | Amino acid substitution | αF6P oxidation activity ratio |
|---|---|---|
| CFP-T7-H20 (Amadoriase 17) | R62D, D106K, Q110L, A113K | 100 |

TABLE 8-continued

| Amadoriase | Amino acid substitution | αF6P oxidation activity ratio |
|---|---|---|
| CFP-T7-H24 (Amadoriase 19) | R62D, L63A, D106K, Q110L, A113K | 123 |
| CFP-T7-H25 (Amadoriase 20) | R62D, L63D, D106K, Q110L, A113K | 24 |
| CFP-T7-H26 (Amadoriase 21) | R62D, L63H, D106K, Q110L, A113K | 142 |
| CFP-T7-H27 (Amadoriase 22) | R62D, L63K, D106K, Q110L, A113K | 7 |

As shown in Table 8, specifically, CFP-T7-H24 and CFP-T7-H26 were found to have improved αF6P oxidation activity, compared with that of CFP-T7-H20.

Crude enzyme solutions containing CFP-T7-H20, CFP-T7-H24, or CFP-T7-H26 were subjected to measurement of oxidation activity on αFV, αFVH, and αF6P by the method described in the "B: Method of activity measurement" above. Table 9 shows oxidation activity on substrates, αF6P/αFVH, and αF6P/αFV of amadoriases, relative to the αFVH oxidation activity designated to be 100.

TABLE 9

| Amadoriase | Amino acid substitution | αFV oxidation activity | αFVH oxidation activity | αF6P oxidation activity | αF6P/αFVH | αF6P/αFV |
|---|---|---|---|---|---|---|
| CFP-T7-H20 (Amadoriase 17) | R62D, D106K, Q110L, A113K | 544 | 100 | 20.5 | 0.205 | 0.0377 |
| CFP-T7-H24 (Amadoriase 19) | R62D, L63A, D106K, Q110L, A113K | 1880 | 100 | 86.7 | 0.867 | 0.0461 |
| CFP-T7-H26 (Amadoriase 21) | R62D, L63H, D106K, Q110L, A113K | 1090 | 100 | 84.3 | 0.843 | 0.0773 |

As shown in Table 9, specifically, CFP-T7-H24 and CFP-T7-H26 were found to have improved reactivity (substrate specificity) with αF6P, compared with that of CFP-T7-H20.

Subsequently, in the same manner as in (2) above, PCR was carried out with the use of DNA of the recombinant plasmid pKK223-3-CFP-T7-H26 as a template, oligonucleotides as shown in SEQ ID NOs: 30 to 33, and KOD-Plus-, strains of *E. coli* JM109 were transformed, and nucleotide sequences of DNAs encoding amadoriases in the plasmid DNAs carried on the grown colonies were determined. As a result, a recombinant plasmid encoding a modified amadoriase comprising an amino acid sequence derived from the amino acid sequence as shown in SEQ ID NO: 1 by substitution of arginine at position 62 with aspartic acid, leucine at position 63 with histidine, aspartic acid at position 106 with lysine, glutamine at position 110 with leucine, alanine at position 113 with lysine, and glutamic acid at position 102 with lysine was obtained (pKK223-3-CFP-T7-H28), and a recombinant plasmid encoding a modified amadoriase comprising an amino acid sequence derived from the amino acid sequence as shown in SEQ ID NO: 1 by substitution of arginine at position 62 with aspartic acid, leucine at position 63 with histidine, aspartic acid at position 106 with lysine, glutamine at position 110 with leucine, alanine at position 113 with lysine, and alanine at position 419 with lysine was obtained (pKK223-3-CFP-T7-H29).

Strains of *E. coli* JM109 carrying pKK223-3-CFP-T7-H26, pKK223-3-CFP-T7-H28, or pKK223-3-CFP-T7-H29 were cultured in the manner described in (3) above, and crude enzyme solutions (0.6 ml each) containing various types of modified amadoriases (CFP-T7-H26, CFP-T7-H28, or CFP-T7-H29) were prepared.

The crude enzyme solutions thus prepared were subjected to measurement of oxidation activity on αF6P by the method described in the "B: Method of activity measurement" above. For the purpose of comparison, the enzyme solution containing CFP-T7-H26 produced from the *E. coli* JM109 strain (pKK223-3-CFP-T7-H26) was subjected to measurement in the same manner. Table 10 shows αF6P oxidation activity of crude enzyme solutions containing amadoriases, relative to the αF6P oxidation activity of a crude enzyme solution containing CFP-T7-H26 designated to be 100.

TABLE 10

| Amadoriase | Amino acid substitution | αF6P oxidation activity ratio |
|---|---|---|
| CFP-T7-H26 (Amadoriase 21) | R62D, L63H, D106K, Q110L, A113K | 100 |
| CFP-T7-H28 (Amadoriase 23) | R62D, L63H, E102K, D106K, Q110L, A113K | 117 |
| CFP-T7-H29 (Amadoriase 24) | R62D, L63H, D106K, Q110L, A113K, A419K | 102 |

As shown in Table 10, specifically, CFP-T7-H28 and CFP-T7-H29 were found to have improved αF6P oxidation activity, compared with that of CFP-T7-H26.

Crude enzyme solutions containing CFP-T7-H26, CFP-T7-H28, or CFP-T7-H29 were subjected to measurement of oxidation activity on αFV, αFVH, and αF6P by the method described in the "B: Method of activity measurement" above. Table 11 shows oxidation activity on substrates, αF6P/αFVH, and αF6P/αFV of amadoriases, relative to the αFVH oxidation activity designated to be 100.

TABLE 11

| Amadoriase | Amino acid substitution | αFV oxidation activity | αFVH oxidation activity | αF6P oxidation activity | αF6P/αFVH | αF6P/αFV |
|---|---|---|---|---|---|---|
| CFP-T7-H26 (Amadoriase 21) | R62D, L63H, D106K, Q110L, A113K | 1090 | 100 | 84.3 | 0.843 | 0.0773 |
| CFP-T7-H28 (Amadoriase 23) | R62D, L63H, E102K, D106K, Q110L, A113K | 1080 | 100 | 134 | 1.34 | 0.124 |

TABLE 11-continued

| Amadoriase | Amino acid substitution | αFV oxidation activity | αFVH oxidation activity | αF6P oxidation activity | αF6P/ αFVH | αF6P/ αFV |
|---|---|---|---|---|---|---|
| CFP-T7-H29 (Amadoriase 24) | R62D, L63H, D106K, Q110L, A113K, A419K | 1000 | 100 | 111 | 1.11 | 0.111 |

As shown in Table 11, specifically, CFP-T7-H28 and CFP-T7-H29 were found to have improved reactivity (substrate specificity) with αF6P, compared with that of CFP-T7-H26.

Subsequently, in the same manner as in (2) above, PCR was carried out with the use of DNA of the recombinant plasmid pKK223-3-CFP-T7-H28 as a template, oligonucleotides as shown in SEQ ID NOs: 34 and 35, and KOD-Plus-, strains of *E. coli* JM109 were transformed, and nucleotide sequences of DNAs encoding amadoriases in the plasmid DNAs carried on the grown colonies were determined. As a result, a recombinant plasmid encoding a modified amadoriase comprising an amino acid sequence derived from the amino acid sequence as shown in SEQ ID NO: 1 by substitution of arginine at position 62 with aspartic acid, leucine at position 63 with histidine, glutamic acid at position 102 with lysine, aspartic acid at position 106 with lysine, glutamine at position 110 with leucine, alanine at position 113 with lysine, and alanine at position 355 with serine was obtained (pKK223-3-CFP-T7-H35).

Strains of *E. coli* JM109 carrying pKK223-3-CFP-T7-H35 were cultured in the manner described in (3) above, and a crude enzyme solution (0.6 ml) containing a modified amadoriase (CFP-T7-H35) was prepared.

The crude enzyme solution thus prepared was subjected to measurement of oxidation activity on αF6P by the method described in the "B: Method of activity measurement" above. For the purpose of comparison, the enzyme solution containing CFP-T7-H20 produced from the strain of *E. coli* JM109 (pKK223-3-CFP-T7-H28) was subjected to measurement in the same manner. Table 12 shows αF6P oxidation activity of crude enzyme solutions containing amadoriases, relative to the αF6P oxidation activity of a crude enzyme solution containing CFP-T7-H26 designated to be 100.

TABLE 12

| Amadoriase | Amino acid variation | αF6P oxidation activity ratio |
|---|---|---|
| CFP-T7-H28 (Amadoriase 23) | R62D, L63H, E102K, D106K, Q110L, A113K | 100 |
| CFP-T7-H35 (Amadoriase 25) | R62D, L63H, E102K, D106K, Q110L, A113K, A355S | 206 |

As shown in Table 12, specifically, CFP-T7-H35 was found to have improved αF6P oxidation activity, compared with that of CFP-T7-H28.

Subsequently, in the same manner as in (2) above, PCR was carried out with the use of DNA of the recombinant plasmid pKK223-3-CFP-T7 as a template, oligonucleotides as shown in SEQ ID NOs: 4 and 10, and KOD-Plus-, strains of *E. coli* JM109 were transformed, and nucleotide sequences of DNAs encoding amadoriases in the plasmid DNAs carried on the grown colonies were determined. As a result, a recombinant plasmid encoding a modified amadoriase comprising an amino acid sequence derived from the amino acid sequence as shown in SEQ ID NO: 1 by substitution of arginine at position 62 with aspartic acid was obtained (pKK223-3-CFP-T7-62D). Subsequently, a strain of *E. coli* JM109 carrying pKK223-3-CFP-T7-62D was prepared.

Example 2

(Production and Purification of Various Types of Amadoriases)

(Production and Purification of Modified Amadoriase Derived from the Genus *Coniochaeta*)

*E. coli* JM109 producing the wild-type amadoriases from the genus *Coniochaeta* and *E. coli* JM109 (pKK223-3-CFP-T7), *E. coli* JM109 (pKK223-3-CFP-T7-62D), *E. coli* JM109 (pKK223-3-CFP-T7-H20), *E. coli* JM109 (pKK223-3-CFP-T7-H21), and *E. coli* JM109 (pKK223-3-CFP-T7-H35) producing modified amadoriases obtained in the manner described above were inoculated into 120 ml of LB-amp media supplemented with IPTG (final concentration: 0.1 mM) and cultured therein at 25° C. for 16 hours. The resulting cultured strains were washed with a 10 mM potassium phosphate buffer (pH 7.0), the washed strains were suspended in the same buffer, the resulting suspension was ultrasonically disintegrated, and the resultant was centrifuged at 20,000×g for 10 minutes to prepare 24 ml of a crude enzyme solution.

The resulting crude enzyme solution was allowed to adsorb to 12 ml of Toyopearl Butyl-650C resin (manufactured by Tosoh) equilibrated with a 10 mM potassium phosphate buffer (pH 7.0) containing 1.35 M $(NH_4)_2SO_4$, the resin was washed with 120 ml of the same buffer, and the amadoriases adsorbed to the resin were then eluted and collected with the aid of a 10 mM potassium phosphate buffer (pH 7.0) containing 84 ml of 1.05 M $(NH_4)_2SO_4$.

The resulting crude enzyme solution containing the amadoriases was introduced into Spectra/Por dialysis tubing (MWCO: 12,000-14,000) and dialyzed against a 10-fold amount of 5 mM potassium phosphate buffer (pH 7.5). This procedure was repeated 3 times to completely remove $(NH_4)_2SO_4$ from the crude enzyme solution containing the amadoriases. Subsequently, the crude enzyme solution containing the amadoriases was applied to HiScreen Capto Q ImpRes (manufactured by GE Healthcare) equilibrated with a 10 mM potassium phosphate buffer (pH 7.5) to allow amadoriases to bind to anion-exchange resin. Thereafter, the concentration of NaCl contained in a 10 mM potassium phosphate buffer (pH 7.5) was linearly increased from 0 mM to 160 mM to elute proteins bound to the resin, and fractions exhibiting amadoriase activity were collected. The obtained fractions exhibiting amadoriase activity were analyzed via SDS-PAGE to confirm that the fractions were sufficiently purified, so that no other contaminating proteins were present therein, and these fractions were designated to be purified samples of the CFP-T7, CFP-T7-62D, CFP-T7-H20, CFP-T7-H21, and pKK223-3-CFP-T7-H35 enzymes.

(Production and Purification of Fructosyl Amino Acid Oxidase Derived from *Aspergillus oryzae* RIB40)

SEQ ID NO: 36 shows the amino acid sequence of fructosyl amino acid oxidase derived from *Aspergillus oryzae* RIB40 (hereafter referred to as "FAOAo2"), a recombinant plasmid obtained by insertion of the gene (SEQ ID NO: 37) encoding the amino acid sequence as shown in SEQ ID NO: 36 (hereafter referred to as "pUC19-FAOAo2") is allowed to express in *E. coli* DH5α to produce FAOAo2, and FAOAo2 reacts with fructosyl hexapeptide (see WO 2008/108385).

The strains of *E. coli* DH5α capable of producing FAOAo2 (pUC19-FAOAo2) were inoculated into LB-amp media supplemented with IPTG (final concentration: 0.1 mM) and cultured therein at 25° C. for 16 hours. The resulting cultured strains were washed with a 10 mM Tris-HCl buffer (pH 8.5), the washed strains were suspended in the same buffer, the resulting suspension was ultrasonically disintegrated, and the resultant was centrifuged at 20,000×g for 10 minutes to prepare a crude enzyme solution.

The resulting crude enzyme solution was allowed to adsorb to Q Sepharose Fast Flow resin (manufactured by GE Healthcare) equilibrated with a 10 mM Tris-HCl buffer (pH 8.5), the resin was washed with a 10 mM Tris-HCl buffer (pH 8.5) containing 50 mM NaCl, and the FAOAo2 adsorbed to the resin was then eluted and collected with the aid of a 10 mM Tris-HCl buffer (pH 8.5) containing 100 mM NaCl.

The resulting crude enzyme solution containing FAOAo2 was applied to the HiLoad 26/600 Superdex 200 column equilibrated with a 20 mM MES-NaOH buffer (pH 7.0) containing 150 mM NaCl so as to elute FAOAo2 with the same buffer, and a fraction exhibiting amadoriase activity was collected. The obtained fraction was analyzed via SDS-PAGE to confirm that the fraction was sufficiently purified, so that no other contaminating proteins were present therein, and the fraction was designated to be a purified enzyme sample of FAOAo2.

(Preparation of Strain Producing Fructosyl Peptide Oxidase Derived from *Phaeosphaeria Nodorum*)

SEQ ID NO: 38 shows the amino acid sequence of fructosyl peptide oxidase derived from *Phaeosphaeria nodorum* (hereafter referred to as "PnFX") (see Biotechnology and Bioengineering, 106, 358-366, 2010). The gene (SEQ ID NO: 39) encoding the amino acid sequence as shown in SEQ ID NO: 38 was obtained via total synthesis of cDNA by a conventional technique of PCR of a gene fragment. The NdeI site and the BamHI were added to the 5' terminus and the 3' terminus of SEQ ID NO: 39, respectively. Also, the full-length amino acid sequence that is deduced based on the cloned gene sequence was confirmed to be consistent with the PnFX sequence as shown in FIG. 1.

In order to express the gene shown in SEQ ID NO: 39 in *E. coli*, subsequently, the following procedures were performed. The gene obtained via total synthesis above was treated with two types of restriction enzymes. NdeI and BamHI (manufactured by Takara Bio Inc.) and inserted into the NdeI-BamHI site of the pET-22b(+) vector (manufactured by Novagen, Inc.). Thus, the recombinant plasmid pET22b-PnFX was obtained. Strains of *E. coli* BL21 (DE3) were transformed under the conditions as described above to obtain a strain of *E. coli* BL21 (DE3) (pET22b-PnFX).

(Production and Purification of Fructosyl Peptide Oxidase Derived from *Phaeosphaeria Nodorum*)

The strains of *E. coli* BL21 (DE3) (pET22b-PnFX) capable of producing PnFX obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 8.0), the washed strains were suspended in the same buffer, the resulting suspension was ultrasonically disintegrated, and the resultant was centrifuged at 20,000×g for 10 minutes to prepare a crude enzyme solution.

The resulting crude enzyme solution containing PnFX was purified in accordance with the method described in the non-patent document (Biotechnology and Bioengineering, 106, 358-366, 2010). Specifically, the crude enzyme solution was fractionated with ammonium sulfate, dialyzed against a 10 mM potassium phosphate buffer (pH 8.0), purified via anion-exchange chromatography (Q Sepharose Fast Flow was used in Example 2), and then purified via gel filtration chromatography (HiLoad 26/600 Superdex 200 was used in Example 2). The obtained fraction was analyzed via SDS-PAGE to confirm that the fraction was sufficiently purified, so that no other contaminating proteins were present therein, and the fraction was designated to be a purified sample of the enzyme PnFX.

By using the purified samples of CFP-T7. CFP-T7-62D, CFP-T7-H20, CFP-T7-H21, CFP-T7-H35, FAOAo2, and PnFX, specific activities thereof relative to αFV, αFVH, and αF6P as substrates were measured. Results are shown in Table 13-1. Incidentally, the concentration of the protein used for calculation of specific activity was determined by using the ultraviolet absorption method which utilizes absorbance at 280 nm (see Protein Sci., 4, 2411-23, 1995).

TABLE 13

| | | Specific activity (U/mg) | | | | |
|---|---|---|---|---|---|---|
| Amadoriase | Amino acid mutation | 1 mM αFV | 1 mM αFVH | 1 mM αF6P | αF6P/ αFVH | αF6P/ αFV |
| CFP-T7 (Comparative Example 1) | None | 11.1 | 16.5 | 0 | 0 | 0 |
| FAOAo2 (Comparative Example 2) | None | Not measured | Not measured | 0.0022 | | |
| PnFX (Comparative Example 3) | None | Not measured | Not measured | 0.0091 | | |
| CFP-T7-62D (Amadoriase 26) | R62D | 13.6 | 1.62 | 0.018 | 0.00132 | 0.00113 |
| CFP-T7-H20 (Amadoriase 17) | R62D, D106K, Q110L, A113K | 21.8 | 4.28 | 0.850 | 0.198 | 0.0389 |

TABLE 13-continued

| Amadoriase | Amino acid mutation | Specific activity (U/mg) 1 mM αFV | 1 mM αFVH | 1 mM αF6P | αF6P/ αFVH | αF6P/ αFV |
|---|---|---|---|---|---|---|
| CFP-T7-H21 (Amadoriase 18) | R62D, D106K, Q110L, A113R | 21.0 | 4.05 | 0.795 | 0.196 | 0.0377 |
| CFP-T7-H35 (Amadoriase 25) | R62D, L63H, E102K, D106K, Q110L, A113K A355S | 13.2 | 1.90 | 4.27 | 2.25 | 0.323 |

The purified CFP-T7 did not react with αF6P, as expected. In contrast, specific activity of CFP-T7-62D, CFP-T7-H20, CFP-T7-H21, or CFP-T7-H35 on αF6P was 0.018 U/mg, 0.850 U/mg, 0.795 U/mg, or 4.27 U/mg, respectively. That is, even in a measurement method in which the influence of protease/peptidase derived from the *E. coli* host was eliminated, sufficiently high reactivity with αF6P was observed.

Specific activities of the reported amadoriases capable of reacting with αF6P, i.e., FAOAo2 (see WO 2008/108385) and PnFX (see WO 2011/15326, referred to as "P.n FPOX" therein) relative to αF6P were 0.0022 U/mg and 0.0091 U/mg, respectively. The modified amadoriases derived from the genus *Coniochaeta* prepared in accordance with the procedure described herein exhibited specific activities that are 2 times (Amadoriase 26/Comparative Example 3) to 1,940 times (Amadoriase 25/Comparative Example 2) greater than those of the reported amadoriases capable of reacting with αF6P. That is, amadoriases exhibiting high reactivity with αF6P were obtained in accordance with the procedures described herein.

There were no significant discrepancies between the αF6P/αFVH values of CFP-T7-H20 and CFP-T7-H21 measured with the use of crude enzyme solutions and those measured with the use of purified enzymes.

With the use of the purified samples of CFP-T7 and CFP-T7-H35, specific activities thereof relative to αFV, αFVH, αF3P, αF4P, αF5P, αF6P, αF8P, and αF16P as substrates were measured. The results are shown in Table 14. Concentration of the protein used for calculation of specific activity was determined by using the ultraviolet absorption method which utilizes the absorbance at 280 nm (see Protein Sci., 4, 2411-23, 1995).

TABLE 14

| Amadoriase | Mutation | Specific activity (U/mg) 1 mM αFV | 1 mM αFVH | 1 mM αF3P | 1 mM αF4P | 1 mM αF5P | 1 mM αF6P | 1 mM αF8P | 1 mM αF16P |
|---|---|---|---|---|---|---|---|---|---|
| CFP-T7 | None | 11.1 | 16.5 | 0 | 0 | 0 | 0 | 0 | 0 |
| CFP-T7-H35 | R62D, L63H, E102K, D106K, Q110L, A113K, A355S | 13.2 | 1.90 | 1.24 | 0.352 | 2.15 | 4.27 | 1.59 | 0.247 |

While the purified CFP-T7 exhibited oxidation activity on αFV and αFVH, it did not exhibit oxidation activity on a glycated peptide with a peptide chain formed by 3 or more amino acids. In contrast, CFP-T7-H35 exhibited oxidation activity on glycated peptides with peptide chains formed by 3 to 16 amino acids in addition to oxidation activity on αFV and αFVH. While CFP-T7-H35 exhibited a high degree of specific activity on αFV and αF6P, it also exhibited a sufficient degree of specific activity on αFVH to αF5P of intermediate chain lengths. From this and the fact that CFP-T7-H35 was capable of reacting with αF6P, αF8P, and αF16P, it is highly plausible that CFP-T7-H35 is also capable of reacting with αF7P and αF9P to αF5P of intermediate chain lengths in a similar manner. Further, since CFP-T7-H35 is also capable of reacting with αF16P, CFP-T7-H35 is also expected to react with substrates with longer chains, such as αF17P to αF32P.

As described above. CFP-T7-H35 was found to be capable of recognizing, as substrates, a wide variety of glycated peptides with long peptide chains, which could not be recognized as substrates by wild-type enzymes (CFP-T7). With the use of such amadoriase, the present invention can provide a method for measurement of HbA1c that enables quantification of HbA1c to be performed rapidly, simply, and accurately with the use of a small amount of a protease and a kit used for such measurement. Further, the present invention can provide a method for measurement of HbA1c that enables quantification of HbA1c to be performed rapidly, simply, and accurately, with high sensitivity with the use of a small amount of a protease and a kit used for such measurement.

Example 3

(Introduction of Point Mutations into Various Amadoriases)

By introducing the mutations described above, reactivity of the amadoriase from the genus *Coniochaeta* with αF6P was enhanced, and reactivity thereof with αF3P, αF4P, αF5P, αF6P, αF8P, and αF16P was also enhanced. Based on this, and by introducing a similar mutation into a corresponding position in the amino acid sequence of the amadoriase derived from another organism species with reference to the information attained by a known sequence alignment processing based on sequence identity, it is expected that reactivity thereof with αF3P, αF4P, αF5P, αF6P, αF8P, and αF16P can also be enhanced. Accordingly, mutations were actually introduced into the corresponding positions of a plurality of amadoriases other than the amadoriase derived from the genus *Coniochaeta.*

1. Introduction of Point Mutation into Gene of Fructosyl Peptide Oxidase Derived from *Eupenicillium terrenum*

SEQ ID NO: 40 shows the amino acid sequence of fructosyl peptide oxidase derived from *Eupenicillium terrenum* (hereafter referred to as "EFP-T5"), and it can be prepared by *E. coli* strains carrying the recombinant plasmid pUTE100K'-EFP-T5 into which the gene (SEQ ID NO: 41) encoding the amino acid sequence as shown in SEQ ID NO: 40 has been inserted. EFP-T5 is confirmed to exhibit oxidation activity on αFV and αFVH (see WO 2007/125779 and WO 2008/018094).

In order to introduce a mutation aimed at improvement of substrate specificity into EFP-T5, in the same manner as in Example 1, PCR was carried out with the use of the recombinant plasmid pUTE100K'-EFP-T5 as a template, synthetic oligonucleotides as shown in SEQ ID NOs: 42 and 43, and KOD-Plus- (manufactured by TOYOBO CO., LTD.), strains of *E. coli* JM109 were transformed, and nucleotide sequences of DNAs encoding the EFP-T5 variant in the plasmid DNAs carried on the grown colonies were determined. As a result, a recombinant plasmid encoding the EFP-T5 gene comprising an amino acid sequence derived from the amino acid sequence as shown in SEQ ID NO: 40 by substitution of arginine at position 62 with aspartic acid was obtained (pUTE100K'-EFP-T5-62D).

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid and asparagine at position 106 with lysine (pUTE100K'-EFP-T5-62D/106K) was obtained with the use of pUTE100K'-EFP-T5-62D as a template and synthetic oligonucleotides as shown in SEQ ID NOs: 44 and 45.

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid, asparagine at position 106 with lysine, and lysine at position 110 with leucine (pUTE100K'-EFP-T5-62D/106K/110L) was obtained with the use of pUTE100K'-EFP-T5-62D/106K as a template and synthetic oligonucleotides as shown in SEQ ID NOs: 46 and 47.

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid, asparagine at position 106 with lysine, lysine at position 110 with leucine, and threonine at position 113 with lysine (pUTE100K'-EFP-T5-62D/106K/110L/113K) was obtained with the use of pUTE100K'-EFP-T5-62D/106K/110L as a template and synthetic oligonucleotides as shown in SEQ ID NOs: 48 and 49.

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid, asparagine at position 106 with lysine, lysine at position 110 with leucine, threonine at position 113 with lysine, and alanine at position 355 with serine (pUTE100K'-EFP-T5-62D/106K/110L/113K/355S) was obtained with the use of pUTE100K'-EFP-T5-62D/106K/110L/113K as a template and synthetic oligonucleotides as shown in SEQ ID NOs: 50 and 51.

Subsequently, in the same manner as described above, a recombinant plasmid encoding the EFP-T5 gene comprising an amino acid sequence derived from the amino acid sequence as shown in SEQ ID NO: 40 by substitution of arginine at position 62 with aspartic acid, leucine at position 63 with histidine, asparagine at position 106 with lysine, lysine at position 110 with leucine, threonine at position 113 with lysine, and alanine at position 355 with serine (pUTE100K'-EFP-T5-62D/63H/106K/110L/113K/355S) was obtained with the use of pUTE100K'-EFP-T5-62D/106K/110L/113K/355S as a template and synthetic oligonucleotides as shown in SEQ ID NOs: 52 and 53.

2. Introduction of Point Mutation into Gene of Ketoamine Oxidase Derived from *Neocosmospora vasinfecta*

SEQ ID NO: 54 shows the amino acid sequence of ketoamine oxidase derived from *Neocosmospora vasinfecta* (hereafter referred to as "NvFX"), and it can be prepared by *E. coli* strains carrying the recombinant plasmid pET22b-NvFX into which the gene (SEQ ID NO: 55) encoding the amino acid sequence as shown in SEQ ID NO: 54 has been inserted. NvFX is confirmed to exhibit oxidation activity on αFV and αFVH (see WO 2012/018094).

In order to introduce a mutation aimed at improvement of substrate specificity into NvFX, in the same manner as in Example 1, PCR was carried out with the use of the recombinant plasmid pET22b-NvFX as a template, synthetic oligonucleotides as shown in SEQ ID NOs: 56 and 57, and KOD-Plus- (manufactured by TOYOBO CO., LTD.), strains of *E. coli* JM109 were transformed, and nucleotide sequences of DNAs encoding the NvFX variant in the plasmid DNAs carried on the grown colonies were determined. As a result, a recombinant plasmid encoding the NvFX gene comprising an amino acid sequence derived from the amino acid sequence as shown in SEQ ID NO: 54 by substitution of arginine at position 62 with aspartic acid was obtained (pET22b-NvFX-62D).

Subsequently, in the same manner as described above, a recombinant plasmid encoding the NvFX gene comprising an amino acid sequence derived from the amino acid sequence as shown in SEQ ID NO: 54 by substitution of arginine at position 62 with aspartic acid and glycine at position 106 with lysine (pET22b-NvFX-62D/106K) was obtained with the use of pET22b-NvFX-62D as a template and synthetic oligonucleotides as shown in SEQ ID NOs: 58 and 59.

Subsequently, in the same manner as described above, a recombinant plasmid encoding the NvFX gene comprising an amino acid sequence derived from the amino acid sequence as shown in SEQ ID NO: 54 by substitution of arginine at position 62 with aspartic acid, arginine at position 106 with lysine, and glutamic acid at position 110 with leucine (pET22b-NvFX-62D/106K/110L) was obtained with the use of pET22b-NvFX-62D/106K as a template and synthetic oligonucleotides as shown in SEQ ID NOs: 60 and 61.

Strains of *E. coli* BL21 (DE3) were transformed under the same conditions as in Example 1 to obtain strains of *E. coli* BL21 (DE3) (pET22b-NvFX-62D/106K/110L).

3. Introduction of Point Mutation into Gene of Fructosyl Amino Acid Oxidase Derived from *Aspergillus nidulans*

SEQ ID NO: 62 shows the amino acid sequence of fructosyl amino acid oxidase derived from *Aspergillus nidulans* resulting from substitution of serine at position 59 with glycine so as to impart the activity of fructosyl peptide oxidase (hereafter referred to as "AnFX"), and it can be prepared by *E. coli* strains carrying the recombinant plasmid pET22b-AnFX into which the gene (SEQ ID NO: 63) encoding the amino acid sequence as shown in SEQ ID NO: 62 has been inserted. AnFX is confirmed to exhibit oxidation activity on αFV and αFVH (see WO 2012/018094).

In order to introduce a mutation aimed at improvement of substrate specificity into AnFX, in the same manner as in Example 1, PCR was carried out with the use of the recombinant plasmid pET22b-AnFX as a template, synthetic oligonucleotides as shown in SEQ ID NOs: 64 and 65, and KOD-Plus- (manufactured by TOYOBO CO., LTD.), strains of *E. coli* JM109 were transformed, and nucleotide sequences of DNAs encoding the AnFX variant in the plasmid DNAs carried on the grown colonies were determined. As a result, a recombinant plasmid encoding the AnFX gene comprising an amino acid sequence derived from the amino acid sequence as shown in SEQ ID NO: 62 by substitution of arginine at position 61 with aspartic acid was obtained (pET22b-AnFX-61D).

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid and glycine at position 105 with lysine (pET22b-AnFX-61D/105K) was obtained with the use of pET22b-AnFX-61D as a template and synthetic oligonucleotides as shown in SEQ ID NOs: 66 and 67.

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, glycine at position 105 with lysine, and lysine at position 109 with leucine (pET22b-AnFX-61D/105K/109L) was obtained with the use of pET22b-AnFX-61D/105K as a template and synthetic oligonucleotides as shown in SEQ ID NOs: 68 and 69.

Strains of *E. coli* BL21 (DE3) were transformed under the same conditions as in Example 1 to obtain strains of *E. coli* BL21 (DE3) (pET22b-AnFX-61D/105K/109L).

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, glycine at position 105 with lysine, lysine at position 109 with leucine, and serine at position 112 with lysine (pET22b-AnFX-61D/105K/109L/112K) was obtained with the use of pET22b-AnFX-61D/105K/109L as a template and synthetic oligonucleotides as shown in SEQ ID NOs: 112 and 70.

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, glycine at position 105 with lysine, lysine at position 109 with leucine, serine at position 112 with lysine, and alanine at position 355 with serine (pET22b-AnFX-61D/105K/109L/112K/355S) was obtained with the use of pET22b-AnFX-61D/105K/109L/112K as a template and synthetic oligonucleotides as shown in SEQ ID NOs: 71 and 72.

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, leucine at position 62 with histidine, glycine at position 105 with lysine, lysine at position 109 with leucine, serine at position 112 with lysine, and alanine at position 355 with serine (pET22b-AnFX-61D/62H/105K/109L/112K/355S) was obtained with the use of pET22b-AnFX-61D/105K/109L/112K/355S as a template and synthetic oligonucleotides as shown in SEQ ID NOs: 73 and 74.

Subsequently, in the same manner as described above, a recombinant plasmid encoding the AnFX gene comprising an amino acid sequence derived from the amino acid sequence as shown in SEQ ID NO: 62 by substitution of arginine at position 61 with aspartic acid, leucine at position 62 with histidine, glutamic acid at position 101 with lysine, glycine at position 105 with lysine, lysine at position 109 with leucine, serine at position 112 with lysine, and alanine at position 355 with serine (pET22b-AnFX-61D/62H/101K/105K/109L/112K/355S) was obtained with the use of pET22b-AnFX-61D/62H/105K/109L/112K/355S as a template and synthetic oligonucleotides as shown in SEQ ID NOs: 75 and 76.

Strains of *E. coli* BL21 (DE3) were transformed under the same conditions as in Example 1 to obtain strains of *E. coli* BL21 (DE3) (pET22b-AnFX-61D/62H/101K/105K/109L/112K/355S).

4. Introduction of Point Mutation into Gene of Fructosyl Peptide Oxidase Derived from *Phaeosphaeria nodorum*

In order to introduce a mutation aimed at improvement of substrate specificity into PnFX, in the same manner as in Example 1, PCR was carried out with the use of the recombinant plasmid pET22b-PnFX prepared in the manner as described above as a template, synthetic oligonucleotides as shown in SEQ ID NOs: 77 and 78, and KOD-Plus- (manufactured by TOYOBO CO., LTD.), strains of *E. coli* JM109 were transformed, and nucleotide sequences of DNAs encoding the PnFX variant in the plasmid DNAs carried on the grown colonies were determined. As a result, a recombinant plasmid encoding the PnFX gene comprising an amino acid sequence derived from the amino acid sequence as shown in SEQ ID NO: 38 by substitution of serine at position 62 with aspartic acid was obtained (pET22b-PnFX-62D).

Subsequently, in the same manner as described above, a recombinant plasmid encoding the PnFX gene comprising an amino acid sequence derived from the amino acid sequence as shown in SEQ ID NO: 38 by substitution of serine at position 62 with aspartic acid and aspartic acid at position 106 with lysine (pET22b-PnFX-62D/106K) was obtained with the use of pET22b-PnFX-62D as a template and synthetic oligonucleotides as shown in SEQ ID NOs: 79 and 80.

Subsequently, in the same manner as described above, a recombinant plasmid encoding the PnFX gene comprising an amino acid sequence derived from the amino acid sequence as shown in SEQ ID NO: 38 by substitution of serine at position 62 with aspartic acid, aspartic acid at position 106 with lysine, and glycine at position 110 with leucine (pET22b-PnFX-62D/106K/110L) was obtained with the use of pET22b-PnFX-62D/106K as a template and synthetic oligonucleotides as shown in SEQ ID NOs: 81 and 82.

Further, in the same manner as described above, a recombinant plasmid encoding the PnFX gene comprising an amino acid sequence derived from the amino acid sequence as shown in SEQ ID NO: 38 by substitution of serine at position 62 with aspartic acid, aspartic acid at position 106 with lysine, glycine at position 110 with leucine, and alanine at position 113 with lysine (pET22b-PnFX-62D/106K/110L/113K) was obtained with the use of pET22b-PnFX-62D/106K/110L as a template and synthetic oligonucleotides as shown in SEQ ID NOs: 83 and 84.

Strains of *E. coli* BL21 (DE3) were transformed under the same conditions as in Example 1 to obtain strains of *E. coli* BL21 (DE3) (pET22b-PnFX-62D/106K/110L/113K).

Further, in the same manner as described above, a recombinant plasmid encoding the PnFX gene comprising an amino acid sequence derived from the amino acid sequence as shown in SEQ ID NO: 38 by substitution of serine at position 62 with aspartic acid, aspartic acid at position 106 with lysine, glycine at position 110 with leucine, alanine at position 113 with lysine, and alanine at position 351 with serine (pET22b-PnFX-62D/106K/110L/113K/351S) was obtained with the use of pET22b-PnFX-62D/106K/110L/113K as a template and synthetic oligonucleotides as shown in SEQ ID NOs: 85 and 86.

Further, in the same manner as described above, a recombinant plasmid encoding the PnFX gene comprising an amino acid sequence derived from the amino acid sequence as shown in SEQ ID NO: 38 by substitution of serine at position 62 with aspartic acid, leucine at position 63 with histidine, aspartic acid at position 106 with lysine, glycine at position 110 with leucine, alanine at position 113 with lysine, and alanine at position 351 with serine (pET22b-PnFX-62D/63H/106K/110L/113K/351S) was obtained with the use of pET22b-PnFX-62D/106K/110L/113K/351S as a template and synthetic oligonucleotides as shown in SEQ ID NOs: 87 and 88.

Strains of *E. coli* BL21 (DE3) were transformed under the same conditions as in Example 1 to obtain strains of *E. coli* BL21 (DE3) (pET22b-PnFX-62D/63H/106K/110L/113K/351S).

5. Introduction of Point Mutation into Gene of Fructosyl Peptide Oxidase Derived from *Cryptococcus neoformans*

SEQ ID NO: 89 shows the amino acid sequence of fructosyl amino acid oxidase derived from *Cryptococcus neoformans* (hereafter referred to as "CnFX"), and it can be prepared by *E. coli* strains carrying the recombinant plasmid pET22b-CnFX into which the gene (SEQ ID NO: 90) encoding the amino acid sequence as shown in SEQ ID NO: 89 has been inserted. CnFX is confirmed to exhibit oxidation activity on αFV and αFVH (see WO 2012/018094).

In order to introduce a mutation aimed at improvement of substrate specificity into CnFX, in the same manner as in Example 1, PCR was carried out with the use of the recombinant plasmid pET22b-CnFX prepared in the manner as described above as a template, synthetic oligonucleotides as shown in SEQ ID NOs: 91 and 92, and KOD-Plus-(manufactured by TOYOBO CO., LTD.), strains of *E. coli* JM109 were transformed, and nucleotide sequences of DNAs encoding the CnFX variant in the plasmid DNAs carried on the grown colonies were determined. As a result, a recombinant plasmid encoding the CnFX gene comprising an amino acid sequence derived from the amino acid sequence as shown in SEQ ID NO: 89 by substitution of arginine at position 62 with aspartic acid was obtained (pET22b-CnFX-62D).

Subsequently, in the same manner as described above, a recombinant plasmid encoding the CnFX gene comprising an amino acid sequence derived from the amino acid sequence as shown in SEQ ID NO: 89 by substitution of arginine at position 62 with aspartic acid and serine at position 106 with lysine (pET22b-CnFX-62D/106K) was obtained with the use of pET22b-CnFX-62D as a template and synthetic oligonucleotides as shown in SEQ ID NOs: 93 and 94.

Subsequently, in the same manner as described above, a recombinant plasmid encoding the CnFX gene comprising an amino acid sequence derived from the amino acid sequence as shown in SEQ ID NO: 89 by substitution of arginine at position 62 with aspartic acid, serine at position 106 with lysine, and serine at position 110 with leucine (pET22b-CnFX-62D/106K/110L) was obtained with the use of pET22b-CnFX-62D/106K as a template and synthetic oligonucleotides as shown in SEQ ID NOs: 95 and 96.

Subsequently, in the same manner as described above, a recombinant plasmid encoding the CnFX gene comprising an amino acid sequence derived from the amino acid sequence as shown in SEQ ID NO: 89 by substitution of arginine at position 62 with aspartic acid, serine at position 106 with lysine, serine at position 110 with leucine, and alanine at position 113 with lysine (pET22b-CnFX-62D/106K/110L/113K) was obtained with the use of pET22b-PnFX-62D/106K/110L as a template and synthetic oligonucleotides as shown in SEQ ID NOs: 97 and 98.

Strains of *E. coli* BL21 (DE3) were transformed under the same conditions as in Example 1 to obtain strains of *E. coli* BL21 (DE3) (pET22b-CnFX-62D/106K/110L/113K).

6. Introduction of Point Mutation into Amadoriase Gene Exhibiting 95% Sequence Identity with Ketoamine Oxidase Derived from *Curvularia clavata*

(Preparation of Amadoriase-Producing Strain Exhibiting 95% Sequence Identity with Ketoamine Oxidase Derived from *Curvularia clavata*)

SEQ ID NO: 99 shows the amino acid sequence of an amadoriase exhibiting 95% sequence identity with ketoamine oxidase derived from *Curvularia clavata* (hereafter referred to as "Cc95FX"). The gene (SEQ ID NO: 100) encoding the amino acid sequence as shown in SEQ ID NO: 99 was obtained via total synthesis of cDNA by a conventional technique of PCR of a gene fragment. The NdeI site and the BamHI were added to the 5' terminus and the 3' terminus of SEQ ID NO: 100, respectively.

In order to express the gene as shown in SEQ ID NO: 100 in *E. coli*, subsequently, the following procedures were performed. The gene obtained via total synthesis above was treated with two types of restriction enzymes, NdeI and BamHI (manufactured by Takara Bio Inc.) and inserted into the NdeI-BamHI site of the pET-22b(+) vector (manufactured by Novagen, Inc.). Thus, the recombinant plasmid pET22b-Cc95FX was obtained. Strains of *E. coli* BL21 (DE3) were transformed under the conditions as described above to obtain strains of *E. coli* BL21 (DE3) (pET22b-Cc95FX). (Introduction of point mutation into amadoriase gene exhibiting 95% sequence identity with ketoamine oxidase derived from *Curvularia clavata*)

In order to introduce a mutation aimed at improvement of substrate specificity into Cc95FX, in the same manner as in Example 1, PCR was carried out with the use of the recombinant plasmid pET22b-Cc95FX prepared in the manner as described above as a template, synthetic oligonucleotides as shown in SEQ ID NOs: 101 and 102, and KOD-Plus-(manufactured by TOYOBO CO., LTD.), strains of *E. coli* JM109 were transformed, and nucleotide sequences of DNAs encoding the Cc95FX variant in the plasmid DNAs carried on the grown colonies were determined. As a result, a recombinant plasmid encoding the Cc95FX gene comprising an amino acid sequence derived from the amino acid sequence as shown in SEQ ID NO: 99 by substitution of arginine at position 62 with aspartic acid was obtained (pET22b-Cc95FX-62D).

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid and aspartic acid at position 106 with lysine (pET22b-Cc95FX-62D/106K) was obtained with the use of pET22b-Cc95FX-62D as a template and synthetic oligonucleotides as shown in SEQ ID NOs: 103 and 104.

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid, aspartic acid at position 106 with lysine, and alanine at position 110 with leucine (pET22h-Cc95FX-62D/106K/110L) was obtained with the use of pET22b-Cc95FX-62D/106K as a template and synthetic oligonucleotides as shown in SEQ ID NOs: 105 and 106.

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid, aspartic acid at position 106 with lysine, alanine at position 110 with leucine, and alanine at position 113 with lysine (pET22b-Cc95FX-62D/106K/110L/113K) was obtained with the use of pET22b-Cc95FX-62D/106K/110L as a template and synthetic oligonucleotides as shown in SEQ ID NOs: 107 and 108.

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid, aspartic acid at position 106 with lysine, alanine at position 110 with leucine, alanine at position 113 with lysine, and alanine at position 353 with serine (pET22b-Cc95FX-62D/106K/110L/113K/353S) was obtained with the use of pET22b-Cc95FX-62D/106K/110L/113K as a template and synthetic oligonucleotides as shown in SEQ 11) NOs: 109 and 110.

Subsequently, in the same manner as described above, a recombinant plasmid encoding the Cc95FX gene comprising an amino acid sequence derived from the amino acid sequence as shown in SEQ ID NO: 99 by substitution of arginine at position 62 with aspartic acid, leucine at position 63 with histidine, aspartic acid at position 106 with lysine, alanine at position 110 with leucine, alanine at position 113 with lysine, and alanine at position 353 with serine (pET22b-Cc95FX-62D/63H/106K/110L/113K/353S) was obtained with the use of pET22b-Cc95FX-62D/106K/110L/113K/353S as a template and synthetic oligonucleotides as shown in SEQ ID NOs: 111 and 102.

Strains of *E. coli* BL21 (DE3) were transformed under the same conditions as in Example 1 to obtain strains of *E. coli* BL21 (DE3) (pET22b-Cc95FX-62D/63H/106K/110L/113K/353S).

Example 4

(Production and Purification of Various Types of Amadoriases)

(Production and Purification of Fructosyl Peptide Oxidase Derived from *Eupenicillium Terrenum*)

*E. coli* JM109 producing wild-type EFP-T5 and *E. coli* JM109 (pUTE100K'-EFP-T5), *E. coli* JM109 (pUTE100K'-EFP-T5-62D), and *E. coli* JM109 (pUTE100K'-EFP-T5-62D/63H/106K/110L/113K/355S) producing the modified EFP-T5 obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 7.0), the washed strains were suspended in the same buffer, the resulting suspension was ultrasonically disintegrated, and the resultant was centrifuged at 20,000×g for 10 minutes to prepare a crude enzyme solution.

To the resulting crude enzyme solution containing the wild-type or modified EFP-T5 enzymes, ammonium sulfate was added to bring the concentration of the solution to 35% saturation, the mixture was agitated, and the resultant was centrifuged at 20,000×g for 10 minutes to collect a supernatant. Subsequently, ammonium sulfate was further added to the supernatant to bring the concentration of the solution to 70% saturation, the mixture was agitated, and the resultant was centrifuged at 20,000×g for 10 minutes. The supernatant was then discarded and the precipitate was dissolved in 10 mM potassium phosphate buffer (pH 7.0).

The resulting crude enzyme solution containing the wild-type or modified EFP-T5 was dialyzed against 10 mM potassium phosphate buffer (pH 6.5), the resultant was applied to 4 ml of Q Sepharose Fast Flow resin (manufactured by GE Healthcare) equilibrated with the buffer, and proteins that are not adsorbed by the resin were eluted with the aid of the buffer. Subsequently, the resulting crude enzyme solution containing the wild-type or modified EFP-T5M enzyme was dialyzed against a 10 mM potassium phosphate buffer (pH 8.0), the resultant was allowed to adsorb to the HiLoad 26/10 Q Sepharose HP column (manufactured by GE Healthcare) equilibrated with the buffer, and the resin was washed with the same buffer. While linearly increasing the concentration of NaCl in the buffer from 0 mM to 100 mM, the wild-type or modified EFP-T5 enzyme which were adsorbed to the resin were then eluted and collected.

The resulting crude enzyme solution containing the wild-type or modified EFP-T5 enzyme was applied to the HiLoad 26/600 Superdex 200 column equilibrated with a 10 mM potassium phosphate buffer (pH 7.0) containing 150 mM NaCl so as to elute the wild-type or modified EFP-T5 enzyme with the same buffer, and a fraction exhibiting activity of fructosyl amino acid oxidase (i.e., amadoriase activity) was collected. The obtained fraction was analyzed via SDS-PAGE to confirm that the fraction was sufficiently purified, so that no other contaminating proteins were present therein, and the fraction was designated to be a purified sample of the wild-type or modified EFP-T5 enzyme.

(Production and Purification of Ketoamine Oxidase Derived from *Neocosmospora vasinfecta*)

*E. coli* BL21 (DE3) producing the wild-type NvFX and *E. coli* BL21 (DE3) (pET22b-NvFX) and *E. coli* BL21 (DE3) (pET22b-NvFX-62D/106K/110L) producing the modified NvFX enzymes obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 8.0), the washed strains were suspended in the same buffer, the resulting suspension was ultrasonically disintegrated, and the resultant was centrifuged at 20,000×g for 10 minutes to prepare a crude enzyme solution.

The resulting crude enzyme solution was allowed to adsorb to Q Sepharose Fast Flow resin (manufactured by GE Healthcare) equilibrated with a 10 mM potassium phosphate buffer (pH 8.0), the resin was washed with a 10 mM potassium phosphate buffer (pH 8.0) containing 20 mM NaCl, and the wild-type or modified NvFX that was adsorbed to the resin was then eluted and collected with the aid of a 10 mM potassium phosphate buffer (pH 8.0) containing 300 mM NaCl.

The resulting crude enzyme solution containing the wild-type or modified NvFX was applied to the HiLoad 26/600 Superdex 200 column equilibrated with a 20 mM MES-NaOH buffer (pH 7.0) containing 150 mM NaCl so as to elute the wild-type or modified NvFX with the same buffer, and a fraction exhibiting activity of fructosyl amino acid oxidase (i.e., amadoriase activity) was collected. The obtained fraction was analyzed via SDS-PAGE to confirm that the fraction was sufficiently purified, so that no other contaminating proteins were present therein, and the fraction was designated to be a purified sample of the wild-type or modified NvFX.

(Production and Purification of Fructosyl Amino Acid Oxidase Derived from *Aspergillus nidulans*)

*E. coli* BL21 (DE3) producing the wild-type AnFX and *E. coli* BL21 (DE3) (pET22b-AnFX-61D/105K/109L) and *E. coli* BL21 (DE3) (pET22b-AnFX-61D/62H/101K/105K/109L/112K/355S) producing the modified AnFX enzymes obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 6.0), the washed strains were suspended in the same buffer, the resulting suspension was ultrasonically disintegrated, and the resultant was centrifuged at 20,000×g for 10 minutes to prepare a crude enzyme solution.

The resulting crude enzyme solution was allowed to adsorb to SP Sepharose Fast Flow resin (manufactured by GE Healthcare) equilibrated with a 10 mM potassium phosphate buffer (pH 6.0), the resin was washed with a 10 mM potassium phosphate buffer (pH 6.0) containing 20 mM NaCl, and the modified AnFX that was adsorbed to the resin was then eluted and collected with the aid of a 10 mM potassium phosphate buffer (pH 6.0) containing 100 mM NaCl.

The resulting crude enzyme solutions containing the modified AnFX were applied to the HiLoad 26/600 Superdex 200 column equilibrated with a 20 mM MES-NaOH buffer (pH 7.0) containing 150 mM NaCl so as to elute modified AnFX with the same buffer, and a fraction exhibiting activity of fructosyl amino acid oxidase (i.e., amadoriase activity) was collected. The obtained fraction was analyzed via SDS-PAGE to confirm that the fraction was sufficiently purified, so that no other contaminating proteins were present therein, and the fraction was designated to be a purified sample of the modified AnFX.

(Production and Purification of Fructosyl Peptide Oxidase Derived from *Phaeosphaeria nodorum*)

*E. coli* BL21 (DE3) (pET22b-PnFX-62D/106K/110L/113K) and *E. coli* BL21 (DE3) (pET22b-PnFX-62D/63H/106K/110L/113K/351S) producing the modified AnFX obtained in the manner described above were purified in accordance with the method for purification of the wild-type PnFX described above. After the completion of purification with the HiLoad 26/600 Superdex 200 column, the degree of purification was analyzed via SDS-PAGE to confirm that the fraction was sufficiently purified, so that no other contaminating proteins were present therein, and the fraction was designated to be a purified sample of the modified PnFX.

(Production and Purification of Ketoamine Oxidase Derived from *Cryptococcus neoformans*)

*E. coli* BL21 (DE3) producing the wild-type CnFX and *E. coli* BL21 (DE3) (pET22h-CnFX) and *E. coli* BL21 (DE3) (pET22h-CnFX-62D/106K/110L/113K) producing the modified CnFX obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 8.0), the washed strains were suspended in the same buffer, the resulting suspension was ultrasonically disintegrated, and the resultant was centrifuged at 20,000×g for 10 minutes to prepare the crude enzyme solution.

The resulting crude enzyme solution was allowed to adsorb to Q Sepharose Fast Flow resin (manufactured by GE Healthcare) equilibrated with a 10 mM potassium phosphate buffer (pH 8.0), the resin was washed with a 10 mM potassium phosphate buffer (pH 8.0) containing 20 mM NaCl, and the wild-type or modified CnFX that was adsorbed to the resin was then eluted and collected with the aid of a 10 mM potassium phosphate buffer (pH 8.0) containing 300 mM NaCl.

The resulting crude enzyme solution containing the wild-type or modified CnFX was applied to the HiLoad 26/600 Superdex 200 column equilibrated with a 20 mM MES-NaOH buffer (pH 7.0) containing 150 mM NaCl so as to elute the wild-type or modified CnFX with the same buffer, and a fraction exhibiting activity of fructosyl amino acid oxidase (i.e., amadoriase activity) was collected. The obtained fraction was analyzed via SDS-PAGE to confirm that the fraction was sufficiently purified, so that no other contaminating proteins were present therein, and the fraction was designated to be a purified sample of the wild-type or modified CnFX.

(Preparation of Amadoriase Exhibiting 95% Sequence Identity with Ketoamine Oxidase Derived from *Curvularia clavata*)

*E. coli* JM109 producing the wild-type Cc95FX and *E. coli* JM109 (pET22b-Cc95FX) and *E. coli* JM109 (pET22b-Cc95FX-62D/63H/106K/110L/113K/355S) producing the modified Cc95FX obtained in the manner described above were inoculated into LB-amp media supplemented with IPTG (final concentration: 0.1 mM) and cultured therein at 25° C. for 16 hours. The resulting cultured strains were washed with a 10 mM potassium phosphate buffer (pH 7.0), the washed strains were suspended in the same buffer, the resulting suspension was ultrasonically disintegrated, and the resultant was centrifuged at 20,000×g for 10 minutes to prepare a crude enzyme solution.

With the use of the purified samples of various types of wild-type amadoriases and modified enzymes, specific activity thereof relative to αF6P as substrates was measured. The results are shown in Table 15. Concentration of a protein used for calculation of specific activity was determined by the ultraviolet absorption method involving the use of the absorbance at 280 nm (see Protein Sci., 4, 2411-23, 1995).

A crude enzyme solution containing Cc95FX or Cc95FX-62D/63H/106K/110L/113K/355S was subjected to measurement of oxidation activity on αFV, αFVH, and αF6P by the method described in the "B: Method of activity measurement" above. Oxidation activity on substrates, αF6P/αFVH, and αF6P/αFV of amadoriases relative to αFVH oxidation activity designated to be 100 are as shown in Table 16.

TABLE 15

| Amadoriase | Amino acid variation | Specific activity (U/mg) 1 mM αF6P |
|---|---|---|
| EFP-T5 (Comparative Example 4) | None | 0 |
| EFP-T5-R62D (Amadoriase 27) | R62D | 0.0043 |
| EFP-T5-62D/63H/106K/110L/113K/355S (Amadoriase 28) | R62D, L63H, N106K, K110L, T113K, A355S | 1.12 |
| NvFX (Comparative Example 5) | None | 0 |
| NvFX-62D/106K/110L (Amadoriase 29) | R62D, G106K, E110L | 0.0030 |
| AnFX (Comparative Example 6) | None | 0 |
| AnFX-61D/105K/109L (Amadoriase 30) | R61D, G105K, K109L | 0.106 |
| AnFX-61D/62H/101K/105K/109L/112K/355S (Amadoriase 31) | R61D, L62H, E101K, G105K, K109L, S112K, A355S | 0.283 |
| PnFX (Comparative Example 3) | None | 0.0091 |
| PnFX-62D/106K/110L/113K (Amadoriase 32) | S62D, D106K, G110L, A113K | 0.125 |
| PnFX-62D/63H/106K/110L/113K/351S (Amadoriase 33) | S62D, L63H, D106K, G110L, A113K, A351S | 0.667 |
| CnFX (Comparative Example 7) | None | 0 |
| CnFX-62D/106K/110L/113K (Amadoriase 34) | R62D, S106K, S110L, A113K | 0.342 |

TABLE 16

| Amadoriase | Amino acid substitution | αFV oxidation activity | αFVH oxidation activity | αF6P oxidation activity | αF6P/ αFVH | αF6P/ αFV |
|---|---|---|---|---|---|---|
| Cc95FX (Comparative Example 8) | None | | 100 | 0 | 0 | 0 |
| Cc95FX-62D/63H/106K/110L/113K/353S (Amadoriase 35) | R62D/L63H/ D106K/A110L/ A113K/A353S | 16400 | 100 | 237 | 2.37 | 0.0144 |

As a result of introducing into various amadoriases the amino acid substitutions which confer or enhance reactivity with αF6P, in comparison with the amadoriase from *Coniochaeta* obtained in accordance with the procedure described herein (CFP-T7; Comparative Example 1), a new trait; i.e., reactivity with αF6P, was newly conferred upon EFP-T5, NvFX, AnFX, and CnFX, as expected. While PnFX had exhibited a minor level of reactivity with αF6P prior to mutation, specific activity on αF6P was elevated by 13.7 fold as a result of introduction of the amino acid substitution described herein.

Further, amino acid substitution aimed at addition or enhancement of reactivity with αF6P relative to the amadoriase derived from *Coniochaeta* obtained in accordance with the procedure described herein (CFP-T7; Comparative Example 1) was introduced into an amadoriase (Cc95FX; Comparative Example 8) exhibiting 95% sequence identity with the ketoamine oxidase derived from *Curvularia clavata* obtained in accordance with the procedure described herein. As a result and as expected, reactivity with αF6P, was newly conferred upon Cc95FX, and regarding Cc95FX-62D/63H/106K/110L/113K/355S, αF6P oxidation activity exceeded αFVH oxidation activity.

Figures 1, 2:
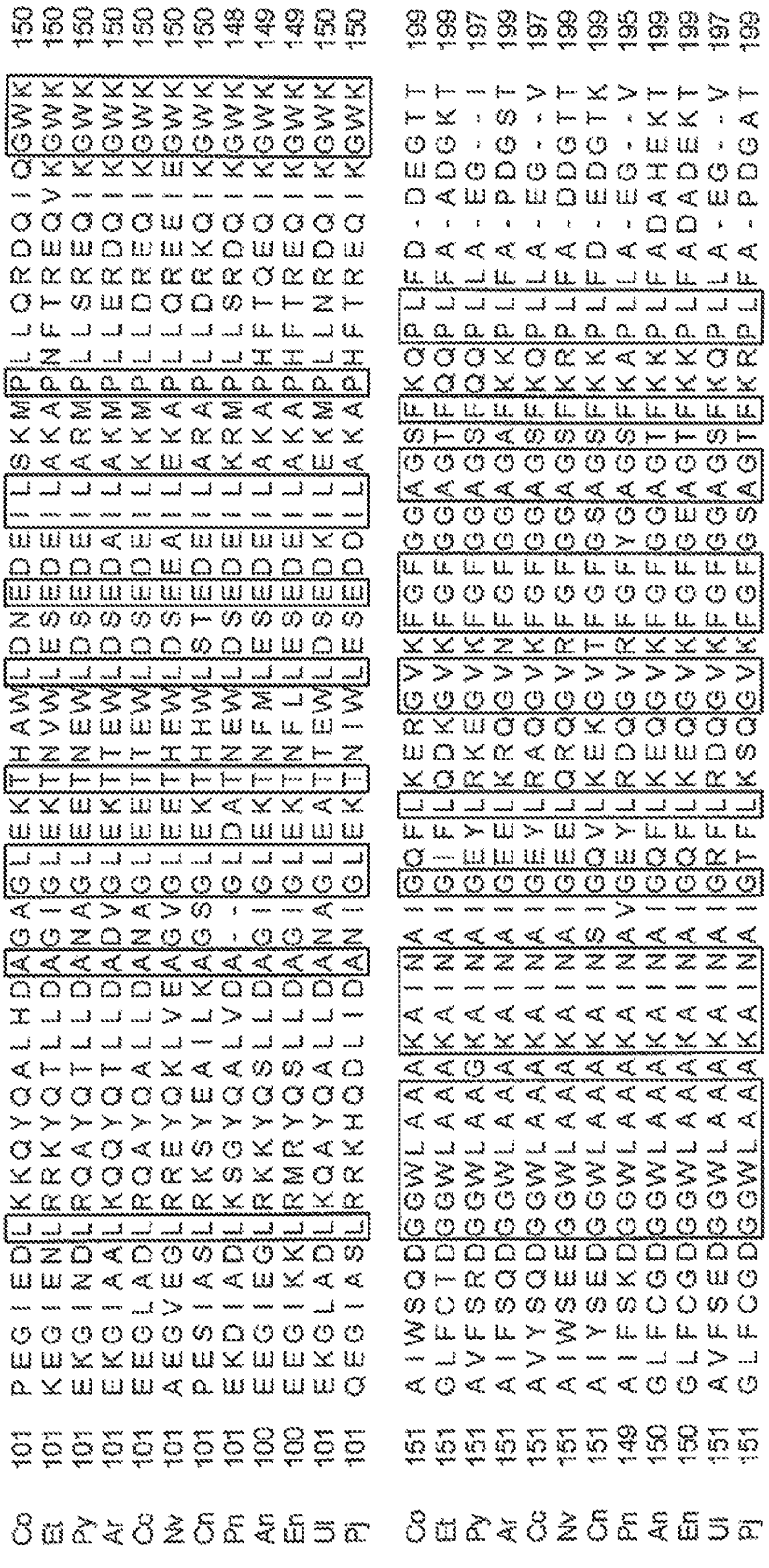

That is, the effects of amino acid substitution aimed at addition or enhancement of reactivity with αF6P to the amadoriase derived from *Coniochaeta* described herein are not limited to the amadoriase derived from *Coniochaeta* but rather, reactivity with αF6P was added to or enhanced similarly in general in amadoriases exhibiting 74% or higher sequence identity with the amadoriase derived from *Coniochaeta* as shown in FIGS. 1 and 2.

The tables below show the amino acids at positions 62, 63, 102, 106, 110, 113, 355, and 419 and amino acids after substitution, if any, of the variants of the present invention and of the Comparative Examples.

TABLE 17

| | Comparative Example 1 | Comparative Example 3 | Comparative Example 5 | Comparative Example 6 | Comparative Example 4 | Comparative Example 7 | Comparative Example 8 | Comparative Example 2 |
|---|---|---|---|---|---|---|---|---|
| Name | CFP-T7 | PnFX | NvFX | AnFX | EFP-T5 | CnFX | Cc95FX | FAOAo2 |
| Origin | *Coniochaeta* sp. | *Phaeosphaeria nodorum* | *Neocosmospora vasinfecta* | *Aspergillus nidulans* | *Eupenicillium terrenum* | *Cryptococcus neoformans* | *Curvularia clavata* | *Aspergillus oryzae* |
| SEQ ID NO<br>aa position | SEQ 1 | SEQ 38 | SEQ 54 | SEQ 62 (SEQ 147) | SEQ 40 (SEQ 145) | SEQ 89 (SEQ 149) | SEQ 99 | SEQ 36 |
| 62 | R | S | R | R61 | R | R | R | |
| 63 | L | L | L | L62 | L | I | L | |
| 102 | E | K | E | E101 | E | E | E | |
| 106 | D | D | G | G105 | N | S | D | |
| 110 | Q | G | E | K109 | K | S | A | |
| 113 | A | A | K | S112 | T | A | A | |
| 355 | A | A351 | S | A | A | A | A353 | |
| 419 | A | S416 | A420 | A420 | G | A420 | S418 | |

TABLE 18

| | Name | | | | | |
|---|---|---|---|---|---|---|
| | PyFX | ArFX | CcFX | EnFX | UlFX | PjFX |
| | Origin | | | | | |
| | *Pyrenochaeta* sp. | *Arthrinium* sp. | *Curvularia clavata* | *Emericella nidulans* | *Ulocladium* sp. | *Penicillium janthinellum* |
| | SEQ ID NO | | | | | |
| aa position | SEQ 113 | SEQ 115 | SEQ 117 | SEQ 119 | SEQ 121 | SEQ 123 |
| 62 | R | R | R | R61 | R | R |
| 63 | L | L | L | L62 | L | L |
| 102 | K | K | E | E101 | K | E |
| 106 | D | A | D | K105 | D | S |
| 110 | A | Q | A | R109 | A | K |
| 113 | T | T | A | S112 | A | D |
| 355 | A353 | A356 | A353 | A | A353 | A |
| 419 | A418 | A421 | A418 | A420 | A418 | S |

TABLE 19

| | Amadoriase 26 | Amadoriase 1 | Amadoriase 2 | Amadoriase 4 | Amadoriase 5 | Amadoriase 6 | Amadoriase 27 |
|---|---|---|---|---|---|---|---|
| | Name | | | | | | |
| | CFP-T7-62D | CFP-T7-H1 | CFP-T7-H2 | CFP-T7-H4 | CFP-T7-H2-62N | CFP-T7-H6 | EFP-T5-R62D |
| | Origin | | | | | | |
| | *Coniochaeta* sp. | *Coniochaeta* sp. | *Coniochaeta* sp. | *Coniochaeta* sp. | *Coniochaeta* sp. | *Coniochaeta* sp. | *Eupenicillium terrenum* |
| | SEQ ID NO | | | | | | |
| aa position | SEQ 153 | SEQ 151 | SEQ 157 | SEQ 159 | SEQ 161 | SEQ 163 | SEQ 155 |
| 62 | R62D | R62A | R62A | R62A | R62N | R62D | R62D |
| 63 | | | | | | | |
| 102 | | | | | | | |
| 106 | | | | | | | |
| 110 | | | Q110L | Q110Y | Q110L | Q110L | |
| 113 | | | | | | | |
| 355 | | | | | | | |
| 419 | | | | | | | |

TABLE 20

| | Amadoriase 12 | Amadoriase 13 | Amadoriase 14 | Amadoriase 15 | Amadoriase 16 | Amadoriase 29 | Amadoriase 30 |
|---|---|---|---|---|---|---|---|
| | Name | | | | | | |
| | CFP-T7-H10 | CFP-T7-H11 | CFP-T7-H12 | CFP-T7-H13 | CFP-T7-H14 | NvFX-62D/106K/110L | AnFX-61D/105K/109L |
| | Origin | | | | | | |
| | *Coniochaeta* sp. | *Coniochaeta* sp. | *Coniochaeta* sp. | *Coniochaeta* sp. | *Coniochaeta* sp. | *Neocosmospora vasinfecta* | *Aspergillus nidulans* |
| | SEQ ID NO | | | | | | |
| aa position | SEQ 165 | SEQ 167 | SEQ 169 | SEQ 171 | SEQ 173 | SEQ 137 | SEQ 139 |
| 62 | R62D | R62D | R62D | R62D | R62D | R62D | R61D |
| 63 | | | | | | | |
| 102 | | | | | | | |
| 106 | D106A | D106K | D106R | | | G106K | G105K |
| 110 | Q110L | Q110L | Q110L | Q110L | Q110L | E110L | K109L |
| 113 | | | | A113K | A113R | | |
| 355 | | | | | | | |
| 419 | | | | | | | |

TABLE 21

| | Amadoriase 17 | Amadoriase 18 | Amadoriase 19 | Amadoriase 21 | Amadoriase 32 | Amadoriase 34 |
|---|---|---|---|---|---|---|
| | Name | | | | | |
| | CFP-T7-H20 | CFP-T7-H21 | CFP-T7-H24 | CFP-T7-H26 | PnFX-62D/ 106K/110L/113K | CnFX-62D/ 106K/110L/113K |
| | Origin | | | | | |
| | *Coniochaeta* sp. | *Coniochaeta* sp. | *Coniochaeta* sp. | *Coniochaeta* sp. | *Phaeosphaeria nodorum* | *Cryptococcus neoformans* |
| | SEQ ID NO | | | | | |
| aa position | SEQ 133 | SEQ 175 | SEQ 177 | SEQ 179 | SEQ 135 | SEQ 1S9 |
| 62 | R62D | R62D | R62D | R62D | S62D | R62D |
| 63 | | | L63A | L63H | | |
| 102 | | | | | | |
| 106 | D106K | D106K | D106K | D106K | D106K | S106K |
| 110 | Q110L | Q110L | Q110L | Q110L | Q110L | S110L |
| 113 | A113K | A113R | A113K | A113K | A113K | A113K |
| 355 | | | | | | |
| 419 | | | | | | |

TABLE 22

| | Amadoriase 23 | Amadoriase 24 | Amadoriase 25 | Amadoriase 33 | Amadoriase 31 | Amadoriase 28 | Amadoriase 35 |
|---|---|---|---|---|---|---|---|
| | Name | | | | | | |
| | CFP-T7H28 | CFP-T7-H29 | CFP-T7-H35 | PnFX-62D/ 106K/110L/ 113K/351S | AnFX-61D/ 62H/101K/ 105K/109L/ 112K/355S | EFP-T5-62D/ 63H/106K/ 110L/113K/ 355S | Cc95FX-62D/ 63H/106K/ 110L/113K/ 353S |
| | Origin | | | | | | |
| | *Coniochaeta* sp. | *Coniochaeta* sp. | *Coniochaeta* sp. | *Phaeosphaeria nodorum* | *Aspergillus nidulans* | *Eupenicillium terrenum* | *Curvularia clavata* |
| | SEQ ID NO | | | | | | |
| aa position | SEQ 181 | SEQ 183 | SEQ 141 | SEQ 187 | SEQ 185 | SEQ 143 | SEQ 191 |
| 62 | R62D | R62D | R62D | S62D | R61D | R62D | R62D |
| 63 | L63H | L63H | L63H | L63H | L62H | L63H | L63H |
| 102 | E102K | | E102K | | E101K | | |
| 106 | D106K | D106K | D106K | D106K | G105K | N106K | D106K |
| 110 | Q110L | Q110L | Q110L | G110L | K109L | K110L | A110L |
| 113 | A113K | A113K | A113K | A113K | S112K | T113K | A113K |
| 355 | | | A355S | A351S | A355S | A355S | A353S |
| 419 | | A419K | | | | | |

As demonstrated above. CFP-T7-H35 was found to recognize, as substrates, not only αFV and αFVH but also glycated peptides with long peptide chains (i.e., αF3P, αF4P, αF5P, αF6P, αF8P, and αF16P), which could not be recognized as substrates by wild-type enzymes (CFP-T7).

Based on such finding, variants comprising similar mutations at positions corresponding to the positions in the amino acid sequence as shown in SEQ ID NO: 1 were prepared in the manner described above and as a result, such variants were also found to exhibit activity on αF6P. Accordingly, such variants are also considered to exhibit activity not only on αFV, αFVH, and αF6P but also on αF3P, αF4P, αF5P, αF8P, and αF16P, as CFP-T7-H35 does. Further, since CFP-T7-H35 was found to recognize αFV, αFVH, αF3P, αF4P, αF5P, αF6P, αF8P, and αF16P as substrates. CFP-T7-H35 is also believed to recognize α-fructosyl peptides including αF7P and αF9P to αF15P (αF1P to αF16P) and α-fructosyl peptides including αFV to αF32P as substrates. Such amadoriase variants can be used for quantification of HbA1c. Since these amadoriases are capable of reacting with α-fructosyl peptides of various lengths, in addition to αFVH, quantification of HbA1c can be performed with high accuracy, regardless of the length of each cleaved α-fructosyl peptide and the proportion thereof within the whole, and even if the protease used for cleaving an α-fructosyl peptide from HbA1c is one that exhibits high cleavage efficiency but low cleavage specificity and complete degradation to αFVH is not achieved. In addition, the protease used for cleaving an α-fructosyl peptide from HbA1c need not be limited to a protease that cleaves αF6P with high cleavage specificity. Rather, other proteases that can readily be obtained with low cleavage specificity can also be used for quantification of HbA1c.

Example 5

(Quantification of α-Fructosyl Peptides)

Reagents for measurement having the compositions described below were prepared and α3P, α4P, α5P, α6P, α8P, and α16P were measured with the use of Bio Majesty JCA-BM1650 (JEOL Ltd.) in the manner as described below.

Sample 1: α-Fructosyl Peptide Solution (Final Concentration: 0.50 to 4.0 μM)

Solutions of α3P, α4P, α5P, α6P, α8P, and α16P at various concentrations (i.e., 4.0 μM, 8.0 μM, 16 μM, 24 μM, and 32

μM) were prepared. Ion exchange water was used as a solution of α-fructosyl peptide at 0 μM.

Reagent 4: Leucodye, Peroxidase Solution 120 mM MES-NaOH buffer (pH 6.5)

0.16 mM N-(carboxymethylaminocarbonyl)-4,4'-bis(dimethylamino)diphenylamine sodium (DA-64, Wako Pure Chemical Industries, Ltd.)

16 U/ml peroxidase (Kikkoman Corporation)

Reagent 5: CFP-T7-H35 Solution 120 mM MES-NaOH buffer (pH 6.5)

100 U/ml (23.4 mg/ml) CFP-T7-H35 (Amadoriase 25)

The unit "U/ml" indicates reactivity with 1 mM αF6P.

Figures 1, 2, 3:
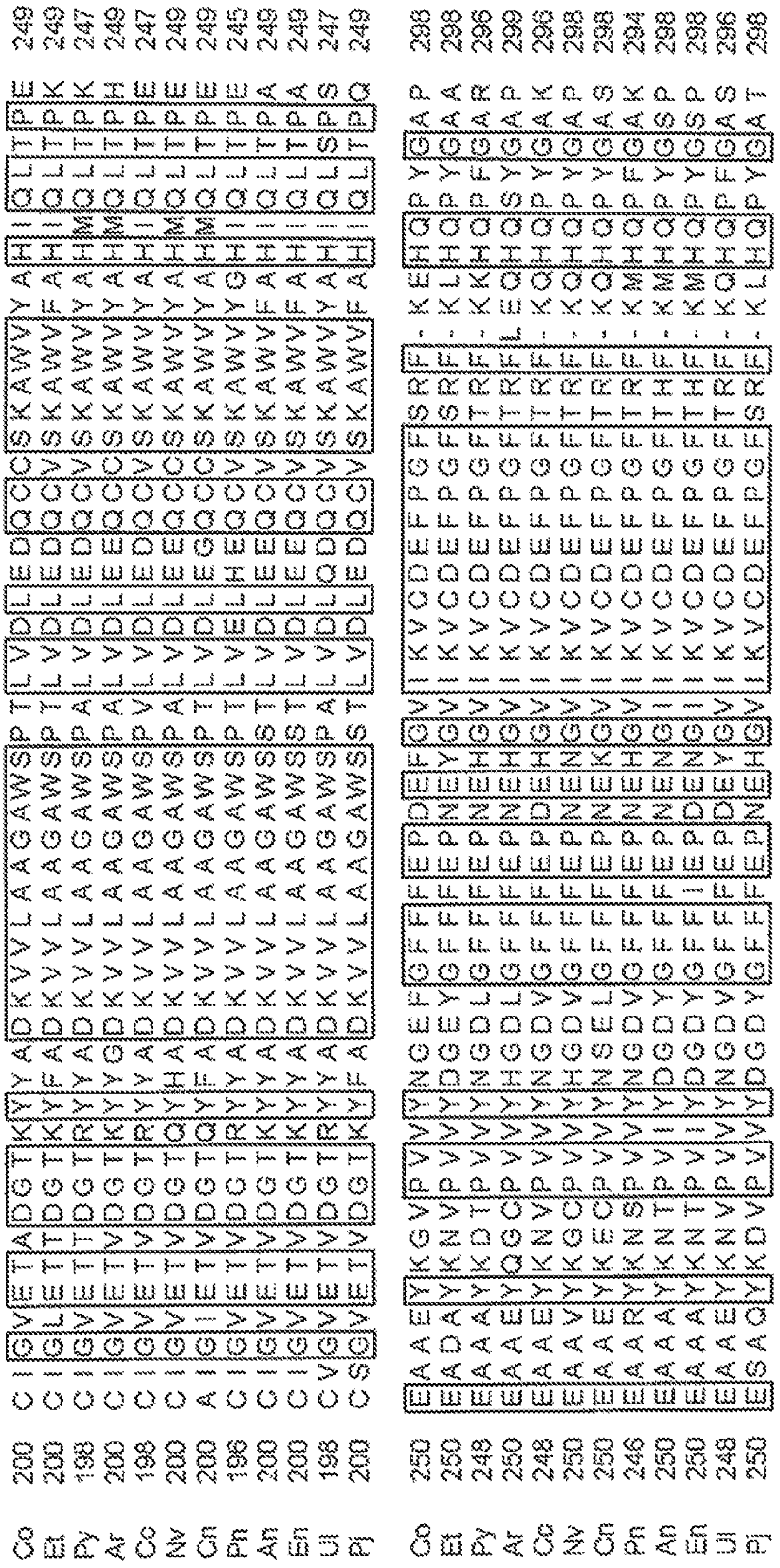
Figures 1, 2:
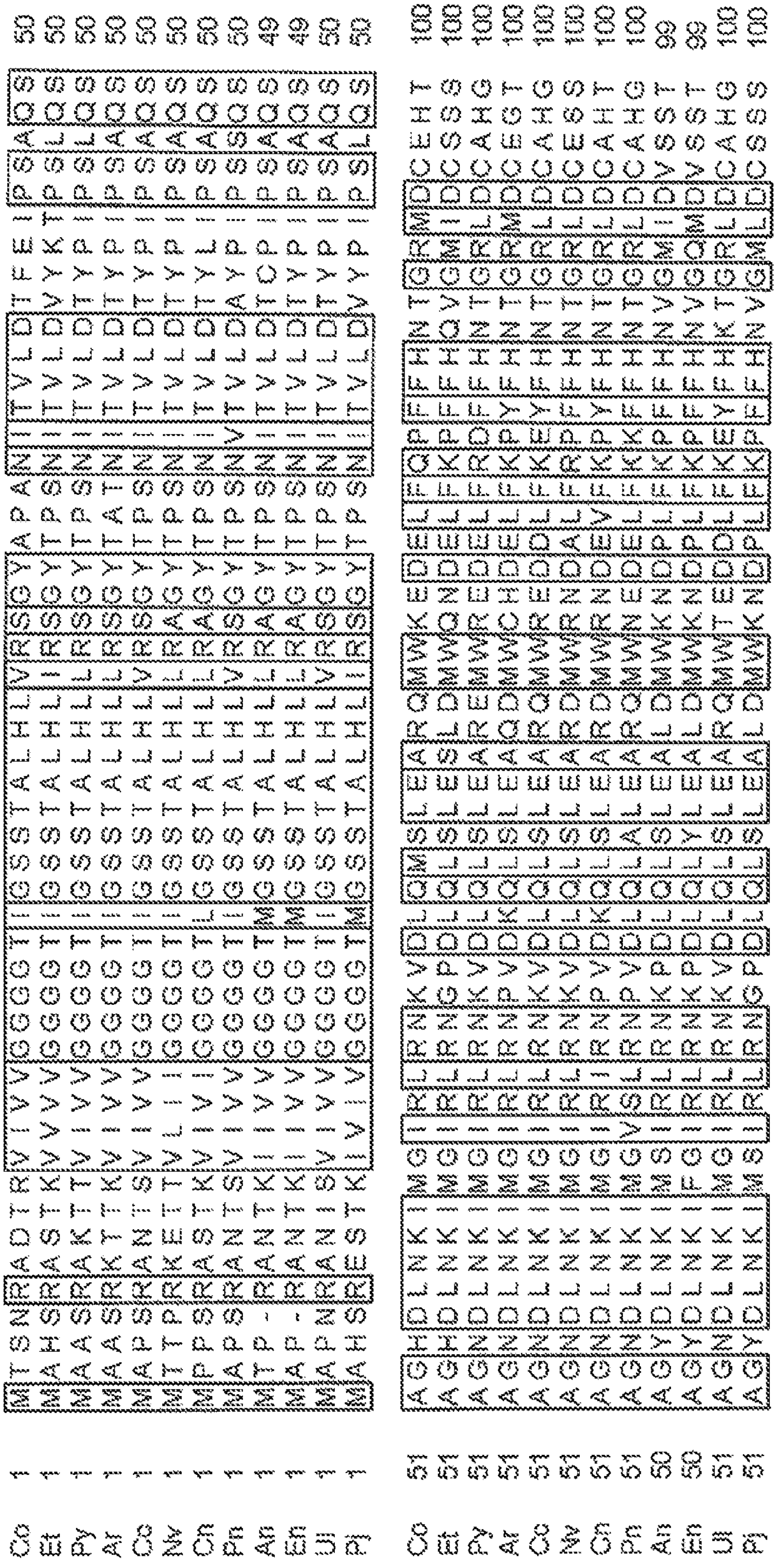
Figures 2, 3:
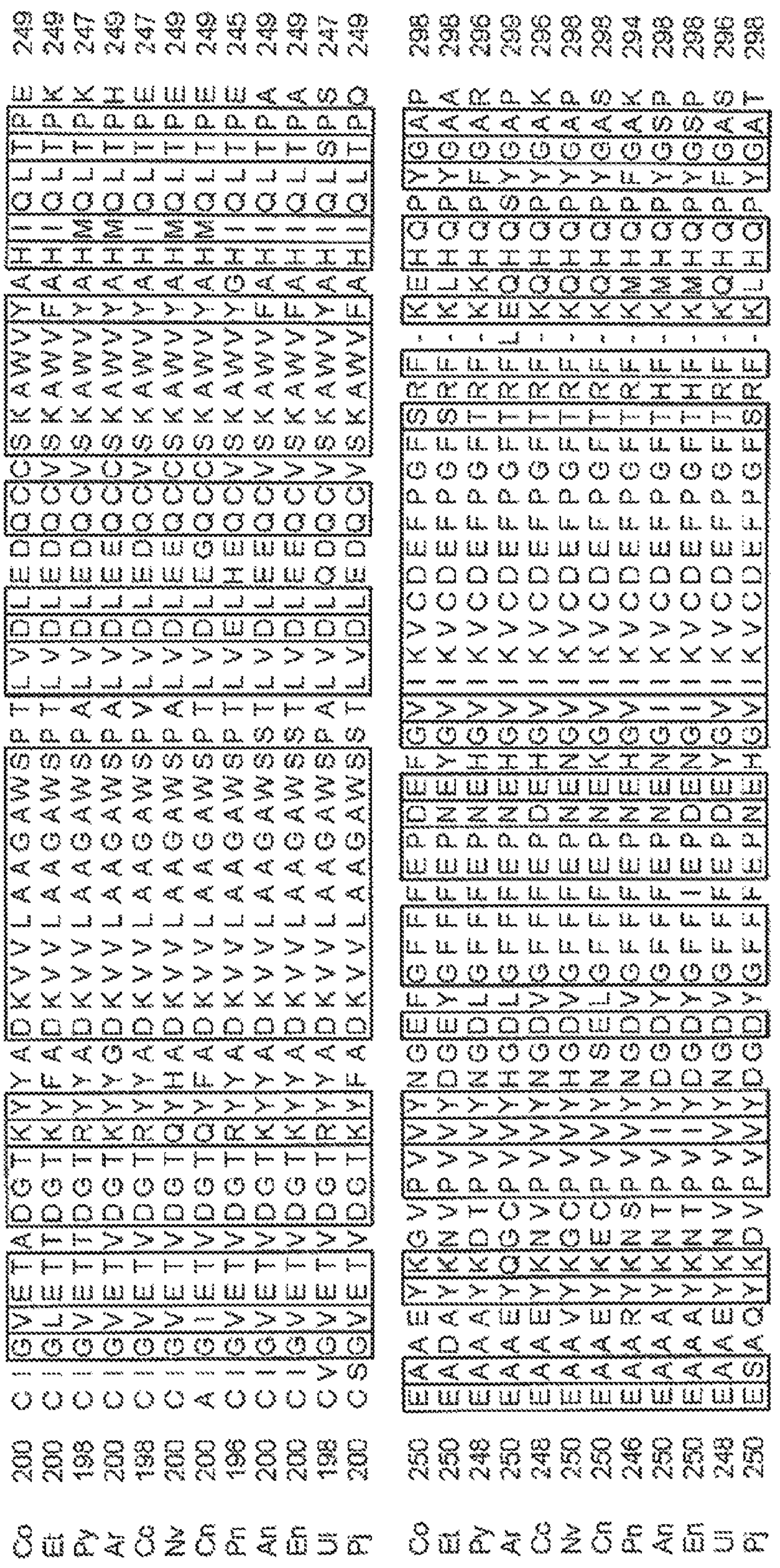
Figures 2, 3, 4:
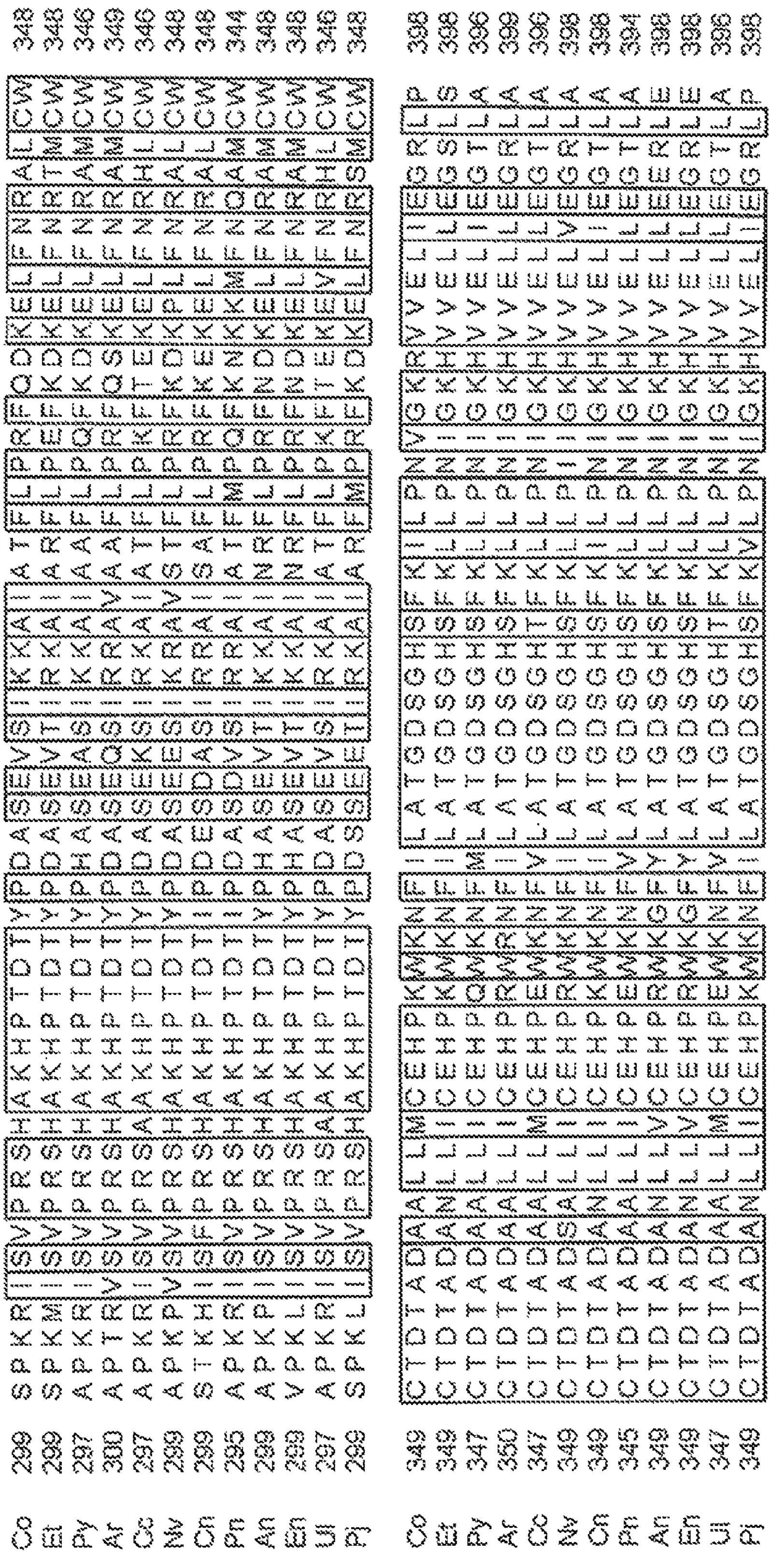
Figures 1, 3:
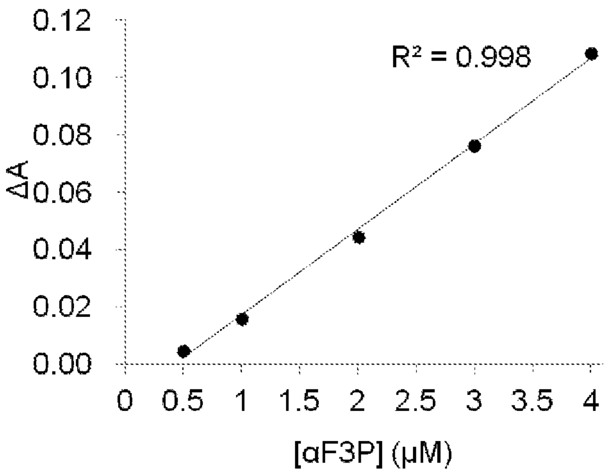
Figures 2, 3:
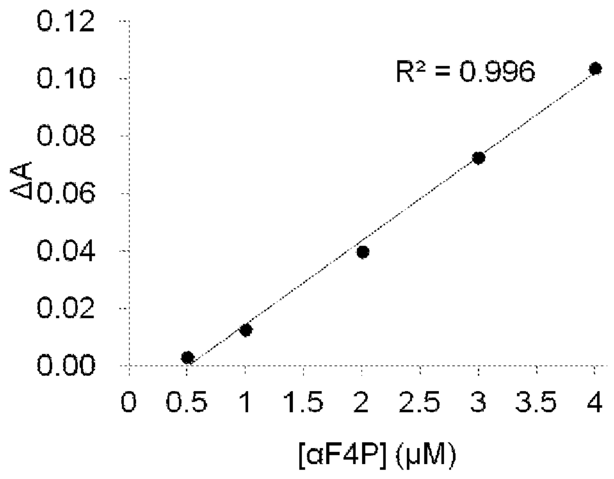
Figure 3:
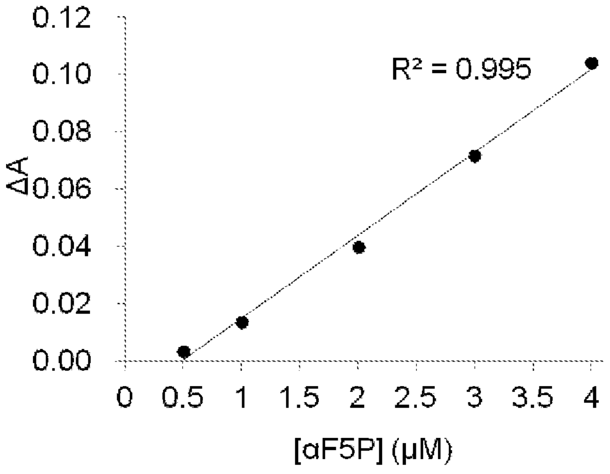
Figures 3, 4:
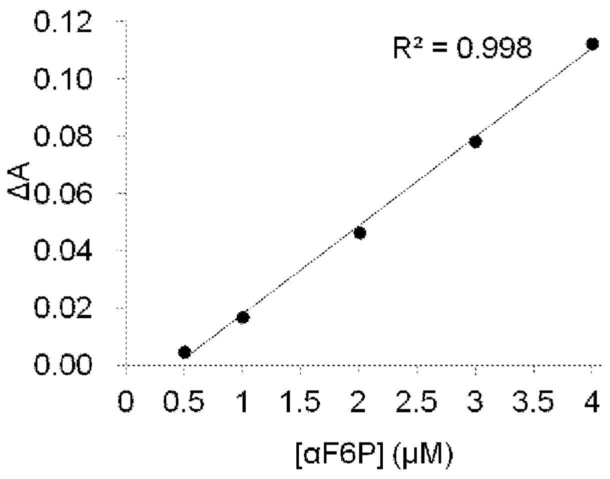
Figures 3, 4, 5:
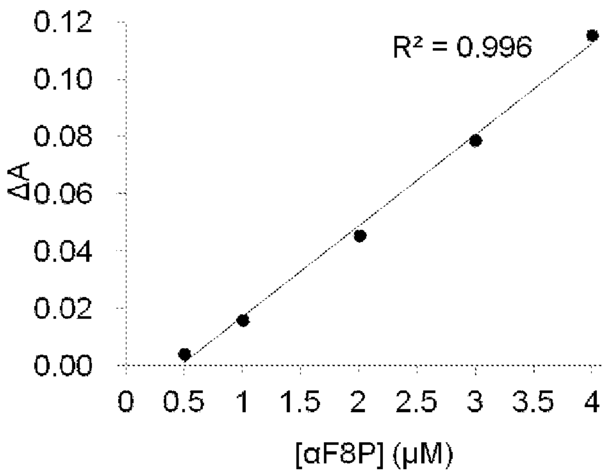
Figures 3, 4, 5, 6:
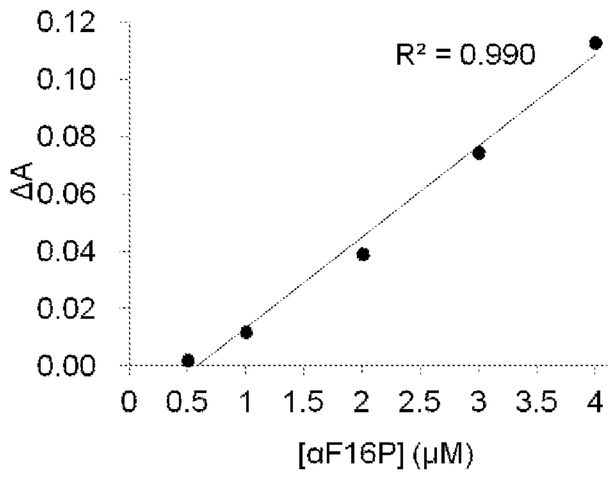

Sample 1 (25 μl) was added to 125 μl of Reagent 4, the resultant was incubated at 37° C. for 5 minutes, and the absorbance of light at 751 nm was then measured ($A_0$). Subsequently, 50 μl of Reagent 5 was added, a quantitative reaction of hydrogen peroxide generated upon oxidation of α-fructosyl peptide was allowed to proceed at 37° C. for 5 minutes, and the absorbance of light at 751 nm was measured again ($A_5$). FIG. 3 shows a chart demonstrating the final concentration of α-fructosyl peptides derived from Sample 1 plotted on the horizontal axis and differences in the absorbance before and after the quantitative reaction of hydrogen peroxide ΔA ($A_5$-$A_0$) plotted on the vertical axis. The differences in the absorbance (ΔA) shown in the chart are values determined by subtracting the value ΔA of the blank measurement (ion exchange water was used as Sample 1).

A favorable correlation was established between ΔA and concentration of each α-fructosyl peptide in the range of the final concentration at 0.50 μM and 4.0 μM (FIGS. 3-1 to 3-6). It was thus demonstrated that quantification of α-fructosyl peptide could be performed rapidly (within 5 minutes) with high sensitivity (up to 0.5 μM) by incorporating the amadoriase of the present invention (CFP-T7-H35) into reagents.

In the present example, substrates (i.e., αF3P, αF4P, αF5P, αF8P, and αF16P) were quantified with the use of the amadoriase of the present invention (CFP-T7-H35). With the use of the amadoriase of the present invention, accordingly, it is believed that quantification of substrates αF7P and αF9P to αF15P can also be performed in a similar manner.

Example 6

(Quantification of α-Fructosyl-Valyl-Histidine Samples Containing α-Fructosyl Peptides)

Reagents for measurement having the compositions described below were prepared and α-fructosyl-valyl-histidine (αF2P) samples containing α-fructosyl peptides were measured with the use of Bio Majesty JCA-BM1650 (JEOL Ltd.) in the manner as described below.

Sample 2: α-Fructosyl-Valyl-Histidine Solutions Containing α-Fructosyl Peptides

Samples (9 types: 2A to 2I) as described below were prepared.

Sample 2A: Ion Exchange Water

Sample 2B: 20 μM α-Fructosyl-Valyl-Histidine (αF2P)

Sample 2C: 16 μM αF2P

Sample 2D: 16 μM αF2P+4 μM αF3P

Sample 2E: 16 μM αF2P+4 μM αF4P

Sample 2F: 16 μM αF2P+4 μM αF5P

Sample 2G: 16 μM αF2P+4 μM αF6P

Sample 2H: 16 μM αF2P+4 μM αF8P

Sample 2I: 16 μM αF2P+4 μM αF16P

Samples 2D to 2I were prepared by complementing the difference in αF2P concentration between Sample 2B and Sample 2C (4 μM, which is equivalent to 0.5 μM in terms of the final concentration) with other α-fructosyl peptides.

Reagent 4: Leucodye, Peroxidase Solution 120 mM MES-NaOH buffer (pH 6.5)

0.16 mM N-(carboxymethylaminocarbonyl)-4,4'-bis(dimethylamino)diphenylamine sodium (DA-64, Wako Pure Chemical Industries, Ltd.)

16 U/ml peroxidase (Kikkoman Corporation)

Reagent 6: CFP-T7-H35 Solution 120 mM MES-NaOH buffer (pH 6.5)

50 U/ml (11.7 mg/ml) CFP-T7-H35 (Amadoriase 25)

The unit "U/ml" indicates reactivity with 1 mM αF6P.

Reagent 7: CFP-T7 Solution 120 mM MES-NaOH buffer (pH 6.5)

11.7 mg/ml CFP-T7 (Comparative Example 1)

Sample 2 (25 μl) was added to 125 μl of Reagent 4, the resultant was incubated at 37° C. for 5 minutes, and the absorbance of light at 751 nm was then measured ($A_0$). Subsequently, 50 μl of Reagent 6 or 7 was added, a quantitative reaction of hydrogen peroxide generated upon oxidation of α-fructosyl peptide was allowed to proceed at 37° C. for 5 minutes, and the absorbance of light at 751 nm was measured again ($A_5$). Table 23 shows the results of measurement attained with the use of Reagent 6, which were attained by determining the differences in the absorbance before and after the quantitative reaction of hydrogen peroxide of each sample ΔA ($A_5$-$A_0$) and subtracting the ΔA value of Sample 2A, which was subjected to blank measurement, from the ΔA values of Samples 2B to 2I. Table 24 shows the results of measurement attained with the use of Reagent 7. Relative values are calculated based on the difference in the absorbance ΔA determined at the time of measurement of Sample 2B designated to be 100%.

TABLE 23

| | Sample | | | | | | | |
|---|---|---|---|---|---|---|---|---|
| | 2B | 2C | 2D | 2E | 2F | 2G | 2H | 2I |
| ΔA | 0.082 | 0.064 | 0.081 | 0.080 | 0.085 | 0.083 | 0.084 | 0.078 |
| Relative value (%) | 100 | 79 | 99 | 98 | 104 | 101 | 103 | 95 |

TABLE 24

| | Sample | | | | | | | |
|---|---|---|---|---|---|---|---|---|
| | 2B | 2C | 2D | 2E | 2F | 2G | 2H | 2I |
| ΔA | 0.109 | 0.087 | 0.089 | 0.087 | 0.089 | 0.090 | 0.089 | 0.089 |
| Relative value (%) | 100 | 79 | 82 | 80 | 81 | 82 | 81 | 82 |

Table 23 shows the values relative to the ΔA values of Samples 2D to 2I that are within ±5% from the value of Sample 2B. This indicates that, when cleaving αF2P from HbA1c by the action of a protease, HbA1c can be accurately quantified with the use of the amadoriase of the present invention even in the presence of remaining α-fructosyl peptides undegraded down to αF2P.

In contrast, Table 24 shows the values relative to the ΔA values of Samples 2D to 2I that are within ±2% from the value of Sample 2C. This indicates that, when cleaving αF2P from HbA1c by the action of a protease, HbA1c cannot be accurately quantified with the use of conventional amadoriases because the difference in the absorbance (ΔA) is at a low value depending on the amount of remaining α-fructosyl peptides undegraded down to α2FP.

According to conventional techniques for measurement of HbA1c using amadoriases, it was necessary to completely degrade HbA1c down to αF2P by the action of a protease. However, it was not confirmed whether or not HbA1c was completely degraded down to αF2P. From the results demonstrated in Table 24 it can be recognized that when using conventional amadoriases and if α-fructosyl peptides undegraded down to α2FP are present, then the difference in the absorbance (ΔA) will be at a low value depending on the remaining amount of undegraded peptides, and HbA1c may not be accurately quantified. However, with the use of the amadoriase of the present invention, even for samples in which various types of α-fructosyl peptides are mixed and present, all of them can be reflected in the HbA1c level. Accordingly, HbA1c can be accurately quantified, regardless of the degree of progress of the HbA1c degradation reaction by the protease. Accordingly, such amadoriase is very advantageous at the industrial level.

When a protease and an enzyme (an amadoriase or peroxidase) are simultaneously formulated (incorporated), the amadoriase or peroxidase will also degraded by the protease, and enzymatic activity will be lost. In conventional techniques of measurement, there were no alternative means other than the use of a protease capable of degrading HbA1c down to αF2P. However, with the use of the amadoriase of the present invention, even for samples in which various types of α-fructosyl peptides are mixed and exist, all of them can be reflected in the HbA1c level and this enables preferential selection of a protease that would be less likely to react with the amadoriase or peroxidase and incorporation of such protease into the reagent for measurement. Such technique is very advantageous at the industrial level.

In order to diagnose diabetes mellitus, it is necessary to be able to detect HbA1c of 6.5% (NGSP), which is the borderline value for diabetes mellitus. An NGSP value of 6.5% is equivalent to 47 mmol/mol in terms of IFCC. When blood hemoglobin level is 13 g/dl and NGSP level is 6.5%, the hemoglobin β-chain level with the glycated amino terminus in the blood is approximately 190 μM. In other words, in order to realize diagnosis of diabetes mellitus on the basis of the NGSP level it is necessary to quantify a glycated peptide at 190 μM or lower or otherwise it is difficult to say the industrial problem is solved. With the use of the amadoriase of the present invention, however, α-fructosyl peptides derived from the amino terminus of the HbA1c β-chain can be detected even if the blood is diluted 47.5 to 380 fold (i.e., even if the final concentration is 0.5 μM to 4 μM in the solution to be analyzed). Thus, the amadoriase of the present invention is very advantageous in terms of industrial applicability.

All publications, patents, and patent applications cited herein are incorporated herein by reference in their entirety.

BRIEF DESCRIPTION OF SEQUENCE LISTING

SEQ ID NO: 1: the amino acid sequence of the amadoriase derived from the *Coniochaeta* sp. NISL 9330 strain;
SEQ ID NO: 2: the nucleotide sequence of the amadoriase as shown in SEQ ID NO: 1;
SEQ ID NOs: 3-33: PCR primers;
SEQ ID NO: 34: PCR primer;
SEQ ID NO: 35: PCR primer;
SEQ ID NO: 36: the amino acid sequence of *Aspergillus oryzae* RIB40 (FAOAo2);
SEQ ID NO: 37: the nucleotide sequence of FAOAo2;
SEQ ID NO: 38: the amino acid sequence of *Phaeosphaeria nodorum* (PnFX);
SEQ ID NO: 39: the nucleotide sequence of PnFX;
SEQ ID NO: 40: the amino acid sequence of *Eupenicillium terrenum* (EFP-T5);
SEQ ID NO: 41: the nucleotide sequence of EFP-T5;
SEQ ID NOs: 42-53: PCR primers;
SEQ ID NO: 54: the amino acid sequence of *Neocosmospora vasinfecta* (NvFX);
SEQ ID NO: 55: the nucleotide sequence of NvFX;
SEQ ID NOs: 56-61: PCR primers;
SEQ ID NO: 62: the amino acid sequence of *Aspergillus nidulans* (AnFX) comprising substitution S59G;
SEQ ID NO: 63: the nucleotide sequence of AnFX;
SEQ ID NOs: 64-88: PCR primers;
SEQ ID NO: 89: the amino acid sequence of *Cryptococcus neoformans* (CnFX);
SEQ ID NO: 90: the nucleotide sequence of CnFX;
SEQ ID NOs: 91-98: PCR primers;
SEQ ID NO: 99: the amino acid sequence of the amadoriase (Cc95FX) exhibiting 95% sequence identity with the ketoamine oxidase derived from *Curvularia clavata;*
SEQ ID NO: 100: the nucleotide sequence of Cc95FX;
SEQ ID NOs: 101-112: PCR primers;
SEQ ID NO: 113: the amino acid sequence of the amadoriase derived from *Pyrenochaeta* sp. (Py);
SEQ ID NO: 114: the nucleotide sequence of the amadoriase derived from *Pyrenochaeta* sp. (Py);
SEQ ID NO: 115: the amino acid sequence of the amadoriase derived from *Arthrinium* sp. (Ar);
SEQ ID NO: 116: the nucleotide sequence of the amadoriase derived from *Arthrinium* sp. (Ar);
SEQ ID NO: 117: the amino acid sequence of the amadoriase derived from *Curvularia clavata* (Cc);
SEQ ID NO: 118: the nucleotide sequence of the amadoriase derived from *Curvularia clavata* (Cc);

SEQ ID NO: 119: the amino acid sequence of the amadoriase derived from *Emericella nidulans* (En);
SEQ ID NO: 120: the nucleotide sequence of the amadoriase derived from *Emericella nidulans* (En);
SEQ ID NO: 121: the amino acid sequence of the amadoriase derived from *Ulocladium* sp. (Ul);
SEQ ID NO: 122: the nucleotide sequence of the amadoriase derived from *Ulocladium* sp. (Ul);
SEQ ID NO: 123: the amino acid sequence of the amadoriase derived from *Penicillium janthinellum* (Pj);
SEQ ID NO: 124: the nucleotide sequence of the amadoriase derived from *Penicillium janthinellum* (Pj);
SEQ ID NO: 125: the amino acid sequence of Amadoriase I derived from *Aspergillus fumigatus;*
SEQ ID NO: 126: the nucleotide sequence of Amadoriase I;
SEQ ID NO: 127: the amino acid sequence of FAOAo1 derived from *Aspergillus oryzae;*
SEQ ID NO: 128: the nucleotide sequence of FAOAo1;
SEQ ID NO: 129: the amino acid sequence of Amadoriase II derived from *Aspergillus fumigatus;*
SEQ ID NO: 130: the nucleotide sequence of Amadoriase II;
SEQ ID NO: 131: the amino acid sequence of FAOD-A derived from *Aspergillus terreus;*
SEQ ID NO: 132: the nucleotide sequence of FAOD-A;
SEQ ID NO: 133: the amino acid sequence of CFP-T7-H20 (R62D, D106K, Q110L, A113K) derived from *Coniochaeta* sp.;
SEQ ID NO: 134: the nucleotide sequence of CFP-T7-H20;
SEQ ID NO: 135: the amino acid sequence of PnFPOX (S62D, D106K, G110L, A113K) derived from *Phaeosphaeria nodorum;*
SEQ ID NO: 136: the nucleotide sequence encoding the amino acid sequence as shown in SEQ ID NO: 135;
SEQ ID NO: 137: the amino acid sequence of NvFX-62D/106K/110L (R62D, G106K, E110L) derived from *Neocosmospora vasinfecta* (Amadoriase 29);
SEQ ID NO: 138: the nucleotide sequence encoding the amino acid sequence as shown in SEQ ID NO: 137;
SEQ ID NO: 139: the amino acid sequence of AnFX-61D/105K/109L (S59G, R61D, G105K, K1091L) derived from *Aspergillus nidulans* (Amadoriase 30);
SEQ ID NO: 140: the nucleotide sequence encoding the amino acid sequence as shown in SEQ ID NO: 139;
SEQ ID NO: 141: the amino acid sequence of CFP-T7-H35 (R62D, L63H, E102K, D106K, Q110L, A113K, A355S) derived from *Coniochaeta* sp. (Amadoriase 25);
SEQ ID NO: 142: the nucleotide sequence of CFP-T7-H35;
SEQ ID NO: 143: the amino acid sequence of EFP-T5-62D/63H/106K/110L/113K/355S derived from *Eupenicillium terrenum;*
SEQ ID NO: 144: the nucleotide sequence encoding the amino acid sequence as shown in SEQ ID NO: 143:
SEQ ID NO: 145: the amino acid sequence of the wild-type amadoriase derived from *Eupenicillium terrenum;*
SEQ ID NO: 146: the nucleotide sequence of the wild-type amadoriase derived from *Eupenicillium terrenum;*
SEQ ID NO: 147: the amino acid sequence of the wild-type amadoriase (AnFX);
SEQ ID NO: 148: the nucleotide sequence of the wild-type amadoriase (AnFX);
SEQ ID NO: 149: the amino acid sequence of the wild-type amadoriase (CnFX);
SEQ ID NO: 150: the nucleotide sequence of the wild-type amadoriase (CnFX);
SEQ ID NO: 151: the amino acid sequence of CFP-T7-H1 (R62A) derived from *Coniochaeta* sp. (Amadoriase 1):
SEQ ID NO: 152: the nucleotide sequence of CFP-T7-H1;
SEQ ID NO: 153: the amino acid sequence of CFP-T7-62D (R62D) derived from *Coniochaeta* sp. (Amadoriase 26);
SEQ ID NO: 154: the nucleotide sequence of CFP-T7-62D;
SEQ ID NO: 155: the amino acid sequence of EFP-T5-R62D (R62D) derived from *Eupenicillium terrenum* (Amadoriase 27);
SEQ ID NO: 156: the nucleotide sequence of EFP-T5-R62D;
SEQ ID NO: 157: the amino acid sequence of CFP-T7-H2 (R62A, Q110L) derived from *Coniochaeta* sp. (Amadoriase 2);
SEQ ID NO: 158: the nucleotide sequence of CFP-T7-H2;
SEQ ID NO: 159: the amino acid sequence of CFP-T7-H4 (R62A, Q110Y) derived from *Coniochaeta* sp. (Amadoriase 4);
SEQ ID NO: 160: the nucleotide sequence of CFP-T7-H4;
SEQ ID NO: 161: the amino acid sequence of CFP-T7-H2-62N (R62N, Q110L) derived from *Coniochaeta* sp. (Amadoriase 5);
SEQ ID NO: 162: the nucleotide sequence of CFP-T7-H2-62N;
SEQ ID NO: 163: the amino acid sequence of CFP-T7-H6 (R62D, Q110L) derived from *Coniochaeta* sp. (Amadoriase 6);
SEQ ID NO: 164: the nucleotide sequence of CFP-T7-H6;
SEQ ID NO: 165: the amino acid sequence of CFP-T7-H10 (R62D, D106A, Q110L) derived from *Coniochaeta* sp. (Amadoriase 12);
SEQ ID NO: 166: the nucleotide sequence of CFP-T7-H10;
SEQ ID NO: 167: the amino acid sequence of CFP-T7-H11 (R62D, D106K, Q110L) derived from *Coniochaeta* sp. (Amadoriase 13);
SEQ ID NO: 168: the nucleotide sequence of CFP-T7-H11;
SEQ ID NO: 169: the amino acid sequence of CFP-T7-H12 (R62D, D106R, Q110L) derived from *Coniochaeta* sp. (Amadoriase 14);
SEQ ID NO: 170: the nucleotide sequence of CFP-T7-H12;
SEQ ID NO: 171: the amino acid sequence of CFP-T7-H13 (R62D, Q110L, A113K) derived from *Coniochaeta* sp. (Amadoriase 15);
SEQ ID NO: 172: the nucleotide sequence of CFP-T7-H13;
SEQ ID NO: 173: the amino acid sequence of CFP-T7-H14 (R62D, Q110L, A113R) derived from *Coniochaeta* sp. (Amadoriase 16);
SEQ ID NO: 174: the nucleotide sequence of CFP-T7-H14;
SEQ ID NO: 175: the amino acid sequence of CFP-T7-H21 (R62D, D106K, Q110L, A113R) derived from *Coniochaeta* sp. (Amadoriase 18);
SEQ ID NO: 176: the nucleotide sequence of CFP-T7-H21;
SEQ ID NO: 177: the amino acid sequence of CFP-T7-H24 (R62D, L63A, D106K, Q110L, A113K) derived from *Coniochaeta* sp. (Amadoriase 19);
SEQ ID NO: 178: the nucleotide sequence of CFP-T7-H24;
SEQ ID NO: 179: the amino acid sequence of CFP-T7-H26 (R62D, L63H, D106K, Q110L, A113K) derived from *Coniochaeta* sp. (Amadoriase 21);
SEQ ID NO: 180: the nucleotide sequence of CFP-T7-H26;
SEQ ID NO: 181: the amino acid sequence of CFP-T7-H28 (R62D, L63H, E102K, D106K, Q110L, A113K) derived from *Coniochaeta* sp. (Amadoriase 23);
SEQ ID NO: 182: the nucleotide sequence of CFP-T7-H28;
SEQ ID NO: 183: the amino acid sequence of CFP-T7-H29 (R62D, L63H, D106K, Q110L, A113K, A419K) derived from *Coniochaeta* sp. (Amadoriase 24);

SEQ ID NO: 184: the nucleotide sequence of CFP-T7-H29;

SEQ ID NO: 185: the amino acid sequence of (AnFX-61D/62H/101K/105K/109L/112K/355S) derived from *Aspergillus nidulans* (Amadoriase 31);

SEQ ID NO: 186: the nucleotide sequence encoding the amino acid sequence as shown in SEQ ID NO: 185;

SEQ ID NO: 187: the amino acid sequence of (PnFX-62D/63H/106K/110L/113K/351S) derived from *Phaeosphaeria nodorum* (Amadoriase 33);

SEQ ID NO: 188: the nucleotide sequence encoding the amino acid sequence as shown in SEQ ID NO: 187;

SEQ ID NO: 189: the amino acid sequence of (CnFX-62D/106K/110L/113K) derived from *Cryptococcus neoformans* (Amadoriase 34);

SEQ ID NO: 190: the nucleotide sequence encoding the amino acid sequence as shown in SEQ ID NO: 189;

SEQ ID NO: 191: the amino acid sequence of (Cc95FX-62D/63H/106K/110L/113K/353S) derived from *Curvularia clavata* (Amadoriase 35);

SEQ ID NO: 192: the nucleotide sequence encoding the amino acid sequence as shown in SEQ ID NO: 191; and SEQ ID NO: 193: the amino acid sequence of the hemoglobin β chain.

The invention claimed is:

1. A method for measurement of α-fructosyl peptide in a sample, said method comprising allowing an amadoriase capable of reacting with one or more α-fructosyl peptides selected from among (a) to (d) below to react with a sample comprising one or more α-fructosyl peptides selected from among (a) to (d) and measuring the amount of hydrogen peroxide generated or oxygen consumed in such reaction:

(a) α-fructosyl-valyl-histidyl-leucyl-threonine (αF4P);

(b) α-fructosyl-valyl-histidyl-leucyl-threonyl-proline (αF5P);

(c) α-fructosyl-valyl-histidyl-leucyl-threonyl-prolyl-glutamyl-glutamyl-lysine (αF8P); and (d) α-fructosyl-valyl-histidyl-leucyl-threonyl-prolyl-glutamyl-glutamyl-lysyl-seryl-alanyl-valyl-threonyl-alanyl-leucyl-tryptophyl-glycine (αF16P).

2. The method according to claim 1, wherein the sample further comprises α-fructosyl-valine (αF1P), α-fructosyl-valyl-histidine (αF2P), α-fructosyl-valyl-histidyl-leucine (αF3P), and/or α-fructosyl-valyl-histidyl-leucyl-threonyl-prolyl-glutamic acid (αF6P), the amadoriase is further capable of reacting with α-fructosyl-valine (αF1P), α-fructosyl-valyl-histidine (αF2P), α-fructosyl-valyl-histidyl-leucine (αF3P), and/or α-fructosyl-valyl-histidyl-leucyl-threonyl-prolyl-glutamic acid (αF6P), and the amount of hydrogen peroxide generated or enzyme oxygen consumed in such reaction is also measured.

3. The method of claim 1, said method further comprising treating the sample with a protease to release a glycated peptide comprising one or more α-fructosyl peptides selected from among (a) to (d):

(a) α-fructosyl-valyl-histidyl-leucyl-threonine (αF4P);

(b) α-fructosyl-valyl-histidyl-leucyl-threonyl-proline (αF5P);

(c) α-fructosyl-valyl-histidyl-leucyl-threonyl-prolyl-glutamyl-glutamyl-lysine (αF8P); and (d) α-fructosyl-valyl-histidyl-leucyl-threonyl-prolyl-glutamyl-glutamyl-lysyl-seryl-alanyl-valyl-threonyl-alanyl-leucyl-tryptophyl-glycine (αF16P).

4. The method according to claim 3, wherein α-fructosyl-valine (αF1P), α-fructosyl-valyl-histidine (αF2P), α-fructosyl-valyl-histidyl-leucine (αF3P), and/or α-fructosyl-valyl-histidyl-leucyl-threonyl-prolyl-glutamic acid (αF6P) is further released by treatment with the protease, the amadoriase is one that is further capable of reacting with α-fructosyl-valine (αF1P), α-fructosyl-valyl-histidine (αF2P), α-fructosyl-valyl-histidyl-leucine (αF3P), and/or α-fructosyl-valyl-histidyl-leucyl-threonyl-prolyl-glutamic acid (αF6P), and the amount of hydrogen peroxide generated or enzyme oxygen consumed in such reaction is also measured.

5. The method for measurement according to claim 1, 2, 3 or 4, wherein the amadoriase is derived from the genus *Coniochaeta, Eupenicillium, Pyrenochaeta, Arthrinium, Curvularia, Neocosmospora, Cryptococcus, Phaeosphaeria, Aspergillus, Emericella, Ulocladium*, or *Penicillium.*

6. The method for measurement according to claim 1, 2, 3 or 4, wherein the amadoriase is derived from *Coniochaeta* sp., *Eupenicillium terrenum, Pyrenochaeta* sp., *Arthrinium* sp., *Curvularia clavata, Neocosmospora vasinfecta, Cryptococcus neoformans, Phaeosphaeria nodorum, Aspergillus nidulans, Emericella nidulans, Ulocladium* sp., or *Penicillium janthinelum.*

7. The method for measurement according to claim 1, 2, 3 or 4, wherein the amadoriase is an amadoriase selected from the group consisting of (i) and (ii) below:

(i) an amadoriase comprising an amino acid sequence derived from the amino acid sequence as shown in SEQ ID NO: 141 by substitution, deletion, or addition of one or several amino acids; and (ii) the amadoriase as defined in (i), wherein the amadoriase comprises an amino acid sequence having 70% or higher sequence identity with the amino acid sequence as shown in SEQ ID NO: 141 over the full length and having 90% or higher sequence identity between the amino acid sequence of a homologous region consisting of amino acids at positions 10 to 32, 36 to 41, 49 to 52, 54 to 58, 73 to 75, 84 to 86, 88 to 90, 120 to 122, 145 to 150, 156 to 162, 164 to 170, 180 to 182, 202 to 205, 207 to 211, 214 to 224, 227 to 230, 236 to 241, 243 to 248, 258 to 261, 266 to 268, 270 to 273, 275 to 287, 295 to 297, 306 to 308, 310 to 316, 324 to 329, 332 to 334, 341 to 344, 346 to 355, 357 to 363, 370 to 383, 385 to 387, 389 to 394, 405 to 410, and 423 to 431 of SEQ ID NO: 141 and the amino acid sequence of the homologous region in corresponding positions of the amadoriase.

8. The method according to claim 1 or 3, further comprising using an amadoriase that oxidizes α-fructosyl-valine or α-fructosyl-valyl-histidine or α-fructosyl-valyl-histidyl-leucine.

9. A method for measurement of α-fructosyl oligopeptide in a sample, said method comprising allowing an amadoriase capable of reacting with α-fructosyl-valyl-histidyl-leucyl-threonine (αF4P) and α-fructosyl-valyl-histidylleucyl-threonyl-proline (αF5P) to react with a sample comprising α-fructosyl-valyl-histidyl-leucyl-threonine (αF4P) and α-fructosyl-valyl-histidyl-leucyl-threonyl-proline (αF5P) and measuring the amount of hydrogen peroxide generated or oxygen consumed in such reaction.

* * * * *

SEQUENCE LISTING

```
<160> NUMBER OF SEQ ID NOS: 193

<210> SEQ ID NO 1
<211> LENGTH: 437
<212> TYPE: PRT
<213> ORGANISM: Coniochaeta sp.

<400> SEQUENCE: 1

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Arg Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285
```

-continued

```
Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 2
<211> LENGTH: 1314
<212> TYPE: DNA
<213> ORGANISM: Coniochaeta sp.

<400> SEQUENCE: 2

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atacgactgc gcaacaaggt ggacctgcaa atgagtctag aggctagaca gatgtggaag     240

gaggatgagt tattccagcc cttctttcac aataccggca gaatggactg cgaacacacg     300

cctgagggta tcgaggacct gaaaaagcag taccaggcac tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840

gacgagttcc caggattctc gcgcttcaag gaacatcaac cctatggcgc ccccatctccg    900

aaacggatat cagtaccacg atcgcacgcc aagcatccca cagacactta tccagacgca     960

tccgaagtca gcatcaaaaa agcaatcgcg acgtttctcc ctcgatttca ggacaaggag    1020

ctcttcaatc gcgccttgtg ctggtgtaca gacactgcgg acgctgctct cttgatgtgt    1080

gaacacccca aatggaagaa tttcattcta gcgaccggcg acagcggaca ctcattcaaa    1140

atcttgccta acgtcggaaa atacgtagtc gagttgatag agggccgcct gccggaggaa    1200
```

-continued atggcttatc aatggaggtg gcggccagga ggcgatgcac tcaagtctag acgtgcggca 1260
ccgccaaaag atcttgcaga catgccagga tggaaacatg atccgaaatt gtaa 1314

<210> SEQ ID NO 3
<211> LENGTH: 30
<212> TYPE: DNA
<213> ORGANISM: Artificial
<220> FEATURE:
<223> OTHER INFORMATION: primer

<400> SEQUENCE: 3
tcatgggaat agcactgcgc aacaaggtgg 30

<210> SEQ ID NO 4
<211> LENGTH: 29
<212> TYPE: DNA
<213> ORGANISM: Artificial
<220> FEATURE:
<223> OTHER INFORMATION: primer

<400> SEQUENCE: 4
tattcccatg atcttgttga gatcatggc 29

<210> SEQ ID NO 5
<211> LENGTH: 29
<212> TYPE: DNA
<213> ORGANISM: Artificial
<220> FEATURE:
<223> OTHER INFORMATION: primer

<400> SEQUENCE: 5
acctgaaaaa gctgtaccag gcactgcac 29

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6
acctgaaaaa gttctaccag gcactgcac 29

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
acctgaaaaa gtattaccag gcactgcac 29

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8
ctttttcagg tcctcgatac cctcaggc 28

<210> SEQ ID NO 9
<211> LENGTH: 30

<212> TYPE: DNA
<213> ORGANISM: Artificial
<220> FEATURE:
<223> OTHER INFORMATION: primer

<400> SEQUENCE: 9
tcatgggaat aaacctgcgc aacaaggtgg 30

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
tcatgggaat agatctgcgc aacaaggtgg 30

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
tcatgggaat acaactgcgc aacaaggtgg 30

<210> SEQ ID NO 12
<211> LENGTH: 30
<212> TYPE: DNA
<213> ORGANISM: Artificial
<220> FEATURE:
<223> OTHER INFORMATION: primer

<400> SEQUENCE: 12
tcatgggaat agaactgcgc aacaaggtgg 30

<210> SEQ ID NO 13
<211> LENGTH: 30
<212> TYPE: DNA
<213> ORGANISM: Artificial
<220> FEATURE:
<223> OTHER INFORMATION: primer

<400> SEQUENCE: 13
tgggaataga tctggccaac aaggtggacc 30

<210> SEQ ID NO 14
<211> LENGTH: 30
<212> TYPE: DNA
<213> ORGANISM: Artificial
<220> FEATURE:
<223> OTHER INFORMATION: primer

<400> SEQUENCE: 14
tgggaataga tctggaaaac aaggtggacc 30

<210> SEQ ID NO 15
<211> LENGTH: 30
<212> TYPE: DNA
<213> ORGANISM: Artificial
<220> FEATURE:
<223> OTHER INFORMATION: primer

<400> SEQUENCE: 15 tgggaatagatctgcacaacaaggtggacc 30

<210> SEQ ID NO 16
<211> LENGTH: 27
<212> TYPE: DNA
<213> ORGANISM: Artificial
<220> FEATURE:
<223> OTHER INFORMATION: primer

<400> SEQUENCE: 16
cagatctatt cccatgatct tgttgag 27

<210> SEQ ID NO 17
<211> LENGTH: 28
<212> TYPE: DNA
<213> ORGANISM: Artificial
<220> FEATURE:
<223> OTHER INFORMATION: primer

<400> SEQUENCE: 17
tgagggtatc gaggccctga aaaagctg 28

<210> SEQ ID NO 18
<211> LENGTH: 28
<212> TYPE: DNA
<213> ORGANISM: Artificial
<220> FEATURE:
<223> OTHER INFORMATION: primer

<400> SEQUENCE: 18
tgagggtatc gagaaactga aaaagctg 28

<210> SEQ ID NO 19
<211> LENGTH: 28
<212> TYPE: DNA
<213> ORGANISM: Artificial
<220> FEATURE:
<223> OTHER INFORMATION: primer

<400> SEQUENCE: 19
tgagggtatc gagcgcctga aaaagctg 28

<210> SEQ ID NO 20
<211> LENGTH: 28
<212> TYPE: DNA
<213> ORGANISM: Artificial
<220> FEATURE:
<223> OTHER INFORMATION: primer

<400> SEQUENCE: 20
ctcgataccc tcaggcgtgt gttcgcag 28

<210> SEQ ID NO 21
<211> LENGTH: 30
<212> TYPE: DNA
<213> ORGANISM: Artificial
<220> FEATURE:
<223> OTHER INFORMATION: primer

<400> SEQUENCE: 21
aaaaagctgt accagaaact gcacgatgcc 30

<210> SEQ ID NO 22
<211> LENGTH: 30
<212> TYPE: DNA
<213> ORGANISM: Artificial

<220> FEATURE:
<223> OTHER INFORMATION: primer

<400> SEQUENCE: 22
gcatcgtgca gtttctggta cagcttttc 30

<210> SEQ ID NO 23
<211> LENGTH: 30
<212> TYPE: DNA
<213> ORGANISM: Artificial
<220> FEATURE:
<223> OTHER INFORMATION: primer

<400> SEQUENCE: 23
aaaaagctgt accagcgtct gcacgatgcc 30

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
gcatcgtgca gacgctggta cagcttttc 30

<210> SEQ ID NO 25
<211> LENGTH: 30
<212> TYPE: DNA
<213> ORGANISM: Artificial
<220> FEATURE:
<223> OTHER INFORMATION: primer

<400> SEQUENCE: 25
tcatgggaat agatgcgcgc aacaaggtgg 30

<210> SEQ ID NO 26
<211> LENGTH: 30
<212> TYPE: DNA
<213> ORGANISM: Artificial
<220> FEATURE:
<223> OTHER INFORMATION: primer

<400> SEQUENCE: 26
tcatgggaat agatgaccgc aacaaggtgg 30

<210> SEQ ID NO 27
<211> LENGTH: 30
<212> TYPE: DNA
<213> ORGANISM: Artificial
<220> FEATURE:
<223> OTHER INFORMATION: primer

<400> SEQUENCE: 27
tcatgggaat agatcatcgc aacaaggtgg 30

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
tcatgggaat agataagcgc aacaaggtgg 30

-continued

<210> SEQ ID NO 29
<211> LENGTH: 29
<212> TYPE: DNA
<213> ORGANISM: Artificial
<220> FEATURE:
<223> OTHER INFORMATION: primer

<400> SEQUENCE: 29
atctattccc atgatcttgt tgagatcat 29

<210> SEQ ID NO 30
<211> LENGTH: 25
<212> TYPE: DNA
<213> ORGANISM: Artificial
<220> FEATURE:
<223> OTHER INFORMATION: primer

<400> SEQUENCE: 30
aggcgtgtgt tcgcagtcca ttctg 25

<210> SEQ ID NO 31
<211> LENGTH: 30
<212> TYPE: DNA
<213> ORGANISM: Artificial
<220> FEATURE:
<223> OTHER INFORMATION: primer

<400> SEQUENCE: 31
gcgaacacac gcctaagggt atcgagaaac 30

<210> SEQ ID NO 32
<211> LENGTH: 29
<212> TYPE: DNA
<213> ORGANISM: Artificial
<220> FEATURE:
<223> OTHER INFORMATION: primer

<400> SEQUENCE: 32
acgtctagac ttgagtgcat cgcctcctg 29

<210> SEQ ID NO 33
<211> LENGTH: 30
<212> TYPE: DNA
<213> ORGANISM: Artificial
<220> FEATURE:
<223> OTHER INFORMATION: primer

<400> SEQUENCE: 33
tcaagtctag acgtaaggca ccgccaaaag 30

<210> SEQ ID NO 34
<211> LENGTH: 30
<212> TYPE: DNA
<213> ORGANISM: Artificial
<220> FEATURE:
<223> OTHER INFORMATION: primer

<400> SEQUENCE: 34
acagacactg cggactctgc tctcttgatg 30

<210> SEQ ID NO 35
<211> LENGTH: 28
<212> TYPE: DNA
<213> ORGANISM: Artificial
<220> FEATURE:
<223> OTHER INFORMATION: primer

<400> SEQUENCE: 35
gtccgcagtg tctgtacacc agcacaag 28

<210> SEQ ID NO 36
<211> LENGTH: 436
<212> TYPE: PRT
<213> ORGANISM: Aspergillus oryzae

<400> SEQUENCE: 36

Met Thr Val Thr Lys Ser Ser Ser Ile Leu Ile Ile Gly Ala Gly Thr
1 5 10 15

Trp Gly Ala Ser Thr Ala Leu His Leu Gly Arg Arg Gly Tyr Thr Asn
20 25 30

Val Thr Val Leu Asp Pro Tyr Thr Val Pro Ser Ala Ile Ser Ala Gly
35 40 45

Asn Asp Val Asn Lys Ile Ile Ser Ser Gly Gln Tyr Ser Asn Lys Lys
50 55 60

Asp Glu Ile Glu Val Asn Glu Ile Leu Ala Glu Glu Ala Phe Lys Gly
65 70 75 80

Trp Thr Thr Asp Pro Leu Phe Lys Pro Tyr Tyr His Asp Thr Gly Val
85 90 95

Val Met Ser Ala Cys Ser Ser Ala Gly Leu Asp Arg Leu Gly Ile Arg
100 105 110

Val Arg Pro Glu Glu Glu Pro Asp Val Ser Glu Val Thr Lys Pro Glu
115 120 125

His Phe Arg Gln Leu Ala Pro Ala Val Leu Lys Gly Asn Phe Pro Gly
130 135 140

Trp Arg Gly Tyr His Ile Arg Ser Asn Ala Gly Trp Ala His Ala Arg
145 150 155 160

Asn Ala Leu Val Ala Ala Ile Arg Glu Ala Glu Lys Leu Gly Val Lys
165 170 175

Phe Val Thr Gly Thr Gln Gly Arg Val Ile Thr Leu Ile Phe Glu Asn
180 185 190

Asn Asp Val Lys Gly Ala Val Thr Ala Asp Gly Lys Ile Trp Arg Ala
195 200 205

Glu Gln Thr Val Leu Cys Ala Gly Ala Asn Ala Ala Gln Phe Leu Asp
210 215 220

Phe Lys Asp Gln Leu Arg Pro Thr Ala Trp Thr Leu Ala His Ile Arg
225 230 235 240

Leu Lys Pro Glu Glu Arg Ala Leu Tyr Lys Asn Leu Pro Val Ile Phe
245 250 255

Asn Ile Glu Lys Gly Phe Phe Phe Glu Pro Asp Glu Glu Arg Gly Glu
260 265 270

Ile Lys Ile Cys Asp Glu His Pro Gly Tyr Thr Asn Met Val Lys Ser
275 280 285

Ala Asp Gly His Leu Thr Ser Leu Pro Phe Glu Lys Thr Gln Ile Pro
290 295 300

Lys Glu Ser Glu Ala Arg Val Arg Ala Leu Leu Ser Glu Thr Met Pro
305 310 315 320

Gln Leu Ala Asp Arg Pro Phe Ser Phe Ala Arg Val Cys Trp Cys Ala
325 330 335

Asp Thr Ala Asn Arg Glu Phe Ile Ile Asp Arg His Pro Glu His Pro
340 345 350

```
Ser Leu Val Leu Gly Cys Gly Ala Ser Gly Arg Gly Phe Lys Tyr Leu
        355                 360                 365

Pro Ser Ile Gly Asn Leu Ile Val Asp Ala Ile Glu Asp Lys Val Pro
    370                 375                 380

Glu Lys Val His Lys Leu Thr Arg Trp Ser Pro Asp Ile Ala Val Asp
385                 390                 395                 400

Arg Lys Trp Arg Asp Thr Leu Gly Arg Phe Gly Gly Pro Asn Arg Val
                405                 410                 415

Met Asp Phe His Asp Val Lys Glu Trp Thr Asn Val Gln Asn Lys Asp
            420                 425                 430

Thr Ala Lys Leu
        435


<210> SEQ ID NO 37
<211> LENGTH: 1311
<212> TYPE: DNA
<213> ORGANISM: Aspergillus oryzae

<400> SEQUENCE: 37

atgactgtca ccaaatcttc ctcaatcctg atcatcggcg caggcacttg ggcgcttca      60

actgcccttc accttggtcg cagaggatac accaatgtca ccgtcctaga cccttacaca    120

gtgccctcag caatttcagc tggaaatgac gtgaacaaga tcatctcctc ggggcaatac    180

agcaacaaaa aggatgagat tgaagttaac gaaattctcg ccgaggaggc attcaaaggc    240

tggacaaccg accctttgtt caagccatac taccacgaca ctggcgttgt aatgtctgct    300

tgcagcagcg ccggtctgga tcgcctcgga atccgagtaa ggccggaaga ggaacctgat    360

gtttccgaag tcacgaagcc ggagcacttc cgccaactgg cccccgctgt gctgaaagga    420

aacttcccgg ggtggagagg ctaccacatt cgttcgaacg ctggctgggc gcacgcccga    480

aatgccctcg tggccgctat acgcgaagca gagaaacttg gtgttaaatt cgtaacaggc    540

acccaaggaa gagtcatcac ccttatcttc gagaacaacg acgtcaaggg cgcagtcacc    600

gccgacggaa agatctggcg cgcggagcaa acagttctct gcgctggcgc aaatgctgcg    660

cagttcttgg attttaagga ccagctccgc ccaacggcat ggacactcgc ccatatccgg    720

ctcaaacctg aggaacgcgc gctctacaaa aacttgccgg tgattttcaa cattgagaaa    780

ggatttttct tcgagcctga tgaggagcgc ggggagatca agatctgcga cgaacatccg    840

ggatacacta acatggttaa atctgcggat ggccacttga cgagtttgcc ctttgagaag    900

acccagatcc ccaaggagtc tgaagctaga gtcagagctt tactatcgga gaccatgcct    960

caattagccg atcgcccatt tagcttcgcc cgcgtttgct ggtgtgcgga caccgcaaac   1020

cgtgaattca tcattgaccg ccaccctgaa cacccgtctc ttgttttggg atgcggtgct   1080

tccggaaggg gtttcaaata tctcccctca atcggcaacc tcattgttga cgccattgaa   1140

gacaaagtcc cagagaaagt tcacaagctt acgaggtgga gtccagacat tgctgttgac   1200

agaaagtgga gggacactct ggggcgcttt ggagggccta accgtgtcat ggacttccat   1260

gatgtcaagg aatggactaa cgtgcagaac aaggatactg cgaagctgta g            1311


<210> SEQ ID NO 38
<211> LENGTH: 437
<212> TYPE: PRT
<213> ORGANISM: Phaeosphaeria nodorum

<400> SEQUENCE: 38

Met Ala Pro Ser Arg Ala Asn Thr Ser Val Ile Val Val Gly Gly Gly
```

-continued

```
1               5                   10                  15

Gly Thr Ile Gly Ser Ser Thr Ala Leu His Leu Val Arg Ser Gly Tyr
            20                  25                  30

Thr Pro Ser Asn Val Thr Val Leu Asp Ala Tyr Pro Ile Pro Ser Ser
        35                  40                  45

Gln Ser Ala Gly Asn Asp Leu Asn Lys Ile Met Gly Val Ser Leu Arg
    50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
                85                  90                  95

Cys Ala His Gly Glu Lys Asp Ile Ala Asp Leu Lys Ser Gly Tyr Gln
            100                 105                 110

Ala Leu Val Asp Ala Gly Leu Asp Ala Thr Asn Glu Trp Leu Asp Ser
        115                 120                 125

Glu Asp Glu Ile Leu Lys Arg Met Pro Leu Leu Ser Arg Asp Gln Ile
    130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
        195                 200                 205

Ala Asp Lys Val Val Leu Ala Ala Gly Ala Trp Ser Pro Thr Leu Val
    210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Phe Glu Pro Asn Glu His Gly Val
            260                 265                 270

Ile Lys Val Cys Asp Glu Phe Pro Gly Phe Thr Arg Phe Lys Met His
        275                 280                 285

Gln Pro Phe Gly Ala Lys Ala Pro Lys Arg Ile Ser Val Pro Arg Ser
    290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
            340                 345                 350

Leu Leu Ile Cys Glu His Pro Glu Trp Lys Asn Phe Val Leu Ala Thr
        355                 360                 365

Gly Asp Ser Gly His Ser Phe Lys Leu Leu Pro Asn Ile Gly Lys His
    370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430
```

Pro Arg Ala Asn Leu
        435

<210> SEQ ID NO 39
<211> LENGTH: 1314
<212> TYPE: DNA
<213> ORGANISM: Phaeosphaeria nodorum

<400> SEQUENCE: 39
atggccccgt cgcgtgctaa tacgtcggtc attgtggttg gtggtggtgg tacgattggc 60
tcatctacgg ctctgcatct ggtccgctca ggctataccc cgtcgaacgt gacggttctg 120
gatgcatacc cgattccgag ctctcagagc gctggcaacg acctgaataa aatcatgggt 180
gtctctctgc gtaatccggt ggatctgcag ctggctctgg aagcgcgcca aatgtggaac 240
gaagacgaac tgttcaagaa gtttttccat aacaccggcc gtctggattg cgcgcacggt 300
gaaaaagata ttgccgacct gaagagcggc tatcaggctc tggtggatgc gggtctggac 360
gccacgaacg aatggctgga tagtgaagac gaaatcctga aacgtatgcc gctgctgtcc 420
cgcgatcaaa ttaaaggctg gaaggcgatc ttttcaaaag acggtggttg gctggcagca 480
gcaaaggcaa ttaatgcagt tggtgaatat ctgcgtgatc agggcgtccg cttcggtttt 540
tacggcgccg gttctttcaa agcaccgctg ctggctgaag gcgtctgcat cggtgtcgaa 600
accgtggatg gcacgcgcta ttacgcagac aaagtggttc tggctgcagg tgcatggtcg 660
ccgaccctgg ttgaactgca tgaacagtgt gtgagcaaag cgtgggttta cggccacatt 720
caactgacgc cggaagaagc cgcacgttat aagaacagcc cggtcgtgta caatggcgat 780
gtgggctttt tctttgaacc gaacgaacat ggcgttatca aagtctgcga tgaatttccg 840
ggttttaccc gcttcaagat gcaccagccg tttggtgcca aagcaccgaa gcgtattagt 900
gtgccgcgct cccatgccaa acacccgacc gatacgatcc cggatgcaag tgacgtttcc 960
attcgtcgcg ctatcgcgac ctttatgccg cagttcaaga acaaaaagat gttcaaccaa 1020
gcgatgtgct ggtgtaccga tacggccgac gctgcgctgc tgatttgtga acatccggaa 1080
tggaaaaact ttgttctggc gaccggcgat tcaggtcatt cgttcaaact gctgccgaat 1140
atcggcaagc acgttgtcga actgctggag ggtacgctgg cagatgacct ggcacacgca 1200
tggcgttggc gtccgggtag tggtgatgca ctgaaaagcc gtcgctctgc tccggcgaaa 1260
gacctggctg atatgccggg ctggaaccat gacaaaccgc gtgctaatct gtaa 1314

<210> SEQ ID NO 40
<211> LENGTH: 437
<212> TYPE: PRT
<213> ORGANISM: Eupenicillium terrenum

<400> SEQUENCE: 40

Met Ala His Ser Arg Ala Ser Thr Lys Val Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Arg Leu Arg
    50                  55                  60

Asn Gly Pro Asp Leu Gln Leu Ser Leu Glu Ser Leu Asp Met Trp Gln
65                  70                  75                  80

-continued

```
Asn Asp Glu Leu Phe Lys Pro Phe Phe His Gln Val Gly Met Ile Asp
                85                  90                  95

Cys Ser Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Asp Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asp
            260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
    290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Leu Leu Pro Asn
    370                 375                 380

Ile Gly Lys Tyr Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
        435
```

<210> SEQ ID NO 41
<211> LENGTH: 1314
<212> TYPE: DNA
<213> ORGANISM: Eupenicillium terrenum

<400> SEQUENCE: 41
atggctcatt cgcgtgcaag caccaaagtc gtcgtggttg ggggaggtgg tacgatcggg      60

-continued

```
tcttcgacgg ctctgcactt aatccgctct ggatataccc cctcaaatat caccgtgctt    120

gacgtataca agaccccttc attgcaatct gcaggacatg atttgaacaa gatcatgggc    180

attcgattgc gcaacgggcc tgacttgcag ctttcgctgg aatcactcga catgtggcaa    240

aacgatgagt tgttcaagcc attctttcac caagtgggca tgattgattg ttcgtcatcc    300

aaagagggta ttgaaaatct tcgacgaaaa taccagaccc tcctcgatgc gggcattggg    360

ctggagaaga cgaacgtttg gctggaatct gaagatgaga tcctcgccaa agcgccgaat    420

ttcacgcgtg aacaagtcaa ggggtggaaa ggcttatttt gcactgatgg aggctggctt    480

gctgcagcca aggctatcaa tgcgatcgga attttcctcc aggacaaagg tgtcaagttt    540

ggctttggag atgctggtac ctttcagcaa cctctgttcg ccgctgatgg aaaaacttgc    600

atcggacttg aaactacaga cggaaccaag tactttgctg acaaggttgt cttggctgct    660

ggtgcgtgga gtcccacctt ggtggatcta gaagatcagt gtgtttcaaa ggcctgggtt    720

ttcgctcata ttcaactcac acccaaagaa gcggacgcgt acaagaatgt gcctgtggtc    780

tatgatggtg aatatgggtt ctttttcgaa cccgacgagt atggggtgat caaagtctgt    840

gacgagttcc ctggtttctc tcgcttcaaa ctgcatcaac cgtacggggc tgcatctccc    900

aagatgatat ccgtaccgcg atcacacgcc aagcatccca cagataccta ccctgatgcc    960

tccgaagtca ccatacgcaa agcgatcgca aggttcctgc cagaatttaa agacaaggag   1020

ctcttcaacc gtaccatgtg ctggtgtaca gatacggccg atgctaactt attgatttgc   1080

gaacacccga agtggaagaa tttcattctg gccactggag atagcggaca ttccttcaag   1140

ctgttgccaa acatcgggaa atacgtagtt gagcttttag agggatctct atcgcaggaa   1200

atggctggtg cctggagatg gagacccgga ggtgatgctc ttagatctag acgcggtgct   1260

ccggcaaagg atcttgctga gatgccggga tggaagcatg atgcacattt gtga         1314
```

```
<210> SEQ ID NO 42
<211> LENGTH: 30
<212> TYPE: DNA
<213> ORGANISM: Artificial
<220> FEATURE:
<223> OTHER INFORMATION: primer

<400> SEQUENCE: 42

aagatcatgg gcattgattt gcgcaacggg                                      30


<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43

aatgcccatg atcttgttca aatcatgtcc                                      30


<210> SEQ ID NO 44
<211> LENGTH: 30
<212> TYPE: DNA
<213> ORGANISM: Artificial
<220> FEATURE:
<223> OTHER INFORMATION: primer

<400> SEQUENCE: 44

gagggtattg aaaaacttcg acgaaaatac                                      30
```

<210> SEQ ID NO 45
<211> LENGTH: 26
<212> TYPE: DNA
<213> ORGANISM: Artificial
<220> FEATURE:
<223> OTHER INFORMATION: primer

<400> SEQUENCE: 45
ttcaataccc tctttggatg acgaac 26

<210> SEQ ID NO 46
<211> LENGTH: 30
<212> TYPE: DNA
<213> ORGANISM: Artificial
<220> FEATURE:
<223> OTHER INFORMATION: primer

<400> SEQUENCE: 46
aaaaacttcg acgattatac cagaccctcc 30

<210> SEQ ID NO 47
<211> LENGTH: 29
<212> TYPE: DNA
<213> ORGANISM: Artificial
<220> FEATURE:
<223> OTHER INFORMATION: primer

<400> SEQUENCE: 47
tcgtcgaagt tttcaatac cctctttgg 29

<210> SEQ ID NO 48
<211> LENGTH: 30
<212> TYPE: DNA
<213> ORGANISM: Artificial
<220> FEATURE:
<223> OTHER INFORMATION: primer

<400> SEQUENCE: 48
cgacgattat accagaaact cctcgatgcg 30

<210> SEQ ID NO 49
<211> LENGTH: 30
<212> TYPE: DNA
<213> ORGANISM: Artificial
<220> FEATURE:
<223> OTHER INFORMATION: primer

<400> SEQUENCE: 49
ctggtataat cgtcgaagtt tttcaatacc 30

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
agatacggcc gattctaact tattgatttg 30

<210> SEQ ID NO 51
<211> LENGTH: 29
<212> TYPE: DNA
<213> ORGANISM: Artificial
<220> FEATURE:
<223> OTHER INFORMATION: primer

<400> SEQUENCE: 51
atcggccgta tctgtacacc agcacatgg 29

<210> SEQ ID NO 52
<211> LENGTH: 30
<212> TYPE: DNA
<213> ORGANISM: Artificial
<220> FEATURE:
<223> OTHER INFORMATION: primer

<400> SEQUENCE: 52
tcatgggcat tgatcatcgc aacgggcctg 30

<210> SEQ ID NO 53
<211> LENGTH: 29
<212> TYPE: DNA
<213> ORGANISM: Artificial
<220> FEATURE:
<223> OTHER INFORMATION: primer

<400> SEQUENCE: 53
atcaatgccc atgatcttgt tcaaatcat 29

<210> SEQ ID NO 54
<211> LENGTH: 441
<212> TYPE: PRT
<213> ORGANISM: Neocosmospora vasinfecta

<400> SEQUENCE: 54

Met Thr Thr Pro Arg Lys Glu Thr Thr Val Leu Ile Ile Gly Gly Gly
1 5 10 15

Gly Thr Ile Gly Ser Ser Thr Ala Leu His Leu Leu Arg Ala Gly Tyr
20 25 30

Thr Pro Ser Asn Ile Thr Val Leu Asp Thr Tyr Pro Ile Pro Ser Ala
35 40 45

Gln Ser Ala Gly Asn Asp Leu Asn Lys Ile Met Gly Ile Arg Leu Arg
50 55 60

Asn Lys Val Asp Leu Gln Leu Ser Leu Glu Ala Arg Asp Met Trp Arg
65 70 75 80

Asn Asp Ala Leu Phe Arg Pro Phe Phe His Asn Thr Gly Arg Leu Asp
85 90 95

Cys Glu Ser Ser Ala Glu Gly Val Glu Gly Leu Arg Arg Glu Tyr Gln
100 105 110

Lys Leu Val Glu Ala Gly Val Gly Leu Glu Glu Thr His Glu Trp Leu
115 120 125

Asp Ser Glu Glu Ala Ile Leu Glu Lys Ala Pro Leu Leu Gln Arg Glu
130 135 140

Glu Ile Glu Gly Trp Lys Ala Ile Trp Ser Glu Glu Gly Gly Trp Leu
145 150 155 160

Ala Ala Ala Lys Ala Ile Asn Ala Ile Gly Glu Glu Leu Gln Arg Gln
165 170 175

Gly Val Arg Phe Gly Phe Gly Gly Ala Gly Ser Phe Lys Arg Pro Leu
180 185 190

Phe Ala Asp Asp Gly Thr Thr Cys Ile Gly Val Glu Thr Val Asp Gly
195 200 205

Thr Gln Tyr His Ala Asp Lys Val Val Leu Ala Ala Gly Ala Trp Ser
210 215 220

Pro Ala Leu Val Asp Leu Glu Glu Gln Cys Cys Ser Lys Ala Trp Val 225 230 235 240

Tyr Ala His Met Gln Leu Thr Pro Glu Glu Ala Ala Val Tyr Lys Gly
245 250 255

Cys Pro Val Val Tyr His Gly Asp Val Gly Phe Phe Phe Glu Pro Asn
260 265 270

Glu Asn Gly Val Ile Lys Val Cys Asp Glu Phe Pro Gly Phe Thr Arg
275 280 285

Phe Lys Gln His Gln Pro Tyr Gly Ala Pro Ala Pro Lys Pro Val Ser
290 295 300

Val Pro Arg Ser His Ala Lys His Pro Thr Asp Thr Tyr Pro Asp Ala
305 310 315 320

Ser Glu Glu Ser Ile Lys Arg Ala Val Ser Thr Phe Leu Pro Arg Phe
325 330 335

Lys Asp Lys Pro Leu Phe Asn Arg Ala Leu Cys Trp Cys Thr Asp Thr
340 345 350

Ala Asp Ser Ala Leu Leu Ile Cys Glu His Pro Arg Trp Lys Asn Phe
355 360 365

Ile Leu Ala Thr Gly Asp Ser Gly His Ser Phe Lys Leu Leu Pro Ile
370 375 380

Ile Gly Lys His Val Val Glu Leu Val Glu Gly Arg Leu Ala Asp Asp
385 390 395 400

Leu Ala Glu Ala Trp Arg Trp Arg Pro Gly Gln Gly Asp Ala Arg Lys
405 410 415

Ser Ile Arg Ala Ala Pro Ala Lys Asp Leu Ala Asp Met Pro Gly Trp
420 425 430

Lys His Asp Gln Asp Ser Glu Ser Arg
435 440

<210> SEQ ID NO 55
<211> LENGTH: 1326
<212> TYPE: DNA
<213> ORGANISM: Neocosmospora vasinfecta

<400> SEQUENCE: 55
atgacgaccc cgcgtaaaga aacgacggtc ctgattattg gtggtggtgg cacgattggt 60
agctcgacgg ctctgcatct gctgcgtgcc ggctataccc cgtctaacat taccgtgctg 120
gatacgtacc cgatcccgag tgcccagtcc gcaggcaacg acctgaataa aattatgggt 180
atccgtctgc gcaataaagt tgatctgcaa ctgagcctgg aagcccgtga tatgtggcgc 240
aacgacgcac tgtttcgtcc gtttttccat aataccggcc gcctggactg cgaaagctct 300
gctgaaggcg tggaaggtct gcgtcgcgaa tatcagaaac tggtggaagc aggcgttggt 360
ctggaagaaa cgcacgaatg gctggatagc gaagaagcta ttctggaaaa agcgccgctg 420
ctgcaacgtg aagaaattga aggttggaaa gccatctggt ctgaagaagg cggttggctg 480
gcggccgcaa aagctattaa cgcgatcggc gaagaactgc agcgtcaagg cgttcgcttc 540
ggttttggcg gtgccggtag ttttaaacgc ccgctgttcg cagatgacgg caccacgtgt 600
atcggtgtcg aaaccgtgga tggcacgcag tatcatgcgg acaaagtggt tctggctgca 660
ggtgcttggt caccggcgct ggtcgatctg gaagaacagt gctgttcgaa agcctgggtg 720
tacgcacaca tgcaactgac cccggaagaa gccgcagttt ataaaggctg cccggtcgtg 780
taccacggcg atgtcggctt tttctttgaa ccgaacgaaa atggcgttat taaagtctgt 840
gacgaattcc cgggttttac gcgtttcaaa cagcatcaac cgtatggtgc ccccggcaccg 900

-continued

```
aaacctgtga gtgttccgcg ctcccatgcg aaacacccga ccgatacgta cccggacgct    960

tcagaagaat cgatcaaacg tgccgtgagt acctttctgc cgcgcttcaa agataaaccg   1020

ctgtttaacc gtgcactgtg ctggtgtacc gatacggccg actccgcact gctgatttgc   1080

gaacacccgc gctggaaaaa ttttatcctg gcgaccggcg atagcggtca ttctttcaaa   1140

ctgctgccga ttatcggcaa acacgttgtc gaactggttg aaggtcgtct ggcggatgac   1200

ctggctgaag cgtggcgttg gcgtccgggt cagggtgatg cacgtaaaag cattcgcgct   1260

gcgccggcga aagacctggc ggatatgccg ggctggaaac acgaccaaga ctcggaatca   1320

cgctga                                                              1326
```

<210> SEQ ID NO 56
<211> LENGTH: 29
<212> TYPE: DNA
<213> ORGANISM: Artificial
<220> FEATURE:
<223> OTHER INFORMATION: primer

<400> SEQUENCE: 56

```
ttatgggtat cgatctgcgc aataaagtt                                       29
```

<210> SEQ ID NO 57
<211> LENGTH: 30
<212> TYPE: DNA
<213> ORGANISM: Artificial
<220> FEATURE:
<223> OTHER INFORMATION: primer

<400> SEQUENCE: 57

```
gctcagttgc agatcaactt tattgcgcag                                      30
```

<210> SEQ ID NO 58
<211> LENGTH: 30
<212> TYPE: DNA
<213> ORGANISM: Artificial
<220> FEATURE:
<223> OTHER INFORMATION: primer

<400> SEQUENCE: 58

```
gaaggcgtgg aaaaactgcg tcgcgaatat                                      30
```

<210> SEQ ID NO 59
<211> LENGTH: 30
<212> TYPE: DNA
<213> ORGANISM: Artificial
<220> FEATURE:
<223> OTHER INFORMATION: primer

<400> SEQUENCE: 59

```
ttccaccagt ttctgatatt cgcgacgcag                                      30
```

<210> SEQ ID NO 60
<211> LENGTH: 27
<212> TYPE: DNA
<213> ORGANISM: Artificial
<220> FEATURE:
<223> OTHER INFORMATION: primer

<400> SEQUENCE: 60

```
ctgcgtcgcc tgtatcagaa actggtg                                         27
```

<210> SEQ ID NO 61
<211> LENGTH: 30

<212> TYPE: DNA
<213> ORGANISM: Artificial
<220> FEATURE:
<223> OTHER INFORMATION: primer

<400> SEQUENCE: 61
accaacgcct gcttccacca gtttctgata 30

<210> SEQ ID NO 62
<211> LENGTH: 438
<212> TYPE: PRT
<213> ORGANISM: Aspergillus nidulans

<400> SEQUENCE: 62

Met Thr Pro Arg Ala Asn Thr Lys Ile Ile Val Val Gly Gly Gly Gly
1 5 10 15

Thr Met Gly Ser Ser Thr Ala Leu His Leu Leu Arg Ala Gly Tyr Thr
20 25 30

Pro Ser Asn Ile Thr Val Leu Asp Thr Cys Pro Ile Pro Ser Ala Gln
35 40 45

Ser Ala Gly Tyr Asp Leu Asn Lys Ile Met Gly Ile Arg Leu Arg Asn
50 55 60

Lys Pro Asp Leu Gln Leu Ser Leu Glu Ala Leu Asp Met Trp Lys Asn
65 70 75 80

Asp Pro Leu Phe Lys Pro Phe Phe His Asn Val Gly Met Ile Asp Val
85 90 95

Ser Ser Thr Glu Glu Gly Ile Glu Gly Leu Arg Lys Lys Tyr Gln Ser
100 105 110

Leu Leu Asp Ala Gly Ile Gly Leu Glu Lys Thr Asn Phe Met Leu Glu
115 120 125

Ser Glu Asp Glu Ile Leu Ala Lys Ala Pro His Phe Thr Gln Glu Gln
130 135 140

Ile Lys Gly Trp Lys Gly Leu Phe Cys Gly Asp Gly Gly Trp Leu Ala
145 150 155 160

Ala Ala Lys Ala Ile Asn Ala Ile Gly Gln Phe Leu Lys Glu Gln Gly
165 170 175

Val Lys Phe Gly Phe Gly Gly Ala Gly Thr Phe Lys Lys Pro Leu Phe
180 185 190

Ala Asp Ala His Glu Lys Thr Cys Ile Gly Val Glu Thr Val Asp Gly
195 200 205

Thr Lys Tyr Tyr Ala Asp Lys Val Val Leu Ala Ala Gly Ala Trp Ser
210 215 220

Ser Thr Leu Val Asp Leu Glu Glu Gln Cys Val Ser Lys Ala Trp Val
225 230 235 240

Phe Ala His Ile Gln Leu Thr Pro Ala Glu Ala Ala Ala Tyr Lys Asn
245 250 255

Thr Pro Val Ile Tyr Asp Gly Asp Tyr Gly Phe Phe Phe Glu Pro Asn
260 265 270

Glu Asn Gly Ile Ile Lys Val Cys Asp Glu Phe Pro Gly Phe Thr His
275 280 285

Phe Lys Met His Gln Pro Tyr Gly Ser Pro Ala Pro Lys Pro Ile Ser
290 295 300

Val Pro Arg Ser His Ala Lys His Pro Thr Asp Thr Tyr Pro His Ala
305 310 315 320

Ser Glu Val Thr Ile Lys Lys Ala Ile Asn Arg Phe Leu Pro Arg Phe
325 330 335

```
Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435


<210> SEQ ID NO 63
<211> LENGTH: 1317
<212> TYPE: DNA
<213> ORGANISM: Aspergillus nidulans

<400> SEQUENCE: 63

atgacgcccc gagccaacac caaaatcatt gtcgtcggcg gcggcggcac aatgggctcg      60

tcgacagccc tacacctcct gcgcgccggc tacacgccgt ccaacattac agtgctcgac     120

acgtgcccta tcccctccgc acagtctgca ggctacgacc tgaacaaaat catggggatc     180

cgtctgcgca acaagcctga tttacagctc tctcttgagg cgctggacat gtggaaaaat     240

gatcctctct tcaagccgtt tttccacaat gttggaatga tcgacgtctc ttcaacagag     300

gaaggcatcg agggtcttcg gaagaaatac cagtctcttc tcgacgcagg cattgggctc     360

gagaagacga atttcatgct ggaaagtgaa gacgagatcc tggctaaagc gccgcatttc     420

acgcaggagc agattaaagg ctggaaaggc ctgttctgtg gcgacggcgg ctggctcgct     480

gcagccaaag ccatcaatgc cattgggcag ttcctcaagg aacagggcgt caagtttgga     540

ttcggcggcg ccggcacgtt caaaaagcca ctcttcgccg atgcccacga gaagacgtgc     600

atcggcgtcg agactgtaga cggcacaaag tactacgccg acaaggtcgt tctagcagct     660

ggtgcctgga gttcgacgtt ggtcgatctg gaggagcagt gcgtttcaaa ggcctgggtc     720

tttgcccaca tccaactgac gcccgctgaa gcagccgcgt ataagaacac tcctgttata     780

tacgacggtg actatgggtt tttctttgag ccgaatgaaa acggcatcat aaaagtctgt     840

gacgaattcc ctggcttcac gcatttcaaa atgcaccagc cgtacggctc gccggcgccc     900

aaacccatct ctgtgcctcg ttcccatgcg aagcacccca cagatacata cccgcacgcg     960

tcggaggtca cgatcaaaaa ggctatcaac cggttcctgc cgaggttcaa tgacaaggaa    1020

ctgtttaaca gggccatgtg ctggtgcacc gataccgcgg atgcaaatct gcttgtttgt    1080

gagcatccac gctggaaggg gttttatctt gcaacagggg acagtgggca ttcgttcaag    1140

ttgctgccga atattggaaa gcatgttgtc gagttattgg aggagaggct ggaaagtgtg    1200

tttaaggatg cttggaggtg gaggcctggc agtggggatg cattaaaaag tagacgggct    1260

gcgcctgcga aggacctggc ggatatgccg gggtggagga atgaggcaaa gatgtag       1317


<210> SEQ ID NO 64
<211> LENGTH: 30
<212> TYPE: DNA
<213> ORGANISM: Artificial
```

-continued

<220> FEATURE:
<223> OTHER INFORMATION: primer

<400> SEQUENCE: 64
atcatgggca tcgatctgcg caacaagcct 30

<210> SEQ ID NO 65
<211> LENGTH: 30
<212> TYPE: DNA
<213> ORGANISM: Artificial
<220> FEATURE:
<223> OTHER INFORMATION: primer

<400> SEQUENCE: 65
agagagctgt aaatcaggct tgttgcgcag 30

<210> SEQ ID NO 66
<211> LENGTH: 30
<212> TYPE: DNA
<213> ORGANISM: Artificial
<220> FEATURE:
<223> OTHER INFORMATION: primer

<400> SEQUENCE: 66
gaaggcatcg agaaacttcg gaagaaatac 30

<210> SEQ ID NO 67
<211> LENGTH: 30
<212> TYPE: DNA
<213> ORGANISM: Artificial
<220> FEATURE:
<223> OTHER INFORMATION: primer

<400> SEQUENCE: 67
gtcgagaaga gactggtatt tcttccgaag 30

<210> SEQ ID NO 68
<211> LENGTH: 27
<212> TYPE: DNA
<213> ORGANISM: Artificial
<220> FEATURE:
<223> OTHER INFORMATION: primer

<400> SEQUENCE: 68
cttcggaagc tgtaccagtc tcttctc 27

<210> SEQ ID NO 69
<211> LENGTH: 30
<212> TYPE: DNA
<213> ORGANISM: Artificial
<220> FEATURE:
<223> OTHER INFORMATION: primer

<400> SEQUENCE: 69
cccaatgcct gcgtcgagaa gagactggta 30

<210> SEQ ID NO 70
<211> LENGTH: 30
<212> TYPE: DNA
<213> ORGANISM: Artificial
<220> FEATURE:
<223> OTHER INFORMATION: primer

<400> SEQUENCE: 70
cttctcgagc ccaatgcctg cgtcgagaag 30

<210> SEQ ID NO 71
<211> LENGTH: 30
<212> TYPE: DNA
<213> ORGANISM: Artificial
<220> FEATURE:
<223> OTHER INFORMATION: primer

<400> SEQUENCE: 71
gataccgcgg atagcaatct gcttgtttgt 30

<210> SEQ ID NO 72
<211> LENGTH: 30
<212> TYPE: DNA
<213> ORGANISM: Artificial
<220> FEATURE:
<223> OTHER INFORMATION: primer

<400> SEQUENCE: 72
ccagcgtgga tgctcacaaa caagcagatt 30

<210> SEQ ID NO 73
<211> LENGTH: 30
<212> TYPE: DNA
<213> ORGANISM: Artificial
<220> FEATURE:
<223> OTHER INFORMATION: primer

<400> SEQUENCE: 73
atcatgggca tcgatcatcg caacaagcct 30

<210> SEQ ID NO 74
<211> LENGTH: 27
<212> TYPE: DNA
<213> ORGANISM: Artificial
<220> FEATURE:
<223> OTHER INFORMATION: primer

<400> SEQUENCE: 74
agagagctgt aaatcaggct tgttgcg 27

<210> SEQ ID NO 75
<211> LENGTH: 30
<212> TYPE: DNA
<213> ORGANISM: Artificial
<220> FEATURE:
<223> OTHER INFORMATION: primer

<400> SEQUENCE: 75
tcttcaacag agaaaggcat cgagaaactt 30

<210> SEQ ID NO 76
<211> LENGTH: 27
<212> TYPE: DNA
<213> ORGANISM: Artificial
<220> FEATURE:
<223> OTHER INFORMATION: primer

<400> SEQUENCE: 76
gtacagcttc cgaagtttct cgatgcc 27

<210> SEQ ID NO 77
<211> LENGTH: 29
<212> TYPE: DNA
<213> ORGANISM: Artificial
<220> FEATURE:
<223> OTHER INFORMATION: primer

<400> SEQUENCE: 77
atcatgggtg tcgatctgcg taatccggt 29

<210> SEQ ID NO 78
<211> LENGTH: 30
<212> TYPE: DNA
<213> ORGANISM: Artificial
<220> FEATURE:
<223> OTHER INFORMATION: primer

<400> SEQUENCE: 78
agccagctgc agatccaccg gattacgcag 30

<210> SEQ ID NO 79
<211> LENGTH: 30
<212> TYPE: DNA
<213> ORGANISM: Artificial
<220> FEATURE:
<223> OTHER INFORMATION: primer

<400> SEQUENCE: 79
aaagatattg ccaaactgaa gagcggctat 30

<210> SEQ ID NO 80
<211> LENGTH: 30
<212> TYPE: DNA
<213> ORGANISM: Artificial
<220> FEATURE:
<223> OTHER INFORMATION: primer

<400> SEQUENCE: 80
atccaccaga gcctgatagc cgctcttcag 30

<210> SEQ ID NO 81
<211> LENGTH: 27
<212> TYPE: DNA
<213> ORGANISM: Artificial
<220> FEATURE:
<223> OTHER INFORMATION: primer

<400> SEQUENCE: 81
ctgaagagcc tgtatcaggc tctggtg 27

<210> SEQ ID NO 82
<211> LENGTH: 30
<212> TYPE: DNA
<213> ORGANISM: Artificial
<220> FEATURE:
<223> OTHER INFORMATION: primer

<400> SEQUENCE: 82
gtccagaccc gcatccacca gagcctgata 30

<210> SEQ ID NO 83
<211> LENGTH: 30
<212> TYPE: DNA
<213> ORGANISM: Artificial
<220> FEATURE:
<223> OTHER INFORMATION: primer

<400> SEQUENCE: 83
agcctgtatc agaaactggt ggatgcgggt 30

<210> SEQ ID NO 84

<211> LENGTH: 30
<212> TYPE: DNA
<213> ORGANISM: Artificial
<220> FEATURE:
<223> OTHER INFORMATION: primer

<400> SEQUENCE: 84
gttcgtggcg tccagacccg catccaccag 30

<210> SEQ ID NO 85
<211> LENGTH: 30
<212> TYPE: DNA
<213> ORGANISM: Artificial
<220> FEATURE:
<223> OTHER INFORMATION: primer

<400> SEQUENCE: 85
gatacggccg acagcgcgct gctgatttgt 30

<210> SEQ ID NO 86
<211> LENGTH: 30
<212> TYPE: DNA
<213> ORGANISM: Artificial
<220> FEATURE:
<223> OTHER INFORMATION: primer

<400> SEQUENCE: 86
ccattccgga tgttcacaaa tcagcagcgc 30

<210> SEQ ID NO 87
<211> LENGTH: 29
<212> TYPE: DNA
<213> ORGANISM: Artificial
<220> FEATURE:
<223> OTHER INFORMATION: primer

<400> SEQUENCE: 87
atgggtgtcg atcatcgtaa tccggtgga 29

<210> SEQ ID NO 88
<211> LENGTH: 30
<212> TYPE: DNA
<213> ORGANISM: Artificial
<220> FEATURE:
<223> OTHER INFORMATION: primer

<400> SEQUENCE: 88
cagagccagc tgcagatcca ccggattacg 30

<210> SEQ ID NO 89
<211> LENGTH: 443
<212> TYPE: PRT
<213> ORGANISM: Cryptococcus neoformans

<400> SEQUENCE: 89

Met Pro Pro Ser Arg Ala Ser Thr Lys Val Ile Val Ile Gly Gly Gly
1 5 10 15

Gly Thr Leu Gly Ser Ser Thr Ala Leu His Leu Leu Arg Ala Gly Tyr
20 25 30

Thr Pro Ser Asn Ile Thr Val Leu Asp Thr Tyr Leu Ile Pro Ser Ala
35 40 45

Gln Ser Ala Gly Asn Asp Leu Asn Lys Ile Met Gly Ile Arg Ile Arg
50 55 60

Asn Pro Val Asp Lys Gln Leu Ser Leu Glu Ala Arg Asp Met Trp Arg

-continued

```
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Ser Leu Arg Lys Ser Tyr Glu
            100                 105                 110

Ala Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
        195                 200                 205

Thr Gln Tyr Phe Ala Asp Lys Val Val Leu Ala Ala Gly Ala Trp Ser
    210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
    290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
            420                 425                 430

Asn His Asp Glu Pro Ser Asp Asp Asp Met Asp
        435                 440
```

<210> SEQ ID NO 90
<211> LENGTH: 1332
<212> TYPE: DNA
<213> ORGANISM: Cryptococcus neoformans

<400> SEQUENCE: 90

-continued

```
atgccgccgt cccgtgcttc aacgaaagtg attgtcattg gtggtggtgg tacgctgggc     60

tcctcaaccg ccctgcatct gctgcgcgcg ggctataccc cgagtaacat taccgtgctg    120

gatacgtacc tgatcccgag tgcccagtcc gcaggcaacg acctgaataa aattatgggt    180

attcgtatcc gcaatccggt ggataaacaa ctgagcctgg aagcccgtga tatgtggcgc    240

aacgacgaag ttttcaaacc gtacttccat aacaccggtc gtctggactg cgctcacacg    300

ccggaatcaa ttgcgtcgct gcgtaaaagc tacgaagcca tcctgaaagc aggctcaggt    360

ctggaaaaaa cccatcactg gctgtcgacg gaagatgaaa tcctggcacg tgcaccgctg    420

ctggaccgta aacagattaa aggttggaaa gcaatctata gtgaagatgg cggttggctg    480

gcggccgcaa aagctattaa ctccatcggc caagtcctga aagaaaaagg tgtgaccttc    540

ggctttggta gcgcaggctc ttttaaaaaa ccgctgttcg atgaagacgg cacgaaagcc    600

attggtatcg aaaccgttga tggtacgcag tattttgccg acaaagtggt tctggctgca    660

ggtgcatgga gcccgaccct ggttgatctg gaaggccagt gctgttctaa agcttgggtc    720

tacgcgcaca tgcaactgac gccggaagaa gccgcagaat ataaagaatg cccggtcgtg    780

tacaacagcg aactgggctt tttctttgaa ccgaacgaaa aaggtgtgat caaagtttgt    840

gatgaattcc cgggctttac ccgtttcaaa cagcatcaac cgtacggtgc tagctctacg    900

aaacacatta gctttccgcg ctctcatgcg aaacacccga ccgatacgat cccggatgaa    960

agtgacgcct ccattcgtcg cgctatctct gcgtttctgc cgcgtttcaa agaaaaagaa   1020

ctgtttaacc gcgcgctgtg ctggtgtacc gatacggctg acgcgaacct gctgatttgt   1080

gaacacccga aatggaaaaa ttttatcctg gccaccggcg attcaggtca ttcgttcaaa   1140

attctgccga atatcggcaa acacgttgtc gaactgattg aaggtaccct ggccgaagat   1200

ctggcagaaa gctggcgttg gcgtccgggc agtggtgacc cgctgatctc ccgtcgcgct   1260

gcgccggcgc gcgacctggc ggacctgccg ggctggaacc acgacgaacc gagcgacgat   1320

gacatggact ga                                                        1332
```

<210> SEQ ID NO 91
<211> LENGTH: 30
<212> TYPE: DNA
<213> ORGANISM: Artificial
<220> FEATURE:
<223> OTHER INFORMATION: primer

<400> SEQUENCE: 91

```
attatgggta ttgatatccg caatccggtg                                       30
```

<210> SEQ ID NO 92
<211> LENGTH: 30
<212> TYPE: DNA
<213> ORGANISM: Artificial
<220> FEATURE:
<223> OTHER INFORMATION: primer

<400> SEQUENCE: 92

```
gctcagttgt ttatccaccg gattgcggat                                       30
```

<210> SEQ ID NO 93
<211> LENGTH: 30
<212> TYPE: DNA
<213> ORGANISM: Artificial
<220> FEATURE:
<223> OTHER INFORMATION: primer

<400> SEQUENCE: 93
gaatcaattg cgaaactgcg taaaagctac 30

<210> SEQ ID NO 94
<211> LENGTH: 30
<212> TYPE: DNA
<213> ORGANISM: Artificial
<220> FEATURE:
<223> OTHER INFORMATION: primer

<400> SEQUENCE: 94
tttcaggatg gcttcgtagc ttttacgcag 30

<210> SEQ ID NO 95
<211> LENGTH: 30
<212> TYPE: DNA
<213> ORGANISM: Artificial
<220> FEATURE:
<223> OTHER INFORMATION: primer

<400> SEQUENCE: 95
ctgcgtaaac tgtacgaagc catcctgaaa 30

<210> SEQ ID NO 96
<211> LENGTH: 30
<212> TYPE: DNA
<213> ORGANISM: Artificial
<220> FEATURE:
<223> OTHER INFORMATION: primer

<400> SEQUENCE: 96
acctgagcct gctttcagga tggcttcgta 30

<210> SEQ ID NO 97
<211> LENGTH: 30
<212> TYPE: DNA
<213> ORGANISM: Artificial
<220> FEATURE:
<223> OTHER INFORMATION: primer

<400> SEQUENCE: 97
aaactgtacg aaaaaatcct gaaagcaggc 30

<210> SEQ ID NO 98
<211> LENGTH: 30
<212> TYPE: DNA
<213> ORGANISM: Artificial
<220> FEATURE:
<223> OTHER INFORMATION: primer

<400> SEQUENCE: 98
tttttccaga cctgagcctg ctttcaggat 30

<210> SEQ ID NO 99
<211> LENGTH: 440
<212> TYPE: PRT
<213> ORGANISM: Curvularia clavata

<400> SEQUENCE: 99

Met Ala Pro Ser Arg Ala Asn Thr Ser Val Ile Val Val Gly Gly Gly
1 5 10 15

Gly Thr Ile Gly Ser Ser Thr Ala Leu His Leu Val Arg Ser Gly Tyr
20 25 30

Thr Pro Ser Asn Ile Thr Val Leu Asp Ala Tyr Pro Ile Pro Ser Ser
35 40 45

```
Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Asp Leu Arg Gln Ala Tyr Gln
            100                 105                 110

Ala Leu Leu Asp Ala Asn Ala Gly Leu Glu Glu Thr Thr Glu Trp Leu
        115                 120                 125

Asp Ser Glu Asp Glu Ile Leu Lys Lys Met Pro Leu Leu Ser Arg Asp
    130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Gly Ala Gly Ser Phe Lys Gln Pro Leu
            180                 185                 190

Leu Ala Glu Gly Val Cys Ile Gly Val Glu Thr Val Asp Gly Thr Arg
        195                 200                 205

Tyr Tyr Ala Asp Lys Val Val Leu Ala Ala Gly Ala Trp Ser Pro Thr
    210                 215                 220

Leu Val Glu Leu His Glu Gln Cys Val Ser Lys Ala Trp Val Tyr Gly
225                 230                 235                 240

His Ile Gln Leu Thr Pro Glu Glu Ala Ala Glu Tyr Lys Asn Ser Pro
                245                 250                 255

Val Val Tyr Asn Gly Asp Val Gly Phe Phe Phe Glu Pro Asn Glu His
            260                 265                 270

Gly Val Ile Lys Val Cys Asp Glu Phe Pro Gly Phe Thr Arg Phe Lys
        275                 280                 285

Met His Gln Pro Phe Gly Ala Lys Ala Pro Lys Arg Ile Ser Val Pro
    290                 295                 300

Arg Ser His Ala Lys His Pro Thr Asp Thr Ile Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
            340                 345                 350

Ala Ala Leu Leu Ile Cys Glu His Pro Glu Trp Lys Asn Phe Val Leu
        355                 360                 365

Ala Thr Gly Asp Ser Gly His Ser Phe Lys Leu Leu Pro Asn Ile Gly
    370                 375                 380

Lys His Val Val Glu Leu Leu Glu Gly Thr Leu Ala Asp Asp Leu Ala
385                 390                 395                 400

His Ala Trp Arg Trp Arg Pro Gly Ser Gly Asp Ala Leu Lys Ser Arg
                405                 410                 415

Arg Ser Ala Pro Ala Lys Asp Leu Ala Asp Met Pro Gly Trp Lys His
            420                 425                 430

Asp Asp Val Val Lys Ser Lys Leu
        435                 440
```

<210> SEQ ID NO 100
<211> LENGTH: 1323

<212> TYPE: DNA
<213> ORGANISM: Curvularia clavata

<400> SEQUENCE: 100
atggccccgt cgcgtgctaa tacgtcggtc attgtggttg gtggtggtgg tacgattggc 60
tcatctacgg ctctgcatct ggtccgctca ggctataccc cgtcgaacat tacggttctg 120
gatgcatacc cgattccgag ctctcagagc gctggcaacg acctgaataa aatcatgggt 180
atccgtctgc gtaataaggt ggatctgcag ctgtctctgg aagcgcgcca aatgtggcgc 240
gaagacgatc tgttcaagga gtatttccat aacaccggcc gtctggattg cgcgcacggt 300
gaagaaggtc ttgccgacct gcgtcaagcc tatcaggctc tgctggatgc gaatgcgggt 360
ctggaagaga cgaccgaatg gctggatagt gaagacgaaa tcctgaaaaa aatgccgctg 420
ctgtcccgcg atcaaattaa aggctggaag gcggtgtatt cacaggacgg tggttggctg 480
gcagcagcaa aggcaattaa tgcaattggt gaatatctgc gtgctcaggg cgtcaaattc 540
ggttttggcg gcgccggttc tttcaaacaa ccgctgctgg ctgaaggcgt ctgcatcggt 600
gtcgaaaccg tggatggcac gcgctattac gcagacaaag tggttctggc tgcaggtgca 660
tggtcgccga ccctggttga actgcatgaa cagtgtgtga gcaaagcgtg ggtttacggc 720
cacattcaac tgacgccgga agaagccgca gaatataaga acagcccggt cgtgtacaat 780
ggcgatgtgg gctttttctt tgaaccgaac gaacatggcg ttatcaaagt ctgcgatgaa 840
tttccgggtt ttacccgctt caagatgcac cagccgtttg gtgccaaagc accgaagcgt 900
attagtgtgc cgcgctccca tgccaaacac ccgaccgata cgatcccgga tgcaagtgaa 960
aaatccattc gtaaagctat cgcgaccttt ctgccgaagt tcacggagaa agagctgttc 1020
aaccgtcatc tgtgctggtg taccgatacg gccgacgctg cgctgctgat ttgtgaacat 1080
ccggaatgga aaaactttgt tctggcgacc ggcgattcag gtcattcgtt caaactgctg 1140
ccgaatatcg gcaagcacgt tgtcgaactg ctggagggta cgctggcaga tgacctggca 1200
cacgcatggc gttggcgtcc gggtagtggt gatgcactga aaagccgtcg ctctgctccg 1260
gcgaaagacc tggctgatat gccgggctgg aaacatgacg atgtggtgaa aagcaaactg 1320
taa 1323

<210> SEQ ID NO 101
<211> LENGTH: 30
<212> TYPE: DNA
<213> ORGANISM: Artificial
<220> FEATURE:
<223> OTHER INFORMATION: primer

<400> SEQUENCE: 101
atcatgggta tcgatctgcg taataaggtg 30

<210> SEQ ID NO 102
<211> LENGTH: 30
<212> TYPE: DNA
<213> ORGANISM: Artificial
<220> FEATURE:
<223> OTHER INFORMATION: primer

<400> SEQUENCE: 102
cagagacagc tgcagatcca ccttattacg 30

<210> SEQ ID NO 103
<211> LENGTH: 30
<212> TYPE: DNA

<213> ORGANISM: Artificial
<220> FEATURE:
<223> OTHER INFORMATION: primer

<400> SEQUENCE: 103
gaaggtcttg ccaaactgcg tcaagcctat 30

<210> SEQ ID NO 104
<211> LENGTH: 30
<212> TYPE: DNA
<213> ORGANISM: Artificial
<220> FEATURE:
<223> OTHER INFORMATION: primer

<400> SEQUENCE: 104
atccagcaga gcctgatagg cttgacgcag 30

<210> SEQ ID NO 105
<211> LENGTH: 30
<212> TYPE: DNA
<213> ORGANISM: Artificial
<220> FEATURE:
<223> OTHER INFORMATION: primer

<400> SEQUENCE: 105
cttgccaaac tgcgtcaact gtatcaggct 30

<210> SEQ ID NO 106
<211> LENGTH: 30
<212> TYPE: DNA
<213> ORGANISM: Artificial
<220> FEATURE:
<223> OTHER INFORMATION: primer

<400> SEQUENCE: 106
acccgcattc gcatccagca gagcctgata 30

<210> SEQ ID NO 107
<211> LENGTH: 30
<212> TYPE: DNA
<213> ORGANISM: Artificial
<220> FEATURE:
<223> OTHER INFORMATION: primer

<400> SEQUENCE: 107
cgtcaactgt atcagaaact gctggatgcg 30

<210> SEQ ID NO 108
<211> LENGTH: 30
<212> TYPE: DNA
<213> ORGANISM: Artificial
<220> FEATURE:
<223> OTHER INFORMATION: primer

<400> SEQUENCE: 108
ctcttccaga cccgcattcg catccagcag 30

<210> SEQ ID NO 109
<211> LENGTH: 30
<212> TYPE: DNA
<213> ORGANISM: Artificial
<220> FEATURE:
<223> OTHER INFORMATION: primer

<400> SEQUENCE: 109
gatacggccg acagcgcgct gctgatttgt 30

<210> SEQ ID NO 110
<211> LENGTH: 30
<212> TYPE: DNA
<213> ORGANISM: Artificial
<220> FEATURE:
<223> OTHER INFORMATION: primer

<400> SEQUENCE: 110
ccattccgga tgttcacaaa tcagcagcgc 30

<210> SEQ ID NO 111
<211> LENGTH: 30
<212> TYPE: DNA
<213> ORGANISM: Artificial
<220> FEATURE:
<223> OTHER INFORMATION: primer

<400> SEQUENCE: 111
atcatgggta tcgatcatcg taataaggtg 30

<210> SEQ ID NO 112
<211> LENGTH: 30
<212> TYPE: DNA
<213> ORGANISM: Artificial
<220> FEATURE:
<223> OTHER INFORMATION: primer

<400> SEQUENCE: 112
aagctgtacc agaaacttct cgacgcaggc 30

<210> SEQ ID NO 113
<211> LENGTH: 440
<212> TYPE: PRT
<213> ORGANISM: Pyrenochaeta sp.

<400> SEQUENCE: 113

```
Met Ala Ala Ser Arg Ala Lys Thr Thr Val Ile Val Val Gly Gly Gly
1               5                   10                  15

Gly Thr Ile Gly Ser Ser Thr Ala Leu His Leu Leu Arg Ser Gly Tyr
            20                  25                  30

Thr Pro Ser Asn Ile Thr Val Leu Asp Thr Tyr Pro Ile Pro Ser Leu
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Glu Met Trp Arg
65                  70                  75                  80

Glu Asp Glu Leu Phe Arg Asp Phe Phe His Asn Thr Gly Arg Leu Asp
                85                  90                  95

Cys Ala His Gly Glu Lys Gly Ile Asn Asp Leu Arg Gln Ala Tyr Gln
            100                 105                 110

Thr Leu Leu Asp Ala Asn Ala Gly Leu Glu Glu Thr Asn Glu Trp Leu
        115                 120                 125

Asp Ser Glu Asp Glu Ile Leu Ala Arg Met Pro Leu Leu Ser Arg Glu
    130                 135                 140

Gln Ile Lys Gly Trp Lys Ala Val Phe Ser Arg Asp Gly Gly Trp Leu
145                 150                 155                 160

Ala Ala Gly Lys Ala Ile Asn Ala Ile Gly Glu Tyr Leu Arg Lys Glu
                165                 170                 175

Gly Val Lys Phe Gly Phe Gly Gly Ala Gly Ser Phe Gln Gln Pro Leu
```

-continued

```
            180                 185                 190

Leu Ala Glu Gly Ile Cys Ile Gly Val Glu Thr Thr Asp Gly Thr Arg
        195                 200                 205

Tyr Tyr Ala Asp Lys Val Val Leu Ala Ala Gly Ala Trp Ser Pro Ala
    210                 215                 220

Leu Val Asp Leu Glu Asp Gln Cys Val Ser Lys Ala Trp Val Tyr Ala
225                 230                 235                 240

His Met Gln Leu Thr Pro Lys Glu Ala Ala Ala Tyr Lys Asp Thr Pro
                245                 250                 255

Val Val Tyr Asn Gly Asp Leu Gly Phe Phe Phe Glu Pro Asn Glu His
            260                 265                 270

Gly Val Ile Lys Val Cys Asp Glu Phe Pro Gly Phe Thr Arg Phe Lys
        275                 280                 285

Lys His Gln Pro Phe Gly Ala Arg Ala Pro Lys Arg Ile Ser Val Pro
    290                 295                 300

Arg Ser His Ala Lys His Pro Thr Asp Thr Tyr Pro His Ala Ser Glu
305                 310                 315                 320

Ala Ser Ile Lys Lys Ala Ile Ala Ala Phe Leu Pro Gln Phe Lys Asp
                325                 330                 335

Lys Glu Leu Phe Asn Arg Ala Met Cys Trp Cys Thr Asp Thr Ala Asp
            340                 345                 350

Ala Ala Leu Leu Ile Cys Glu His Pro Gln Trp Lys Asn Phe Met Leu
        355                 360                 365

Ala Thr Gly Asp Ser Gly His Ser Phe Lys Leu Leu Pro Asn Ile Gly
    370                 375                 380

Lys His Val Val Glu Leu Ile Glu Gly Thr Leu Ala Ala Asp Leu Ala
385                 390                 395                 400

His Ala Trp Arg Trp Arg Pro Gly Ile Gly Asp Ala Leu Gln Ser Arg
                405                 410                 415

Arg Ala Ala Pro Ala Lys Asp Leu Ala Asp Met Pro Gly Trp Asn His
            420                 425                 430

Asp Glu Ser Pro Arg Ala Lys Leu
        435                 440
```

<210> SEQ ID NO 114
<211> LENGTH: 1323
<212> TYPE: DNA
<213> ORGANISM: Pyrenochaeta sp.

<400> SEQUENCE: 114

```
atggccgctt cacgagcaaa gacgacagtg atcgtcgtgg gtggcggcgg taccattggg      60

tcatcaacag cgctccacct tctacgttca ggttatactc catcgaatat cacagttttg     120

gacacatatc caattccttc attacagtcc gcgggcaatg atttaaacaa gattatgggc     180

attcgcttgc gaaacaaagt cgacctccaa ttgagtttag aggctaggga gatgtggaga     240

gaagatgaac tttttagaga ttttttttcac aatactgggc gactggattg tgcccatggc     300

gaaaaaggaa tcaatgatct taggcaggca tatcaaacac tactcgacgc caatgccggt     360

ttggaagaga cgaacgagtg gctggactct gaggacgaaa ttctggcaag aatgccgctc     420

ttgagtcgag agcagatcaa gggctggaaa gcggtcttca gccgagacgg cggttggctc     480

gccgcaggta aggccatcaa tgcaattggc gagtatctgc gcaaggaagg agtcaagttt     540

ggctttggcg gcgcgggatc gttccagcag ccgcttcttg cagagggtat ttgcattggc     600

gtggaaacaa cggatggaac tagatactac gccgacaaag ttgtcctggc agctggtgca     660
```

-continued

```
tggagtcctg cattggtgga cttggaagac cagtgtgttt caaaagcatg ggtctatgct    720

cacatgcagc tcaccccgaa ggaggctgcg gcatacaaag acacaccagt agtctacaat    780

ggcgatctgg gatttttctt tgaaccaaac gagcatggcg tgatcaaagt ctgcgacgag    840

ttcccaggct tcacacgttt taagaagcat caaccatttg gtgcaagggc accaaaacgg    900

atatcggttc ccagatctca tgccaaacac cctactgata cttatcctca cgcatccgaa    960

gccagtatca agaaagctat tgcggcattc ttaccacagt tcaaggacaa ggagctgttc   1020

aaccgcgcaa tgtgctggtg cacagataca gctgatgcag ccttgttgat ctgcgaacac   1080

ccgcaatgga agaatttcat gcttgctact ggagacagcg ggcactcatt taagctctta   1140

ccaaatatcg gcaagcatgt agttgaactg attgaaggca ctctggcggc agatcttgcc   1200

catgcttgga ggtggcgacc tgggattggt gacgctttgc agtcaaggcg agcggcacct   1260

gcgaaggatc tggcggacat gccaggatgg aatcatgatg aatctcctag ggcgaaattg   1320

taa                                                                 1323


<210> SEQ ID NO 115
<211> LENGTH: 452
<212> TYPE: PRT
<213> ORGANISM: Arthrinium sp.

<400> SEQUENCE: 115

Met Ala Ala Ser Arg Lys Thr Thr Lys Val Ile Val Val Gly Gly Gly
1               5                   10                  15

Gly Thr Ile Gly Ser Ser Thr Ala Leu His Leu Leu Arg Ser Gly Tyr
            20                  25                  30

Thr Ala Thr Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Pro Val Asp Lys Gln Leu Ser Leu Glu Ala Gln Asp Met Trp Cys
65                  70                  75                  80

His Asp Glu Leu Phe Lys Pro Tyr Phe His Asn Thr Gly Arg Met Asp
                85                  90                  95

Cys Glu Gly Thr Glu Lys Gly Ile Ala Ala Leu Lys Gln Gln Tyr Gln
            100                 105                 110

Thr Leu Leu Asp Ala Asp Val Gly Leu Glu Lys Thr Thr Glu Trp Leu
        115                 120                 125

Asp Ser Glu Asp Ala Ile Leu Ala Lys Met Pro Leu Leu Glu Arg Asp
    130                 135                 140

Gln Ile Lys Gly Trp Lys Ala Ile Phe Ser Gln Asp Gly Gly Trp Leu
145                 150                 155                 160

Ala Ala Ala Lys Ala Ile Asn Ala Ile Gly Glu Glu Leu Lys Arg Gln
                165                 170                 175

Gly Val Asn Phe Gly Phe Gly Gly Ala Gly Ala Phe Lys Lys Pro Leu
            180                 185                 190

Phe Ala Pro Asp Gly Ser Thr Cys Ile Gly Val Glu Thr Val Asp Gly
        195                 200                 205

Thr Lys Tyr Tyr Gly Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro His Glu Ala Ala Glu Tyr Gln Gly
```

```
                245                 250                 255

Cys Pro Val Val Tyr His Gly Asp Leu Gly Phe Phe Phe Glu Pro Asn
            260                 265                 270

Glu His Gly Val Ile Lys Val Cys Asp Glu Phe Pro Gly Phe Thr Arg
        275                 280                 285

Phe Leu Glu Gln His Gln Ser Tyr Gly Ala Pro Ala Pro Thr Arg Val
    290                 295                 300

Ser Val Pro Arg Ser His Ala Lys His Pro Thr Asp Thr Tyr Pro Asp
305                 310                 315                 320

Ala Ser Glu Gln Ser Ile Arg Arg Ala Val Ala Ala Phe Leu Pro Arg
                325                 330                 335

Phe Gln Ser Lys Glu Leu Phe Asn Arg Ala Met Cys Trp Cys Thr Asp
            340                 345                 350

Thr Ala Asp Ala Ala Leu Leu Ile Cys Glu His Pro Arg Trp Arg Asn
        355                 360                 365

Phe Ile Leu Ala Thr Gly Asp Ser Gly His Ser Phe Lys Leu Leu Pro
    370                 375                 380

Asn Ile Gly Lys His Val Val Glu Leu Leu Glu Gly Arg Leu Ala Asp
385                 390                 395                 400

Asp Leu Ala Gln Ala Trp Arg Trp Arg Pro Gly Gln Gly Asp Ala Leu
                405                 410                 415

Lys Ser Arg Arg Ala Ala Pro Ala Lys Asp Leu Ala Asp Met Pro Gly
            420                 425                 430

Trp Asn His Asp Gly Asp Ser Gly Asn Ala Thr Ser Gly Thr Ser Ser
        435                 440                 445

Glu His Lys Leu
    450
```

<210> SEQ ID NO 116
<211> LENGTH: 1359
<212> TYPE: DNA
<213> ORGANISM: Arthrinium sp.

<400> SEQUENCE: 116

```
atggcggcgt cacgaaagac caccaaagtg attgtcgtgg gcggcggagg caccatcggc      60

tcatccacgg ctctacatct tctccggtcg ggtatacgg ccaccaacat taccgtcctg       120

gacacctacc ccatcccctc ggcgcagtcg gccggcaacg acctgaacaa gattatgggg     180

atccgcctgc ggaacccggt cgacaagcag ctcagccttg aagcccagga catgtggtgc     240

catgacgagc tcttcaagcc ctacttccac aacaccggca ggatggactg cgagggcacc     300

gagaagggca tcgcggcgct caagcagcag taccagacct tgcttgacgc cgacgtgggc     360

ctcgagaaga cgacggagtg gctcgacagt gaggatgcca tcctggcaaa gatgccactc     420

ctggagcgcg accaaatcaa aggatggaaa gcgatattta gccaggacgg cggttggctg     480

gccgcagcta aagccatcaa cgcgataggc gaggaactga agaggcaggg cgtcaacttc     540

gggttcggcg gggcgggcgc cttcaagaag cccctttcg ccccggacgg atccacctgc      600

atcggcgtcg agacggtgga tggaaccaag tactacggcg acaaggtcgt cctggccgcg     660

ggcgcgtgga gccctgcgct ggtcgacctg gaagagcagt gctgctccaa ggcctgggtg     720

tacgcccaca tgcagctgac gccgcacgag gcagccgagt accagggctg tccggtcgtg     780

taccacggcg acctcggctt cttcttcgag cccaacgagc acggcgtcat caaggtgtgc     840

gacgagttcc ccggcttcac gcggttcctc gagcagcacc agtcgtacgg cgcgccggcg     900
```

-continued

```
ccgacgcgcg tctcggtgcc ccggtcgcac gcgaagcacc ccaccgacac atacccggac    960

gcgtcggagc agtcgatccg gcgggccgtg gccgcgttcc tgccgcgatt ccaaagcaaa   1020

gagcttttca accgcgccat gtgctggtgc accgacacgg ccgacgccgc gctgctgatc   1080

tgcgagcacc cccgctggcg caattttatt ctggctacgg gcgacagcgg acactcgttc   1140

aagctcctgc ccaacatcgg caagcacgtg gtcgagctgc tggaaggccg gctagcggat   1200

gacctggcgc aggcgtggag gtggcgcccc ggtcaggggg atgcgttgaa gtctagacgg   1260

gcggctccgg ctaaggatct ggcggatatg ccagggtgga atcatgacgg ggattcaggg   1320

aatgctacgt ctggaacaag ctcggagcac aaattgtag                          1359


<210> SEQ ID NO 117
<211> LENGTH: 440
<212> TYPE: PRT
<213> ORGANISM: Curvularia clavata

<400> SEQUENCE: 117

Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Asp Leu Arg Gln Ala Tyr Gln
            100                 105                 110

Ala Leu Leu Asp Ala Asn Ala Gly Leu Glu Glu Thr Thr Glu Trp Leu
        115                 120                 125

Asp Ser Glu Asp Glu Ile Leu Lys Lys Met Pro Leu Leu Asp Arg Glu
    130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Gly Ala Gly Ser Phe Lys Gln Pro Leu
            180                 185                 190

Leu Ala Glu Gly Val Cys Ile Gly Val Glu Thr Val Asp Gly Thr Arg
        195                 200                 205

Tyr Tyr Ala Asp Lys Val Val Leu Ala Ala Gly Ala Trp Ser Pro Val
    210                 215                 220

Leu Val Asp Leu Glu Asp Gln Cys Val Ser Lys Ala Trp Val Tyr Ala
225                 230                 235                 240

His Ile Gln Leu Thr Pro Glu Glu Ala Ala Glu Tyr Lys Asn Val Pro
                245                 250                 255

Val Val Tyr Asn Gly Asp Val Gly Phe Phe Phe Glu Pro Asp Glu His
            260                 265                 270

Gly Val Ile Lys Val Cys Asp Glu Phe Pro Gly Phe Thr Arg Phe Lys
        275                 280                 285

Gln His Gln Pro Tyr Gly Ala Lys Ala Pro Lys Arg Ile Ser Val Pro
```

```
    290                 295                 300

Arg Ser Ala Ala Lys His Pro Thr Asp Thr Tyr Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
            340                 345                 350

Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly
    370                 375                 380

Lys His Val Val Glu Leu Leu Glu Gly Thr Leu Ala Glu Asp Leu Ala
385                 390                 395                 400

His Ala Trp Arg Trp Arg Pro Gly Thr Gly Asp Ala Leu Lys Ser Arg
                405                 410                 415

Arg Ala Ala Pro Ala Lys Asp Leu Ala Asp Met Pro Gly Trp Lys His
            420                 425                 430

Asp Asp Val Val Lys Ser Lys Leu
        435                 440


<210> SEQ ID NO 118
<211> LENGTH: 1323
<212> TYPE: DNA
<213> ORGANISM: Curvularia clavata

<400> SEQUENCE: 118

atggcgccct caagagcaaa cacttctgtt atcgttgtcg gtggcggtgg cactattggc     60

tcttcaaccg ctcttcatct agtccgctcg ggctacacac catctaacat caccgttctt    120

gacacatacc ctatcccatc agcgcagtca gctggaaatg acctgaataa gatcatgggt    180

atccgcttgc ggaacaaggt cgatctccaa ttgagtctag aagccaggca gatgtggaga    240

gaggatgacc tattcaaaga gtatttccac aacactggaa gactcgactg tgcacatggg    300

gaagagggac ttgcagattt gagacaggca taccaggctc tgctcgacgc taacgcgggt    360

ctcgaagaaa caacagaatg gcttgactcc gaagacgaaa ttctaaagaa aatgccgctt    420

ctggaccgcg agcaaatcaa gggctggaaa gcggtttaca gccaagacgg cggctggctg    480

gctgcagcaa aagccatcaa tgctataggc gagtacttgc gagcccaagg agttaagttt    540

ggttttggtg gtgctggatc gttcaagcag cctcttttgg ccgagggagt gtgcattggc    600

gtagagacag tcgacgggac gaggtactac gccgataaag ttgtgcttgc agctggtgct    660

tggagtccgg tattggtcga cctggaagat caatgcgttt caaaagcttg ggtatatgct    720

cacatacagc ttacgcctga ggaagcagca gagtacaaaa acgtgcctgt ggtatacaac    780

ggcgacgtcg gcttcttctt cgagcctgac gagcacggcg ttatcaaggt ttgtgacgaa    840

tttccaggtt ttacacgctt caagcaacat cagccatatg gcgccaaagc accgaaacgt    900

atctccgtgc ccagatcggc agcgaagcac ccgacggata cttaccccga tgcgtcggag    960

aagagcatcc gcaaggccat tgcaactttc ctgcccaagt tcacagagaa ggagctattc   1020

aaccggcatc tatgttggtg tacggatacg gctgacgctg cgctattgat gtgtgagcat   1080

cccgagtgga agaactttgt gctggcgaca ggggacagcg ggcacacatt caaacttttg   1140

ccaaatatcg gcaagcatgt ggttgagctt ctcgagggta cactcgcgga ggatctggca   1200

catgcatgga gatggcggcc tggtactggc gatgcgctga aatcaagaag agcggcaccg   1260
```

-continued

```
gcgaaggatt tagcagatat gcctggctgg aagcatgacg atgttgtcaa gtccaagtta   1320

tag                                                                 1323


<210> SEQ ID NO 119
<211> LENGTH: 438
<212> TYPE: PRT
<213> ORGANISM: Emericella nidulans

<400> SEQUENCE: 119

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Phe Gly Ile Arg Leu Arg Asn
    50                  55                  60

Lys Pro Asp Leu Gln Leu Tyr Leu Glu Ala Leu Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Lys Leu Arg Met Arg Tyr Gln Ser
            100                 105                 110

Leu Leu Asp Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
```

-continued

```
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435


<210> SEQ ID NO 120
<211> LENGTH: 1317
<212> TYPE: DNA
<213> ORGANISM: Emericella nidulans

<400> SEQUENCE: 120

atggcgcccc gagccaacac caaaatcatc gtcgtcggcg gcggcggcac aatgggctcg      60

tcgacagccc tacacctcct gcgcgccggc tacacgccgt ccaacatcac agtgctcgac     120

acgtacccta tcccttccgc acagtctgca ggctacgacc tgaacaaaat cttcggcatc     180

aggctgcgca acaagcctga cttacaactc tatcttgagg cgctggacat gtggaaaaat     240

gatcctctat tcaagccgtt tttccacaat gttggacaga tggacgtctc ttcaacagaa     300

gaaggcatca aaaagcttcg catgagatac cagtctcttc tcgacgcagg cattgggctc     360

gagaagacga atttcctgct ggaaagtgaa gacgagatcc tggctaaagc gccgcatttc     420

acgcgggagc agattaaagg ctggaaaggg ctgttctgtg gcgacggcgg ttggctcgct     480

gcagccaaag ccatcaatgc catcgggcag ttcctcaagg aacagggcgt caagtttgga     540

tttggcgagg ccggcacgtt caaaaagcca ctcttcgccg atgccgacga gaagacgtgc     600

atcggcgtcg aaactgtaga cggcacaaaa tactacgccg acaaggtcgt tctagcagct     660

ggtgcctgga gttcgacgtt ggtcgatctg gaggagcagt gcgtttcaaa ggcctgggtc     720

tttgcccaca tccaactgac gcccgctgaa gcagccgcgt acaagaacac tcctgttata     780

tacgacggtg actatgggtt tttcattgag ccggacgaga acggcatcat aaaagtctgc     840

gacgaattcc ctggcttcac gcacttcaag atgcaccagc cgtacggctc accggtgccc     900

aaattgatct ctgtgcctcg ctcccatgcg aagcacccca cagatacata cccgcacgcg     960

tcggaggtca ccatcaaaaa ggctatcaac cggttcctgc cgaggttcaa tgacaaggaa    1020

ctgtttaaca gggccatgtg ctggtgcacc gataccgcgg atgcaaatct gcttgtttgt    1080

gagcatccac gctggaaggg gttttatctt gcaacagggg acagcgggca ttcgttcaag    1140

ttgctgccga atattggaaa gcacgttgtc gagttattgg aggggaggct ggaaagtgtg    1200

tttaaggatg cttggaggtg gaggcctggc agtggggatg cattaaagag tagacgggct    1260

gcgcctgcga aggacctggc ggatatgccg ggtggaggga atgaggcaaa gatgtag       1317


<210> SEQ ID NO 121
<211> LENGTH: 441
<212> TYPE: PRT
<213> ORGANISM: Ulocladium sp.

<400> SEQUENCE: 121

Met Ala Pro Asn Arg Ala Asn Ile Ser Val Ile Val Val Gly Gly Gly
1               5                   10                  15
```

-continued

```
Gly Thr Ile Gly Ser Ser Thr Ala Leu His Leu Val Arg Ser Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Arg Leu Arg
    50                  55                  60

Asn Lys Val Asp Leu Gln Leu Ser Leu Glu Ala Arg Gln Met Trp Thr
65                  70                  75                  80

Glu Asp Asp Leu Phe Lys Glu Tyr Phe His Lys Thr Gly Arg Leu Asp
                85                  90                  95

Cys Ala His Gly Glu Lys Gly Leu Ala Asp Leu Lys Gln Ala Tyr Gln
            100                 105                 110

Ala Leu Leu Asp Ala Asn Ala Gly Leu Glu Ala Thr Thr Glu Trp Leu
        115                 120                 125

Asp Ser Glu Asp Lys Ile Leu Glu Lys Met Pro Leu Leu Asn Arg Asp
    130                 135                 140

Gln Ile Lys Gly Trp Lys Ala Val Phe Ser Glu Asp Gly Gly Trp Leu
145                 150                 155                 160

Ala Ala Ala Lys Ala Ile Asn Ala Ile Gly Arg Phe Leu Arg Asp Gln
                165                 170                 175

Gly Val Lys Phe Gly Phe Gly Gly Ala Gly Ser Phe Lys Gln Pro Leu
            180                 185                 190

Leu Ala Glu Gly Val Cys Val Gly Val Glu Thr Val Asp Gly Thr Arg
        195                 200                 205

Tyr Tyr Ala Asp Lys Val Val Leu Ala Ala Gly Ala Trp Ser Pro Ala
    210                 215                 220

Leu Val Asp Leu Gln Asp Gln Cys Val Ser Lys Ala Trp Val Tyr Ala
225                 230                 235                 240

His Ile Gln Leu Ser Pro Ser Glu Ala Ala Glu Tyr Lys Asn Val Pro
                245                 250                 255

Val Val Tyr Asn Gly Asp Val Gly Phe Phe Phe Glu Pro Asp Glu Tyr
            260                 265                 270

Gly Val Ile Lys Val Cys Asp Glu Phe Pro Gly Phe Thr Arg Phe Lys
        275                 280                 285

Gln His Gln Pro Phe Gly Ala Ser Ala Pro Lys Arg Ile Ser Val Pro
    290                 295                 300

Arg Ser Ala Ala Lys His Pro Thr Asp Thr Tyr Pro Asp Ala Ser Glu
305                 310                 315                 320

Val Ser Ile Arg Lys Ala Ile Ala Thr Phe Leu Pro Lys Phe Thr Glu
                325                 330                 335

Lys Glu Val Phe Asn Arg His Leu Cys Trp Cys Thr Asp Thr Ala Asp
            340                 345                 350

Ala Ala Leu Leu Met Cys Glu His Pro Glu Trp Lys Asn Phe Val Leu
        355                 360                 365

Ala Thr Gly Asp Ser Gly His Thr Phe Lys Leu Leu Pro Asn Ile Gly
    370                 375                 380

Lys His Val Val Glu Leu Leu Glu Gly Thr Leu Ala Asp Asp Leu Ala
385                 390                 395                 400

His Ala Trp Arg Trp Arg Pro Gly Thr Gly Asp Ala Leu Lys Ser Arg
                405                 410                 415

Arg Ala Ala Arg Ala Lys Asp Leu Ala Asp Met Pro Gly Trp Asn His
            420                 425                 430
```

Asp Gly Glu Ala Pro Arg Ala Lys Leu
        435                 440

<210> SEQ ID NO 122
<211> LENGTH: 1326
<212> TYPE: DNA
<213> ORGANISM: Ulocladium sp.

<400> SEQUENCE: 122
atggcaccta acagagctaa tatttctgtc atcgtcgtgg gtggtggcgg caccattggg 60
tcttcaacgg cccttcatct cgtacgctcg ggatacacac cgtcgaatat cacggttctg 120
gacacttatc caattccatc agcgcaatca gctggcaatg acttgaacaa gatcatgggt 180
atccgtttgc ggaacaaggt ggatttgcag ttgagcttag aggcgagaca aatgtggaca 240
gaagacgatc tgttcaagga gtactttcat aaaaccgggc ggctcgactg cgcacatggc 300
gagaaaggcc ttgcagatct caaacaagcc taccaagccc ttcttgatgc gaacgctggc 360
ctggaggcga cgacagaatg gttagattcc gaggacaaga ttcttgagaa gatgccgctt 420
ctcaatcgcg atcagatcaa aggatggaaa gccgtcttca gcgaagacgg cggatggctc 480
gctgcggcaa aagccatcaa cgctatcggt agatttctgc gcgatcaagg cgtcaagttt 540
ggctttggcg gagcaggatc attcaaacaa cctcttcttg ccgagggtgt ttgtgttggt 600
gttgaaacag ttgacgggac gagatattat gctgacaagg ttgtgttggc ggctggtgcg 660
tggagtcctg cattggtcga tctacaagac caatgtgtgt cgaaagcatg ggtatacgct 720
cacatccaac tgtccccgag cgaggcggcg gaatacaaaa atgttcctgt agtctataat 780
ggcgacgtgg gcttcttctt cgagcctgac gaatacggcg tcatcaaagt ctgtgacgag 840
tttccaggtt ttacgcgctt caagcagcat caacctttcg gcgcatcggc tccaaagcgc 900
atttctgtgc ctcgatctgc cgcaaaacac cccacagata cctatccgga cgcctcggaa 960
gtcagtatcc gcaaggccat cgcgacgttc ctgcccaagt tcacagaaaa ggaagtgttc 1020
aacaggcatc tgtgttggtg tactgatacg gctgatgcgg cgcttttgat gtgcgaacat 1080
cctgagtgga agaactttgt tttggccacg ggtgacagtg gtcacacctt caagcttcta 1140
cctaacatcg gtaagcatgt ggtcgagcta ctagagggta cattagcaga cgacctagcg 1200
catgcgtgga gatggcgtcc cggtaccggc gatgcgctga agtcgcgaag ggcggcgcgt 1260
gcgaaagacc ttgcagatat gccaggatgg aatcatgacg gggaagcccc cagagcgaag 1320
ctgtga 1326

<210> SEQ ID NO 123
<211> LENGTH: 437
<212> TYPE: PRT
<213> ORGANISM: Penicillium janthinellum

<400> SEQUENCE: 123

Met Ala His Ser Arg Glu Ser Thr Lys Ile Val Ile Val Gly Gly Gly
1               5                   10                  15

Gly Thr Met Gly Ser Ser Thr Ala Leu His Leu Ile Arg Ser Gly Tyr
            20                  25                  30

Thr Pro Ser Asn Ile Thr Val Leu Asp Val Tyr Pro Ile Pro Ser Leu
        35                  40                  45

Gln Ser Ala Gly Tyr Asp Leu Asn Lys Ile Met Ser Ile Arg Leu Arg
    50                  55                  60

Asn Gly Pro Asp Leu Gln Leu Ser Leu Glu Ala Leu Asp Met Trp Lys
65                  70                  75                  80

```
Asn Asp Pro Leu Phe Lys Pro Phe Phe His Asn Val Gly Met Leu Asp
                85                  90                  95

Cys Ser Ser Ser Gln Glu Gly Ile Ala Ser Leu Arg Arg Lys His Gln
            100                 105                 110

Asp Leu Ile Asp Ala Asn Ile Gly Leu Glu Lys Thr Asn Ile Trp Leu
        115                 120                 125

Glu Ser Glu Asp Asp Ile Leu Ala Lys Ala Pro His Phe Thr Arg Glu
    130                 135                 140

Gln Ile Lys Gly Trp Lys Gly Leu Phe Cys Gly Asp Gly Gly Trp Leu
145                 150                 155                 160

Ala Ala Ala Lys Ala Ile Asn Ala Ile Gly Thr Phe Leu Lys Ser Gln
                165                 170                 175

Gly Val Lys Phe Gly Phe Gly Ser Ala Gly Thr Phe Lys Arg Pro Leu
            180                 185                 190

Phe Ala Pro Asp Gly Ala Thr Cys Ser Gly Val Glu Thr Val Asp Gly
        195                 200                 205

Thr Lys Tyr Phe Ala Asp Lys Val Val Leu Ala Ala Gly Ala Trp Ser
    210                 215                 220

Ser Thr Leu Val Asp Leu Glu Asp Gln Cys Val Ser Lys Ala Trp Val
225                 230                 235                 240

Phe Ala His Ile Gln Leu Thr Pro Gln Glu Ser Ala Gln Tyr Lys Asp
                245                 250                 255

Val Pro Val Val Tyr Asp Gly Asp Tyr Gly Phe Phe Phe Glu Pro Asn
            260                 265                 270

Glu His Gly Val Ile Lys Val Cys Asp Glu Phe Pro Gly Phe Ser Arg
        275                 280                 285

Phe Lys Leu His Gln Pro Tyr Gly Ala Thr Ser Pro Lys Leu Ile Ser
    290                 295                 300

Val Pro Arg Ser His Ala Lys His Pro Thr Asp Thr Tyr Pro Asp Ser
305                 310                 315                 320

Ser Glu Glu Thr Ile Arg Lys Ala Ile Ala Arg Phe Met Pro Arg Phe
                325                 330                 335

Lys Asp Lys Glu Leu Phe Asn Arg Ser Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Val Leu Pro Asn
    370                 375                 380

Ile Gly Lys His Val Val Glu Leu Ile Glu Gly Arg Leu Pro Gln Asp
385                 390                 395                 400

Leu Ala Gly Ala Trp Arg Trp Arg Pro Gly Gly Asp Ala Leu Lys Ser
                405                 410                 415

Lys Arg Ser Ala Pro Ala Lys Asp Leu Ala Glu Met Pro Gly Trp Lys
            420                 425                 430

His Asp Ala Lys Leu
        435
```

<210> SEQ ID NO 124
<211> LENGTH: 1314
<212> TYPE: DNA
<213> ORGANISM: Penicillium janthinellum

<400> SEQUENCE: 124

```
atggctcatt cgcgagaaag cacaaagatt gtcattgtcg ggggaggtgg cacaatggga     60
```

```
tcttcaaccg cgctacacct gatacgctct ggatacaccc cgtcaaacat caccgtcctt    120

gatgtatacc caattccatc cttgcaatcc gcaggatatg atcttaacaa gatcatgagc    180

atccgattac gcaacgggcc tgacttgcaa ctttccctgg aggctctcga tatgtggaaa    240

aacgatccgt tgttcaagcc tttctttcac aacgttggca tgctagactg ttcatcgtca    300

caagagggta ttgcaagcct tcgacggaag caccaagacc tcatagacgc gaatatcgga    360

ctagagaaga cgaatatctg gttagagagt gaagatgata ttctggcaaa agccccgcac    420

ttcacgcggg aacagatcaa ggggtggaag ggcttgtttt gcggcgatgg aggatggctt    480

gctgcagcca aggccatcaa tgcgatcgga acctttctaa aaagtcaagg cgtcaagttc    540

ggatttggaa gtgccgggac tttcaagcga cctttgtttg ctccagatgg ggcgacatgc    600

agcggtgttg agacagtaga tggaacaaaa tacttcgccg acaaggtggt tttggccgct    660

ggtgcttgga gttcgacgtt agtagatttg gaggaccaat gtgtttcgaa ggcctgggtc    720

ttcgctcata tccaactcac gccccaagaa tcggcccagt acaaggacgt gcccgtagta    780

tacgacggtg attatggctt tttcttcgag cccaacgaac acggagtaat caaagtctgc    840

gatgagttcc ccgggttctc ccgcttcaag ctgcatcaac cttacggtgc cacctctcct    900

aagcttatat ccgttcctcg atcacacgcc aagcatccca ccgataccta cccagattct    960

tctgaagaga ccattcgaaa agcgattgcg aggtttatgc cacgcttcaa ggataaggag   1020

ctttttaata ggagcatgtg ctggtgcacc gatactgctg atgccaactt gttgatctgc   1080

gagcaccccca agtggaagaa ctttatcttg gccacaggag acagcggcca tagtttcaag   1140

gttttgccca atataggaaa acatgtcgtt gagttgatag aaggacgcct accacaagac   1200

ctggctggtg cgtggagatg gagaccaggg ggagatgccc ttaagtccaa acgcagtgct   1260

ccggcaaagg accttgctga aatgccgggc tggaagcatg atgcgaagct ctga          1314
```

<210> SEQ ID NO 125
<211> LENGTH: 445
<212> TYPE: PRT
<213> ORGANISM: Aspergillus fumigatus

<400> SEQUENCE: 125

```
Met Ala Pro Ser Ile Leu Ser Thr Glu Ser Ser Ile Ile Val Ile Gly
1               5                   10                  15

Ala Gly Thr Trp Gly Cys Ser Thr Ala Leu His Leu Ala Arg Arg Gly
            20                  25                  30

Tyr Lys Asp Val Thr Val Leu Asp Pro His Pro Val Pro Ser Pro Ile
        35                  40                  45

Ala Ala Gly Asn Asp Ile Asn Lys Ile Met Glu His Ser Glu Leu Lys
    50                  55                  60

Asp Gly Ser Ser Asp Pro Arg Ser Ala Ala Phe Ser Thr Phe Thr Arg
65                  70                  75                  80

Ala Ala Leu Lys Ala Trp Lys Thr Asp Pro Val Phe Gln Pro Tyr Phe
                85                  90                  95

His Glu Thr Gly Phe Ile Ile Ser Gly His Thr Pro Ala Leu Ile Asp
            100                 105                 110

His Ile Arg Lys Asp Glu Val Glu Pro Ser Glu Thr Asn Phe Val Lys
        115                 120                 125

Leu Glu Thr Ala Glu Asp Phe Arg Arg Thr Met Pro Pro Gly Val Leu
    130                 135                 140

Thr Gly Asp Phe Pro Gly Trp Lys Gly Trp Leu His Lys Ser Gly Ala
```

-continued

```
145                 150                 155                 160

Gly Trp Ile His Ala Lys Lys Ala Met Ile Ser Ala Phe Asn Glu Ala
                165                 170                 175

Lys Arg Leu Gly Val Arg Phe Val Thr Gly Ser Pro Glu Gly Asn Val
            180                 185                 190

Val Ser Leu Val Tyr Glu Asp Gly Asp Val Val Gly Ala Arg Thr Ala
        195                 200                 205

Asp Gly Arg Val His Lys Ala His Arg Thr Ile Leu Ser Ala Gly Ala
    210                 215                 220

Gly Ser Asp Ser Leu Leu Asp Phe Lys Lys Gln Leu Arg Pro Thr Ala
225                 230                 235                 240

Trp Thr Leu Cys His Ile Gln Met Gly Pro Glu Glu Val Lys Gln Tyr
                245                 250                 255

Arg Asn Leu Pro Val Leu Phe Asn Ile Ala Lys Gly Phe Phe Met Glu
            260                 265                 270

Pro Asp Glu Asp Lys His Glu Leu Lys Ile Cys Asp Glu His Pro Gly
        275                 280                 285

Tyr Cys Asn Phe Leu Pro Asp Pro Asn Arg Pro Gly Gln Glu Lys Ser
    290                 295                 300

Val Pro Phe Ala Lys His Gln Ile Pro Leu Glu Ala Glu Ala Arg Ala
305                 310                 315                 320

Arg Asp Phe Leu His Asp Thr Met Pro His Leu Ala Asp Arg Pro Leu
                325                 330                 335

Ser Phe Ala Arg Ile Cys Trp Asp Ala Asp Thr Pro Asp Arg Ala Phe
            340                 345                 350

Leu Ile Asp Arg His Pro Glu His Pro Ser Leu Leu Val Ala Val Gly
        355                 360                 365

Gly Ser Gly Asn Gly Ala Met Gln Met Pro Thr Ile Gly Gly Phe Ile
    370                 375                 380

Ala Asp Ala Leu Glu Ser Lys Leu Gln Lys Glu Val Lys Asp Ile Val
385                 390                 395                 400

Arg Trp Arg Pro Glu Thr Ala Val Asp Arg Asp Trp Arg Ala Thr Gln
                405                 410                 415

Asn Arg Phe Gly Gly Pro Asp Arg Ile Met Asp Phe Gln Gln Val Gly
            420                 425                 430

Glu Asp Gln Trp Thr Lys Ile Gly Glu Ser Arg Gly Pro
        435                 440                 445
```

<210> SEQ ID NO 126
<211> LENGTH: 1338
<212> TYPE: DNA
<213> ORGANISM: Aspergillus fumigatus

<400> SEQUENCE: 126

```
atggcgcctt caattttgag cactgaatct tccattatcg ttatcggagc aggcacatgg      60

ggctgctcaa ctgctctgca cctcgctcgt cgaggctaca aagatgtcac tgttctcgac     120

cctcatccag ttccttcgcc cattgcagca ggcaatgaca tcaacaagat tatggagcac     180

agcgagctga aagatggctc atccgaccct cgaagcgcag ccttctcgac atttacgcga     240

gctgctctta aggcgtggaa aactgacccg gttttccagc cttactttca cgaaactggc     300

tttatcatat cggggcacac acctgctctg attgaccaca tacgaaaaga cgaggtagaa     360

ccgtcagaaa caaacttcgt caagctggag acagccgagg acttccgccg gaccatgccg     420

ccaggtgtac tgacaggcga cttccctggc tggaaaggct ggttgcacaa gtctggtgct     480
```

-continued

```
gggtggattc atgccaaaaa ggctatgatc tctgctttca atgaagctaa gcgcttggga    540

gtcagatttg tcactggctc tccggaaggg aatgttgtat cgttggtata cgaggacgga    600

gacgtcgttg gagccagaac tgccgatggt cgcgtgcaca aagcccatcg cactattctt    660

tcggcaggtg ctggcagtga cagtctccta gacttcaaga agcagcttcg gcctaccgcg    720

tggactctct gtcatattca gatgggccct gaagaggtca agcaatatcg gaaccttcct    780

gtgttgttca acatcgccaa agggttcttc atggagcctg atgaggataa acacgagctc    840

aagatttgtg acgagcatcc agggtactgc aactttctcc ctgacccaaa cagaccgggc    900

caggagaaga gtgtcccctt cgcaaagcat cagatcccgc tcgaggccga agcccgcgca    960

cgagactttc tccatgatac aatgccgcat ctggctgacc ggccactgtc tttcgcgcgt   1020

atttgctggg atgctgatac cccagaccgt gctttcttga tcgatagaca tcctgaacac   1080

ccctcactgc tagtcgctgt tggaggttcc ggcaatggcg ccatgcaaat gcctacaatt   1140

ggcggtttta tcgcagatgc tctagagagt aaactacaga aggaggtgaa ggacatcgtt   1200

cgatggaggc cagagacggc tgtcgatcga gattggagag cgactcagaa tcgctttggc   1260

gggcctgaca ggatcatgga ttttcagcag gtcggagagg atcagtggac caagattgga   1320

gagagcagag gtccgtaa                                                 1338
```

<210> SEQ ID NO 127
<211> LENGTH: 445
<212> TYPE: PRT
<213> ORGANISM: Aspergillus oryzae

<400> SEQUENCE: 127

```
Met Thr Ser Ser Lys Leu Thr Pro Thr Ser Ser Ile Leu Ile Val Gly
1               5                   10                  15

Ala Gly Thr Trp Gly Cys Ser Thr Ala Leu His Leu Ala Arg Arg Gly
            20                  25                  30

Tyr Lys Asn Val Thr Val Leu Asp Pro His Pro Val Pro Ser Pro Ile
        35                  40                  45

Ala Ala Gly Asn Asp Ile Asn Lys Ile Met Glu His Arg Glu Val Lys
    50                  55                  60

Ala Ser Glu Thr Asp Pro Trp Ser Ile Ala Phe Ser Thr Cys Thr Arg
65                  70                  75                  80

Ala Ala Leu Lys Gly Trp Lys Asn Asp Pro Val Phe Gln Pro Tyr Phe
                85                  90                  95

His Glu Thr Gly Ala Ile Val Ser Gly His Thr Ala Ser Leu Ile Lys
            100                 105                 110

His Ile Gln Glu His Glu Ile Asp Ser Ser Asp Ala Glu Phe Ile Lys
        115                 120                 125

Leu Asn Thr Ala Glu Asp Phe Arg Lys Thr Met Pro Pro Gly Ile Leu
    130                 135                 140

Thr Gly Asn Phe Pro Gly Trp Lys Gly Trp Leu Asn Lys Thr Gly Ala
145                 150                 155                 160

Gly Trp Ile His Ala Lys Lys Ala Met Phe Ser Ala Tyr Thr Glu Ala
                165                 170                 175

Lys Arg Leu Gly Val Thr Phe Ile Thr Gly Ser Pro Glu Gly Asp Val
            180                 185                 190

Val Ser Leu Ile Tyr Glu Asn Gly Asp Val Val Gly Ala Arg Thr Ala
        195                 200                 205

Asp Gly Thr Val His Arg Ala Asp His Thr Ile Leu Ser Ala Gly Ala
```

-continued

```
    210                 215                 220

Gly Ser Asp Arg Leu Leu Asp Phe Lys Lys Gln Leu Arg Pro Thr Ala
225                 230                 235                 240

Trp Thr Leu Cys His Ile Arg Met Thr Pro Asp Glu Ala Lys Lys Tyr
                245                 250                 255

Arg Asn Leu Pro Val Leu Phe Asn Val Ala Lys Gly Phe Phe Met Glu
            260                 265                 270

Pro Asp Glu Asp Asn His Glu Leu Lys Ile Cys Asp Glu His Pro Gly
        275                 280                 285

Tyr Cys Asn Phe Val Pro Asp Pro Lys His Gly Gly Glu Val Arg Ser
    290                 295                 300

Ile Pro Phe Ala Lys His Gln Ile Pro Leu Glu Ala Glu Ala Arg Ala
305                 310                 315                 320

Arg Asp Phe Leu Arg Asp Thr Met Pro His Leu Ala Asp Arg Pro Leu
                325                 330                 335

Ser Phe Ala Arg Ile Cys Trp Asp Ala Asp Thr Val Asp Arg Ala Phe
            340                 345                 350

Leu Ile Asp Arg His Pro Glu Tyr Arg Ser Leu Leu Leu Ala Val Gly
        355                 360                 365

Gly Ser Gly Asn Gly Ala Met Gln Met Pro Thr Ile Gly Gly Phe Ile
    370                 375                 380

Ala Asp Ala Leu Glu Gly Asn Leu Gln Lys Glu Leu Lys His Ala Leu
385                 390                 395                 400

Arg Trp Arg Pro Glu Ile Ala Ala Gln Arg Asp Trp Lys Asp Thr Gln
                405                 410                 415

Asn Arg Phe Gly Gly Pro Asn Lys Val Met Asp Phe Gln Lys Val Gly
            420                 425                 430

Glu Asn Glu Trp Thr Lys Ile Gly Asp Lys Ser Arg Leu
        435                 440                 445
```

<210> SEQ ID NO 128
<211> LENGTH: 1338
<212> TYPE: DNA
<213> ORGANISM: Aspergillus oryzae

<400> SEQUENCE: 128

```
atgacatcct ccaagttgac tcccacatca tctatcttaa ttgtcggtgc agggacctgg      60

ggttgttcta ctgctttaca tcttgcccgt cgaggataca aaaatgtcac ggtcctagat     120

ccgcacccgg tcccttctcc cattgcagct ggcaatgaca ttaacaagat tatggagcac     180

agggaggtaa aagcctctga aaccgatcct tggagtatcg ccttctcaac atgcacacga     240

gctgcactga aaggttggaa aaacgaccca gtattccagc catacttcca tgaaacgggg     300

gcaatagttt ctggccacac cgcctctttg attaaacata tacaagaaca cgaaatcgac     360

tcgtcagacg ccgagttcat aaaattgaac accgcagagg atttccgcaa aactatgccc     420

ccgggaatcc tcactggcaa cttccccggc tggaagggct ggctgaacaa gaccggcgcc     480

ggatggatcc acgccaagaa ggccatgttc tccgcataca ccgaagcaaa gcgcctagga     540

gtcactttca tcaccggctc ccctgaagga gacgttgtat ctctaattta cgagaatgga     600

gacgtagtcg gagccagaac ggccgacggc accgtccacc gagcagacca taccattctt     660

tccgcagggg ctggcagtga tcgtctcctg gactttaaga aacagctccg tcctaccgcc     720

tggacgctct gccacatcag aatgacgccc gacgaggcca agaagtaccg gaatcttcct     780

gtgctgttca acgtcgctaa ggggttcttc atggaacctg atgaggataa tcatgagctt     840
```

```
aagatctgcg acgagcatcc tggatattgc aacttcgtcc cggacccgaa gcacggcggt    900

gaggtgcgca gtatcccatt tgcaaagcat cagattcctc ttgaagccga ggcccgtgca    960

agggacttcc tccgtgatac gatgcctcat cttgctgatc gaccactgtc ttttgctcgt   1020

atatgctggg atgctgatac agtggatcgc gccttcttga tcgataggca tcctgagtat   1080

cgctctttac tgcttgctgt cggtggatct ggtaatggag ccatgcaaat gcctaccatt   1140

ggtgggttca tagcggatgc tctggaggga aacctgcaaa aggaactgaa gcatgcacta   1200

cggtggaggc ctgagattgc cgcccaacga gactggaagg atacgcaaaa tagattcgga   1260

ggtccgaata aagtaatgga tttccaaaag gttggagaga atgagtggac caagattggc   1320

gataagagtc ggctttaa                                                 1338


<210> SEQ ID NO 129
<211> LENGTH: 438
<212> TYPE: PRT
<213> ORGANISM: Aspergillus fumigatus

<400> SEQUENCE: 129

Met Ala Val Thr Lys Ser Ser Ser Leu Leu Ile Val Gly Ala Gly Thr
1               5                   10                  15

Trp Gly Thr Ser Thr Ala Leu His Leu Ala Arg Arg Gly Tyr Thr Asn
            20                  25                  30

Val Thr Val Leu Asp Pro Tyr Pro Val Pro Ser Ala Ile Ser Ala Gly
        35                  40                  45

Asn Asp Val Asn Lys Val Ile Ser Ser Gly Gln Tyr Ser Asn Asn Lys
    50                  55                  60

Asp Glu Ile Glu Val Asn Glu Ile Leu Ala Glu Glu Ala Phe Asn Gly
65                  70                  75                  80

Trp Lys Asn Asp Pro Leu Phe Lys Pro Tyr Tyr His Asp Thr Gly Leu
                85                  90                  95

Leu Met Ser Ala Cys Ser Gln Glu Gly Leu Asp Arg Leu Gly Val Arg
            100                 105                 110

Val Arg Pro Gly Glu Asp Pro Asn Leu Val Glu Leu Thr Arg Pro Glu
        115                 120                 125

Gln Phe Arg Lys Leu Ala Pro Glu Gly Val Leu Gln Gly Asp Phe Pro
    130                 135                 140

Gly Trp Lys Gly Tyr Phe Ala Arg Ser Gly Ala Gly Trp Ala His Ala
145                 150                 155                 160

Arg Asn Ala Leu Val Ala Ala Ala Arg Glu Ala Gln Arg Met Gly Val
                165                 170                 175

Lys Phe Val Thr Gly Thr Pro Gln Gly Arg Val Val Thr Leu Ile Phe
            180                 185                 190

Glu Asn Asn Asp Val Lys Gly Ala Val Thr Gly Asp Gly Lys Ile Trp
        195                 200                 205

Arg Ala Glu Arg Thr Phe Leu Cys Ala Gly Ala Ser Ala Gly Gln Phe
    210                 215                 220

Leu Asp Phe Lys Asn Gln Leu Arg Pro Thr Ala Trp Thr Leu Val His
225                 230                 235                 240

Ile Ala Leu Lys Pro Glu Glu Arg Ala Leu Tyr Lys Asn Ile Pro Val
                245                 250                 255

Ile Phe Asn Ile Glu Arg Gly Phe Phe Phe Glu Pro Asp Glu Glu Arg
            260                 265                 270

Gly Glu Ile Lys Ile Cys Asp Glu His Pro Gly Tyr Thr Asn Met Val
```

-continued

```
        275                 280                 285

Gln Ser Ala Asp Gly Thr Met Met Ser Ile Pro Phe Glu Lys Thr Gln
    290                 295                 300

Ile Pro Lys Glu Ala Glu Thr Arg Val Arg Ala Leu Leu Lys Glu Thr
305                 310                 315                 320

Met Pro Gln Leu Ala Asp Arg Pro Phe Ser Phe Ala Arg Ile Cys Trp
                325                 330                 335

Cys Ala Asp Thr Ala Asn Arg Glu Phe Leu Ile Asp Arg His Pro Gln
            340                 345                 350

Tyr His Ser Leu Val Leu Gly Cys Gly Ala Ser Gly Arg Gly Phe Lys
        355                 360                 365

Tyr Leu Pro Ser Ile Gly Asn Leu Ile Val Asp Ala Met Glu Gly Lys
    370                 375                 380

Val Pro Gln Lys Ile His Glu Leu Ile Lys Trp Asn Pro Asp Ile Ala
385                 390                 395                 400

Ala Asn Arg Asn Trp Arg Asp Thr Leu Gly Arg Phe Gly Gly Pro Asn
                405                 410                 415

Arg Val Met Asp Phe His Asp Val Lys Glu Trp Thr Asn Val Gln Tyr
            420                 425                 430

Arg Asp Ile Ser Lys Leu
        435
```

```
<210> SEQ ID NO 130
<211> LENGTH: 1317
<212> TYPE: DNA
<213> ORGANISM: Aspergillus fumigatus

<400> SEQUENCE: 130

atggcggtaa ccaagtcatc ttccctttttg atcgtggggg caggcacctg gggcacatcg      60

actgctctcc acctggcacg aagaggatac acaaatgtga cggttctaga tccctacccc     120

gttccctcag ccatctcggc tgggaatgat gtgaacaagg tcatctcctc cggccaatat     180

agcaacaaca aggacgaaat tgaggtcaac gagattctgg ctgaagaagc gttcaatggc     240

tggaagaacg accccttgtt caaaccatac tatcacgata ctggattgct catgtccgcc     300

tgctcccagg aaggcttgga ccgccttgga gtccgtgtca ggcccggtga ggaccccaac     360

cttgtggaac tgacacggcc ggagcaattc cgcaaattag ctcctgaggg tgttctacag     420

ggagatttcc ccggctggaa gggctacttt gcgcgttcag gagctggttg ggcccatgct     480

cgcaatgcac tcgtggctgc tgcaagggag gctcagagaa tgggcgtgaa gttcgtaact     540

ggcactcctc agggcagagt agtcactcta atatttgaga ataacgatgt caaaggtgcc     600

gttaccggag acggcaagat ttggcgtgca gagcgcacat tcctctgcgc cggtgccagc     660

gctggtcagt tcctcgactt caagaatcag ttgcgtccaa cggcatggac gctggttcat     720

attgctctga agcctgagga gcgggctctt tacaagaata tcccagttat cttcaacatt     780

gagaggggggt tcttcttcga accagatgag gagcgcggtg agattaagat ctgcgacgaa     840

catccggggt ataccaatat ggtacagtct gccgacggca cgatgatgag cattcctttt     900

gaaaagactc agattcctaa agaagccgag acgagggtta gagctctgct taaagagacg     960

atgccacagc ttgcagaccg tccattcagt ttcgccagga tttgctggtg cgccgacact    1020

gccaaccggg agttcttgat cgatcgccat cctcagtacc attcgcttgt gctgggctgc    1080

ggcgcttccg gcagaggatt caaatatcta ccttcaattg gcaatctcat cgttgatgct    1140

atggaaggca aggtccctca aaagatccac gaactgatta aatggaaccc agatattgct    1200
```

gccaatcgca actggaggga tactttgggg agattcgggg gtcccaacag agtaatggac 1260
ttccacgacg tcaaggagtg gacaaatgta caatatagag atatttccaa gttataa 1317

<210> SEQ ID NO 131
<211> LENGTH: 437
<212> TYPE: PRT
<213> ORGANISM: Aspergillus terreus

<400> SEQUENCE: 131

Met Pro Val Thr Lys Ser Ser Ser Ile Leu Ile Ile Gly Ala Gly Thr
1 5 10 15

Trp Gly Cys Ser Thr Ala Leu His Leu Ala Arg Arg Gly Tyr Thr Asn
20 25 30

Val Thr Val Leu Asp Pro Tyr Pro Val Pro Ser Ala Ile Ser Ala Gly
35 40 45

Asn Asp Val Asn Lys Ile Ile Ser Ser Gly Gln Tyr Ser Ser Lys Lys
50 55 60

Asp Glu Val Glu Val Asn Glu Ile Ile Ala Glu Gln Ala Phe Asn Gly
65 70 75 80

Trp Lys Asn Asp Pro Ile Phe Lys Pro Tyr Tyr His Asp Thr Gly Val
85 90 95

Val Met Ser Ala Thr Thr Gln Glu Gly Leu Glu Arg Leu Gly Val Arg
100 105 110

Val Arg Pro Glu Asp Glu Pro Asp Val Ala Glu Leu Thr Arg Pro Glu
115 120 125

Gln Phe Arg Gln Leu Ala Pro Gly Val Leu Lys Gly Asn Phe Pro Gly
130 135 140

Trp Arg Gly Tyr His Ile Arg Ser Asn Ala Gly Trp Ala His Ala Arg
145 150 155 160

Asn Ala Leu Val Ala Ala Ala Arg Glu Ala Gln Arg Leu Gly Val Arg
165 170 175

Phe Val Ala Gly Ser Pro Gln Gly Arg Val Ile Thr Leu Ile Phe Glu
180 185 190

Asn Asn Asp Val Lys Gly Ala Val Thr Ala Asp Gly Lys Ile Trp Arg
195 200 205

Ala Glu Gln Thr Ile Leu Cys Ala Gly Ala Ala Ala Gly Gln Phe Leu
210 215 220

Asp Phe Lys Asp Gln Leu Arg Pro Thr Ala Trp Thr Leu Val His Ile
225 230 235 240

Gln Leu Lys Pro Glu Glu Arg Ala Gln Tyr Lys Asn Met Pro Val Val
245 250 255

Phe Asn Ile Glu Lys Gly Phe Phe Phe Glu Pro Asp Glu Glu Arg Gly
260 265 270

Glu Ile Lys Ile Cys Asp Glu His Pro Gly Tyr Thr Asn Met Thr Thr
275 280 285

Gly Ala Asp Gly Arg Val Arg Ser Ile Pro Phe Glu Lys Thr Gln Val
290 295 300

Pro Arg Glu Ala Glu Met Arg Val Arg Lys Leu Leu Ser Glu Thr Met
305 310 315 320

Pro Gln Leu Ala Asp Arg Pro Phe Ser Phe Ala Arg Ile Cys Trp Cys
325 330 335

Ala Asp Thr Pro Asn Arg Glu Phe Ile Ile Asp Arg His Pro Glu Tyr
340 345 350

```
Pro Ser Leu Val Leu Gly Cys Gly Ala Ser Gly Arg Gly Phe Lys Tyr
        355                 360                 365

Leu Pro Ser Ile Gly Ser Ile Ile Ala Asp Ala Met Glu Asp Lys Thr
    370                 375                 380

Pro Ala Lys Ile His Lys Leu Ile Arg Trp Ser Pro Glu Ile Ala Ile
385                 390                 395                 400

Asn Arg Asn Trp Gly Asp Arg Leu Gly Arg Phe Gly Gly Pro Asn Arg
                405                 410                 415

Val Met Asp Phe Asn Glu Val Lys Glu Trp Thr Asn Val Thr Gln Arg
            420                 425                 430

Asp Ile Ser Lys Leu
        435
```

<210> SEQ ID NO 132
<211> LENGTH: 1314
<212> TYPE: DNA
<213> ORGANISM: Aspergillus terreus

<400> SEQUENCE: 132

```
atgccagtca ccaagtcttc gtcgatattg atcatcgggg cgggcacctg gggttgctca     60

actgccctgc atcttgcccg cagaggatac accaatgtca ctgtccttga cccgtacccg    120

gttccatcag ccatttcggc cggcaacgac gtcaacaaga tcatctcgtc cggccagtac    180

agcagcaaga aggacgaggt cgaagtcaat gagattatcg ccgaacaggc cttcaatggc    240

tggaaaaatg accccatctt caagccgtac taccacgaca ccggcgtcgt gatgtccgcc    300

accacacagg aaggattgga gcgtctgggg gtccgcgtgc gacctgaaga tgaacccgat    360

gtagccgaat tgactcggcc ggagcagttc cgccagctgg cccccggcgt cttgaagggt    420

aacttccccg gttggagggg gtaccacatt cgctcaaacg cgggctgggc gcatgcgcgc    480

aacgccctgg tcgccgcggc gcgggaggca cagcgcctgg gtgtgcgctt cgtcgcggga    540

tcgccgcagg gcagagtcat cacgttgatt tttgagaaca acgatgtgaa gggtgccgtc    600

acggcggacg gcaagatctg gcgggccgag cagactatcc tctgcgctgg tgcggccgcc    660

ggccagtttc tggatttcaa ggaccaactg cgtcccactg cgtggactct ggtccacatc    720

cagttgaagc cggaagagcg tgcccagtat aaaaacatgc cggtggtctt caacatcgag    780

aaggggttct tcttcgagcc ggatgaggag cgtggtgaaa tcaagatctg cgacgaacac    840

cccgggtaca cgaatatgac cacgggggcc gacggccgcg tgaggagcat tcccttcgag    900

aagacgcagg ttcctcgaga agcggagatg cgcgtccgca agcttctgtc tgaaacgatg    960

cctcagcttg cggaccggcc gttcagtttc gcaaggatct gctggtgtgc ggataccccc   1020

aatcgcgagt ttatcattga ccgtcatccc gaatacccgt cgcttgttct tgggtgtggt   1080

gcttcaggac gaggcttcaa atatcttccc tcgatcggaa gcatcatcgc agacgccatg   1140

gaggacaaaa ccccggcaaa aatccacaag ctgatccgct ggagcccgga aatcgcgatc   1200

aaccgtaact gggggacag attaggtcga tttggagggc ccaaccgggt catggatttc   1260

aatgaagtga aggagtggac taatgtcacc caaagggaca tctcgaagtt atag         1314
```

<210> SEQ ID NO 133
<211> LENGTH: 437
<212> TYPE: PRT
<213> ORGANISM: Coniochaeta sp.

<400> SEQUENCE: 133

```
Met Thr Ser Asn Arg Ala Asp Thr Arg Val Ile Val Val Gly Gly Gly
```

-continued

```
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430
```

His Asp Pro Lys Leu
435

<210> SEQ ID NO 134
<211> LENGTH: 1314
<212> TYPE: DNA
<213> ORGANISM: Coniochaeta sp.

<400> SEQUENCE: 134
atgacgtcga atcgtgcaga tacaagggtg attgtcgtcg gtggcggagg aacgattggt 60
tcctcgacag cgctgcatct tgtgaggagt ggttatgctc ccgcaaatat cacggtcttg 120
gacacatttg agattccatc ggctcaatca gccggccatg atctcaacaa gatcatggga 180
atagatctgc gcaacaaggt ggacctgcaa atgagtctag aggctagaca gatgtggaag 240
gaggatgagt tattccagcc cttctttcac aataccggca gaatggactg cgaacacacg 300
cctgagggta tcgagaaact gaaaaagctg taccagaaac tgcacgatgc cggtgcgggt 360
ctggagaaga ctcatgcctg gttggacaac gaggatgaga tcttatccaa gatgccgttg 420
cttcaacgtg accaaataca aggatggaaa gcaatatgga gtcaagatgg cggctggtta 480
gctgcggcaa aggccatcaa tgcgatcgga cagttcttga aagaacgtgg tgtaaagttc 540
ggattcggcg gcgctggatc cttcaagcaa ccccttttcg acgatgaagg cacaacttgc 600
attggcgttg agacggcaga tggtaccaaa tattacgctg acaaggtggt cttagcagct 660
ggcgcatgga gcccaaccct ggtggacctg gaagatcaat gttgctcgaa ggcttgggtg 720
tatgctcata ttcagttgac gcctgaagag gccgctgagt ataagggtgt cccagttgtg 780
tataatggcg aatttggctt cttctttgag cctgatgagt ttggtgtaat aaaggtgtgc 840
gacgagttcc caggattctc gcgcttcaag gaacatcaac cctatggcgc ccccatctccg 900
aaacggatat cagtaccacg atcgcacgcc aagcatccca cagacactta tccagacgca 960
tccgaagtca gcatcaaaaa agcaatcgcg acgtttctcc ctcgatttca ggacaaggag 1020
ctcttcaatc gcgccttgtg ctggtgtaca gacactgcgg acgctgctct cttgatgtgt 1080
gaacacccca aatggaagaa tttcattcta gcgaccggcg acagcggaca ctcattcaaa 1140
atcttgccta acgtcggaaa atacgtagtc gagttgatag agggccgcct gccggaggaa 1200
atggcttatc aatggaggtg gcggccagga ggcgatgcac tcaagtctag acgtgcggca 1260
ccgccaaaag atcttgcaga catgccagga tggaaacatg atccgaaatt gtaa 1314

<210> SEQ ID NO 135
<211> LENGTH: 437
<212> TYPE: PRT
<213> ORGANISM: Phaeosphaeria nodorum

<400> SEQUENCE: 135

Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Val Thr Val Leu Asp Ala Tyr Pro Ile Pro Ser Ser
        35                  40                  45

Gln Ser Ala Gly Asn Asp Leu Asn Lys Ile Met Gly Val Asp Leu Arg
    50                  55                  60

Asn Pro Val Asp Leu Gln Leu Ala Leu Glu Ala Arg Gln Met Trp Asn
65                  70                  75                  80

-continued

```
Glu Asp Glu Leu Phe Lys Lys Phe Phe His Asn Thr Gly Arg Leu Asp
                85                  90                  95

Cys Ala His Gly Glu Lys Asp Ile Ala Lys Leu Lys Ser Leu Tyr Gln
            100                 105                 110

Lys Leu Val Asp Ala Gly Leu Asp Ala Thr Asn Glu Trp Leu Asp Ser
        115                 120                 125

Glu Asp Glu Ile Leu Lys Arg Met Pro Leu Leu Ser Arg Asp Gln Ile
    130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
        195                 200                 205

Ala Asp Lys Val Val Leu Ala Ala Gly Ala Trp Ser Pro Thr Leu Val
    210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Phe Glu Pro Asn Glu His Gly Val
            260                 265                 270

Ile Lys Val Cys Asp Glu Phe Pro Gly Phe Thr Arg Phe Lys Met His
        275                 280                 285

Gln Pro Phe Gly Ala Lys Ala Pro Lys Arg Ile Ser Val Pro Arg Ser
    290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ala Ala
            340                 345                 350

Leu Leu Ile Cys Glu His Pro Glu Trp Lys Asn Phe Val Leu Ala Thr
        355                 360                 365

Gly Asp Ser Gly His Ser Phe Lys Leu Leu Pro Asn Ile Gly Lys His
    370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
        435
```

<210> SEQ ID NO 136
<211> LENGTH: 1314
<212> TYPE: DNA
<213> ORGANISM: Phaeosphaeria nodorum

<400> SEQUENCE: 136
atggccccgt cgcgtgctaa tacgtcggtc attgtggttg gtggtggtgg tacgattggc     60

```
tcatctacgg ctctgcatct ggtccgctca ggctataccc cgtcgaacgt gacggttctg    120

gatgcatacc cgattccgag ctctcagagc gctggcaacg acctgaataa aatcatgggt    180

gtcgatctgc gtaatccggt ggatctgcag ctggctctgg aagcgcgcca aatgtggaac    240

gaagacgaac tgttcaagaa gtttttccat aacaccggcc gtctggattg cgcgcacggt    300

gaaaaagata ttgccaaact gaagagcctg tatcagaaac tggtggatgc gggtctggac    360

gccacgaacg aatggctgga tagtgaagac gaaatcctga aacgtatgcc gctgctgtcc    420

cgcgatcaaa ttaaaggctg gaaggcgatc ttttcaaaag acggtggttg gctggcagca    480

gcaaaggcaa ttaatgcagt tggtgaatat ctgcgtgatc agggcgtccg cttcggtttt    540

tacggcgccg gttctttcaa agcaccgctg ctggctgaag gcgtctgcat cggtgtcgaa    600

accgtggatg gcacgcgcta ttacgcagac aaagtggttc tggctgcagg tgcatggtcg    660

ccgaccctgg ttgaactgca tgaacagtgt gtgagcaaag cgtgggttta cggccacatt    720

caactgacgc cggaagaagc cgcacgttat aagaacagcc cggtcgtgta caatggcgat    780

gtgggctttt tctttgaacc gaacgaacat ggcgttatca aagtctgcga tgaatttccg    840

ggttttaccc gcttcaagat gcaccagccg tttggtgcca aagcaccgaa gcgtattagt    900

gtgccgcgct cccatgccaa acacccgacc gatacgatcc cggatgcaag tgacgtttcc    960

attcgtcgcg ctatcgcgac ctttatgccg cagttcaaga acaaaaagat gttcaaccaa   1020

gcgatgtgct ggtgtaccga tacggccgac gctgcgctgc tgatttgtga acatccggaa   1080

tggaaaaact ttgttctggc gaccggcgat tcaggtcatt cgttcaaact gctgccgaat   1140

atcggcaagc acgttgtcga actgctggag ggtacgctgg cagatgacct ggcacacgca   1200

tggcgttggc gtccgggtag tggtgatgca ctgaaaagcc gtcgctctgc tccggcgaaa   1260

gacctggctg atatgccggg ctggaaccat gacaaaccgc gtgctaatct gtaa         1314
```

<210> SEQ ID NO 137
<211> LENGTH: 441
<212> TYPE: PRT
<213> ORGANISM: Neocosmospora vasinfecta

<400> SEQUENCE: 137

```
Met Thr Thr Pro Arg Lys Glu Thr Thr Val Leu Ile Ile Gly Gly Gly
1               5                   10                  15

Gly Thr Ile Gly Ser Ser Thr Ala Leu His Leu Leu Arg Ala Gly Tyr
            20                  25                  30

Thr Pro Ser Asn Ile Thr Val Leu Asp Thr Tyr Pro Ile Pro Ser Ala
        35                  40                  45

Gln Ser Ala Gly Asn Asp Leu Asn Lys Ile Met Gly Ile Asp Leu Arg
    50                  55                  60

Asn Lys Val Asp Leu Gln Leu Ser Leu Glu Ala Arg Asp Met Trp Arg
65                  70                  75                  80

Asn Asp Ala Leu Phe Arg Pro Phe Phe His Asn Thr Gly Arg Leu Asp
                85                  90                  95

Cys Glu Ser Ser Ala Glu Gly Val Glu Lys Leu Arg Arg Leu Tyr Gln
            100                 105                 110

Lys Leu Val Glu Ala Gly Val Gly Leu Glu Glu Thr His Glu Trp Leu
        115                 120                 125

Asp Ser Glu Glu Ala Ile Leu Glu Lys Ala Pro Leu Leu Gln Arg Glu
    130                 135                 140

Glu Ile Glu Gly Trp Lys Ala Ile Trp Ser Glu Glu Gly Gly Trp Leu
145                 150                 155                 160
```

```
Ala Ala Ala Lys Ala Ile Asn Ala Ile Gly Glu Glu Leu Gln Arg Gln
                165                 170                 175

Gly Val Arg Phe Gly Phe Gly Gly Ala Gly Ser Phe Lys Arg Pro Leu
            180                 185                 190

Phe Ala Asp Asp Gly Thr Thr Cys Ile Gly Val Glu Thr Val Asp Gly
        195                 200                 205

Thr Gln Tyr His Ala Asp Lys Val Val Leu Ala Ala Gly Ala Trp Ser
    210                 215                 220

Pro Ala Leu Val Asp Leu Glu Glu Gln Cys Cys Ser Lys Ala Trp Val
225                 230                 235                 240

Tyr Ala His Met Gln Leu Thr Pro Glu Glu Ala Ala Val Tyr Lys Gly
                245                 250                 255

Cys Pro Val Val Tyr His Gly Asp Val Gly Phe Phe Phe Glu Pro Asn
            260                 265                 270

Glu Asn Gly Val Ile Lys Val Cys Asp Glu Phe Pro Gly Phe Thr Arg
        275                 280                 285

Phe Lys Gln His Gln Pro Tyr Gly Ala Pro Ala Pro Lys Pro Val Ser
    290                 295                 300

Val Pro Arg Ser His Ala Lys His Pro Thr Asp Thr Tyr Pro Asp Ala
305                 310                 315                 320

Ser Glu Glu Ser Ile Lys Arg Ala Val Ser Thr Phe Leu Pro Arg Phe
                325                 330                 335

Lys Asp Lys Pro Leu Phe Asn Arg Ala Leu Cys Trp Cys Thr Asp Thr
            340                 345                 350

Ala Asp Ser Ala Leu Leu Ile Cys Glu His Pro Arg Trp Lys Asn Phe
        355                 360                 365

Ile Leu Ala Thr Gly Asp Ser Gly His Ser Phe Lys Leu Leu Pro Ile
    370                 375                 380

Ile Gly Lys His Val Val Glu Leu Val Glu Gly Arg Leu Ala Asp Asp
385                 390                 395                 400

Leu Ala Glu Ala Trp Arg Trp Arg Pro Gly Gln Gly Asp Ala Arg Lys
                405                 410                 415

Ser Ile Arg Ala Ala Pro Ala Lys Asp Leu Ala Asp Met Pro Gly Trp
            420                 425                 430

Lys His Asp Gln Asp Ser Glu Ser Arg
        435                 440
```

<210> SEQ ID NO 138
<211> LENGTH: 1326
<212> TYPE: DNA
<213> ORGANISM: Neocosmospora vasinfecta

<400> SEQUENCE: 138

```
atgacgaccc cgcgtaaaga aacgacggtc ctgattattg gtggtggtgg cacgattggt      60

agctcgacgg ctctgcatct gctgcgtgcc ggctataccc cgtctaacat taccgtgctg     120

gatacgtacc cgatcccgag tgcccagtcc gcaggcaacg acctgaataa aattatgggt     180

atcgatctgc gcaataaagt tgatctgcaa ctgagcctgg aagcccgtga tatgtggcgc     240

aacgacgcac tgtttcgtcc gtttttccat aataccggcc gcctggactg cgaaagctct     300

gctgaaggcg tggaaaaact gcgtcgcctg tatcagaaac tggtggaagc aggcgttggt     360

ctggaagaaa cgcacgaatg gctggatagc gaagaagcta ttctggaaaa agcgccgctg     420

ctgcaacgtg aagaaattga aggttggaaa gccatctggt ctgaagaagg cggttggctg     480
```

-continued

```
gcggccgcaa aagctattaa cgcgatcggc gaagaactgc agcgtcaagg cgttcgcttc    540

ggttttggcg gtgccggtag ttttaaacgc ccgctgttcg cagatgacgg caccacgtgt    600

atcggtgtcg aaaccgtgga tggcacgcag tatcatgcgg acaaagtggt tctggctgca    660

ggtgcttggt caccggcgct ggtcgatctg gaagaacagt gctgttcgaa agcctgggtg    720

tacgcacaca tgcaactgac cccggaagaa gccgcagttt ataaaggctg cccggtcgtg    780

taccacggcg atgtcggctt tttctttgaa ccgaacgaaa atggcgttat taaagtctgt    840

gacgaattcc cgggttttac gcgtttcaaa cagcatcaac cgtatggtgc cccggcaccg    900

aaacctgtga gtgttccgcg ctcccatgcg aaacacccga ccgatacgta cccggacgct    960

tcagaagaat cgatcaaacg tgccgtgagt acctttctgc cgcgcttcaa agataaaccg   1020

ctgtttaacc gtgcactgtg ctggtgtacc gatacggccg actccgcact gctgatttgc   1080

gaacacccgc gctggaaaaa ttttatcctg gcgaccggcg atagcggtca ttctttcaaa   1140

ctgctgccga ttatcggcaa acacgttgtc gaactggttg aaggtcgtct ggcggatgac   1200

ctggctgaag cgtggcgttg gcgtccgggt cagggtgatg cacgtaaaag cattcgcgct   1260

gcgccggcga aagacctggc ggatatgccg ggctggaaac acgaccaaga ctcggaatca   1320

cgctga                                                              1326


<210> SEQ ID NO 139
<211> LENGTH: 438
<212> TYPE: PRT
<213> ORGANISM: Aspergillus nidulans

<400> SEQUENCE: 139

Met Thr Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
        35                  40                  45

Ser Ala Gly Tyr Asp Leu Asn Lys Ile Met Gly Ile Asp Leu Arg Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe Phe His Asn Val Gly Met Ile Asp Val
                85                  90                  95

Ser Ser Thr Glu Glu Gly Ile Glu Lys Leu Arg Lys Leu Tyr Gln Ser
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220
```

```
Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Ala Tyr Lys Asn
                245                 250                 255

Thr Pro Val Ile Tyr Asp Gly Asp Tyr Gly Phe Phe Phe Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Ala Pro Lys Pro Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435


<210> SEQ ID NO 140
<211> LENGTH: 1317
<212> TYPE: DNA
<213> ORGANISM: Aspergillus nidulans

<400> SEQUENCE: 140

atgacgcccc gagccaacac caaaatcatt gtcgtcggcg gcggcggcac aatgggctcg      60

tcgacagccc tacacctcct gcgcgccggc tacacgccgt ccaacattac agtgctcgac     120

acgtgcccta tcccctccgc acagtctgca ggctacgacc tgaacaaaat catgggcatc     180

gatctgcgca acaagcctga tttacagctc tctcttgagg cgctggacat gtggaaaaat     240

gatcctctct tcaagccgtt tttccacaat gttggaatga tcgacgtctc ttcaacagag     300

gaaggcatcg agaaacttcg gaagctgtac cagtctcttc tcgacgcagg cattgggctc     360

gagaagacga atttcatgct ggaaagtgaa gacgagatcc tggctaaagc gccgcatttc     420

acgcaggagc agattaaagg ctggaaaggc ctgttctgtg gcgacggcgg ctggctcgct     480

gcagccaaag ccatcaatgc cattgggcag ttcctcaagg aacagggcgt caagtttgga     540

ttcggcggcg ccggcacgtt caaaaagcca ctcttcgccg atgcccacga gaagacgtgc     600

atcggcgtcg agactgtaga cggcacaaag tactacgccg acaaggtcgt tctagcagct     660

ggtgcctgga gttcgacgtt ggtcgatctg gaggagcagt gcgtttcaaa ggcctgggtc     720

tttgcccaca tccaactgac gcccgctgaa gcagccgcgt ataagaacac tcctgttata     780

tacgacggtg actatgggtt tttctttgag ccgaatgaaa acggcatcat aaaagtctgt     840
```

```
gacgaattcc ctggcttcac gcatttcaaa atgcaccagc cgtacggctc gccggcgccc    900

aaacccatct ctgtgcctcg ttcccatgcg aagcacccca cagatacata cccgcacgcg    960

tcggaggtca cgatcaaaaa ggctatcaac cggttcctgc cgaggttcaa tgacaaggaa   1020

ctgtttaaca gggccatgtg ctggtgcacc gataccgcgg atgcaaatct gcttgtttgt   1080

gagcatccac gctggaaggg gttttatctt gcaacagggg acagtgggca ttcgttcaag   1140

ttgctgccga atattggaaa gcatgttgtc gagttattgg aggagaggct ggaaagtgtg   1200

tttaaggatg cttggaggtg gaggcctggc agtggggatg cattaaaaag tagacgggct   1260

gcgcctgcga aggacctggc ggatatgccg gggtggagga atgaggcaaa gatgtag      1317


<210> SEQ ID NO 141
<211> LENGTH: 437
<212> TYPE: PRT
<213> ORGANISM: Coniochaeta sp.

<400> SEQUENCE: 141

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
```

-continued

```
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ser Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435


<210> SEQ ID NO 142
<211> LENGTH: 1314
<212> TYPE: DNA
<213> ORGANISM: Coniochaeta sp.

<400> SEQUENCE: 142

atgacgtcga atcgtgcaga tacaagggtg attgtcgtcg gtggcggagg aacgattggt     60

tcctcgacag cgctgcatct tgtgaggagt ggttatgctc ccgcaaatat cacggtcttg    120

gacacatttg agattccatc ggctcaatca gccggccatg atctcaacaa gatcatggga    180

atagatcatc gcaacaaggt ggacctgcaa atgagtctag aggctagaca gatgtggaag    240

gaggatgagt tattccagcc cttctttcac aataccggca gaatggactg cgaacacacg    300

cctaagggta tcgagaaact gaaaaagctg taccagaaac tgcacgatgc cggtgcgggt    360

ctggagaaga ctcatgcctg gttggacaac gaggatgaga tcttatccaa gatgccgttg    420

cttcaacgtg accaaataca aggatggaaa gcaatatgga gtcaagatgg cggctggtta    480

gctgcggcaa aggccatcaa tgcgatcgga cagttcttga aagaacgtgg tgtaaagttc    540

ggattcggcg gcgctggatc cttcaagcaa ccccttttcg acgatgaagg cacaacttgc    600

attggcgttg agacggcaga tggtaccaaa tattacgctg acaaggtggt cttagcagct    660

ggcgcatgga gcccaaccct ggtggacctg gaagatcaat gttgctcgaa ggcttgggtg    720

tatgctcata ttcagttgac gcctgaagag gccgctgagt ataagggtgt cccagttgtg    780

tataatggcg aatttggctt cttctttgag cctgatgagt ttggtgtaat aaaggtgtgc    840

gacgagttcc caggattctc gcgcttcaag gaacatcaac cctatggcgc cccatctccg    900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg actctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtgcggca   1260
```

-continued

```
ccgccaaaag atcttgcaga catgccagga tggaaacatg atccgaaatt gtaa        1314


<210> SEQ ID NO 143
<211> LENGTH: 437
<212> TYPE: PRT
<213> ORGANISM: Eupenicillium terrenum

<400> SEQUENCE: 143

Met Ala His Ser Arg Ala Ser Thr Lys Val Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Asp His Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe Phe His Gln Val Gly Met Ile Asp
                85                  90                  95

Cys Ser Ser Ser Lys Glu Gly Ile Glu Lys Leu Arg Arg Leu Tyr Gln
            100                 105                 110

Lys Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Asp Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asp
            260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
    290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ser Asn Leu Leu Ile Cys Glu His Pro Lys Trp Lys Asn Phe
        355                 360                 365
```

```
Ile Leu Ala Thr Gly Asp Ser Gly His Ser Phe Lys Leu Leu Pro Asn
    370                 375                 380

Ile Gly Lys Tyr Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
        435


<210> SEQ ID NO 144
<211> LENGTH: 1314
<212> TYPE: DNA
<213> ORGANISM: Eupenicillium terrenum

<400> SEQUENCE: 144

atggctcatt cgcgtgcaag caccaaagtc gtcgtggttg ggggaggtgg tacgatcggg     60

tcttcgacgg ctctgcactt aatccgctct ggatataccc cctcaaatat caccgtgctt    120

gacgtataca agaccccttc attgcaatct gcaggacatg atttgaacaa gatcatgggc    180

attgatcatc gcaacgggcc tgacttgcag ctttcgctgg aatcactcga catgtggcaa    240

aacgatgagt tgttcaagcc attctttcac caagtgggca tgattgattg ttcgtcatcc    300

aaagagggta ttgaaaaact tcgacgatta taccagaaac tcctcgatgc gggcattggg    360

ctggagaaga cgaacgtttg gctggaatct gaagatgaga tcctcgccaa agcgccgaat    420

ttcacgcgtg aacaagtcaa ggggtggaaa ggcttatttt gcactgatgg aggctggctt    480

gctgcagcca aggctatcaa tgcgatcgga attttcctcc aggacaaagg tgtcaagttt    540

ggctttggag atgctggtac ctttcagcaa cctctgttcg ccgctgatgg aaaaacttgc    600

atcggacttg aaactacaga cggaaccaag tactttgctg acaaggttgt cttggctgct    660

ggtgcgtgga gtcccacctt ggtggatcta gaagatcagt gtgtttcaaa ggcctgggtt    720

ttcgctcata ttcaactcac acccaaagaa gcggacgcgt acaagaatgt gcctgtggtc    780

tatgatggtg aatatgggtt ctttttcgaa cccgacgagt atggggtgat caaagtctgt    840

gacgagttcc ctggtttctc tcgcttcaaa ctgcatcaac cgtacggggc tgcatctccc    900

aagatgatat ccgtaccgcg atcacacgcc aagcatccca cagataccta ccctgatgcc    960

tccgaagtca ccatacgcaa agcgatcgca aggttcctgc cagaatttaa agacaaggag   1020

ctcttcaacc gtaccatgtg ctggtgtaca gatacggccg attctaactt attgatttgc   1080

gaacacccga agtggaagaa tttcattctg gccactggag atagcggaca ttccttcaag   1140

ctgttgccaa acatcgggaa atacgtagtt gagcttttag agggatctct atcgcaggaa   1200

atggctggtg cctggagatg gagacccgga ggtgatgctc ttagatctag acgcggtgct   1260

ccggcaaagg atcttgctga gatgccggga tggaagcatg atgcacattt gtga          1314


<210> SEQ ID NO 145
<211> LENGTH: 437
<212> TYPE: PRT
<213> ORGANISM: Eupenicillium terrenum

<400> SEQUENCE: 145

Met Ala His Ser Arg Ala Ser Thr Lys Val Val Val Val Gly Gly Gly
1               5                   10                  15

Gly Thr Ile Gly Ser Ser Thr Ala Leu His Leu Ile Arg Ser Gly Tyr
```

-continued

```
                20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Arg Leu Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe Phe His Gln Val Gly Met Ile Asp
                85                  90                  95

Cys Ser Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Gly Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asn
            260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
    290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Leu Leu Pro Asn
    370                 375                 380

Ile Gly Lys His Val Val Glu Leu Leu Glu Gly Ser Leu Ser Gln Glu
385                 390                 395                 400

Met Ala Gly Ala Trp Arg Trp Arg Pro Gly Gly Asp Ala Leu Arg Ser
                405                 410                 415

Arg Arg Gly Ala Pro Ala Lys Asp Leu Ala Glu Met Pro Gly Trp Lys
            420                 425                 430

His Asp Ala His Leu
        435
```

<210> SEQ ID NO 146
<211> LENGTH: 1314
<212> TYPE: DNA
<213> ORGANISM: Eupenicillium terrenum

<400> SEQUENCE: 146
atggctcatt cgcgtgcaag caccaaagtc gtcgtggttg ggggaggtgg tacgatcggg 60
tcttcgacgg ctctgcactt aatccgctct ggatataccc cctcaaatat caccgtgctt 120
gacgtataca agaccccttc attgcaatct gcaggacatg atttgaacaa gatcatgggc 180
attcgattgc gcaacgggcc tgacttgcag ctttcgctgg aatcactcga catgtggcaa 240
aacgatgagt tgttcaagcc attctttcac caagtgggca tgattgattg ttcgtcatcc 300
aaagagggta ttgaaaatct tcgacgaaaa taccagaccc tcctcgatgc gggcattggg 360
ctggagaaga cgaacgtttg gctggaatct gaagatgaga tcctcgccaa agcgccgaat 420
ttcacgcgtg aacaagtcaa ggggtggaaa ggcttatttt gcactgatgg aggctggctt 480
gctgcagcca aggctatcaa tgcgatcgga attttcctcc aggacaaagg tgtcaagttt 540
ggctttggag gtgctggaac atttcagcaa cctctgttcg ccgctgatgg aaaaacttgc 600
atcggacttg aaactacaga cggaaccaag tactttgctg acaaggttgt cttggctgct 660
ggtgcgtgga gtcccacctt ggtggatcta gaagatcagt gtgtttcaaa ggcctgggtt 720
ttcgctcata ttcaactcac acccaaagaa gcggacgcgt acaagaatgt gcctgtggtc 780
tatgatggtg aatatgggtt ctttttgag cccaacgagt atggggtgat caaagtctgt 840
gacgagttcc ctggtttctc tcgcttcaaa ctgcatcaac cgtacggggc tgcatctccc 900
aagatgatat ccgtaccgcg atcacacgcc aagcatccca cagataccta ccctgatgcc 960
tccgaagtca ccatacgcaa agcgatcgca aggttcctgc cagaatttaa agacaaggag 1020
ctcttcaacc gtaccatgtg ctggtgtaca gatacggccg atgctaactt attgatttgc 1080
gaacacccga agtggaagaa tttcattctg gccactggag atagcggaca ttccttcaag 1140
ctgttgccaa acatcgggaa acacgttgtt gagcttttag agggatctct atcgcaggaa 1200
atggctggtg cctggagatg gagacccgga ggtgatgctc ttagatctag acgcggtgct 1260
ccggcaaagg atcttgctga gatgccggga tggaagcatg atgcacattt gtga 1314

<210> SEQ ID NO 147
<211> LENGTH: 438
<212> TYPE: PRT
<213> ORGANISM: Aspergillus nidulans

<400> SEQUENCE: 147

Met Thr Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
        35                  40                  45

Ser Ala Gly Tyr Asp Leu Asn Lys Ile Met Ser Ile Arg Leu Arg Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe Phe His Asn Val Gly Met Ile Asp Val
                85                  90                  95

-continued

```
Ser Ser Thr Glu Glu Gly Ile Glu Gly Leu Arg Lys Lys Tyr Gln Ser
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Ala Tyr Lys Asn
                245                 250                 255

Thr Pro Val Ile Tyr Asp Gly Asp Tyr Gly Phe Phe Phe Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Ala Pro Lys Pro Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435


<210> SEQ ID NO 148
<211> LENGTH: 1317
<212> TYPE: DNA
<213> ORGANISM: Aspergillus nidulans

<400> SEQUENCE: 148

atgacgcccc gagccaacac caaaatcatt gtcgtcggcg gcggcggcac aatgggctcg      60

tcgacagccc tacacctcct gcgcgccggc tacacgccgt ccaacattac agtgctcgac     120

acgtgcccta tcccctccgc acagtctgca ggctacgacc tgaacaaaat catgagcatc     180
```

-continued

```
aggctgcgca acaagcctga tttacagctc tctcttgagg cgctggacat gtggaaaaat    240

gatcctctct tcaagccgtt tttccacaat gttggaatga tcgacgtctc ttcaacagag    300

gaaggcatcg agggtcttcg gaagaaatac cagtctcttc tcgacgcagg cattgggctc    360

gagaagacga atttcatgct ggaaagtgaa gacgagatcc tggctaaagc gccgcatttc    420

acgcaggagc agattaaagg ctggaaaggc ctgttctgtg gcgacggcgg ctggctcgct    480

gcagccaaag ccatcaatgc cattgggcag ttcctcaagg aacagggcgt caagtttgga    540

ttcggcggcg ccggcacgtt caaaaagcca ctcttcgccg atgcccacga gaagacgtgc    600

atcggcgtcg agactgtaga cggcacaaag tactacgccg acaaggtcgt tctagcagct    660

ggtgcctgga gttcgacgtt ggtcgatctg gaggagcagt gcgtttcaaa ggcctgggtc    720

tttgcccaca tccaactgac gcccgctgaa gcagccgcgt ataagaacac tcctgttata    780

tacgacggtg actatgggtt tttctttgag ccgaatgaaa acggcatcat aaaagtctgt    840

gacgaattcc ctggcttcac gcatttcaaa atgcaccagc cgtacggctc gccggcgccc    900

aaacccatct ctgtgcctcg ttcccatgcg aagcacccca cagatacata cccgcacgcg    960

tcggaggtca cgatcaaaaa ggctatcaac cggttcctgc cgaggttcaa tgacaaggaa   1020

ctgtttaaca gggccatgtg ctggtgcacc gataccgcgg atgcaaatct gcttgtttgt   1080

gagcatccac gctggaaggg gttttatctt gcaacagggg acagtgggca ttcgttcaag   1140

ttgctgccga atattggaaa gcatgttgtc gagttattgg aggagaggct ggaaagtgtg   1200

tttaaggatg cttggaggtg gaggcctggc agtggggatg cattaaaaag tagacgggct   1260

gcgcctgcga aggacctggc ggatatgccg ggtggagga atgaggcaaa gatgtag        1317

<210> SEQ ID NO 149
<211> LENGTH: 477
<212> TYPE: PRT
<213> ORGANISM: Cryptococcus neoformans

<400> SEQUENCE: 149

Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Arg Ile Arg
    50                  55                  60

Asn Pro Val Asp Lys Gln Leu Ser Leu Glu Ala Arg Asp Met Trp Arg
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Ser Leu Arg Lys Ser Tyr Glu
            100                 105                 110

Ala Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175
```

```
Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
        195                 200                 205

Thr Gln Tyr Phe Ala Asp Lys Val Val Leu Ala Ala Gly Ala Trp Ser
    210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
    290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350

Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
            420                 425                 430

Asn His Asp Glu Pro Ser Asp Asp Asp Met Asp Val Lys Asp Val Ala
        435                 440                 445

Val Ser Leu Ala Ser Val Lys Ile Gly Glu Asn Ile Gly Glu Lys Val
    450                 455                 460

Val Glu Asp Gly Ala Arg Val Gly Val Lys Val Leu Ala
465                 470                 475
```

<210> SEQ ID NO 150
<211> LENGTH: 1434
<212> TYPE: DNA
<213> ORGANISM: Cryptococcus neoformans

<400> SEQUENCE: 150

```
atgccacctt cgcgcgccag tactaaggtc atagttatcg ggggcggtgg tactctcggg     60

tcctctactg ctcttcacct tttacgagcc ggttacactc catccaacat cactgtgctt    120

gacacgtatc taatcccatc agcacagtcg gctggcaatg acctcaataa gatcatgggt    180

attcgtatca ggaatcctgt agataaacag ttgagcctgg aagcaagaga catgtggagg    240

aatgatgaag ttttcaagcc ttatttccac aacacgggaa gacttgattg tgctcataca    300

ccggagagca ttgcatcttt gcgtaaatcg tacgaggcta tcttaaaggc cgggagcggg    360

ctcgagaaga cccaccattg gctgagtaca gaagatgaaa tactggctag agcccctttg    420
```

```
ttggatcgga aacagatcaa aggatggaaa gctatttaca gcgaagatgg gggctggctt    480

gcggcggcga aagctatcaa cagtatcggc caggtgttga aagagaaagg tgtgacattc    540

ggattcggga gtgcgggctc attcaagaaa cccttgtttg acgaagacgg taccaaggcc    600

atcggcattg agacagttga tggtacgcaa tattttgccg acaaggtcgt tctggctgcc    660

ggagcttgga gtcctaccct cgtggatttg gaagggcaat gctgttcaaa ggcttgggtt    720

tacgcccata tgcaattgac accagaagag gctgccgaat acaaggagtg tcctgtggtg    780

tacaactctg aacttgggtt cttcttcgag cccaatgaaa aaggagtcat caaagtgtgc    840

gacgaattcc cagggttcac ccgtttcaag caacatcaac cttacggcgc ctcctctact    900

aaacacatct ctttcccgcg ctcccatgcc aaacacccta ccgataccat tccggacgag    960

tcggacgcat ctatccgccg tgctatctct gcctttttac cgagattcaa agaaaaagaa   1020

ctgttcaaca gagcactgtg ctggtgtaca gataccgccg atgccaatct tttgatatgc   1080

gaacatccca aatggaaaaa ttttatctta gctacagggg atagtggaca ttcattcaaa   1140

attcttccca atatcggtaa acatgtcgtt gaacttatag aaggtaccct tgccgaggac   1200

ttggctgaga gctggagatg gagacctgga agcggtgacc ccctgatctc tcgtcgggca   1260

gcccctgcaa gggatcttgc tgatcttcca ggatggaacc atgatgagcc ctcggatgac   1320

gatatggatg taaaggatgt cgctgtatcg cttgcttctg tgaaaattgg cgaaaaacatc  1380

ggggagaagg ttgtggaaga tggagcacga gtcggagtca aagttctagc ttag         1434


<210> SEQ ID NO 151
<211> LENGTH: 437
<212> TYPE: PRT
<213> ORGANISM: Coniochaeta sp.

<400> SEQUENCE: 151

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Ala Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190
```

-continued

```
Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 152
<211> LENGTH: 1314
<212> TYPE: DNA
<213> ORGANISM: Coniochaeta sp.

<400> SEQUENCE: 152

```
atgacgtcga atcgtgcaga tacaagggtg attgtcgtcg gtggcggagg aacgattggt     60

tcctcgacag cgctgcatct tgtgaggagt ggttatgctc ccgcaaatat cacggtcttg    120

gacacatttg agattccatc ggctcaatca gccggccatg atctcaacaa gatcatggga    180

atagcactgc gcaacaaggt ggacctgcaa atgagtctag aggctagaca gatgtggaag    240

gaggatgagt tattccagcc cttctttcac aataccggca gaatggactg cgaacacacg    300

cctgagggta tcgaggacct gaaaaagcag taccaggcac tgcacgatgc cggtgcgggt    360

ctggagaaga ctcatgcctg gttggacaac gaggatgaga tcttatccaa gatgccgttg    420

cttcaacgtg accaaataca aggatggaaa gcaatatgga gtcaagatgg cggctggtta    480

gctgcggcaa aggccatcaa tgcgatcgga cagttcttga aagaacgtgg tgtaaagttc    540

ggattcggcg gcgctggatc cttcaagcaa ccccttttcg acgatgaagg cacaacttgc    600

attggcgttg agacggcaga tggtaccaaa tattacgctg acaaggtggt cttagcagct    660

ggcgcatgga gcccaaccct ggtggacctg gaagatcaat gttgctcgaa ggcttgggtg    720
```

```
tatgctcata ttcagttgac gcctgaagag gccgctgagt ataagggtgt cccagttgtg    780

tataatggcg aatttggctt cttctttgag cctgatgagt ttggtgtaat aaaggtgtgc    840

gacgagttcc caggattctc gcgcttcaag gaacatcaac cctatggcgc cccatctccg    900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtgcggca   1260

ccgccaaaag atcttgcaga catgccagga tggaaacatg atccgaaatt gtaa         1314
```

<210> SEQ ID NO 153
<211> LENGTH: 437
<212> TYPE: PRT
<213> ORGANISM: Coniochaeta sp.

<400> SEQUENCE: 153

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Gln Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270
```

```
Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435


<210> SEQ ID NO 154
<211> LENGTH: 1314
<212> TYPE: DNA
<213> ORGANISM: Coniochaeta sp.

<400> SEQUENCE: 154

atgacgtcga atcgtgcaga tacaagggtg attgtcgtcg gtggcggagg aacgattggt     60

tcctcgacag cgctgcatct tgtgaggagt ggttatgctc ccgcaaatat cacggtcttg    120

gacacatttg agattccatc ggctcaatca gccggccatg atctcaacaa gatcatggga    180

atagatctgc gcaacaaggt ggacctgcaa atgagtctag aggctagaca gatgtggaag    240

gaggatgagt tattccagcc cttctttcac aataccggca gaatggactg cgaacacacg    300

cctgagggta tcgaggacct gaaaaagcag taccaggcac tgcacgatgc cggtgcgggt    360

ctggagaaga ctcatgcctg gttggacaac gaggatgaga tcttatccaa gatgccgttg    420

cttcaacgtg accaaataca aggatggaaa gcaatatgga gtcaagatgg cggctggtta    480

gctgcggcaa aggccatcaa tgcgatcgga cagttcttga aagaacgtgg tgtaaagttc    540

ggattcggcg gcgctggatc cttcaagcaa ccccttttcg acgatgaagg cacaacttgc    600

attggcgttg agacggcaga tggtaccaaa tattacgctg acaaggtggt cttagcagct    660

ggcgcatgga gcccaaccct ggtggacctg gaagatcaat gttgctcgaa ggcttgggtg    720

tatgctcata ttcagttgac gcctgaagag gccgctgagt ataagggtgt cccagttgtg    780

tataatggcg aatttggctt cttctttgag cctgatgagt ttggtgtaat aaaggtgtgc    840

gacgagttcc caggattctc gcgcttcaag gaacatcaac cctatggcgc ccccatctccg    900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140
```

```
atcttgccta acgtcggaaa atacgtagtc gagttgatag agggccgcct gccggaggaa   1200

atggcttatc aatggaggtg gcggccagga ggcgatgcac tcaagtctag acgtgcggca   1260

ccgccaaaag atcttgcaga catgccagga tggaaacatg atccgaaatt gtaa         1314


<210> SEQ ID NO 155
<211> LENGTH: 437
<212> TYPE: PRT
<213> ORGANISM: Eupenicillium terrenum

<400> SEQUENCE: 155

Met Ala His Ser Arg Ala Ser Thr Lys Val Val Val Val Gly Gly Gly
1               5                   10                  15

Gly Thr Ile Gly Ser Ser Thr Ala Leu His Leu Ile Arg Ser Gly Tyr
            20                  25                  30

Thr Pro Ser Asn Ile Thr Val Leu Asp Val Tyr Lys Thr Pro Ser Leu
        35                  40                  45

Gln Ser Ala Gly His Asp Leu Asn Lys Ile Met Gly Ile Asp Leu Arg
    50                  55                  60

Asn Gly Pro Asp Leu Gln Leu Ser Leu Glu Ser Leu Asp Met Trp Gln
65                  70                  75                  80

Asn Asp Glu Leu Phe Lys Pro Phe Phe His Gln Val Gly Met Ile Asp
                85                  90                  95

Cys Ser Ser Ser Lys Glu Gly Ile Glu Asn Leu Arg Arg Lys Tyr Gln
            100                 105                 110

Thr Leu Leu Asp Ala Gly Ile Gly Leu Glu Lys Thr Asn Val Trp Leu
        115                 120                 125

Glu Ser Glu Asp Glu Ile Leu Ala Lys Ala Pro Asn Phe Thr Arg Glu
    130                 135                 140

Gln Val Lys Gly Trp Lys Gly Leu Phe Cys Thr Asp Gly Gly Trp Leu
145                 150                 155                 160

Ala Ala Ala Lys Ala Ile Asn Ala Ile Gly Ile Phe Leu Gln Asp Lys
                165                 170                 175

Gly Val Lys Phe Gly Phe Gly Asp Ala Gly Thr Phe Gln Gln Pro Leu
            180                 185                 190

Phe Ala Ala Asp Gly Lys Thr Cys Ile Gly Leu Glu Thr Thr Asp Gly
        195                 200                 205

Thr Lys Tyr Phe Ala Asp Lys Val Val Leu Ala Ala Gly Ala Trp Ser
    210                 215                 220

Pro Thr Leu Val Asp Leu Glu Asp Gln Cys Val Ser Lys Ala Trp Val
225                 230                 235                 240

Phe Ala His Ile Gln Leu Thr Pro Lys Glu Ala Asp Ala Tyr Lys Asn
                245                 250                 255

Val Pro Val Val Tyr Asp Gly Glu Tyr Gly Phe Phe Phe Glu Pro Asp
            260                 265                 270

Glu Tyr Gly Val Ile Lys Val Cys Asp Glu Phe Pro Gly Phe Ser Arg
        275                 280                 285

Phe Lys Leu His Gln Pro Tyr Gly Ala Ala Ser Pro Lys Met Ile Ser
    290                 295                 300

Val Pro Arg Ser His Ala Lys His Pro Thr Asp Thr Tyr Pro Asp Ala
305                 310                 315                 320

Ser Glu Val Thr Ile Arg Lys Ala Ile Ala Arg Phe Leu Pro Glu Phe
                325                 330                 335

Lys Asp Lys Glu Leu Phe Asn Arg Thr Met Cys Trp Cys Thr Asp Thr
```

340 345 350

Ala Asp Ala Asn Leu Leu Ile Cys Glu His Pro Lys Trp Lys Asn Phe
355 360 365

Ile Leu Ala Thr Gly Asp Ser Gly His Ser Phe Lys Leu Leu Pro Asn
370 375 380

Ile Gly Lys Tyr Val Val Glu Leu Leu Glu Gly Ser Leu Ser Gln Glu
385 390 395 400

Met Ala Gly Ala Trp Arg Trp Arg Pro Gly Gly Asp Ala Leu Arg Ser
405 410 415

Arg Arg Gly Ala Pro Ala Lys Asp Leu Ala Glu Met Pro Gly Trp Lys
420 425 430

His Asp Ala His Leu
435

<210> SEQ ID NO 156
<211> LENGTH: 1314
<212> TYPE: DNA
<213> ORGANISM: Eupenicillium terrenum

<400> SEQUENCE: 156
atggctcatt cgcgtgcaag caccaaagtc gtcgtggttg ggggaggtgg tacgatcggg 60
tcttcgacgg ctctgcactt aatccgctct ggatataccc cctcaaatat caccgtgctt 120
gacgtataca agaccccttc attgcaatct gcaggacatg atttgaacaa gatcatgggc 180
attgatttgc gcaacgggcc tgacttgcag ctttcgctgg aatcactcga catgtggcaa 240
aacgatgagt tgttcaagcc attctttcac caagtgggca tgattgattg ttcgtcatcc 300
aaagagggta ttgaaaatct tcgacgaaaa taccagaccc tcctcgatgc gggcattggg 360
ctggagaaga cgaacgtttg gctggaatct gaagatgaga tcctcgccaa agcgccgaat 420
ttcacgcgtg aacaagtcaa ggggtggaaa ggcttatttt gcactgatgg aggctggctt 480
gctgcagcca aggctatcaa tgcgatcgga attttcctcc aggacaaagg tgtcaagttt 540
ggctttggag atgctggtac ctttcagcaa cctctgttcg ccgctgatgg aaaaacttgc 600
atcggacttg aaactacaga cggaaccaag tactttgctg acaaggttgt cttggctgct 660
ggtgcgtgga gtcccacctt ggtggatcta gaagatcagt gtgtttcaaa ggcctgggtt 720
ttcgctcata ttcaactcac acccaaagaa gcggacgcgt acaagaatgt gcctgtggtc 780
tatgatggtg aatatgggtt ctttttcgaa cccgacgagt atggggtgat caaagtctgt 840
gacgagttcc ctggtttctc tcgcttcaaa ctgcatcaac cgtacggggc tgcatctccc 900
aagatgatat ccgtaccgcg atcacacgcc aagcatccca cagataccta ccctgatgcc 960
tccgaagtca ccatacgcaa agcgatcgca aggttcctgc cagaatttaa agacaaggag 1020
ctcttcaacc gtaccatgtg ctggtgtaca gatacggccg atgctaactt attgatttgc 1080
gaacacccga agtggaagaa tttcattctg gccactggag atagcggaca ttccttcaag 1140
ctgttgccaa acatcgggaa atacgtagtt gagcttttag agggatctct atcgcaggaa 1200
atggctggtg cctggagatg gagacccgga ggtgatgctc ttagatctag acgcggtgct 1260
ccggcaaagg atcttgctga gatgccggga tggaagcatg atgcacattt gtga 1314

<210> SEQ ID NO 157
<211> LENGTH: 437
<212> TYPE: PRT
<213> ORGANISM: Coniochaeta sp.

<400> SEQUENCE: 157

Met Thr Ser Asn Arg Ala Asp Thr Arg Val Ile Val Val Gly Gly Gly
1 5 10 15

Gly Thr Ile Gly Ser Ser Thr Ala Leu His Leu Val Arg Ser Gly Tyr
20 25 30

Ala Pro Ala Asn Ile Thr Val Leu Asp Thr Phe Glu Ile Pro Ser Ala
35 40 45

Gln Ser Ala Gly His Asp Leu Asn Lys Ile Met Gly Ile Ala Leu Arg
50 55 60

Asn Lys Val Asp Leu Gln Met Ser Leu Glu Ala Arg Gln Met Trp Lys
65 70 75 80

Glu Asp Glu Leu Phe Gln Pro Phe Phe His Asn Thr Gly Arg Met Asp
85 90 95

Cys Glu His Thr Pro Glu Gly Ile Glu Asp Leu Lys Lys Leu Tyr Gln
100 105 110

Ala Leu His Asp Ala Gly Ala Gly Leu Glu Lys Thr His Ala Trp Leu
115 120 125

Asp Asn Glu Asp Glu Ile Leu Ser Lys Met Pro Leu Leu Gln Arg Asp
130 135 140

Gln Ile Gln Gly Trp Lys Ala Ile Trp Ser Gln Asp Gly Gly Trp Leu
145 150 155 160

Ala Ala Ala Lys Ala Ile Asn Ala Ile Gly Gln Phe Leu Lys Glu Arg
165 170 175

Gly Val Lys Phe Gly Phe Gly Gly Ala Gly Ser Phe Lys Gln Pro Leu
180 185 190

Phe Asp Asp Glu Gly Thr Thr Cys Ile Gly Val Glu Thr Ala Asp Gly
195 200 205

Thr Lys Tyr Tyr Ala Asp Lys Val Val Leu Ala Ala Gly Ala Trp Ser
210 215 220

Pro Thr Leu Val Asp Leu Glu Asp Gln Cys Cys Ser Lys Ala Trp Val
225 230 235 240

Tyr Ala His Ile Gln Leu Thr Pro Glu Glu Ala Ala Glu Tyr Lys Gly
245 250 255

Val Pro Val Val Tyr Asn Gly Glu Phe Gly Phe Phe Phe Glu Pro Asp
260 265 270

Glu Phe Gly Val Ile Lys Val Cys Asp Glu Phe Pro Gly Phe Ser Arg
275 280 285

Phe Lys Glu His Gln Pro Tyr Gly Ala Pro Ser Pro Lys Arg Ile Ser
290 295 300

Val Pro Arg Ser His Ala Lys His Pro Thr Asp Thr Tyr Pro Asp Ala
305 310 315 320

Ser Glu Val Ser Ile Lys Lys Ala Ile Ala Thr Phe Leu Pro Arg Phe
325 330 335

Gln Asp Lys Glu Leu Phe Asn Arg Ala Leu Cys Trp Cys Thr Asp Thr
340 345 350

Ala Asp Ala Ala Leu Leu Met Cys Glu His Pro Lys Trp Lys Asn Phe
355 360 365

Ile Leu Ala Thr Gly Asp Ser Gly His Ser Phe Lys Ile Leu Pro Asn
370 375 380

Val Gly Lys Tyr Val Val Glu Leu Ile Glu Gly Arg Leu Pro Glu Glu
385 390 395 400

Met Ala Tyr Gln Trp Arg Trp Arg Pro Gly Gly Asp Ala Leu Lys Ser
405 410 415

Arg Arg Ala Ala Pro Pro Lys Asp Leu Ala Asp Met Pro Gly Trp Lys
420 425 430

His Asp Pro Lys Leu
435

<210> SEQ ID NO 158
<211> LENGTH: 1314
<212> TYPE: DNA
<213> ORGANISM: Coniochaeta sp.

<400> SEQUENCE: 158
atgacgtcga atcgtgcaga tacaagggtg attgtcgtcg gtggcggagg aacgattggt 60
tcctcgacag cgctgcatct tgtgaggagt ggttatgctc ccgcaaatat cacggtcttg 120
gacacatttg agattccatc ggctcaatca gccggccatg atctcaacaa gatcatggga 180
atagcactgc gcaacaaggt ggacctgcaa atgagtctag aggctagaca gatgtggaag 240
gaggatgagt tattccagcc cttctttcac aataccggca gaatggactg cgaacacacg 300
cctgagggta tcgaggacct gaaaaagctg taccaggcac tgcacgatgc cggtgcgggt 360
ctggagaaga ctcatgcctg gttggacaac gaggatgaga tcttatccaa gatgccgttg 420
cttcaacgtg accaaataca aggatggaaa gcaatatgga gtcaagatgg cggctggtta 480
gctgcggcaa aggccatcaa tgcgatcgga cagttcttga aagaacgtgg tgtaaagttc 540
ggattcggcg gcgctggatc cttcaagcaa ccccttttcg acgatgaagg cacaacttgc 600
attggcgttg agacggcaga tggtaccaaa tattacgctg acaaggtggt cttagcagct 660
ggcgcatgga gcccaaccct ggtggacctg gaagatcaat gttgctcgaa ggcttgggtg 720
tatgctcata ttcagttgac gcctgaagag gccgctgagt ataagggtgt cccagttgtg 780
tataatggcg aatttggctt cttctttgag cctgatgagt ttggtgtaat aaaggtgtgc 840
gacgagttcc caggattctc gcgcttcaag gaacatcaac cctatggcgc cccatctccg 900
aaacggatat cagtaccacg atcgcacgcc aagcatccca cagacactta tccagacgca 960
tccgaagtca gcatcaaaaa agcaatcgcg acgtttctcc ctcgatttca ggacaaggag 1020
ctcttcaatc gcgccttgtg ctggtgtaca gacactgcgg acgctgctct cttgatgtgt 1080
gaacacccca aatggaagaa tttcattcta gcgaccggcg acagcggaca ctcattcaaa 1140
atcttgccta acgtcggaaa atacgtagtc gagttgatag agggccgcct gccggaggaa 1200
atggcttatc aatggaggtg gcggccagga ggcgatgcac tcaagtctag acgtgcggca 1260
ccgccaaaag atcttgcaga catgccagga tggaaacatg atccgaaatt gtaa 1314

<210> SEQ ID NO 159
<211> LENGTH: 437
<212> TYPE: PRT
<213> ORGANISM: Coniochaeta sp.

<400> SEQUENCE: 159

Met Thr Ser Asn Arg Ala Asp Thr Arg Val Ile Val Val Gly Gly Gly
1 5 10 15

Gly Thr Ile Gly Ser Ser Thr Ala Leu His Leu Val Arg Ser Gly Tyr
20 25 30

Ala Pro Ala Asn Ile Thr Val Leu Asp Thr Phe Glu Ile Pro Ser Ala
35 40 45

Gln Ser Ala Gly His Asp Leu Asn Lys Ile Met Gly Ile Ala Leu Arg
50 55 60

Asn Lys Val Asp Leu Gln Met Ser Leu Glu Ala Arg Gln Met Trp Lys

```
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Tyr Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 160
<211> LENGTH: 1314
<212> TYPE: DNA
<213> ORGANISM: Coniochaeta sp.

<400> SEQUENCE: 160

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagcactgc gcaacaaggt ggacctgcaa atgagtctag aggctagaca gatgtggaag     240

gaggatgagt tattccagcc cttctttcac aataccggca gaatggactg cgaacacacg     300

cctgagggta tcgaggacct gaaaaagtat taccaggcac tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840

gacgagttcc caggattctc gcgcttcaag gaacatcaac cctatggcgc cccatctccg     900

aaacggatat cagtaccacg atcgcacgcc aagcatccca cagacactta tccagacgca     960

tccgaagtca gcatcaaaaa agcaatcgcg acgtttctcc ctcgatttca ggacaaggag    1020

ctcttcaatc gcgccttgtg ctggtgtaca gacactgcgg acgctgctct cttgatgtgt    1080

gaacacccca aatggaagaa tttcattcta gcgaccggcg acagcggaca ctcattcaaa    1140

atcttgccta acgtcggaaa atacgtagtc gagttgatag agggccgcct gccggaggaa    1200

atggcttatc aatggaggtg gcggccagga ggcgatgcac tcaagtctag acgtgcggca    1260

ccgccaaaag atcttgcaga catgccagga tggaaacatg atccgaaatt gtaa          1314
```

```
<210> SEQ ID NO 161
<211> LENGTH: 437
<212> TYPE: PRT
<213> ORGANISM: Coniochaeta sp.

<400> SEQUENCE: 161

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asn Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140
```

-continued

```
Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 162
<211> LENGTH: 1314
<212> TYPE: DNA
<213> ORGANISM: Coniochaeta sp.

<400> SEQUENCE: 162

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

ataaacctgc gcaacaaggt ggacctgcaa atgagtctag aggctagaca gatgtggaag     240

gaggatgagt tattccagcc cttctttcac aataccggca gaatggactg cgaacacacg     300

cctgagggta tcgaggacct gaaaaagctg taccaggcac tgcacgatgc cggtgcgggt     360

ctggagaaga ctcatgcctg gttggacaac gaggatgaga tcttatccaa gatgccgttg     420
```

-continued

```
cttcaacgtg accaaataca aggatggaaa gcaatatgga gtcaagatgg cggctggtta    480
gctgcggcaa aggccatcaa tgcgatcgga cagttcttga aagaacgtgg tgtaaagttc    540
ggattcggcg gcgctggatc cttcaagcaa cccctttcg acgatgaagg cacaacttgc    600
attggcgttg agacggcaga tggtaccaaa tattacgctg acaaggtggt cttagcagct    660
ggcgcatgga gcccaaccct ggtggacctg gaagatcaat gttgctcgaa ggcttgggtg    720
tatgctcata ttcagttgac gcctgaagag gccgctgagt ataagggtgt cccagttgtg    780
tataatggcg aatttggctt cttctttgag cctgatgagt ttggtgtaat aaaggtgtgc    840
gacgagttcc caggattctc gcgcttcaag gaacatcaac cctatggcgc ccatctccg     900
aaacggatat cagtaccacg atcgcacgcc aagcatccca cagacactta tccagacgca    960
tccgaagtca gcatcaaaaa agcaatcgcg acgtttctcc ctcgatttca ggacaaggag   1020
ctcttcaatc gcgccttgtg ctggtgtaca gacactgcgg acgctgctct cttgatgtgt   1080
gaacacccca aatggaagaa tttcattcta gcgaccggcg acagcggaca ctcattcaaa   1140
atcttgccta acgtcggaaa atacgtagtc gagttgatag agggccgcct gccggaggaa   1200
atggcttatc aatggaggtg gcggccagga ggcgatgcac tcaagtctag acgtgcggca   1260
ccgccaaaag atcttgcaga catgccagga tggaaacatg atccgaaatt gtaa         1314
```

```
<210> SEQ ID NO 163
<211> LENGTH: 437
<212> TYPE: PRT
<213> ORGANISM: Coniochaeta sp.

<400> SEQUENCE: 163

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220
```

```
Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 164
<211> LENGTH: 1314
<212> TYPE: DNA
<213> ORGANISM: Coniochaeta sp.

<400> SEQUENCE: 164

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatctgc gcaacaaggt ggacctgcaa atgagtctag aggctagaca gatgtggaag     240

gaggatgagt tattccagcc cttctttcac aataccggca gaatggactg cgaacacacg     300

cctgagggta tcgaggacct gaaaaagctg taccaggcac tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840
```

-continued

```
gacgagttcc caggattctc gcgcttcaag gaacatcaac cctatggcgc cccatctccg    900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtgcggca   1260

ccgccaaaag atcttgcaga catgccagga tggaaacatg atccgaaatt gtaa         1314


<210> SEQ ID NO 165
<211> LENGTH: 437
<212> TYPE: PRT
<213> ORGANISM: Coniochaeta sp.

<400> SEQUENCE: 165

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Ala Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
```

```
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435


<210> SEQ ID NO 166
<211> LENGTH: 1314
<212> TYPE: DNA
<213> ORGANISM: Coniochaeta sp.

<400> SEQUENCE: 166

atgacgtcga atcgtgcaga tacaagggtg attgtcgtcg gtggcggagg aacgattggt     60

tcctcgacag cgctgcatct tgtgaggagt ggttatgctc ccgcaaatat cacggtcttg    120

gacacatttg agattccatc ggctcaatca gccggccatg atctcaacaa gatcatggga    180

atagatctgc gcaacaaggt ggacctgcaa atgagtctag aggctagaca gatgtggaag    240

gaggatgagt tattccagcc cttctttcac aataccggca gaatggactg cgaacacacg    300

cctgagggta tcgaggccct gaaaaagctg taccaggcac tgcacgatgc cggtgcgggt    360

ctggagaaga ctcatgcctg gttggacaac gaggatgaga tcttatccaa gatgccgttg    420

cttcaacgtg accaaataca aggatggaaa gcaatatgga gtcaagatgg cggctggtta    480

gctgcggcaa aggccatcaa tgcgatcgga cagttcttga aagaacgtgg tgtaaagttc    540

ggattcggcg gcgctggatc cttcaagcaa ccccttttcg acgatgaagg cacaacttgc    600

attggcgttg agacggcaga tggtaccaaa tattacgctg acaaggtggt cttagcagct    660

ggcgcatgga gcccaaccct ggtggacctg gaagatcaat gttgctcgaa ggcttgggtg    720

tatgctcata ttcagttgac gcctgaagag gccgctgagt ataagggtgt cccagttgtg    780

tataatggcg aatttggctt cttctttgag cctgatgagt ttggtgtaat aaaggtgtgc    840

gacgagttcc caggattctc gcgcttcaag gaacatcaac cctatggcgc cccatctccg    900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtgcggca   1260
```

```
ccgccaaaag atcttgcaga catgccagga tggaaacatg atccgaaatt gtaa         1314


<210> SEQ ID NO 167
<211> LENGTH: 437
<212> TYPE: PRT
<213> ORGANISM: Coniochaeta sp.

<400> SEQUENCE: 167

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365
```

-continued

```
Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 168
<211> LENGTH: 1314
<212> TYPE: DNA
<213> ORGANISM: Coniochaeta sp.

<400> SEQUENCE: 168

```
atgacgtcga atcgtgcaga tacaagggtg attgtcgtcg gtggcggagg aacgattggt     60

tcctcgacag cgctgcatct tgtgaggagt ggttatgctc ccgcaaatat cacggtcttg    120

gacacatttg agattccatc ggctcaatca gccggccatg atctcaacaa gatcatggga    180

atagatctgc gcaacaaggt ggacctgcaa atgagtctag aggctagaca gatgtggaag    240

gaggatgagt tattccagcc cttctttcac aataccggca gaatggactg cgaacacacg    300

cctgagggta tcgagaaact gaaaaagctg taccaggcac tgcacgatgc cggtgcgggt    360

ctggagaaga ctcatgcctg gttggacaac gaggatgaga tcttatccaa gatgccgttg    420

cttcaacgtg accaaataca aggatggaaa gcaatatgga gtcaagatgg cggctggtta    480

gctgcggcaa aggccatcaa tgcgatcgga cagttcttga aagaacgtgg tgtaaagttc    540

ggattcggcg gcgctggatc cttcaagcaa ccccttttcg acgatgaagg cacaacttgc    600

attggcgttg agacggcaga tggtaccaaa tattacgctg acaaggtggt cttagcagct    660

ggcgcatgga gcccaaccct ggtggacctg gaagatcaat gttgctcgaa ggcttgggtg    720

tatgctcata ttcagttgac gcctgaagag gccgctgagt ataagggtgt cccagttgtg    780

tataatggcg aatttggctt cttctttgag cctgatgagt ttggtgtaat aaaggtgtgc    840

gacgagttcc caggattctc gcgcttcaag gaacatcaac cctatggcgc cccatctccg    900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtgcggca   1260

ccgccaaaag atcttgcaga catgccagga tggaaacatg atccgaaatt gtaa         1314
```

<210> SEQ ID NO 169
<211> LENGTH: 437
<212> TYPE: PRT
<213> ORGANISM: Coniochaeta sp.

<400> SEQUENCE: 169

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
```

-continued

```
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Arg Leu Lys Lys Leu Tyr Gln
            100                 105                 110

Ala Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 170
<211> LENGTH: 1314
<212> TYPE: DNA
<213> ORGANISM: Coniochaeta sp.

<400> SEQUENCE: 170
atgacgtcga atcgtgcaga tacaagggtg attgtcgtcg gtggcggagg aacgattggt 60
tcctcgacag cgctgcatct tgtgaggagt ggttatgctc ccgcaaatat cacggtcttg 120
gacacatttg agattccatc ggctcaatca gccggccatg atctcaacaa gatcatggga 180
atagatctgc gcaacaaggt ggacctgcaa atgagtctag aggctagaca gatgtggaag 240
gaggatgagt tattccagcc cttctttcac aataccggca gaatggactg cgaacacacg 300
cctgagggta tcgagcgcct gaaaaagctg taccaggcac tgcacgatgc cggtgcgggt 360
ctggagaaga ctcatgcctg gttggacaac gaggatgaga tcttatccaa gatgccgttg 420
cttcaacgtg accaaataca aggatggaaa gcaatatgga gtcaagatgg cggctggtta 480
gctgcggcaa aggccatcaa tgcgatcgga cagttcttga aagaacgtgg tgtaaagttc 540
ggattcggcg gcgctggatc cttcaagcaa ccccttttcg acgatgaagg cacaacttgc 600
attggcgttg agacggcaga tggtaccaaa tattacgctg acaaggtggt cttagcagct 660
ggcgcatgga gcccaaccct ggtggacctg gaagatcaat gttgctcgaa ggcttgggtg 720
tatgctcata ttcagttgac gcctgaagag gccgctgagt ataagggtgt cccagttgtg 780
tataatggcg aatttggctt cttctttgag cctgatgagt ttggtgtaat aaaggtgtgc 840
gacgagttcc caggattctc gcgcttcaag gaacatcaac cctatggcgc cccatctccg 900
aaacggatat cagtaccacg atcgcacgcc aagcatccca cagacactta tccagacgca 960
tccgaagtca gcatcaaaaa agcaatcgcg acgtttctcc ctcgatttca ggacaaggag 1020
ctcttcaatc gcgccttgtg ctggtgtaca gacactgcgg acgctgctct cttgatgtgt 1080
gaacacccca aatggaagaa tttcattcta gcgaccggcg acagcggaca ctcattcaaa 1140
atcttgccta acgtcggaaa atacgtagtc gagttgatag agggccgcct gccggaggaa 1200
atggcttatc aatggaggtg gcggccagga ggcgatgcac tcaagtctag acgtgcggca 1260
ccgccaaaag atcttgcaga catgccagga tggaaacatg atccgaaatt gtaa 1314

<210> SEQ ID NO 171
<211> LENGTH: 437
<212> TYPE: PRT
<213> ORGANISM: Coniochaeta sp.

<400> SEQUENCE: 171

Met Thr Ser Asn Arg Ala Asp Thr Arg Val Ile Val Val Gly Gly Gly
1 5 10 15

Gly Thr Ile Gly Ser Ser Thr Ala Leu His Leu Val Arg Ser Gly Tyr
20 25 30

Ala Pro Ala Asn Ile Thr Val Leu Asp Thr Phe Glu Ile Pro Ser Ala
35 40 45

Gln Ser Ala Gly His Asp Leu Asn Lys Ile Met Gly Ile Asp Leu Arg
50 55 60

Asn Lys Val Asp Leu Gln Met Ser Leu Glu Ala Arg Gln Met Trp Lys
65 70 75 80

Glu Asp Glu Leu Phe Gln Pro Phe Phe His Asn Thr Gly Arg Met Asp
85 90 95

-continued

```
Cys Glu His Thr Pro Glu Gly Ile Glu Asp Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 172
<211> LENGTH: 1314
<212> TYPE: DNA
<213> ORGANISM: Coniochaeta sp.

<400> SEQUENCE: 172

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180
```

```
atagatctgc gcaacaaggt ggacctgcaa atgagtctag aggctagaca gatgtggaag    240

gaggatgagt tattccagcc cttctttcac aataccggca gaatggactg cgaacacacg    300

cctgagggta tcgaggacct gaaaaagctg taccagaaac tgcacgatgc cggtgcgggt    360

ctggagaaga ctcatgcctg gttggacaac gaggatgaga tcttatccaa gatgccgttg    420

cttcaacgtg accaaataca aggatggaaa gcaatatgga gtcaagatgg cggctggtta    480

gctgcggcaa aggccatcaa tgcgatcgga cagttcttga aagaacgtgg tgtaaagttc    540

ggattcggcg gcgctggatc cttcaagcaa ccccttttcg acgatgaagg cacaacttgc    600

attggcgttg agacggcaga tggtaccaaa tattacgctg acaaggtggt cttagcagct    660

ggcgcatgga gcccaaccct ggtggacctg gaagatcaat gttgctcgaa ggcttgggtg    720

tatgctcata ttcagttgac gcctgaagag gccgctgagt ataagggtgt cccagttgtg    780

tataatggcg aatttggctt cttctttgag cctgatgagt ttggtgtaat aaaggtgtgc    840

gacgagttcc caggattctc gcgcttcaag gaacatcaac cctatggcgc ccatctccg     900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtgcggca   1260

ccgccaaaag atcttgcaga catgccagga tggaaacatg atccgaaatt gtaa         1314
```

<210> SEQ ID NO 173
<211> LENGTH: 437
<212> TYPE: PRT
<213> ORGANISM: Coniochaeta sp.

<400> SEQUENCE: 173

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Asp Leu Lys Lys Leu Tyr Gln
            100                 105                 110

Arg Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175
```

-continued

```
Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 174
<211> LENGTH: 1314
<212> TYPE: DNA
<213> ORGANISM: Coniochaeta sp.

<400> SEQUENCE: 174

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatctgc gcaacaaggt ggacctgcaa atgagtctag aggctagaca gatgtggaag     240

gaggatgagt tattccagcc cttctttcac aataccggca gaatggactg cgaacacacg     300

cctgagggta tcgaggacct gaaaaagctg taccagcgtc tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600
```

-continued

```
attggcgttg agacggcaga tggtaccaaa tattacgctg acaaggtggt cttagcagct    660

ggcgcatgga gcccaaccct ggtggacctg gaagatcaat gttgctcgaa ggcttgggtg    720

tatgctcata ttcagttgac gcctgaagag gccgctgagt ataagggtgt cccagttgtg    780

tataatggcg aatttggctt cttctttgag cctgatgagt ttggtgtaat aaaggtgtgc    840

gacgagttcc caggattctc gcgcttcaag gaacatcaac cctatggcgc ccatctccg     900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtgcggca   1260

ccgccaaaag atcttgcaga catgccagga tggaaacatg atccgaaatt gtaa         1314
```

```
<210> SEQ ID NO 175
<211> LENGTH: 437
<212> TYPE: PRT
<213> ORGANISM: Coniochaeta sp.

<400> SEQUENCE: 175

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Leu Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Arg Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
```

```
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435


<210> SEQ ID NO 176
<211> LENGTH: 1314
<212> TYPE: DNA
<213> ORGANISM: Coniochaeta sp.

<400> SEQUENCE: 176

atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatctgc gcaacaaggt ggacctgcaa atgagtctag aggctagaca gatgtggaag     240

gaggatgagt tattccagcc cttctttcac aataccggca gaatggactg cgaacacacg     300

cctgagggta tcgagaaact gaaaaagctg taccagcgtc tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840

gacgagttcc caggattctc gcgcttcaag gaacatcaac cctatggcgc cccatctccg     900

aaacggatat cagtaccacg atcgcacgcc aagcatccca cagacactta tccagacgca     960

tccgaagtca gcatcaaaaa agcaatcgcg acgtttctcc ctcgatttca ggacaaggag    1020
```

-continued

```
ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtgcggca   1260

ccgccaaaag atcttgcaga catgccagga tggaaacatg atccgaaatt gtaa         1314


<210> SEQ ID NO 177
<211> LENGTH: 437
<212> TYPE: PRT
<213> ORGANISM: Coniochaeta sp.

<400> SEQUENCE: 177

Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp Ala Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320
```

```
Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 178
<211> LENGTH: 1314
<212> TYPE: DNA
<213> ORGANISM: Coniochaeta sp.

<400> SEQUENCE: 178

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatgcgc gcaacaaggt ggacctgcaa atgagtctag aggctagaca gatgtggaag     240

gaggatgagt tattccagcc cttctttcac aataccggca gaatggactg cgaacacacg     300

cctgagggta tcgagaaact gaaaaagctg taccagaaac tgcacgatgc cggtgcgggt     360

ctggagaaga ctcatgcctg gttggacaac gaggatgaga tcttatccaa gatgccgttg     420

cttcaacgtg accaaataca aggatggaaa gcaatatgga gtcaagatgg cggctggtta     480

gctgcggcaa aggccatcaa tgcgatcgga cagttcttga aagaacgtgg tgtaaagttc     540

ggattcggcg gcgctggatc cttcaagcaa ccccttttcg acgatgaagg cacaacttgc     600

attggcgttg agacggcaga tggtaccaaa tattacgctg acaaggtggt cttagcagct     660

ggcgcatgga gcccaaccct ggtggacctg gaagatcaat gttgctcgaa ggcttgggtg     720

tatgctcata ttcagttgac gcctgaagag gccgctgagt ataagggtgt cccagttgtg     780

tataatggcg aatttggctt cttctttgag cctgatgagt ttggtgtaat aaaggtgtgc     840

gacgagttcc caggattctc gcgcttcaag gaacatcaac cctatggcgc cccatctccg     900

aaacggatat cagtaccacg atcgcacgcc aagcatccca cagacactta tccagacgca     960

tccgaagtca gcatcaaaaa agcaatcgcg acgtttctcc ctcgatttca ggacaaggag    1020

ctcttcaatc gcgccttgtg ctggtgtaca gacactgcgg acgctgctct cttgatgtgt    1080

gaacacccca aatggaagaa tttcattcta gcgaccggcg acagcggaca ctcattcaaa    1140

atcttgccta acgtcggaaa atacgtagtc gagttgatag agggccgcct gccggaggaa    1200

atggcttatc aatggaggtg gcggccagga ggcgatgcac tcaagtctag acgtgcggca    1260

ccgccaaaag atcttgcaga catgccagga tggaaacatg atccgaaatt gtaa          1314
```

<210> SEQ ID NO 179
<211> LENGTH: 437

<212> TYPE: PRT
<213> ORGANISM: Coniochaeta sp.

<400> SEQUENCE: 179

```
Met Thr Ser Asn Arg Ala Asp Thr Arg Val Ile Val Val Gly Gly Gly
1               5                   10                  15

Gly Thr Ile Gly Ser Ser Thr Ala Leu His Leu Val Arg Ser Gly Tyr
            20                  25                  30

Ala Pro Ala Asn Ile Thr Val Leu Asp Thr Phe Glu Ile Pro Ser Ala
        35                  40                  45

Gln Ser Ala Gly His Asp Leu Asn Lys Ile Met Gly Ile Asp His Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Glu Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400
```

Met Ala Tyr Gln Trp Arg Trp Arg Pro Gly Gly Asp Ala Leu Lys Ser
405 410 415

Arg Arg Ala Ala Pro Pro Lys Asp Leu Ala Asp Met Pro Gly Trp Lys
420 425 430

His Asp Pro Lys Leu
435

<210> SEQ ID NO 180
<211> LENGTH: 1314
<212> TYPE: DNA
<213> ORGANISM: Coniochaeta sp.

<400> SEQUENCE: 180
atgacgtcga atcgtgcaga tacaagggtg attgtcgtcg gtggcggagg aacgattggt 60
tcctcgacag cgctgcatct tgtgaggagt ggttatgctc ccgcaaatat cacggtcttg 120
gacacatttg agattccatc ggctcaatca gccggccatg atctcaacaa gatcatggga 180
atagatcatc gcaacaaggt ggacctgcaa atgagtctag aggctagaca gatgtggaag 240
gaggatgagt tattccagcc cttctttcac aataccggca gaatggactg cgaacacacg 300
cctgagggta tcgagaaact gaaaaagctg taccagaaac tgcacgatgc cggtgcgggt 360
ctggagaaga ctcatgcctg gttggacaac gaggatgaga tcttatccaa gatgccgttg 420
cttcaacgtg accaaataca aggatggaaa gcaatatgga gtcaagatgg cggctggtta 480
gctgcggcaa aggccatcaa tgcgatcgga cagttcttga aagaacgtgg tgtaaagttc 540
ggattcggcg gcgctggatc cttcaagcaa ccccttttcg acgatgaagg cacaacttgc 600
attggcgttg agacggcaga tggtaccaaa tattacgctg acaaggtggt cttagcagct 660
ggcgcatgga gcccaaccct ggtggacctg gaagatcaat gttgctcgaa ggcttgggtg 720
tatgctcata ttcagttgac gcctgaagag gccgctgagt ataagggtgt cccagttgtg 780
tataatggcg aatttggctt cttctttgag cctgatgagt ttggtgtaat aaaggtgtgc 840
gacgagttcc caggattctc gcgcttcaag gaacatcaac cctatggcgc cccatctccg 900
aaacggatat cagtaccacg atcgcacgcc aagcatccca cagacactta tccagacgca 960
tccgaagtca gcatcaaaaa agcaatcgcg acgtttctcc ctcgatttca ggacaaggag 1020
ctcttcaatc gcgccttgtg ctggtgtaca gacactgcgg acgctgctct cttgatgtgt 1080
gaacacccca aatggaagaa tttcattcta gcgaccggcg acagcggaca ctcattcaaa 1140
atcttgccta acgtcggaaa atacgtagtc gagttgatag agggccgcct gccggaggaa 1200
atggcttatc aatggaggtg gcggccagga ggcgatgcac tcaagtctag acgtgcggca 1260
ccgccaaaag atcttgcaga catgccagga tggaaacatg atccgaaatt gtaa 1314

<210> SEQ ID NO 181
<211> LENGTH: 437
<212> TYPE: PRT
<213> ORGANISM: Coniochaeta sp.

<400> SEQUENCE: 181

Met Thr Ser Asn Arg Ala Asp Thr Arg Val Ile Val Val Gly Gly Gly
1 5 10 15

Gly Thr Ile Gly Ser Ser Thr Ala Leu His Leu Val Arg Ser Gly Tyr
20 25 30

Ala Pro Ala Asn Ile Thr Val Leu Asp Thr Phe Glu Ile Pro Ser Ala
35 40 45

```
Gln Ser Ala Gly His Asp Leu Asn Lys Ile Met Gly Ile Asp His Arg
    50                  55                  60

Asn Lys Val Asp Leu Gln Met Ser Leu Glu Ala Arg Gln Met Trp Lys
65                  70                  75                  80

Glu Asp Glu Leu Phe Gln Pro Phe Phe His Asn Thr Gly Arg Met Asp
                85                  90                  95

Cys Glu His Thr Pro Lys Gly Ile Glu Lys Leu Lys Lys Leu Tyr Gln
            100                 105                 110

Lys Leu His Asp Ala Gly Ala Gly Leu Glu Lys Thr His Ala Trp Leu
        115                 120                 125

Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Ala Ala Pro Pro Lys Asp Leu Ala Asp Met Pro Gly Trp Lys
            420                 425                 430

His Asp Pro Lys Leu
        435
```

<210> SEQ ID NO 182
<211> LENGTH: 1314
<212> TYPE: DNA

<213> ORGANISM: Coniochaeta sp.

<400> SEQUENCE: 182
atgacgtcga atcgtgcaga tacaagggtg attgtcgtcg gtggcggagg aacgattggt 60
tcctcgacag cgctgcatct tgtgaggagt ggttatgctc ccgcaaatat cacggtcttg 120
gacacatttg agattccatc ggctcaatca gccggccatg atctcaacaa gatcatggga 180
atagatcatc gcaacaaggt ggacctgcaa atgagtctag aggctagaca gatgtggaag 240
gaggatgagt tattccagcc cttctttcac aataccggca gaatggactg cgaacacacg 300
cctaagggta tcgagaaact gaaaaagctg taccagaaac tgcacgatgc cggtgcgggt 360
ctggagaaga ctcatgcctg gttggacaac gaggatgaga tcttatccaa gatgccgttg 420
cttcaacgtg accaaataca aggatggaaa gcaatatgga gtcaagatgg cggctggtta 480
gctgcggcaa aggccatcaa tgcgatcgga cagttcttga aagaacgtgg tgtaaagttc 540
ggattcggcg gcgctggatc cttcaagcaa ccccttttcg acgatgaagg cacaacttgc 600
attggcgttg agacggcaga tggtaccaaa tattacgctg acaaggtggt cttagcagct 660
ggcgcatgga gcccaaccct ggtggacctg gaagatcaat gttgctcgaa ggcttgggtg 720
tatgctcata ttcagttgac gcctgaagag gccgctgagt ataagggtgt cccagttgtg 780
tataatggcg aatttggctt cttctttgag cctgatgagt ttggtgtaat aaaggtgtgc 840
gacgagttcc caggattctc gcgcttcaag gaacatcaac cctatggcgc cccatctccg 900
aaacggatat cagtaccacg atcgcacgcc aagcatccca cagacactta tccagacgca 960
tccgaagtca gcatcaaaaa agcaatcgcg acgtttctcc ctcgatttca ggacaaggag 1020
ctcttcaatc gcgccttgtg ctggtgtaca gacactgcgg acgctgctct cttgatgtgt 1080
gaacacccca aatggaagaa tttcattcta gcgaccggcg acagcggaca ctcattcaaa 1140
atcttgccta acgtcggaaa atacgtagtc gagttgatag agggccgcct gccggaggaa 1200
atggcttatc aatggaggtg gcggccagga ggcgatgcac tcaagtctag acgtgcggca 1260
ccgccaaaag atcttgcaga catgccagga tggaaacatg atccgaaatt gtaa 1314

<210> SEQ ID NO 183
<211> LENGTH: 437
<212> TYPE: PRT
<213> ORGANISM: Coniochaeta sp.

<400> SEQUENCE: 183

Met Thr Ser Asn Arg Ala Asp Thr Arg Val Ile Val Val Gly Gly Gly
1 5 10 15

Gly Thr Ile Gly Ser Ser Thr Ala Leu His Leu Val Arg Ser Gly Tyr
20 25 30

Ala Pro Ala Asn Ile Thr Val Leu Asp Thr Phe Glu Ile Pro Ser Ala
35 40 45

Gln Ser Ala Gly His Asp Leu Asn Lys Ile Met Gly Ile Asp His Arg
50 55 60

Asn Lys Val Asp Leu Gln Met Ser Leu Glu Ala Arg Gln Met Trp Lys
65 70 75 80

Glu Asp Glu Leu Phe Gln Pro Phe Phe His Asn Thr Gly Arg Met Asp
85 90 95

Cys Glu His Thr Pro Glu Gly Ile Glu Lys Leu Lys Lys Leu Tyr Gln
100 105 110

Lys Leu His Asp Ala Gly Ala Gly Leu Glu Lys Thr His Ala Trp Leu
115 120 125

```
Asp Asn Glu Asp Glu Ile Leu Ser Lys Met Pro Leu Leu Gln Arg Asp
    130                 135                 140

Gln Ile Gln Gly Trp Lys Ala Ile Trp Ser Gln Asp Gly Gly Trp Leu
145                 150                 155                 160

Ala Ala Ala Lys Ala Ile Asn Ala Ile Gly Gln Phe Leu Lys Glu Arg
                165                 170                 175

Gly Val Lys Phe Gly Phe Gly Gly Ala Gly Ser Phe Lys Gln Pro Leu
            180                 185                 190

Phe Asp Asp Glu Gly Thr Thr Cys Ile Gly Val Glu Thr Ala Asp Gly
        195                 200                 205

Thr Lys Tyr Tyr Ala Asp Lys Val Val Leu Ala Ala Gly Ala Trp Ser
    210                 215                 220

Pro Thr Leu Val Asp Leu Glu Asp Gln Cys Cys Ser Lys Ala Trp Val
225                 230                 235                 240

Tyr Ala His Ile Gln Leu Thr Pro Glu Glu Ala Ala Glu Tyr Lys Gly
                245                 250                 255

Val Pro Val Val Tyr Asn Gly Glu Phe Gly Phe Phe Phe Glu Pro Asp
            260                 265                 270

Glu Phe Gly Val Ile Lys Val Cys Asp Glu Phe Pro Gly Phe Ser Arg
        275                 280                 285

Phe Lys Glu His Gln Pro Tyr Gly Ala Pro Ser Pro Lys Arg Ile Ser
    290                 295                 300

Val Pro Arg Ser His Ala Lys His Pro Thr Asp Thr Tyr Pro Asp Ala
305                 310                 315                 320

Ser Glu Val Ser Ile Lys Lys Ala Ile Ala Thr Phe Leu Pro Arg Phe
                325                 330                 335

Gln Asp Lys Glu Leu Phe Asn Arg Ala Leu Cys Trp Cys Thr Asp Thr
            340                 345                 350

Ala Asp Ala Ala Leu Leu Met Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Val Gly Lys Tyr Val Val Glu Leu Ile Glu Gly Arg Leu Pro Glu Glu
385                 390                 395                 400

Met Ala Tyr Gln Trp Arg Trp Arg Pro Gly Gly Asp Ala Leu Lys Ser
                405                 410                 415

Arg Arg Lys Ala Pro Pro Lys Asp Leu Ala Asp Met Pro Gly Trp Lys
            420                 425                 430

His Asp Pro Lys Leu
        435
```

<210> SEQ ID NO 184
<211> LENGTH: 1314
<212> TYPE: DNA
<213> ORGANISM: Coniochaeta sp.

<400> SEQUENCE: 184

```
atgacgtcga atcgtgcaga tacaagggtg attgtcgtcg gtggcggagg aacgattggt      60

tcctcgacag cgctgcatct tgtgaggagt ggttatgctc ccgcaaatat cacggtcttg     120

gacacatttg agattccatc ggctcaatca gccggccatg atctcaacaa gatcatggga     180

atagatcatc gcaacaaggt ggacctgcaa atgagtctag aggctagaca gatgtggaag     240

gaggatgagt tattccagcc cttctttcac aataccggca gaatggactg cgaacacacg     300
```

-continued

```
cctgagggta tcgagaaact gaaaaagctg taccagaaac tgcacgatgc cggtgcgggt    360

ctggagaaga ctcatgcctg gttggacaac gaggatgaga tcttatccaa gatgccgttg    420

cttcaacgtg accaaataca aggatggaaa gcaatatgga gtcaagatgg cggctggtta    480

gctgcggcaa aggccatcaa tgcgatcgga cagttcttga aagaacgtgg tgtaaagttc    540

ggattcggcg gcgctggatc cttcaagcaa cccctttcg acgatgaagg cacaacttgc    600

attggcgttg agacggcaga tggtaccaaa tattacgctg acaaggtggt cttagcagct    660

ggcgcatgga gcccaaccct ggtggacctg gaagatcaat gttgctcgaa ggcttgggtg    720

tatgctcata ttcagttgac gcctgaagag gccgctgagt ataagggtgt cccagttgtg    780

tataatggcg aatttggctt cttctttgag cctgatgagt ttggtgtaat aaaggtgtgc    840

gacgagttcc caggattctc gcgcttcaag gaacatcaac cctatggcgc cccatctccg    900

aaacggatat cagtaccacg atcgcacgcc aagcatccca cagacactta tccagacgca    960

tccgaagtca gcatcaaaaa agcaatcgcg acgtttctcc ctcgatttca ggacaaggag   1020

ctcttcaatc gcgccttgtg ctggtgtaca gacactgcgg acgctgctct cttgatgtgt   1080

gaacacccca aatggaagaa tttcattcta gcgaccggcg acagcggaca ctcattcaaa   1140

atcttgccta acgtcggaaa atacgtagtc gagttgatag agggccgcct gccggaggaa   1200

atggcttatc aatggaggtg gcggccagga ggcgatgcac tcaagtctag acgtaaggca   1260

ccgccaaaag atcttgcaga catgccagga tggaaacatg atccgaaatt gtaa         1314
```

<210> SEQ ID NO 185
<211> LENGTH: 438
<212> TYPE: PRT
<213> ORGANISM: Aspergillus nidulans

<400> SEQUENCE: 185

```
Met Thr Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Cys Pro Ile Pro Ser Ala Gln
        35                  40                  45

Ser Ala Gly Tyr Asp Leu Asn Lys Ile Met Gly Ile Asp His Arg Asn
    50                  55                  60

Lys Pro Asp Leu Gln Leu Ser Leu Glu Ala Leu Asp Met Trp Lys Asn
65                  70                  75                  80

Asp Pro Leu Phe Lys Pro Phe Phe His Asn Val Gly Met Ile Asp Val
                85                  90                  95

Ser Ser Thr Glu Lys Gly Ile Glu Lys Leu Arg Lys Leu Tyr Gln Lys
            100                 105                 110

Leu Leu Asp Ala Gly Ile Gly Leu Glu Lys Thr Asn Phe Met Leu Glu
        115                 120                 125

Ser Glu Asp Glu Ile Leu Ala Lys Ala Pro His Phe Thr Gln Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala His Glu Lys Thr Cys Ile Gly Val Glu Thr Val Asp Gly
```

-continued

```
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Ala Tyr Lys Asn
                245                 250                 255

Thr Pro Val Ile Tyr Asp Gly Asp Tyr Gly Phe Phe Phe Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Ala Pro Lys Pro Ile Ser
    290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ser Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Glu Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435
```

<210> SEQ ID NO 186
<211> LENGTH: 1317
<212> TYPE: DNA
<213> ORGANISM: Aspergillus nidulans

<400> SEQUENCE: 186

```
atgacgcccc gagccaacac caaaatcatt gtcgtcggcg gcggcggcac aatgggctcg      60

tcgacagccc tacacctcct gcgcgccggc tacacgccgt ccaacattac agtgctcgac     120

acgtgcccta tcccctccgc acagtctgca ggctacgacc tgaacaaaat catgggcatc     180

gatcatcgca acaagcctga tttacagctc tctcttgagg cgctggacat gtggaaaaat     240

gatcctctct tcaagccgtt tttccacaat gttggaatga tcgacgtctc ttcaacagag     300

aaaggcatcg agaaacttcg gaagctgtac cagaaacttc tcgacgcagg cattgggctc     360

gagaagacga atttcatgct ggaaagtgaa gacgagatcc tggctaaagc gccgcatttc     420

acgcaggagc agattaaagg ctggaaaggc ctgttctgtg gcgacggcgg ctggctcgct     480

gcagccaaag ccatcaatgc cattgggcag ttcctcaagg aacagggcgt caagtttgga     540

ttcggcggcg ccggcacgtt caaaaagcca ctcttcgccg atgcccacga gaagacgtgc     600

atcggcgtcg agactgtaga cggcacaaag tactacgccg acaaggtcgt tctagcagct     660

ggtgcctgga gttcgacgtt ggtcgatctg gaggagcagt gcgtttcaaa ggcctgggtc     720
```

```
tttgcccaca tccaactgac gcccgctgaa gcagccgcgt ataagaacac tcctgttata    780

tacgacggtg actatgggtt tttctttgag ccgaatgaaa acggcatcat aaaagtctgt    840

gacgaattcc ctggcttcac gcatttcaaa atgcaccagc cgtacggctc gccggcgccc    900

aaacccatct ctgtgcctcg ttcccatgcg aagcacccca cagatacata cccgcacgcg    960

tcggaggtca cgatcaaaaa ggctatcaac cggttcctgc cgaggttcaa tgacaaggaa   1020

ctgtttaaca gggccatgtg ctggtgcacc gataccgcgg atagcaatct gcttgtttgt   1080

gagcatccac gctggaaggg gttttatctt gcaacagggg acagtgggca ttcgttcaag   1140

ttgctgccga atattggaaa gcatgttgtc gagttattgg aggagaggct ggaaagtgtg   1200

tttaaggatg cttggaggtg gaggcctggc agtggggatg cattaaaaag tagacgggct   1260

gcgcctgcga aggacctggc ggatatgccg ggtggagga atgaggcaaa gatgtag      1317
```

```
<210> SEQ ID NO 187
<211> LENGTH: 437
<212> TYPE: PRT
<213> ORGANISM: Phaeosphaeria nodorum

<400> SEQUENCE: 187

Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Val Thr Val Leu Asp Ala Tyr Pro Ile Pro Ser Ser
        35                  40                  45

Gln Ser Ala Gly Asn Asp Leu Asn Lys Ile Met Gly Val Asp His Arg
    50                  55                  60

Asn Pro Val Asp Leu Gln Leu Ala Leu Glu Ala Arg Gln Met Trp Asn
65                  70                  75                  80

Glu Asp Glu Leu Phe Lys Lys Phe Phe His Asn Thr Gly Arg Leu Asp
                85                  90                  95

Cys Ala His Gly Glu Lys Asp Ile Ala Lys Leu Lys Ser Leu Tyr Gln
            100                 105                 110

Lys Leu Val Asp Ala Gly Leu Asp Ala Thr Asn Glu Trp Leu Asp Ser
        115                 120                 125

Glu Asp Glu Ile Leu Lys Arg Met Pro Leu Leu Ser Arg Asp Gln Ile
    130                 135                 140

Lys Gly Trp Lys Ala Ile Phe Ser Lys Asp Gly Gly Trp Leu Ala Ala
145                 150                 155                 160

Ala Lys Ala Ile Asn Ala Val Gly Glu Tyr Leu Arg Asp Gln Gly Val
                165                 170                 175

Arg Phe Gly Phe Tyr Gly Ala Gly Ser Phe Lys Ala Pro Leu Leu Ala
            180                 185                 190

Glu Gly Val Cys Ile Gly Val Glu Thr Val Asp Gly Thr Arg Tyr Tyr
        195                 200                 205

Ala Asp Lys Val Val Leu Ala Ala Gly Ala Trp Ser Pro Thr Leu Val
    210                 215                 220

Glu Leu His Glu Gln Cys Val Ser Lys Ala Trp Val Tyr Gly His Ile
225                 230                 235                 240

Gln Leu Thr Pro Glu Glu Ala Ala Arg Tyr Lys Asn Ser Pro Val Val
                245                 250                 255

Tyr Asn Gly Asp Val Gly Phe Phe Phe Glu Pro Asn Glu His Gly Val
            260                 265                 270
```

```
Ile Lys Val Cys Asp Glu Phe Pro Gly Phe Thr Arg Phe Lys Met His
        275                 280                 285

Gln Pro Phe Gly Ala Lys Ala Pro Lys Arg Ile Ser Val Pro Arg Ser
    290                 295                 300

His Ala Lys His Pro Thr Asp Thr Ile Pro Asp Ala Ser Asp Val Ser
305                 310                 315                 320

Ile Arg Arg Ala Ile Ala Thr Phe Met Pro Gln Phe Lys Asn Lys Lys
                325                 330                 335

Met Phe Asn Gln Ala Met Cys Trp Cys Thr Asp Thr Ala Asp Ser Ala
            340                 345                 350

Leu Leu Ile Cys Glu His Pro Glu Trp Lys Asn Phe Val Leu Ala Thr
        355                 360                 365

Gly Asp Ser Gly His Ser Phe Lys Leu Leu Pro Asn Ile Gly Lys His
    370                 375                 380

Val Val Glu Leu Leu Glu Gly Thr Leu Ala Asp Asp Leu Ala His Ala
385                 390                 395                 400

Trp Arg Trp Arg Pro Gly Ser Gly Asp Ala Leu Lys Ser Arg Arg Ser
                405                 410                 415

Ala Pro Ala Lys Asp Leu Ala Asp Met Pro Gly Trp Asn His Asp Lys
            420                 425                 430

Pro Arg Ala Asn Leu
        435


<210> SEQ ID NO 188
<211> LENGTH: 1314
<212> TYPE: DNA
<213> ORGANISM: Phaeosphaeria nodorum

<400> SEQUENCE: 188

atggccccgt cgcgtgctaa tacgtcggtc attgtggttg gtggtggtgg tacgattggc      60

tcatctacgg ctctgcatct ggtccgctca ggctataccc cgtcgaacgt gacggttctg     120

gatgcatacc cgattccgag ctctcagagc gctggcaacg acctgaataa aatcatgggt     180

gtcgatcatc gtaatccggt ggatctgcag ctggctctgg aagcgcgcca aatgtggaac     240

gaagacgaac tgttcaagaa gtttttccat aacaccggcc gtctggattg cgcgcacggt     300

gaaaaagata ttgccaaact gaagagcctg tatcagaaac tggtggatgc gggtctggac     360

gccacgaacg aatggctgga tagtgaagac gaaatcctga aacgtatgcc gctgctgtcc     420

cgcgatcaaa ttaaaggctg gaaggcgatc ttttcaaaag acggtggttg gctggcagca     480

gcaaaggcaa ttaatgcagt tggtgaatat ctgcgtgatc agggcgtccg cttcggtttt     540

tacggcgccg gttctttcaa agcaccgctg ctggctgaag gcgtctgcat cggtgtcgaa     600

accgtggatg gcacgcgcta ttacgcagac aaagtggttc tggctgcagg tgcatggtcg     660

ccgaccctgg ttgaactgca tgaacagtgt gtgagcaaag cgtgggttta cggccacatt     720

caactgacgc cggaagaagc cgcacgttat aagaacagcc cggtcgtgta caatggcgat     780

gtgggctttt tctttgaacc gaacgaacat ggcgttatca aagtctgcga tgaatttccg     840

ggttttaccc gcttcaagat gcaccagccg tttggtgcca aagcaccgaa gcgtattagt     900

gtgccgcgct cccatgccaa acacccgacc gatacgatcc cggatgcaag tgacgtttcc     960

attcgtcgcg ctatcgcgac ctttatgccg cagttcaaga acaaaaagat gttcaaccaa    1020

gcgatgtgct ggtgtaccga tacggccgac agcgcgctgc tgatttgtga acatccggaa    1080

tggaaaaact ttgttctggc gaccggcgat tcaggtcatt cgttcaaact gctgccgaat    1140
```

```
atcggcaagc acgttgtcga actgctggag ggtacgctgg cagatgacct ggcacacgca   1200

tggcgttggc gtccgggtag tggtgatgca ctgaaaagcc gtcgctctgc tccggcgaaa   1260

gacctggctg atatgccggg ctggaaccat gacaaaccgc gtgctaatct gtaa         1314


<210> SEQ ID NO 189
<211> LENGTH: 443
<212> TYPE: PRT
<213> ORGANISM: Cryptococcus neoformans

<400> SEQUENCE: 189

Met Pro Pro Ser Arg Ala Ser Thr Lys Val Ile Val Ile Gly Gly Gly
1               5                   10                  15

Gly Thr Leu Gly Ser Ser Thr Ala Leu His Leu Leu Arg Ala Gly Tyr
            20                  25                  30

Thr Pro Ser Asn Ile Thr Val Leu Asp Thr Tyr Leu Ile Pro Ser Ala
        35                  40                  45

Gln Ser Ala Gly Asn Asp Leu Asn Lys Ile Met Gly Ile Asp Ile Arg
    50                  55                  60

Asn Pro Val Asp Lys Gln Leu Ser Leu Glu Ala Arg Asp Met Trp Arg
65                  70                  75                  80

Asn Asp Glu Val Phe Lys Pro Tyr Phe His Asn Thr Gly Arg Leu Asp
                85                  90                  95

Cys Ala His Thr Pro Glu Ser Ile Ala Lys Leu Arg Lys Leu Tyr Glu
            100                 105                 110

Lys Ile Leu Lys Ala Gly Ser Gly Leu Glu Lys Thr His His Trp Leu
        115                 120                 125

Ser Thr Glu Asp Glu Ile Leu Ala Arg Ala Pro Leu Leu Asp Arg Lys
    130                 135                 140

Gln Ile Lys Gly Trp Lys Ala Ile Tyr Ser Glu Asp Gly Gly Trp Leu
145                 150                 155                 160

Ala Ala Ala Lys Ala Ile Asn Ser Ile Gly Gln Val Leu Lys Glu Lys
                165                 170                 175

Gly Val Thr Phe Gly Phe Gly Ser Ala Gly Ser Phe Lys Lys Pro Leu
            180                 185                 190

Phe Asp Glu Asp Gly Thr Lys Ala Ile Gly Ile Glu Thr Val Asp Gly
        195                 200                 205

Thr Gln Tyr Phe Ala Asp Lys Val Val Leu Ala Ala Gly Ala Trp Ser
    210                 215                 220

Pro Thr Leu Val Asp Leu Glu Gly Gln Cys Cys Ser Lys Ala Trp Val
225                 230                 235                 240

Tyr Ala His Met Gln Leu Thr Pro Glu Glu Ala Ala Glu Tyr Lys Glu
                245                 250                 255

Cys Pro Val Val Tyr Asn Ser Glu Leu Gly Phe Phe Phe Glu Pro Asn
            260                 265                 270

Glu Lys Gly Val Ile Lys Val Cys Asp Glu Phe Pro Gly Phe Thr Arg
        275                 280                 285

Phe Lys Gln His Gln Pro Tyr Gly Ala Ser Ser Thr Lys His Ile Ser
    290                 295                 300

Phe Pro Arg Ser His Ala Lys His Pro Thr Asp Thr Ile Pro Asp Glu
305                 310                 315                 320

Ser Asp Ala Ser Ile Arg Arg Ala Ile Ser Ala Phe Leu Pro Arg Phe
                325                 330                 335

Lys Glu Lys Glu Leu Phe Asn Arg Ala Leu Cys Trp Cys Thr Asp Thr
            340                 345                 350
```

```
Ala Asp Ala Asn Leu Leu Ile Cys Glu His Pro Lys Trp Lys Asn Phe
        355                 360                 365

Ile Leu Ala Thr Gly Asp Ser Gly His Ser Phe Lys Ile Leu Pro Asn
    370                 375                 380

Ile Gly Lys His Val Val Glu Leu Ile Glu Gly Thr Leu Ala Glu Asp
385                 390                 395                 400

Leu Ala Glu Ser Trp Arg Trp Arg Pro Gly Ser Gly Asp Pro Leu Ile
                405                 410                 415

Ser Arg Arg Ala Ala Pro Ala Arg Asp Leu Ala Asp Leu Pro Gly Trp
            420                 425                 430

Asn His Asp Glu Pro Ser Asp Asp Asp Met Asp
        435                 440
```

<210> SEQ ID NO 190
<211> LENGTH: 1332
<212> TYPE: DNA
<213> ORGANISM: Cryptococcus neoformans

<400> SEQUENCE: 190

```
atgccgccgt cccgtgcttc aacgaaagtg attgtcattg gtggtggtgg tacgctgggc     60

tcctcaaccg ccctgcatct gctgcgcgcg ggctataccc cgagtaacat taccgtgctg    120

gatacgtacc tgatcccgag tgcccagtcc gcaggcaacg acctgaataa aattatgggt    180

attgatatcc gcaatccggt ggataaacaa ctgagcctgg aagcccgtga tatgtggcgc    240

aacgacgaag ttttcaaacc gtacttccat aacaccggtc gtctggactg cgctcacacg    300

ccggaatcaa ttgcgaaact gcgtaaactg tacgaaaaaa tcctgaaagc aggctcaggt    360

ctggaaaaaa cccatcactg gctgtcgacg gaagatgaaa tcctggcacg tgcaccgctg    420

ctggaccgta aacagattaa aggttggaaa gcaatctata gtgaagatgg cggttggctg    480

gcggccgcaa aagctattaa ctccatcggc caagtcctga aagaaaaagg tgtgaccttc    540

ggctttggta gcgcaggctc ttttaaaaaa ccgctgttcg atgaagacgg cacgaaagcc    600

attggtatcg aaaccgttga tggtacgcag tattttgccg acaaagtggt tctggctgca    660

ggtgcatgga gcccgaccct ggttgatctg gaaggccagt gctgttctaa agcttgggtc    720

tacgcgcaca tgcaactgac gccggaagaa gccgcagaat ataaagaatg cccggtcgtg    780

tacaacagcg aactgggctt tttctttgaa ccgaacgaaa aaggtgtgat caaagtttgt    840

gatgaattcc cgggctttac ccgtttcaaa cagcatcaac cgtacggtgc tagctctacg    900

aaacacatta gctttccgcg ctctcatgcg aaacacccga ccgatacgat cccggatgaa    960

agtgacgcct ccattcgtcg cgctatctct gcgtttctgc cgcgtttcaa agaaaaagaa   1020

ctgtttaacc gcgcgctgtg ctggtgtacc gatacggctg acgcgaacct gctgatttgt   1080

gaacacccga aatggaaaaa ttttatcctg gccaccggcg attcaggtca ttcgttcaaa   1140

attctgccga atatcggcaa acacgttgtc gaactgattg aaggtaccct ggccgaagat   1200

ctggcagaaa gctggcgttg gcgtccgggc agtggtgacc cgctgatctc ccgtcgcgct   1260

gcgccggcgc gcgacctggc ggacctgccg ggctggaacc acgacgaacc gagcgacgat   1320

gacatggact ga                                                       1332
```

<210> SEQ ID NO 191
<211> LENGTH: 440
<212> TYPE: PRT
<213> ORGANISM: Curvularia clavata

<400> SEQUENCE: 191

```
Met Ala Pro Ser Arg Ala Asn Thr Ser Val Ile Val Val Gly Gly Gly
1               5                   10                  15

Gly Thr Ile Gly Ser Ser Thr Ala Leu His Leu Val Arg Ser Gly Tyr
            20                  25                  30

Thr Pro Ser Asn Ile Thr Val Leu Asp Ala Tyr Pro Ile Pro Ser Ser
        35                  40                  45

Gln Ser Ala Gly Asn Asp Leu Asn Lys Ile Met Gly Ile Asp His Arg
    50                  55                  60

Asn Lys Val Asp Leu Gln Leu Ser Leu Glu Ala Arg Gln Met Trp Arg
65                  70                  75                  80

Glu Asp Asp Leu Phe Lys Glu Tyr Phe His Asn Thr Gly Arg Leu Asp
                85                  90                  95

Cys Ala His Gly Glu Glu Gly Leu Ala Lys Leu Arg Gln Leu Tyr Gln
            100                 105                 110

Lys Leu Leu Asp Ala Asn Ala Gly Leu Glu Glu Thr Thr Glu Trp Leu
        115                 120                 125

Asp Ser Glu Asp Glu Ile Leu Lys Lys Met Pro Leu Leu Ser Arg Asp
    130                 135                 140

Gln Ile Lys Gly Trp Lys Ala Val Tyr Ser Gln Asp Gly Gly Trp Leu
145                 150                 155                 160

Ala Ala Ala Lys Ala Ile Asn Ala Ile Gly Glu Tyr Leu Arg Ala Gln
                165                 170                 175

Gly Val Lys Phe Gly Phe Gly Gly Ala Gly Ser Phe Lys Gln Pro Leu
            180                 185                 190

Leu Ala Glu Gly Val Cys Ile Gly Val Glu Thr Val Asp Gly Thr Arg
        195                 200                 205

Tyr Tyr Ala Asp Lys Val Val Leu Ala Ala Gly Ala Trp Ser Pro Thr
    210                 215                 220

Leu Val Glu Leu His Glu Gln Cys Val Ser Lys Ala Trp Val Tyr Gly
225                 230                 235                 240

His Ile Gln Leu Thr Pro Glu Glu Ala Ala Glu Tyr Lys Asn Ser Pro
                245                 250                 255

Val Val Tyr Asn Gly Asp Val Gly Phe Phe Phe Glu Pro Asn Glu His
            260                 265                 270

Gly Val Ile Lys Val Cys Asp Glu Phe Pro Gly Phe Thr Arg Phe Lys
        275                 280                 285

Met His Gln Pro Phe Gly Ala Lys Ala Pro Lys Arg Ile Ser Val Pro
    290                 295                 300

Arg Ser His Ala Lys His Pro Thr Asp Thr Ile Pro Asp Ala Ser Glu
305                 310                 315                 320

Lys Ser Ile Arg Lys Ala Ile Ala Thr Phe Leu Pro Lys Phe Thr Glu
                325                 330                 335

Lys Glu Leu Phe Asn Arg His Leu Cys Trp Cys Thr Asp Thr Ala Asp
            340                 345                 350

Ser Ala Leu Leu Ile Cys Glu His Pro Glu Trp Lys Asn Phe Val Leu
        355                 360                 365

Ala Thr Gly Asp Ser Gly His Ser Phe Lys Leu Leu Pro Asn Ile Gly
    370                 375                 380

Lys His Val Val Glu Leu Leu Glu Gly Thr Leu Ala Asp Asp Leu Ala
385                 390                 395                 400

His Ala Trp Arg Trp Arg Pro Gly Ser Gly Asp Ala Leu Lys Ser Arg
                405                 410                 415
```

```
Arg Ser Ala Pro Ala Lys Asp Leu Ala Asp Met Pro Gly Trp Lys His
            420                 425                 430

Asp Asp Val Val Lys Ser Lys Leu
        435                 440


<210> SEQ ID NO 192
<211> LENGTH: 1323
<212> TYPE: DNA
<213> ORGANISM: Curvularia clavata

<400> SEQUENCE: 192

atggccccgt cgcgtgctaa tacgtcggtc attgtggttg gtggtggtgg tacgattggc      60

tcatctacgg ctctgcatct ggtccgctca ggctataccc cgtcgaacat tacggttctg     120

gatgcatacc cgattccgag ctctcagagc gctggcaacg acctgaataa aatcatgggt     180

atcgatcatc gtaataaggt ggatctgcag ctgtctctgg aagcgcgcca aatgtggcgc     240

gaagacgatc tgttcaagga gtatttccat aacaccggcc gtctggattg cgcgcacggt     300

gaagaaggtc ttgccaaact gcgtcaactg tatcagaaac tgctggatgc gaatgcgggt     360

ctggaagaga cgaccgaatg gctggatagt gaagacgaaa tcctgaaaaa aatgccgctg     420

ctgtcccgcg atcaaattaa aggctggaag gcggtgtatt cacaggacgg tggttggctg     480

gcagcagcaa aggcaattaa tgcaattggt gaatatctgc gtgctcaggg cgtcaaattc     540

ggttttggcg gcgccggttc tttcaaacaa ccgctgctgg ctgaaggcgt ctgcatcggt     600

gtcgaaaccg tggatggcac gcgctattac gcagacaaag tggttctggc tgcaggtgca     660

tggtcgccga ccctggttga actgcatgaa cagtgtgtga gcaaagcgtg ggtttacggc     720

cacattcaac tgacgccgga agaagccgca gaatataaga acagcccggt cgtgtacaat     780

ggcgatgtgg gctttttctt tgaaccgaac gaacatggcg ttatcaaagt ctgcgatgaa     840

tttccgggtt ttacccgctt caagatgcac cagccgtttg gtgccaaagc accgaagcgt     900

attagtgtgc cgcgctccca tgccaaacac ccgaccgata cgatcccgga tgcaagtgaa     960

aaatccattc gtaaagctat cgcgaccttt ctgccgaagt tcacggagaa agagctgttc    1020

aaccgtcatc tgtgctggtg taccgatacg gccgacagcg cgctgctgat ttgtgaacat    1080

ccggaatgga aaaactttgt tctggcgacc ggcgattcag gtcattcgtt caaactgctg    1140

ccgaatatcg gcaagcacgt tgtcgaactg ctggagggta cgctggcaga tgacctggca    1200

cacgcatggc gttggcgtcc gggtagtggt gatgcactga aaagccgtcg ctctgctccg    1260

gcgaaagacc tggctgatat gccgggctgg aaacatgacg atgtggtgaa aagcaaactg    1320

taa                                                                   1323


<210> SEQ ID NO 193
<211> LENGTH: 146
<212> TYPE: PRT
<213> ORGANISM: Homo sapiens

<400> SEQUENCE: 193

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
```

-continued

```
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145
```